(12) United States Patent
Mc Allister et al.

(10) Patent No.: US 8,440,679 B2
(45) Date of Patent: May 14, 2013

(54) BICYCLIC COMPOUNDS AND THEIR USES AS DUAL C-SRC / JAK INHIBITORS

(75) Inventors: Andrès Mc Allister, Genève (CH);
Maximilien Murone, Epalinges (CH);
Saumitra Sengupta, Kolkata (IN);
Shankar Jayaram Shetty, Bangalore (IN)

(73) Assignees: Debiopharm S.A., Lausanne (CH);
Aurigene Discovery Technologies Ltd, Bangalore (IN)

( * ) Notice: Subject to any disclaimer, the term of this patent is extended or adjusted under 35 U.S.C. 154(b) by 0 days.

(21) Appl. No.: 13/578,656

(22) PCT Filed: Feb. 17, 2011

(86) PCT No.: PCT/IB2011/050669
§ 371 (c)(1),
(2), (4) Date: Sep. 27, 2012

(87) PCT Pub. No.: WO2011/101806
PCT Pub. Date: Aug. 25, 2011

(65) Prior Publication Data
US 2013/0012518 A1    Jan. 10, 2013

(30) Foreign Application Priority Data

Feb. 17, 2010   (IN) .............................. 415/CHE/2010

(51) Int. Cl.
*C07D 471/04*   (2006.01)
*A61K 31/519*   (2006.01)
*A61P 35/00*    (2006.01)

(52) U.S. Cl.
USPC ...................... 514/264.1; 544/279

(58) Field of Classification Search ................. 544/279; 514/264.1
See application file for complete search history.

(56) References Cited

FOREIGN PATENT DOCUMENTS

| | | |
|---|---|---|
| WO | WO 99/61444 | 12/1999 |
| WO | WO 2005/034869 | 4/2005 |
| WO | WO 2007/088014 | 8/2007 |

OTHER PUBLICATIONS

International Search Report and Written Opinion for PCT/IB2011/050669 with mail date May 13, 2011.

*Primary Examiner* — Susanna Moore
(74) *Attorney, Agent, or Firm* — Harness, Dickey & Pierce, P.L.C.

(57) ABSTRACT

The present invention relates to substituted aromatic bicyclic compounds containing pyrimidine and pyridine rings of formula (I) having the structure as well as pharmaceutically acceptable salts thereof. The compounds of the present invention are useful as tyrosine kinase inhibitors, preferably SRC family kinases (SFKs) inhibitors, in particular as multi SFK/JAK. kinases inhibitors and even preferably as dual c-SRC/JAK kinases inhibitors, thereby inhibiting the STAT3 activation and therefore abnormal growth of particular cell types. Notably, the compounds of the present invention are useful for the treatment or inhibition of certain diseases that are the result of deregulation of STAT3.

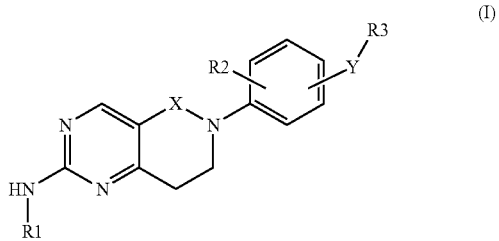

9 Claims, 2 Drawing Sheets

BICYCLIC COMPOUNDS AND THEIR USES AS DUAL C-SRC / JAK INHIBITORS

PRIORITY STATEMENT

This application is a national phase under 35 U.S.C. §371 of PCT International Application No. PCT/IB2011/050669 which has an International filing date of 17 Feb. 2011, which claims priority under 35 U.S.C. §119 to Indian Application No. 00415/CHE/2010, filed on 17 Feb. 2010. The contents of each application recited above are incorporated herein by reference in their entirety.

FIELD OF THE INVENTION

The present invention relates to substituted aromatic bicyclic compounds containing pyrimidine and pyridine rings as well as pharmaceutically acceptable salts thereof. The compounds of the present invention are useful as tyrosine kinase inhibitors, preferably SRC family kinases (SFKs) inhibitors, in particular as multi SFK/JAK kinases inhibitors and even preferably as dual c-SRC/JAK kinases inhibitors, thereby inhibiting the STAT3 activation and therefore abnormal growth of particular cell types. Notably, the compounds of the present invention are useful for the treatment or inhibition of certain diseases that are the result of deregulation of STAT3.

BACKGROUND OF THE INVENTION

Inflammation and cancer are linked by both oncogenic (intrinsic) and environmental (extrinsic) pathways (Yu et al., Nature Reviews Cancer 2009). The intrinsic pathway is activated by genetic or epigenetic alterations in transformed cells. Such alterations include those that cause the overexpression or the persistent activation of growth factor receptors with intrinsic tyrosine kinase activity and cytokine receptors with associated Janus kinase (JAK) family tyrosine kinases. Oncogenic mutations in receptor-associated JAK family members also underlie some types of cancer. These receptors, as well as non-receptor tyrosine kinases such as c-SRC, can be activated by extrinsic pathways—environmental factors that are associated with cancer inflammation—which include ultraviolet (UV) radiation, chemical carcinogens, infection, stress and cigarette smoke. Activated tyrosine kinases induced by both intrinsic and extrinsic pathways phosphorylate and activate the transcription factor signal transducer and activator of transcription 3 (STAT3), which in turn forms dimers that translocate to the nucleus, where they directly regulate the expression of a battery of target genes. In addition to upregulating numerous genes involved in proliferation, survival, invasion and metastasis, STAT3 induces the expression of many cytokines, chemokines and other mediators, such as interleukin-6 and cyclooxygenase 4 that are associated with cancer-promoting inflammation. Importantly, receptors for many of these cytokines, chemokines and mediators in turn further activate STAT3, thus forming autocrine and paracrine feedforward loops that result in a stable change to the genetic program and the promotion of cancer inflammation.

STAT3 is suggested to have a crucial role in selectively inducing and maintaining a procarcinogenic inflammatory microenvironment, both at the initiation of malignant transformation and during cancer progression. Persistent activation of STAT3 mediates the propagation of tumor-promoting inflammation and increases tumor cell proliferation, survival and invasion while suppressing anti-tumor immunity. Thus, STAT3 is an attractive molecular target for the development of novel cancer therapeutics or for modulating immune responses to improve cancer therapy.

Several small molecule inhibitors, that effectively block the STAT3 signaling pathway, are already known in the prior art (Deng et al., Current Cancer Drug Targets, 2007). These inhibitors, from a structural point of view, are divided into five classes of compounds. They include (1) natural products and derivatives, such as curcumin, resveratrol and others, (2) tyrphostins, (3) platinum-containing complexes, (4) peptidomimetics, and (5) azaspiranes.

It is also known from the prior art that instead of directly and specifically inhibiting STAT3, it is possible to effectively block the STAT3 signaling pathway by inhibiting the upstream targets. Indeed, as mentioned above, the STAT3 transcription factor is a downstream effector of both JAK and c-SRC kinases and is activated by tyrosine phosphorylation on tyrosine 705 (Y705) by these kinases, which is a prerequisite for STAT3 dimerization and activation of the transcription factor function of STAT3.

Thus c-SRC and JAK act upstream of the transcription factor STAT3, and their inhibition will lead to block STAT3 signaling pathway in a subset of STAT3 dependent tumors. It has been reported (Johnson et al., Clin. Cancer Res, 2007 and WO 2008/077062, Board of Regents, The University of Texas System) that c-SRC and JAK inhibitors have synergistic anti-tumor effects. Indeed, c-SRC can be rapidly and durably inhibited by, for example, Dasatinib, whereas STAT3 undergoes only transient inactivation. The addition of JAK inhibitors, such as pyridone 6 or AG490, during Dasatinib incubation resulted in sustained inhibition of STAT3, although JAK activation by Dasatinib was not shown. Combined c-SRC and JAK inhibition resulted in synergistic cytotoxicity due to increased apoptosis. Therefore with the combination treatment, the durable inhibition of several pathways, such as STAT3 signaling pathway, known to be important for cancer cell survival and proliferation can be obtained.

The SRC family of kinases (SFKs) is composed of nonreceptor tyrosine kinases with key roles in regulating signal transduction pathways that control cell proliferation, motility, adhesion and survival. SFKs and certain growth factor receptors are overexpressed in various cancers. Halpern M. S., England J. M., Kopen G. C, Christou A. A., Taylor R. L. Jr., Endogenous c-src as a Determinant of the Tumorigenicity of src Oncogenes, Proc Natl Acad Sd USA. 1996 93(2): 824-827. Haura, E. B., Zheng, Z., Song, L., Cantor, A., Bepler, G., Activated Epidermal Growth Factor Receptor-Stat-3 Signaling Promotes Tumor Survival In Vivo in Non-Small Cell Lung Cancer, Clin. Cancer Res. 2005, 11(23): 8288-8294. c-SRC plays a role in responses to regional hypoxia, limited nutrients, and internal cellular effects to self-destruct. Aberrant expression and/or activity of c-SRC are observed in numerous solid and liquid tumors, and play critical roles in affecting chemoresistance. Almost any growth factor leading to activation of receptor tyrosine kinases can be shown to activate c-SRC, making c-SRC a very attractive target for cancer therapy. Since the activation and perhaps over-expression of c-SRC has been implicated in cancer, osteoporosis, stroke, myocardial infarction, and vascular leak, among others, a small molecule inhibitor of c-SRC can be beneficial for the treatment of several disease states. However, inhibition of SFKs using a tyrosine kinase inhibitor has been shown to result in cytotoxicity, cell cycle arrest, and apoptosis in head and neck squamous carcinoma and non-small cell lung cancer cell lines. Johnson, F. M., Saigal, B., Talpaz, M., and Donate, N. J., Dasatinib (BMS-354825) Tyrosine Kinase Inhibitor Suppresses Invasion and Induces Cell Cycle Arrest and Apoptosis of Head and Neck Squamous Cell Carcinoma and Non-small Cell Lung Cancer Cells, Clin Cancer Res, 11: 6924-6932, 2005. In head and neck squamous carcinoma and non-small cell lung cancer cell lines, Dasatinib results in cytotoxicity, cell cycle arrest and apoptosis. However, despite the durable inhibition of SFKs and initial inhibition of STAT3, STAT3 is not durably inhibited.

The Janus kinases (JAKs) are cellular kinases and consist of four members—JAK1, JAK2, JAK3 and TYK2. The JAKs may play a crucial role in regulating cell behavior induced by a number of cytokines and are crucial components of diverse signal transduction pathways that govern cellular survival, proliferation, differentiation and apoptosis. The over-activation of JAK kinases has been implicated in tumorigenesis. In 2005, a recurrent mutation in JAK2 (JAK2V6I7F) leading to a constitutively active JAK2 was identified in a large number of patients with myeloproliferative disorders, including polycythaemia vera, essential thrombocythaemia and primary myelo fibrosis.

Several selective SRC family kinase inhibitors, such as SU6656, Dasatinib, WO 99/61444 (Warner-Lambert Company) or WO 2007/088014 (F. Hoffmann La Roche AG), and selective JAK inhibitors, such as pyridone 6, AG490 or those disclosed in WO 2009/054941 (Merck & Co., Inc), WO 2009/029998 (Cytopia Research PTY LTD) or WO/2008/157208 (Incyte Corporation), have been reported. SFKs also mediate STAT growth pathways in various cancers. Xi, S., Zhang, Q., Dyer, K. F., Lerner, E. C, Smithgall, T. E., Gooding, W. E., Kamens, J., and Grandis, J. R., Src kinases Mediate STAT Growth Pathways in Squamous Cell Carcinoma of the Head and Neck, J Biol Chem, 278: 31574-31583, 2003. An important need exists, therefore, for pharmaceutical composition and/or method of treatment for cancer that will inhibit both SFKs and STATs.

However there is a further need to develop a multi-targeted kinase inhibitor. A single compound which inhibits a combination of several targets, such as SFKs and JAKs, offers the advantage of inhibiting simultaneously several key signal transduction pathways, thereby interfering with several oncogenic processes, while making the treatment easier and improving the patients comfort. It would therefore be desirable to generate small molecule kinase inhibitor molecules able to simultaneously inhibit SFKs (in particular c-SRC) and JAKs.

By combining a dual inhibitory activity, such as SFKs (in particular c-SRC) and JAKs, in a single molecule, the advantage resides in (i) reducing the risks related to off-target toxicity encountered when two different kinase inhibitors targeting SFKs (in particular c-SRC) and JAKs are administered, (ii) reducing the costs of treatment, (iii) increasing the patients compliance, and (iv) blocking simultaneously parallel ways of activating the STAT3 pathway will lead to a better anti-tumoral response. Moreover, as the status of STAT3 activation can be monitored across tumor types, a multi SFKs (in particular c-SRC) and JAKs targeted kinase inhibitor could be used in various types of diseases based on the status of STAT3 in those tumors.

Accordingly, the present invention aims to provide compounds which simultaneously inhibit several key signal transduction pathways especially directed towards the status of STAT3 activation. Those compounds have the unexpected advantage to present either:
- an inhibition for efficient STAT3 blockade following the inhibition of c-Src and JAK2;
- an inhibition of STAT3 phosphorylation by in-cell Western preferably having an IC50≦500 nM;
- in an established xenograft models using A431 and A549 (STAT3 positive cell lines) an inhibition of growth (>60%) of established tumors at a dose below MTD with a clear dose-response (highest dose close to MTD) and an inhibition of STAT3 phosphorylation in tumors.

The compounds of the invention represent compounds showing a particular and unexpected good compromise between these 3 criteria.

SUMMARY OF THE INVENTION

This goal has been achieved by the Applicants, who surprisingly generated novel small kinase inhibitor molecules of c-SRC, JAK-1, JAK-2.

The present invention provides compounds which affect the STAT3 pathway. The compounds of the invention are useful as pharmaceutical compositions, for example where modulation of the STAT3 pathway is indicated for the treatment of various human diseases, such as cancer and/or autoimmune diseases.

The present invention provides a compound of formula (I) having the structure

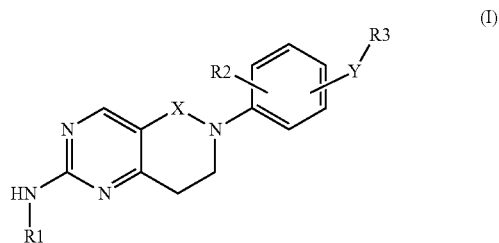

wherein
R1 is H, aryl, substituted aryl, alkyl, substituted alkyl, heteroaryl, substituted hetero aryl, heterocyclyl, substituted heterocyclyl, heterocyclylalkyl or substituted heterocyclylalkyl,
X is $CH_2$ or C=O
R2 is H, $(C_1-C_6)$alkyl, halogen, $CF_3$, or —O—$(C_1-C_6)$alkyl
Y is —NHCO—, —CONH—, —$NHSO_2^-$, —NH—, —$NCH_3$—CO—, —$NHCH_2$—, O, —NHCONH— or —$NHCOCH_2$—
R3 is alkyl, substituted alkyl, aryl, or substituted aryl, heteroaryl, substituted heteroaryl, cyclo alkyl, substituted cycloalkyl or heterocycloalkyl
or a pharmaceutically acceptable salt thereof.

Preferably the present invention provides a compound of formula (II) having the structure

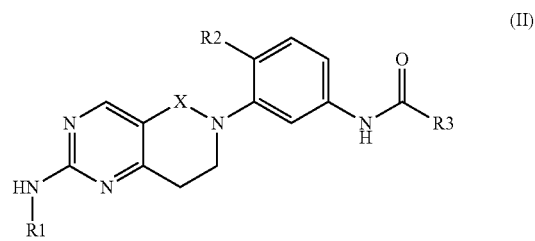

wherein
R1 is hydrogen, $(C_1-C_4)$alkyl, phenyl, substituted phenyl, pyridine, or substituted pyridine, preferably R1 is substituted phenyl or substituted pyridine,
X is $CH_2$ or C=O
R2 is H, $(C_1-C_6)$alkyl, halogen, or —O—$(C_1-C_6)$alkyl, preferably R2 is H, $CH_3$, Cl or F R3 is (C₁-C₆)alkyl, cycloalkyl, substituted cycloalkyl, heterocycloalkyl, aryl, substituted aryl, heteroaryl, substituted heteroaryl,

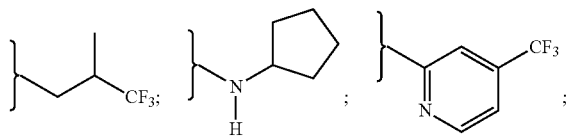

and wherein the substituents are selected from the group comprising $C_1$-$C_4$ linear or branched alkyl, halo or nitrile substituted $C_1$-$C_4$ alkyl, —O-alkyl($C_1$-$C_4$), halogen;

or a pharmaceutically acceptable salt thereof.

Preferably R3 is selected from the group consisting of:

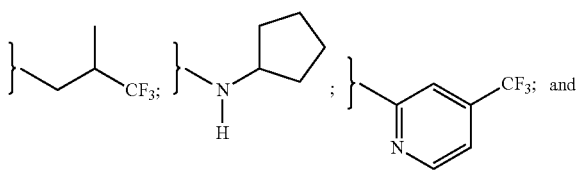

substituted phenyl, wherein the substituents are selected from the group comprising Cl, F, Br, $CF_3$ and $CH_3$.

The compounds of the invention for use in therapy and for use in a method for treating diseases associated with activation of STAT3 pathway, through multi-target inhibition of c-SRC and JAK2 are also encompassed in the present invention.

Preferably the diseases associated with activation of STAT3 pathway are cancer, auto-immune, bone related and heamatological diseases.

Further object of the present invention is to provide a pharmaceutical composition comprising the compounds of the invention and at least one pharmaceutically acceptable excipient, carrier or diluent.

DETAILED DESCRIPTION OF THE INVENTION

Figure 1:
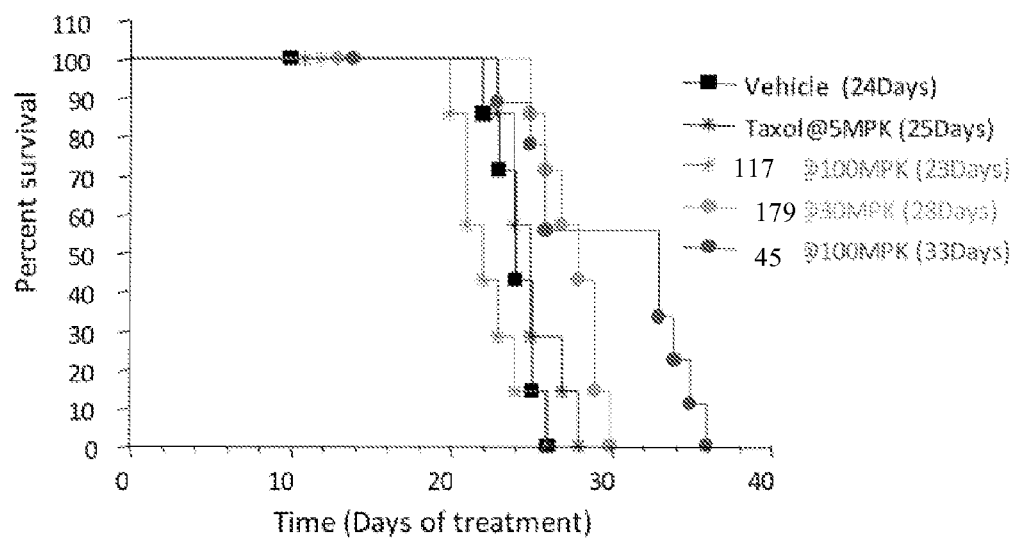
FIG. 1 shows inhibition activity of the compounds of the invention compared to Taxol®

Unless defined otherwise, all technical and scientific terms used herein have the same meaning as is commonly understood by one of skill in art to which the subject matter herein belongs. As used herein, the following definitions are supplied in order to facilitate the understanding of the present invention. In the case of conflict, the present specification, including definitions, will control.

The term "comprise" is generally used in the sense of include, that is to say permitting the presence of one or more features or components.

As used in the specification and claims, the singular form "a", "an" and "the" include plural references unless the context clearly dictates otherwise.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons.

Likewise, "cycloalkyl" refers to a saturated or partially saturated, monocyclic or fused or spiro polycyclic, carbocycle preferably containing from 3 to 10 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

The term "substituted alkyls" refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "heterocycloalkyl" or "heterocyclyl" as used herein, refers to a non-aromatic partially unsaturated or fully saturated 3 to 10 membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized. The heterocyclic ring may be substituted at one or more ring positions with substituents such as alkyl, carbonyl, halogen, alkoxy, hydroxyalkyl and the like. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The group may be a terminal group or a bridging group.

The term "heteroatom" refers to an atom of any element other than carbon or hydrogen. Illustrative heteroatoms include boron, nitrogen, oxygen, phosphorus, sulfur and selenium.

The term "aralkyl" refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively. The term "alkylene" refers to an organic radical formed from an unsaturated aliphatic hydrocarbon; "alkenylene" denotes an acyclic carbon chain which includes a carbon-to-carbon double bond.

The term "nitro" refers to —$NO_2$.

The term "halogen" represents chlorine, fluorine, bromine or iodine.

The term "sulfhydryl" refers to —SH.

The term "hydroxyl" means —OH.

The term "sulfonyl" refers to —$SO_2$.

The terms "amine" and "amino" refer to both unsubstituted and substituted amines (—$NH_2$). The substituted amine may be substituted at one or both hydrogen positions with, for example, an alkyl, an alkenyl, an aryl, a cycloalkyl, a cycloalkenyl, or a heterocycle. Thus, the term "alkylamine" includes an amine group, as defined above, having a substituted or unsubstituted alkyl attached thereto.

The term "amido" refers to an amino-substituted carbonyl (—$CONH_2$—), wherein the amine moiety may be substituted at one or both hydrogen positions with, for example, an alkyl, hydroxyalkyl, an alkenyl, an aryl, a cycloalkyl, a cycloalkenyl, heterocycloalkylalkyl or a heterocycle.

The term "acylamino" may be represented by the general formula:

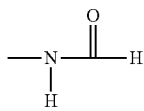

wherein one or both hydrogen positions may be substituted with, for example, an alkyl, an alkenyl, an aryl, a cycloalkyl, a cycloalkenyl, or a heterocycle.

The term "alkylthio" refers to an alkyl group, as defined above, having a sulfur radical attached thereto. In certain embodiments, the "alkylthio" moiety is represented by one of —S-alkyl, —S-alkenyl, or —S-alkynyl. Representative alkylthio groups include methylthio, ethyl thio, and the like.

The term "carbonyl" refers to the general formula:

wherein the hydrogen atom may be substituted with, for example, an alkyl, an alkenyl, an aryl, a cycloalkyl, a cycloalkenyl, or a heterocycle.

The term "aryl" as used herein refers to a mono-, bi-, or other multi-carbocyclic, aromatic ring system. The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, alkylsulfonyl, sulfonamido, cycloalkyl sulfonamido, ketone, aldehyde, ester, heterocyclyl, heterocyclyl carbonyl, heterocyclyl alkoxy, heterocycloalkylalkyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, heterocycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic or heterocyclic moieties such as 5,6,7,8-tetrahydronaphthyl, benzo[1,3]dioxolyl, benzo[1,4]dioxinyl.

The terms "heteroaryl" refers to a 5-15 membered mono-, bi-, or other multi-cyclic, aromatic ring system containing one or more heteroatoms, for example one to four heteroatoms, such as nitrogen, oxygen, and sulfur. Heteroaryls can also be fused to non-aromatic rings. The heteroaryl ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. Illustrative examples of heteroaryl groups include, but are not limited to, acridinyl, benzimidazolyl, benzofuryl, benzothiazolyl, benzothienyl, benzoxazolyl, carbazolyl, carbolinyl, cinnolinyl, furazanyl, furyl, imidazolyl, indazolyl, indolizinyl, indolyl, isobenzofuryl, isoindolyl, isoquinolinyl, isothiazolyl, isoxazolyl, naphthyridinyl, oxadiazolyl, oxazolyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyrazyl, pyridazinyl, pyridinyl, pyrimidilyl, pyrimidyl, pyrrolyl, quinolinyl, quinolizinyl, quinoxalinyl, quinoxaloyl, quinazolinyl, tetrazolyl, thiadiazolyl, thianthrenyl, thiazolyl, thienyl, thiophenyl, triazinyl, (1,2,3,)- and (1,2,4)-triazolyl, and the like. Exemplary heteroaryl groups include, but are not limited to, a monocyclic aromatic ring, wherein the ring comprises 2 to 5 carbon atoms and 1 to 3 heteroatoms.

The term "carbocycle" is art-recognized and refers to an aromatic or non-aromatic ring in which each atom of the ring is carbon.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl.

The term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy and the like.

The term "haloalkyl" and "haloalkoxy" means alkyl or alkoxy, as the case may be, substituted with one or more halogen atoms, where alkyl and alkoxy groups are as defined above. The term "halo" is used herein interchangeably with the term "halogen" means F, Cl, Br or I. Examples of "haloalkyl" include but are not limited to trifluoromethyl, difluoromethyl, 2,2,2-trifluoroethyl, pentafluoroethyl, pentachloroethyl 4,4,4-trifluorobutyl, 4,4-difluorocyclohexyl, chloromethyl, dichloromethyl, trichloromethyl, 1-bromoethyl and the like. Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy, 1-bromoethoxy and the like.

The term "heterocyclylcarbonyl" or "heterocyclylalkoxy" means carbonyl or alkoxy, as the case may be, linked with heterocyclyl group, where alkoxy and heterocyclyl groups are as defined above.

The term "heterocyclylalkyl" or "heterocycloalkylalkyl" refers to a heterocyclic ring radical directly bonded to an alkyl group. The heterocyclyl or heterocycloalkyl radical as defined above may be attached to the main structure at any carbon atom in the alkyl group that results in the creation of a stable structure.

Unless otherwise specified, the term "substituted" as used herein refers to substitution with any one or more or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine.

The terms ortho, meta and para refer to 1,2-, 1,3- and 1,4-disubstituted benzenes, respectively. For example, the names 1,2-dimethylbenzene and ortho-dimethylbenzene are synonymous.

The present invention provides a compound of formula (I) having the structure

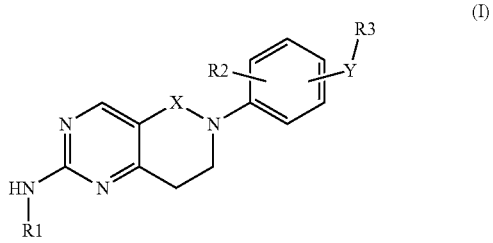

(I)

wherein
R1 is H, aryl, substituted aryl, alkyl, substituted alkyl, heteroaryl, substituted hetero aryl, heterocyclyl, substituted heterocyclyl, heterocyclylalkyl or substituted heterocyclylalkyl,
X is CH$_2$ or C=O
R2 is H, (C$_1$-C$_6$)alkyl, halogen, CF$_3$, or —O—(C$_1$-C$_6$)alkyl
Y is —NHCO—, —CONH—, —NHSO$_2$-, —NH—, —NCH$_3$—CO—, —NHCH$_2$—, O, —NHCONH— or —NHCOCH$_2$—
R3 is alkyl, substituted alkyl, aryl, or substituted aryl, heteroaryl, substituted heteroaryl, cycloalkyl, substituted cycloalkyl or heterocycloalkyl;
or a pharmaceutically acceptable salt thereof.
Preferably Y is —NHCO—.

According to a particular embodiment, the invention provides a compound of formula (II) having the structure

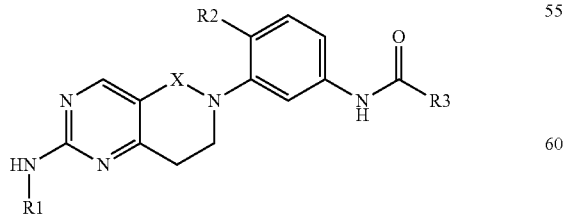

(II)

wherein
R1 is hydrogen, (C$_1$-C$_4$)alkyl, phenyl, substituted phenyl, pyridine, or substituted pyridine,
X is CH$_2$ or C=O
R2 is H, (C$_1$-C$_6$)alkyl, halogen, or —O—(C$_1$-C$_6$)alkyl,
R3 is (C$_1$-C$_6$)alkyl, cycloalkyl, substituted cycloalkyl, heterocycloalkyl, aryl, substituted aryl, heteroaryl, substituted heteroaryl,

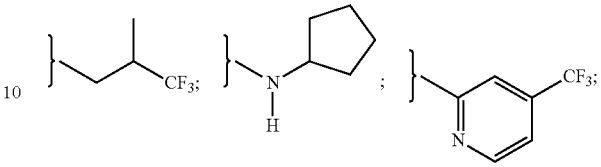

and wherein the substituents are selected from the group comprising C$_1$-C$_4$ linear or branched alkyl, halo or nitrile substituted C$_1$-C$_4$ alkyl, —O-alkyl(C$_1$-C$_4$), halogen;
or a pharmaceutically acceptable salt thereof.
Preferably R3 is selected from the group consisting of

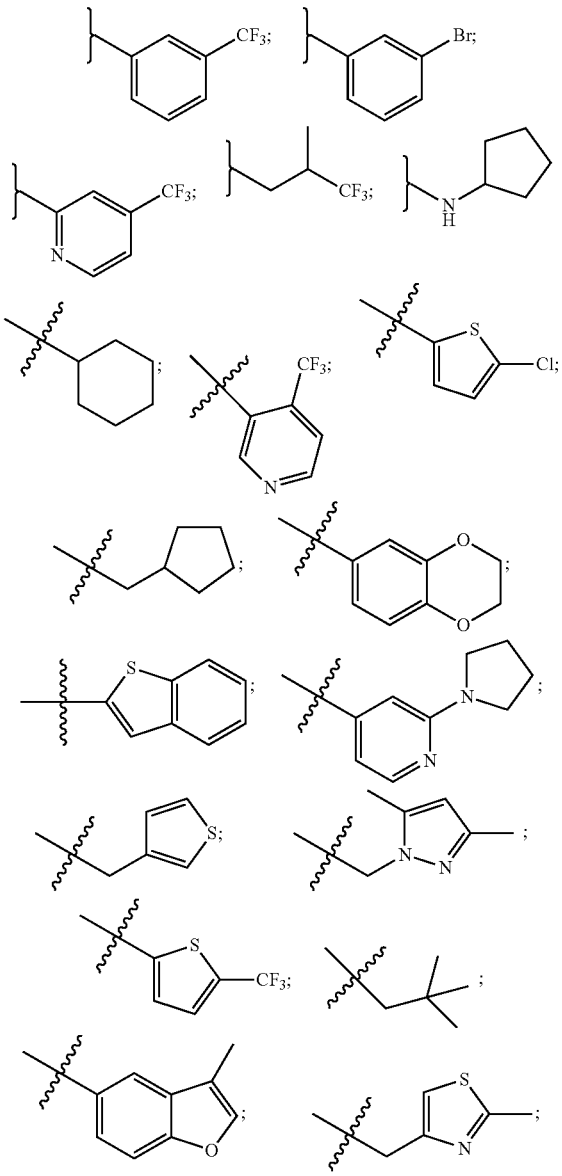

-continued

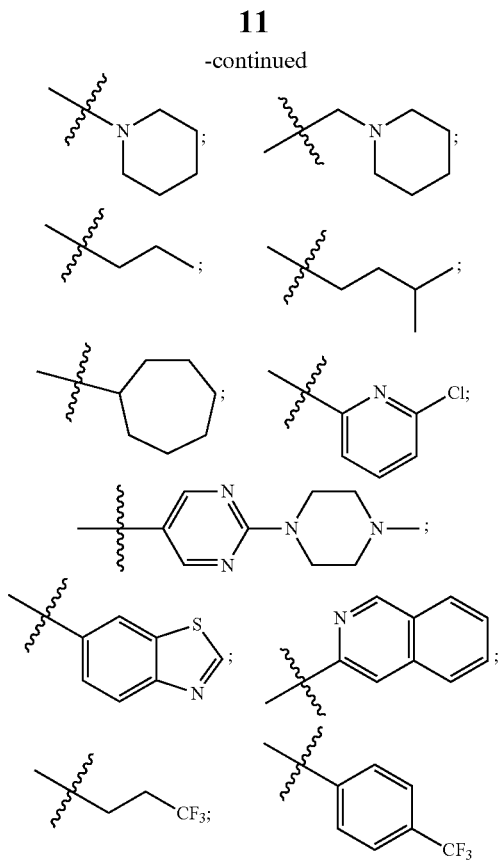

Preferably R1 is substituted phenyl or substituted pyridine,
Preferably X is CH₂ or C=O
Preferably R2 is H, CH₃, Cl or F;
More preferably R3 is selected from the group consisting of:

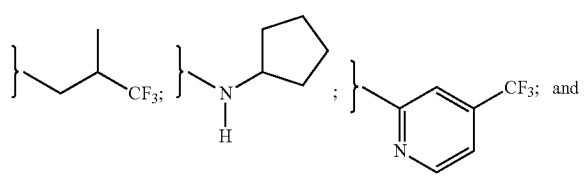

substituted phenyl, wherein the substituents are selected from the group comprising Cl, F, Br, CF₃ and CH₃.
More preferably R1 is selected from the group consisting of:

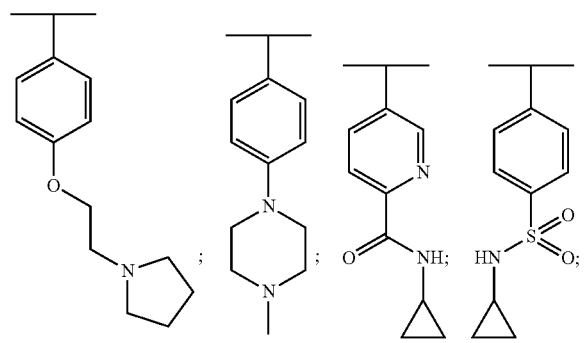

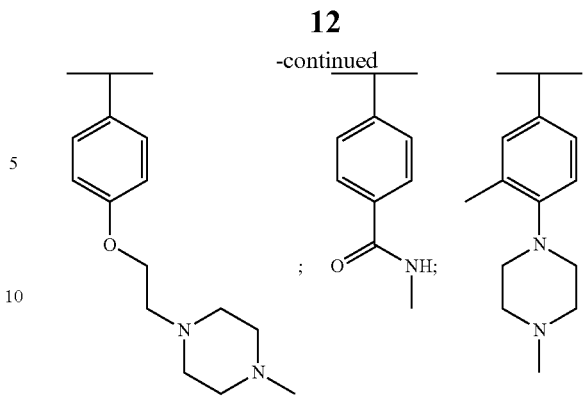

Even more preferably R3 is selected from the group consisting of:

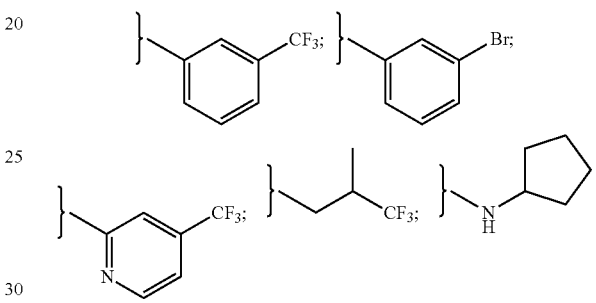

Preferably the present invention comprises a compound selected from the group consisting of:
N-(4-Methyl-3-{2-[4-(4-methyl-piperazine-1-carbonyl)-phenylamino]-7,8-dihydro-5H-pyrido[4,3-d]pyrimidin-6-yl}-phenyl)-3-trifluoromethyl-benzamide
N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide
5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide
N-{3-[2-(4-Cyclopropylsulfamoyl-phenylamino)-7,8-dihydro-5H-pyrido[4,3-d]pyrimidin-6-yl]-4-methyl-phenyl}-3-trifluoromethyl-benzamide
N-(4-Chloro-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide
4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide
4,4,4-Trifluoro-3-methyl-N-[4-methyl-3-(2-{4-[2-(4-methyl-piperazin-1-yl)-ethoxy]-phenylamino}-7,8-dihydro-5H-pyrido[4,3-d]pyrimidin-6-yl)-phenyl]-butyramide
1-Cyclopentyl-3-(4-methyl-3-{2-[4-(2-pyrrolidin-1-yl-ethoxy)-phenylamino]-7,8-dihydro-5H-pyrido[4,3-d]pyrimidin-6-yl}-phenyl)-urea
N-(4-Methyl-3-{5-oxo-2-[4-(2-pyrrolidin-1-yl-ethoxy)-phenylamino]-7,8-dihydro-5H-pyrido[4,3-d]pyrimidin-6-yl}-phenyl)-3-trifluoromethyl-benzamide
N-{4-Chloro-3-[2-(4-(cyclopropylcarbamoylmethoxy)phenylamino)-5-oxo-7,8-dihydro-5H-pyrido[4,3-d]pyrimidin-6-yl]-phenyl}-3-trifluoromethyl-benzamide
N-(4-Chloro-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide 3-Bromo-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide N-(4-Chloro-3-{2-[4-(4-methyl-piperazin-1-ylmethyl)-phenylamino]-5-oxo-7,8-dihydro-5H-pyrido[4,3-d]pyrimidin-6-yl}-phenyl)-3-trifluoromethyl-benzamide or a pharmaceutically acceptable salt thereof.

According to another particular embodiment, the present invention provides a compound selected from the group consisting of:

N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide 4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide or a pharmaceutically acceptable salt thereof.

According to further particular embodiment, the present invention provides a compound selected from the group consisting of:

N-(4-Chloro-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide N-{4-Chloro-3-[2-(4-(cyclopropylcarbamoylmethoxy)phenylamino)-5-oxo-7,8-dihydro-5H-pyrido[4,3-d]pyrimidin-6-yl]-phenyl}-3-trifluoromethyl-benzamide or a pharmaceutically acceptable salt thereof.

Further examples of compounds encompassed by the present invention include the compounds of Table 1. Last column represents the example number (Ex) used for the preparation of each compound appearing on the following table.

TABLE 1

| No | Structure | Physical Data [$^1$HNMR and/or MS] | IUPAC NAME | Ex |
|---|---|---|---|---|
| 1 | 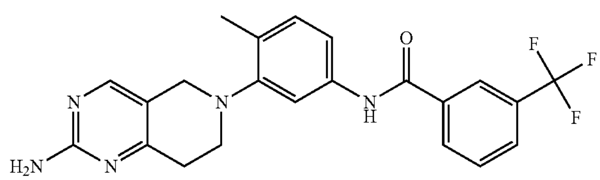 [SMILES: Cc1ccc(NC(=O)c2cccc(C(F)(F)F)c2)cc1N1CCc2nc(N)ncc2C1] | $^1$H NMR (300 MHz, CD$_3$OD) δ 8.15-8.0 (m, 3H), 7.9-7.76 (m, 2H), 7.66-7.55 (m, 2H), 7.22-7.12 (m, 2H), 4.95 (s, 2H), 4.0 (s, 2H), 3.3-3.2 (m, 2H), 2.96-2.85 (m, 2H), 2.3 (s, 3H) MS: m/z 428.0 (M + 1). | N-[3-(2-Amino-7,8-dihydro-5H-pyrido[4,3-d]pyrimidin-6-yl)-4-methyl-phenyl]-3-trifluoromethyl-benzamide | 1 |
| 6 | 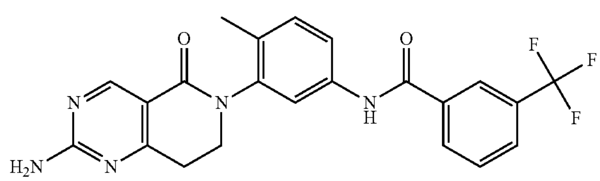 [SMILES: Cc1ccc(NC(=O)c2cccc(C(F)(F)F)c2)cc1N1CCc2nc(N)ncc2C1=O] | $^1$H NMR (300 MHz, DMSO-D$_6$) δ 10.5 (s, 1H), 8.62 (s, 1H), 8.32-8.29 (br s, 1H), 8.29-8.23 (d, 1H), 8.0-7.95 (m, 1H), 7.8 (t, 1H), 7.7-7.62 (m, 2H), 7.46-7.36 (br s, 2H), 7.34-7.27 (m, 1H), 4.0-3.88 (m, 1H), 3.76-3.66 (m, 1H), 3.18-3.04 (m, 1H), 2.78-2.86 (m, 1H), 2.16 (s, 3H) MS m/z 442.2 (M + 1), | N-[3-(2-Amino-5-oxo-7,8-dihydro-5H-pyrido[4,3-d]pyrimidin-6-yl)-4-methyl-phenyl]-3-trifluoromethyl-benzamide | 3 |
| 7 | 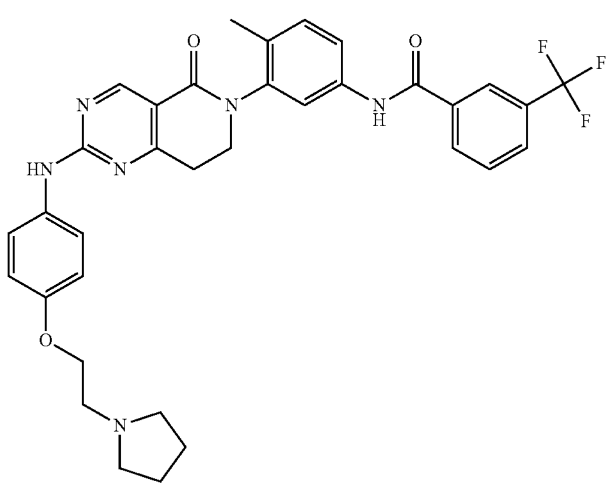 [SMILES: Cc1ccc(NC(=O)c2cccc(C(F)(F)F)c2)cc1N1CCc2nc(Nc3ccc(OCCN4CCCC4)cc3)ncc2C1=O] | $^1$H NMR (300 MHz, CDCl$_3$) δ 9.4-9.1 (br s, 1H), 8.95-8.85 (m, 2H), 8.2-8.0 (m, 2H), 7.8-7.7 (m, 1H), 7.7-7.5 (m, 5H), 7.2-7.1 (d, 1H), 6.9-6.8 (d, 2H), 4.4-4.3 (t, 2H), 4.05-3.7 (m, 4H), 3.5 (t, 2H), 3.2-3.1 (m, 2H), 3.05-2.9 (m, 2H), 2.2-2.0 (m, 4H), 1.95 (s, 3H) MS: m/z 631.2 (M + 1), | N-(4-Methyl-3-{5-oxo-2-[4-(2-pyrrolidin-1-yl-ethoxy)-phenylamino]-7,8-dihydro-5H-pyrido[4,3-d]pyrimidin-6-yl}phenyl)-3-trifluoromethyl-benzamide | 3 |

TABLE 1-continued

| No | Structure | Physical Data [¹HNMR and/or MS] | IUPAC NAME | Ex |
|---|---|---|---|---|
| 8 | 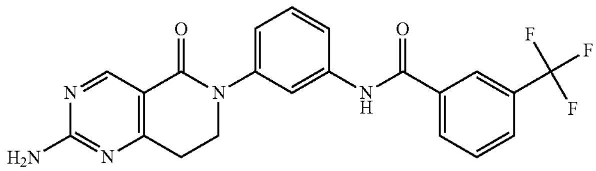 [SMILES: Nc1ncc2c(n1)CCN(c1cccc(NC(=O)c3cccc(C(F)(F)F)c3)c1)C2=O] | ¹H NMR (300 MHz, CD₃OD) δ 8.74 (s, 1H), 8.29-8.18 (m, 2H), 7.94-7.87 (m, 1H), 7.83 (t, 1H), 7.78-7.7 (m, 1H), 7.68-7.62 (m, 1H), 7.44 (t, 1H), 7.23-6.96 (m, 1H), 4.05 (t, 2H), 3.1 (t, 2H) MS m/z 428.1 (M + 1), | N-[3-(2-Amino-5-oxo-7,8-dihydro-5H-pyrido[4,3-d]pyrimidin-6-yl)-trifluoromethyl-benzamide | 3 |
| 9 | 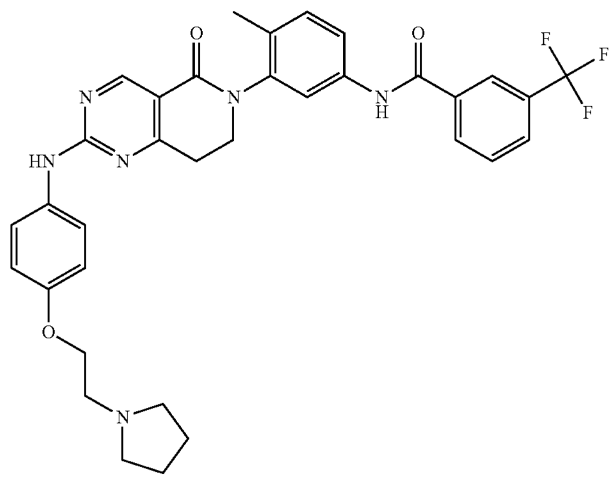 | ¹H NMR (300 MHz, CDCl₃) δ 12.5-12.2 (br. s, 1H), 11.9 (s, 1H), 8.16-8.12 (br s, 1H), 8.1-8.04 (m, 1H), 8.0-7.96 (br s, 1H), 7.86-7.8 (m, 1H), 7.76-7.72 (br s, 1H), 7.7-7.58 (m, 2H), 7.24-7.22 (br s, 1H), 7.16-7.1 (m, 1H), 6.9-6.86 (m, 2H), 4.4-4.3 (t, 2H), 4.1 (s, 2H), 4.0-3.7 (m, 2H), 3.55 (t, 2H), 3.3 (t, 2H), 3.2 (t, 2H), 3.1-2.9 (m, 2H), 2.3 (s, 3H), 2.2-2.1 (m, 4H) MS m/z 617.2 (M + 1), | N-(4-Methyl-3-{2-[4-(2-pyrrolidin-1-yl-ethoxy)-phenylamino]-7,8-dihydro-5H-pyrido[4,3-d]pyrimidin-6-yl}-phenyl)-3-trifluoromethyl-benzamide | 2 |
| 14 | 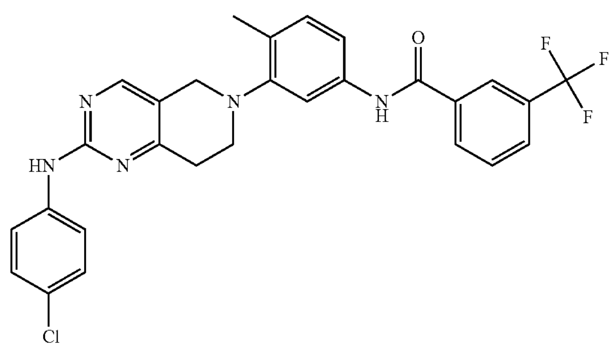 [SMILES: Cc1ccc(NC(=O)c2cccc(C(F)(F)F)c2)cc1N1CCc2nc(Nc3ccc(Cl)cc3)ncc2C1] | ¹H NMR (300 MHz, CDCl₃) δ 8.22 (s, 1H), 8.13 (s, 1H), 8.06 (d, 1H), 7.84-7.78 (m, 1H), 7.75-7.7 (br s, 1H), 7.68-7.6 (m, 3H), 7.34-7.27 (m, 2H), 7.24-7.19 (m, 1H), 7.15-7.08 (m, 1H), 4.06 (s, 2H), 3.35-3.26 (m, 2H), 3.18-3.09 (m, 2H), 2.3 (s, 3H) MS m/z 538.1 (M + 1), | N-{3-[2-(4-Chloro-phenylamino)-7,8-dihydro-5H-pyrido[4,3-d]pyrimidin-6-yl]-4-methyl-phenyl}-3-trilfuoromethyl-benzamide | |
| 15 | 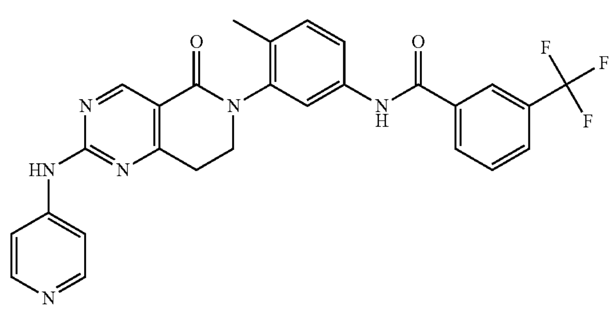 | ¹H NMR (300 MHz, DMSO-D₆) δ 9.1-8.9 (m, 1H), 8.35-8.14 (m, 5H), 7.76-7.66 (m, 4H), 7.56 (t, 1H), 7.46-7.37 (m, 1H), 7.32-7.26 (m, 1H), 7.16-704 (m, 1H), 4.02 (s, 2H), 3.3-3.2 (m, 2H), 3.05-2.96 (m, 2H), 2.25 (s, 3H) MS m/z 505.0 (M + 1), | N-{4-Methyl-3-[2-(pyridin-4-yl-amino)-7,8-dihydro-5H-pyrido[4,3-d]pyrimidin-6-yl]-phenyl}-3-trifluoromethyl-benzamide | 2 |
| 16 | 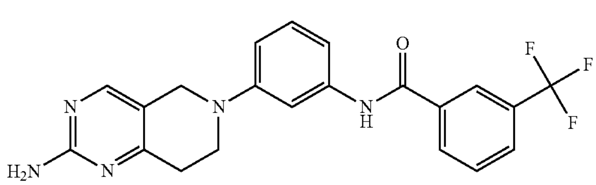 [SMILES: Nc1ncc2c(n1)CCN(c1cccc(NC(=O)c3cccc(C(F)(F)F)c3)c1)C2] | ¹H NMR (300 MHz, DMSO-D₆) δ 10.34 (s, 1H), 8.32-8.22 (m, 2H), 8.11 (s, 1H), 7.98 (d, 1H), 7.8 (t, 1H), 7.5-7.4 (br s, 1H), 7.3-7.15 (m, 2H), 6.85-6.76 (m, 1H), 6.41 (s, 2H), 4.21 (s, 2H), 3.58 (t, 2H), 2.75 (t, 2H) MS m/z 414.1 (M + 1), | N-[3-(2-Amino-7,8-dihydro-5H-pyrido[4,3-d]pyrimidin-6-yl)-phenyl]-3-trifluoromethyl-benzamide | 1 |

TABLE 1-continued

| No | Structure | Physical Data [¹HNMR and/or MS] | IUPAC NAME | Ex |
|---|---|---|---|---|
| 17 | 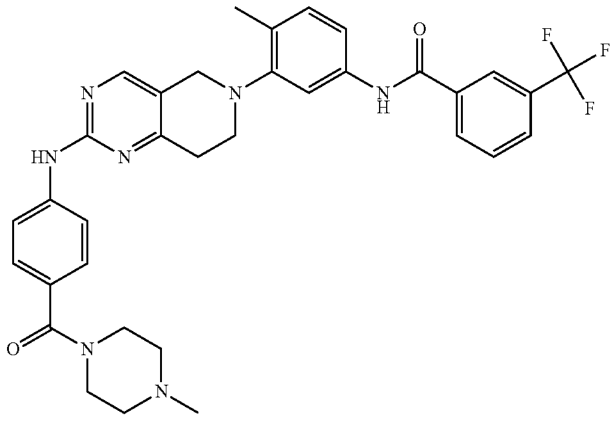 [SMILES: Cc1ccc(NC(=O)c2cccc(C(F)(F)F)c2)cc1N1CCc2nc(Nc3ccc(C(=O)N4CCN(C)CC4)cc3)ncc2C1] | ¹H NMR (300 MHz, DMSO-D₆) δ 10.4 (s, 1H), 9.8 (s, 1H), 8.36 (s, 1H), 8.32-8.24 (m, 2H), 8.0-7.76 (m, 1H), 7.9-7.74 (m, 3H), 7.66-7.62 (m, 1H), 7.52-7.44 (m, 1H), 7.38-7.3 (m, 2H), 7.24-7.18 (m, 1H), 4.05 (s, 2H), 3.6-3.49 (m, 2H), 3.3-3.1 (m, 2H), 3.0-2.9 (m, 2H), 2.75-2.7 (m, 2H), 2.6-2.55 (m, 2H), 2.45-2.4 (m, 2H), 2.3 (s, 3H), 1.9 (s, 3H) MS m/z 630.2 (M + 1), | N-(4-Methyl-3-{2-[4-(4-methyl-piperazine-1-carbonyl)-phenylamino]-7,8-dihydro-5H-pyrido[4,3-d]pyrimidin-6-yl}-phenyl)-3-trifluoromethyl-benzamide | 2 |
| 18 | 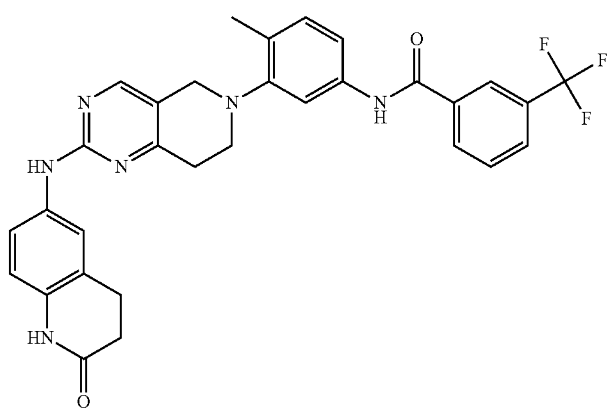 [SMILES: Cc1ccc(NC(=O)c2cccc(C(F)(F)F)c2)cc1N1CCc2nc(Nc3ccc4c(c3)CCC(=O)N4)ncc2C1] | ¹H NMR (300 MHz, CD₃OD) δ 8.3-8.16 (m, 3H), 7.94-7.86 (m, 1H), 7.64-7.78 (m, 2H), 7.48-7.2 (m, 4H), 6.84-6.92 (m, 1H), 4.1 (s, 2H), 3.4-3.3 (m, 2H), 3.1-2.9 (m, 4H), 2.6 (t, 2H), 2.3 (s, 3H) MS m/z 573.1 (M + 1), | N-{4-Methyl-3-[2-(2-oxo-1,2,3,4-tetrahydro-quinolin-6-ylamino)-7,8-dihydro-5H-pyrido[4,3-d]pyrimidin-6-yl]-phenyl}-3-trifluoromethyl-benzamide | 2 |
| 19 | 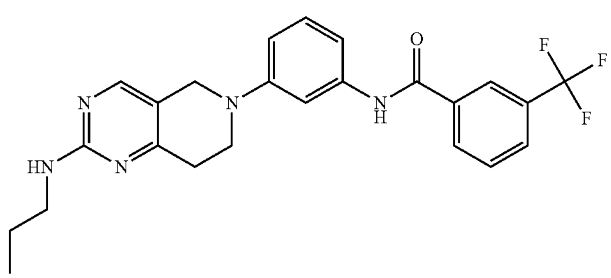 [SMILES: CCCNc1ncc2c(n1)CCN(c1cccc(NC(=O)c3cccc(C(F)(F)F)c3)c1)C2] | ¹H NMR (300 MHz, CDCl₃) δ 10.37 (s, 1H), 8.32-8.24 (m, 2H), 8.14 (s, 1H), 7.98 (d, 1H), 7.8 (t, 1H), 7.48-7.42 (m, 1H), 7.3-7.18 (m, 2H), 6.96 (t, 1H), 6.84-6.78 (m, 1H), 4.22 (s, 2H), 3.58 (t, 2H), 3.2 (q, 2H), 2.76 (t, 2H), 1.5 (quin, 2H), 0.87 (t, 3H) MS m/z 456.1 (M + 1), | N-[3-(2-Propyl-amino-7,8-dihydro-5H-pyrido[4,3-d]pyrimidin-6-yl)-phenyl]-3-trifluoromethyl-benzamide | 1 |
| 20 | 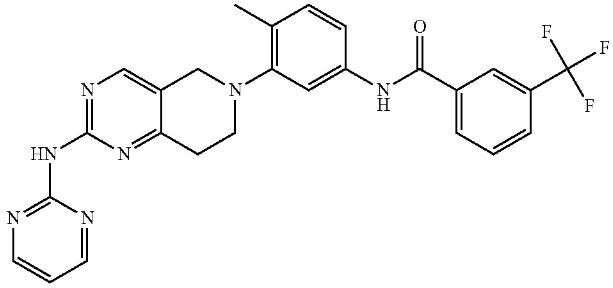 [SMILES: Cc1ccc(NC(=O)c2cccc(C(F)(F)F)c2)cc1N1CCc2nc(Nc3ncccn3)ncc2C1] | ¹H NMR (300 MHz, CDCl₃) δ 8.62 (d, 2H), 8.42 (s, 1H), 8.19-8.04 (m, 3H), 7.9-7.8 (m, 2H), 7.7-7.6 (m, 2H), 7.26-7.14 (m, 2H), 6.92 (t, 1H), 4.14 (s, 2H), 3.38-3.28 (t, 2H), 3.14-3.04 (m, 2H), 2.34 (s, 3H) MS m/z 506.1 (M + 1), | N-{4-Methyl-3-[2-(pyrimidin-2-ylamino)-7,8-dihydro-5H-pyrido[4,3-d]pyrimidin-6-yl]-phenyl}-3-trifluoromethyl-benzamide | 2 |

TABLE 1-continued

| No | Structure | Physical Data [¹HNMR and/or MS] | IUPAC NAME | Ex |
|---|---|---|---|---|
| 21 | 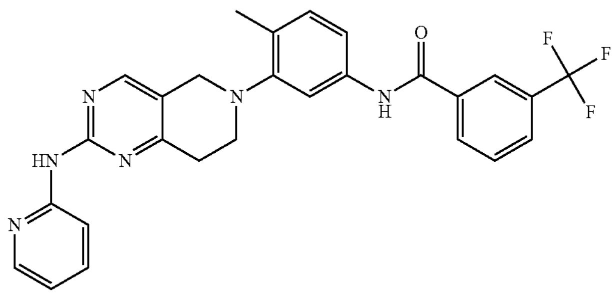 [SMILES: Cc1ccc(NC(=O)c2cccc(C(F)(F)F)c2)cc1N1CCc2nc(Nc3ccccn3)ncc2C1] | ¹H NMR (300 MHz, CDCl₃) δ 8.77 (s, 1H), 8.42 (d, 1H), 8.3-8.24 (m, 1H), 8.22 (s, 2H), 8.12 (d, 1H), 8.01 (s, 1H), 7.82-7.58 (m, 4H), 7.25-7.16 (m, 2H), 6.94-6.86 (m, 1H), 4.06 (s, 2H), 3.32-3.26 (t, 2H), 3.8-3.0 (t, 2H), 2.3 (s, 3H) MS m/z 505.0 (M + 1), | N-{4-Methyl-3-[2-(pyridin-2-ylamino)-7,8-dihydro-5H-pyrido[4,3-d]pyrimidin-6-yl]-phenyl}-3-trifluoromethyl-benzamide | 2 |
| 22 | 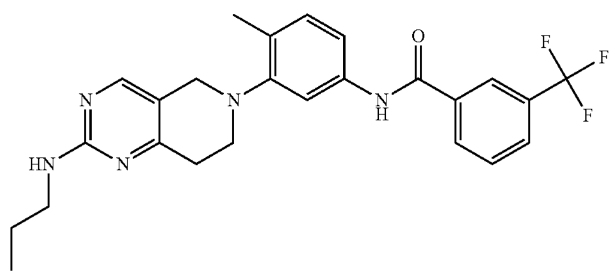 [SMILES: CCCNc1ncc2c(n1)CCN(c1cc(NC(=O)c3cccc(C(F)(F)F)c3)ccc1C)C2] | ¹H NMR (300 MHz, CD₃OD) δ 8.25 (s, 1H), 8.2 (d, 1H), 8.05 (s, 1H), 7.91-7.86 (m, 1H), 7.76-7.68 (m, 1H), 7.6-7.55 (m, 1H), 7.35 (dd, 1H), 7.24-7.18 (m, 1H), 5.5 (s, 1H), 3.97 (s, 2H), 3.36-3.32 (m, 2H), 3.28-3.24 (m, 2H), 2.9 (t, 2H), 2.32 (s, 3H), 1.62 (quin, 2H), 1.0-0.98 (m, 3H) MS m/z 470.1 (M + 1), | N-[4-Methyl-3-(2-propylamino-7,8-dihydro-5H-pyrido[4,3-d]pyrimidin-6-yl)-phenyl]-3-trifluoromethyl-benzamide | 1 |
| 23 | 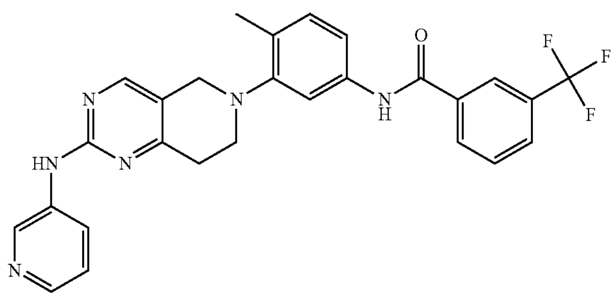 [SMILES: Cc1ccc(NC(=O)c2cccc(C(F)(F)F)c2)cc1N1CCc2nc(Nc3cccnc3)ncc2C1] | ¹H NMR (300 MHz, CDCl₃) δ 8.8-8.76 (m, 1H), 8.3-8.04 (m, 6H), 7.84-7.78 (m, 1H), 7.68-7.6 (m, 2H), 7.32-7.28 (m, 1H), 7.24-7.16 (m, 2H), 4.06 (s, 2H), 3.3 (t, 2H), 3.04 (t, 2H), 2.33 (s, 3H) MS m/z 504.7 (M + 1), | N-{4-Methyl-3-[2-(pyridin-3-ylamino)-7,8-dihydro-5H-pyrido[4,3-d]pyrimidin-6-yl]-phenyl}-3-trifluoromethyl-benzamide | 2 |
| 25 | 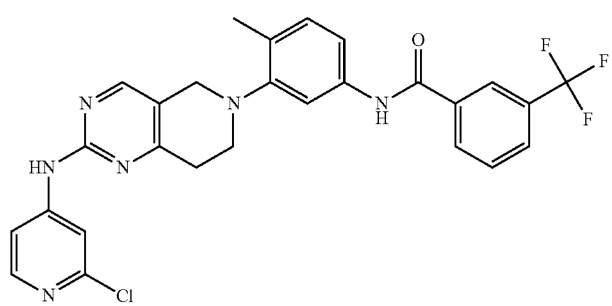 [SMILES: Cc1ccc(NC(=O)c2cccc(C(F)(F)F)c2)cc1N1CCc2nc(Nc3ccnc(Cl)c3)ncc2C1] | ¹H NMR (300 MHz, CDCl₃) δ 8.25 (s, 1H), 8.21-8.12 (m, 3H), 8.08 (d, 1H), 7.98-7.89 (m, 2H), 7.82 (d, 1H), 7.72-7.6 (m, 2H), 7.44 (dd, 1H), 7.25-7.2 (m, 1H), 7.16-7.1 (m, 1H), 4.1 (s, 2H), 3.32 (t, 2H), 3.08 (t, 2H), 2.32 (s, 3H) MS m/z 539.1 (M + 1), | N-{3-[2-(2-Chloro-pyridin-4-ylamino)-7,8-dihydro-5H-pyrido[4,3-d]pyrimidin-6-yl]-4-methyl-phenyl}-3-trifluoromethyl-benzamide | 2 |
| 26 | 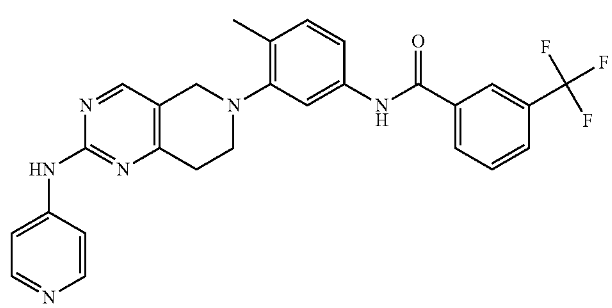 | ¹H NMR (300 MHz, CD₃OD) δ 9.14 (s, 1H), 8.6-8.5 (m, 2H), 8.48-8.39 (m, 2H), 8.3-8.16 (m, 2H), 7.94-7.83 (m, 2H), 7.78-7.7 (t, 1H), 7.6-7.52 (m, 1H), 7.42-7.34 (m, 1H), 4.3-4.1 (m, 1H), 4.08-3.9 (m, 1H), 3.58-3.36 (m, 2H), 2.3 (s, 3H) MS m/z 518.6 (M + 1), | N-{4-Methyl-3-[5-oxo-2-(pyridin-4-ylamino)-7,8-dihydro-5H-pyrido[4,3-d]pyrimidin-6-yl]-phenyl}-3-trifluoromethyl-benzamide | 4 |

TABLE 1-continued

| No | Structure | Physical Data [¹HNMR and/or MS] | IUPAC NAME | Ex |
|---|---|---|---|---|
| 27 | 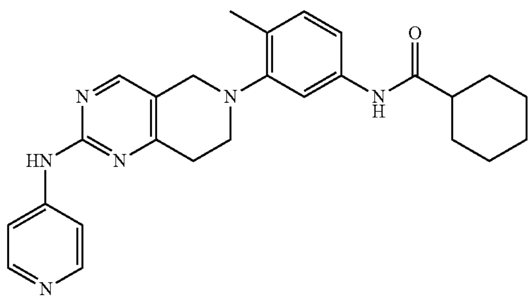 [SMILES: Cc1ccc(NC(=O)C2CCCCC2)cc1N1CCc2nc(Nc3ccncc3)ncc2C1] | ¹H NMR (300 MHz, CDCl₃) δ 8.82-8.74 (br s, 2H), 8.54 (d, 2H), 8.32 (s, 1H), 8.2-8.1 (m, 2H), 7.85-7.8 (m, 1H), 7.2-7.1 (m, 1H), 6.9-6.8 (m, 1H), 4.1 (s, 2H), 3.3 (t, 2H), 3.1 (t, 2H), 2.3 (s, 3H), 2.25-2.15 (m, 1H), 2.0-1.9 (m, 2H), 1.9-1.8 (m, 2H), 1.75-1.65 (m, 1H), 1.6-1.49 (m, 2H), 1.44-1.3 (m, 2H) MS m/z 442.9 (M + 1), | Cyclohexane-carboxylic acid {4-methyl-3-[2-(pyridin-4-ylamino)-7,8-dihydro-5H-pyrido[4,3-d]pyrimidin-6-yl]-phenyl}-amide | 2 |
| 29 | 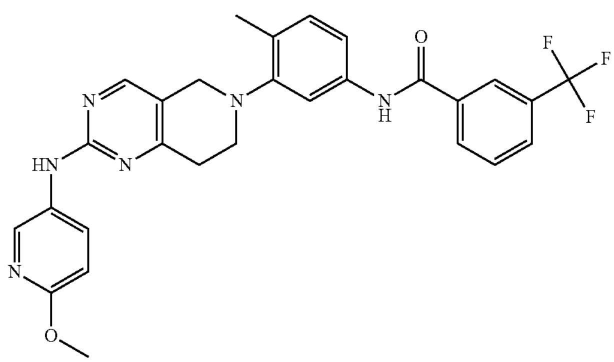 [SMILES: COc1ccc(Nc2ncc3c(n2)CCN(c2cc(NC(=O)c4cccc(C(F)(F)F)c4)ccc2C)C3)cn1] | ¹H NMR (300 MHz, CDCl₃) δ 8.38 (d, 1H), 8.25 (s, 2H), 8.08 (d, 1H), 7.94 (dd, 1H), 7.88 (s, 1H), 7.82 (d, 1H), 7.7-7.6 (m, 2H), 7.26-7.1 (m, 3H), 6.76 (d, 1H), 4.05 (s, 2H), 3.93 (s, 3H), 3.28 (t, 2H), 3.02 (t, 2H), 2.32 (s, 3H) MS m/z 535.2 (M + 1), | N-{3-[2-(6-Methoxy-pyridin-3-ylamino)-7,8-dihydro-5H-pyrido[4,3-d]pyrimidin-6-yl]-4-methyl-phenyl]-3-trifluoromethyl-benzamide | 2 |
| 30 | 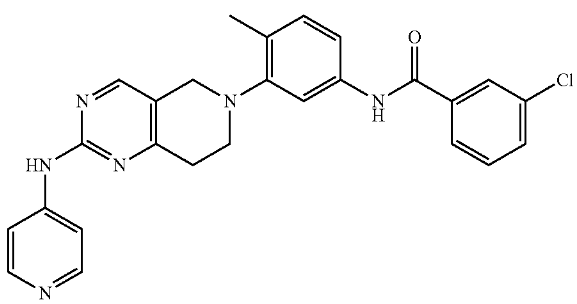 [SMILES: Cc1ccc(NC(=O)c2cccc(Cl)c2)cc1N1CCc2nc(Nc3ccncc3)ncc2C1] | ¹H NMR (300 MHz, CD3OD) δ 8.49 (s, 1H), 8.45-8.4 (m, 2H), 8.4-8.2 (br s, 2H), 7.78-7.82 (m, 2H), 7.69-7.46 (m, 3H), 7.33-7.19 (m, 2H), 4.16 (s, 2H), 3.4-3.32 (m, 2H), 3.18-3.08 (m, 2H), 2.33 (s, 3H) MS m/z 471.0 (M + 1), | 3-Chloro-N-{4-methyl-3-[2-(pyridin-4-ylamino)-7,8-dihydro-5H-pyrido[4,3-d]pyrimidin-6-yl]-phenyl}-benzamide | 2 |
| 31 | 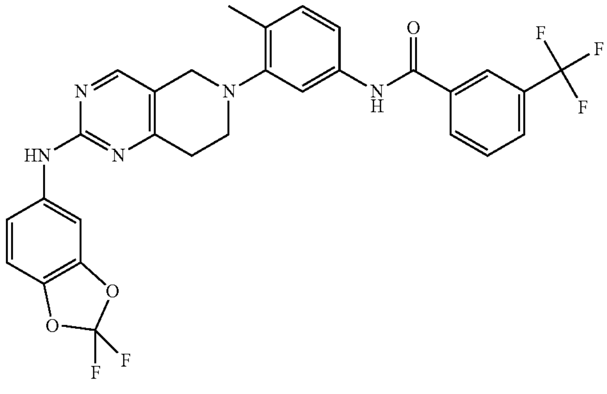 [SMILES: Cc1ccc(NC(=O)c2cccc(C(F)(F)F)c2)cc1N1CCc2nc(Nc3ccc4c(c3)OC(F)(F)O4)ncc2C1] | ¹H NMR (300 MHz, CDCl₃) δ 8.2-8.12 (m, 2H), 8.06 (s, 1H), 7.88-7.78 (m, 3H), 7.7-7.6 (m, 2H), 7.26-7.1 (m, 3H), 7.03-6.96 (m, 2H), 4.06 (s, 2H), 3.3 (t, 2H), 3.02 (t, 2H), 2.32 (s, 3H) MS m/z 584.1 (M + 1), | N-{3-[2-(2,2-Difluoro-benzo[1,3]dioxol-5-ylamino)-7,8-dihydro-5H-pyrido[4,3-d]pyrimidin-6-yl]-4-methyl-phenyl}-3-trifluoromethyl-benzamide | 2 |

TABLE 1-continued

| No | Structure | Physical Data [¹HNMR and/or MS] | IUPAC NAME | Ex |
|---|---|---|---|---|
| 32 | 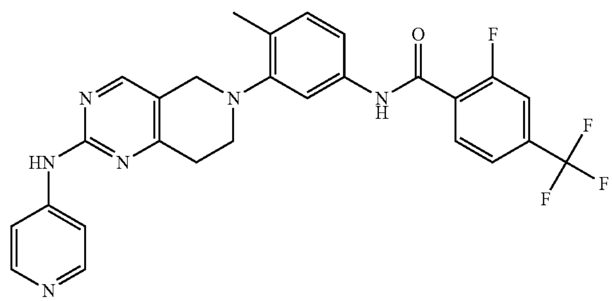 [SMILES: Cc1ccc(NC(=O)c2ccc(C(F)(F)F)cc2F)cc1N1CCc2nc(Nc3ccncc3)ncc2C1] | ¹H NMR (300 MHz, CD₃OD) δ 8.5 (s, 1H), 8.47-8.25 (m, 4H), 7.94-7.86 (m, 1H), 7.72-7.6 (m, 3H), 7.3-7.2 (m, 2H), 4.17 (s, 2H), 3.36 (t, 2H), 3.14 (t, 2H), 2.35 (s, 3H) MS m/z 523.1 (M + 1), | 2-Fluoro-N-{4-methyl-3-[2-(pyridin-4-ylamino)-7,8-dihydro-5H-pyrido[4,3-d]pyrimidin-6-yl]-phenyl}-4-trifluoromethyl-benzamide | 2 |
| 34 | 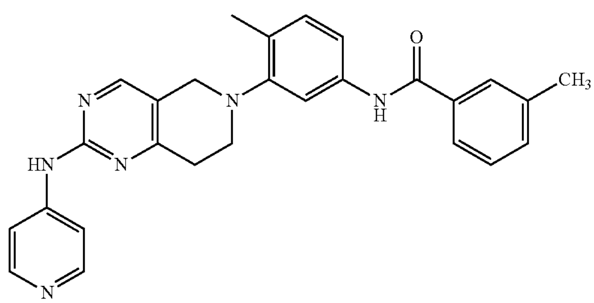 [SMILES: Cc1cccc(C(=O)Nc2ccc(C)c(N3CCc4nc(Nc5ccncc5)ncc4C3)c2)c1] | ¹H NMR (300 MHz, CD₃OD) δ 8.53-8.19 (m, 5H), 7.8-7.6 (m, 3H), 7.45-7.15 (m, 4H), 4.15 (s, 2H), 3.42-3.32 (m, 2H), 3.18-3.1 (m, 2H), 2.44 (s, 3H), 2.34 (s, 3H) MS m/z 451.0 (M + 1) | 3-Methyl-N-{4-methyl-3-[2-(pyridin-4-ylamino)-7,8-dihydro-5H-pyrido[4,3-d]pyrimidin-6-yl]-phenyl}-benzamide | 2 |
| 36 | 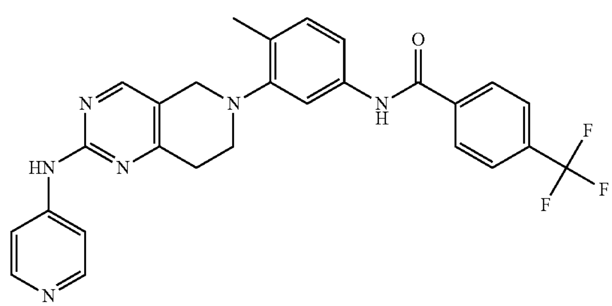 [SMILES: Cc1ccc(NC(=O)c2ccc(C(F)(F)F)cc2)cc1N1CCc2nc(Nc3ccncc3)ncc2C1] | ¹H NMR (300 MHz, CDCl₃) δ 8.48-8.42 (m, 2H), 8.25 (s, 1H), 8.04-7.92 (m, 3H), 7.81-7.62 (m, 6H), 7.25-7.2 (m, 1H), 7.15-7.08 (m, 1H), 4.1 (s, 2H), 3.32 (t, 2H), 3.08 (t, 2H), 2.33 (s, 3H) MS m/z 505.1 (M + 1), | N-{4-Methyl-3-[2-(pyridin-4-ylamino)-7,8-dihydro-5H-pyrido[4,3-d]pyrimidin-6-yl]-phenyl}-4-trifluoromethyl-benzamide | 2 |
| 37 | 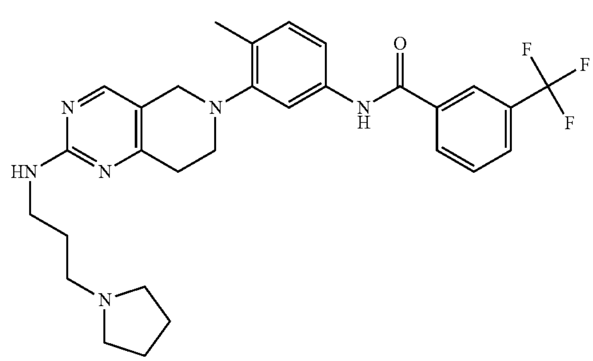 [SMILES: Cc1ccc(NC(=O)c2cccc(C(F)(F)F)c2)cc1N1CCc2nc(NCCCN3CCCC3)ncc2C1] | ¹H NMR (300 MHz, CDCl₃) δ 8.55 (s, 1H), 8.18 (s, 1H), 8.1 (d, 1H), 7.95 (s, 1H), 7.76 (d, 1H), 7.64-7.52 (m, 2H), 7.26-7.12 (m, 2H), 6.66-6.58 (m, 1H), 3.75 (s, 2H), 3.3-3.4 (m, 2H), 3.22-3.08 (m, 5H), 2.86 (t, 2H), 2.28 (s, 3H), 2.13-1.98 (m, 9H) MS m/z 539.2 (M + 1), | N-{4-Methyl-3-[2-(3-pyrrolidin-1-yl-propylamino)-7,8-dihydro-5H-pyrido[4,3-d]pyrimidin-6-yl]-phenyl}-3-trifluoromethyl-benzamide | 1 |

TABLE 1-continued

| No | Structure | Physical Data [¹HNMR and/or MS] | IUPAC NAME | Ex |
|---|---|---|---|---|
| 38 | 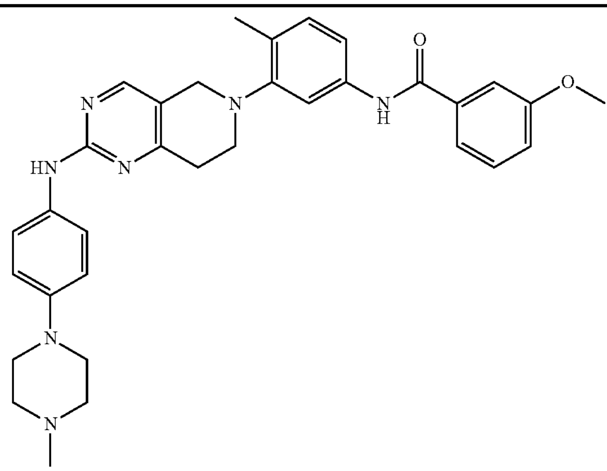 | ¹H NMR (300 MHz, DMSO-D₆) δ 10.16 (s, 1H), 8.24 (s, 1H), 7.7-7.38 (m, 7H), 7.2-7.1 (m, 2H), 6.95 (d, 2H), 3.97 (s, 2H), 3.83 (s, 3H), 3.4-3.1 (m, 8H), 2.96-2.86 (m, 2H), 2.8 (s, 3H), 2.24 (s, 3H) MS m/z 564.2 (M + 1), | 3-Methoxy-N-(4-methyl-3-{2-[4-(4-methyl-piperazin-1-yl)-phenylamino]-7,8-dihydro-5H-pyrido[4,3-d]pyrimidin-6-yl}-phenyl)-benzamide | 1 |
| 39 | 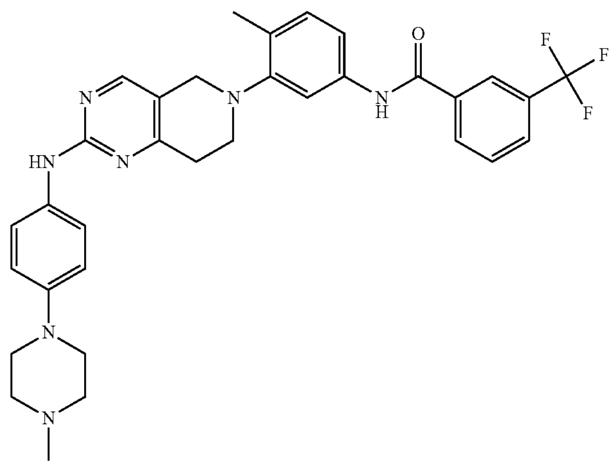 [SMILES: Cc1ccc(NC(=O)c2cccc(C(F)(F)F)c2)cc1N1CCc2nc(Nc3ccc(N4CCN(C)CC4)cc3)ncc2C1] | ¹H NMR (300 MHz, CDCl₃) δ 11.76 (s, 1H), 8.3-8.18 (br s, 1H), 8.16-8.04 (m, 3H), 7.82 (d, 1H), 7.73 (s, 1H), 7.7-7.56 (m, 3H), 7.24-7.18 (m, 1H), 7.16-7.02 (m, 1H), 6.94 (d, 2H), 4.07 (s, 2H), 3.76-3.56 (m, 4H), 3.4-3.02 (m, 8H), 2.92 (s, 3H), 2.29 (s, 3H) MS m/z 602.2 (M + 1), | N-(4-Methyl-3-{2-[4-(4-methyl-piperazin-1-1-yl)-phenyl-amino]-7,8-dihydro-5H-pyrido[4,3-d]pyrimidin-6-yl}-phenyl)-3-trifluoromethyl-benzamide | 1 |
| 40 | 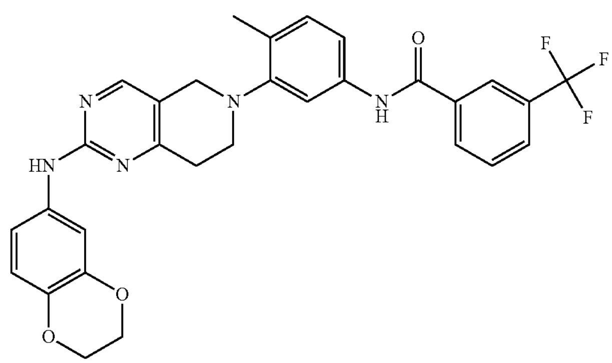 [SMILES: Cc1ccc(NC(=O)c2cccc(C(F)(F)F)c2)cc1N1CCc2nc(Nc3ccc4c(c3)OCCO4)ncc2C1] | ¹H NMR (300 MHz, CD₃OD) δ 8.28-8.16 (m, 3H), 7.92-7.86 (m, 1H), 7.78-7.7 (m, 1H), 7.61 (d, 1H), 7.35 (dd, 1H), 7.28-7.2 (m, 2H), 6.96 (dd, 1H), 6.81-6.76 (m, 1H), 4.3-4.2 (m, 4H), 4.05 (s, 2H), 3.3-3.26 (m, 2H), 3.05-2.96 (m, 2H), 2.35 (s, 3H) MS m/z 562.2 (M + 1), | N-{3-[2-(2,3-Dihydro-benzo[1,4]dioxin-6-ylamino)-7,8-dihydro-5H-pyrido[4,3-d]pyrimidin-6-yl]-4-methyl-phenyl}-3-trifluoromethyl-benzamide | 2 |
| 41 | 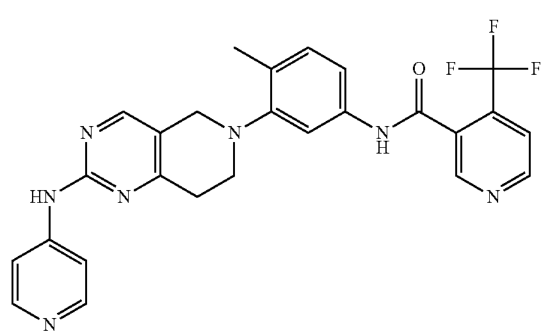 [SMILES: Cc1ccc(NC(=O)c2cnccc2C(F)(F)F)cc1N1CCc2nc(Nc3ccncc3)ncc2C1] | ¹H NMR (300 MHz, CD₃OD) δ 9.0-8.92 (m, 2H), 8.53 (s, 1H), 8.46 (d, 2H), 8.4-8.3 (br s, 2H), 7.85 (d, 1H), 7.66 (s, 1H), 7.28-7.22 (m, 2H), 4.18 (s, 2H), 3.39-3.37 (m, 2H), 3.2-3.1 (m, 2H), 2.35 (s, 3H) MS m/z 506.1 (M + 1), | N-{4-Methyl-3-[2-(pyridin-4-ylamino)-7,8-dihydro-5H-pyrido[4,3-d]pyrimidin-6-yl]-phenyl}-4-trifluoromethyl-nicotinamide | 2 |

TABLE 1-continued

| No | Structure | Physical Data [¹HNMR and/or MS] | IUPAC NAME | Ex |
|---|---|---|---|---|
| 42 | 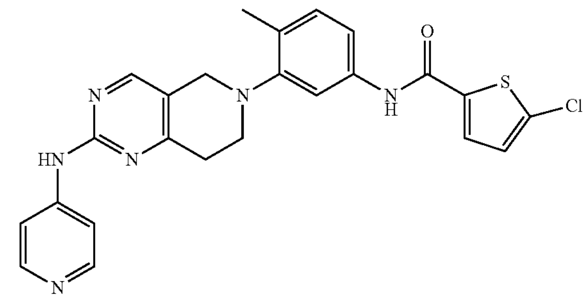 [SMILES: Cc1ccc(NC(=O)c2ccc(Cl)s2)cc1N1CCc2nc(Nc3ccncc3)ncc2C1] | 1H NMR (300 MHz, CDCl₃) δ 8.45 (d, 2H), 8.25 (s, 1H), 7.72-7.56 (m, 4H), 7.4 (d, 1H), 7.32-7.28 (m, 1H), 7.22-7.18 (m, 1H), 7.06-7.0 (m, 1H), 6.97 (d, 1H), 4.08 (s, 2H), 3.3 (t, 2H), 3.07 (t, 2H), 2.32 (s, 3H) MS m/z 477.0 (M + 1), | 5-Chloro-thiophene-2-carboxylic acid {4-methyl-3-[2-(pyridin-4-ylamino)-7,8-dihydro-5H-pyrido[4,3-d]pyrimidin-6-yl]-phenyl}-amide | 2 |
| 43 | 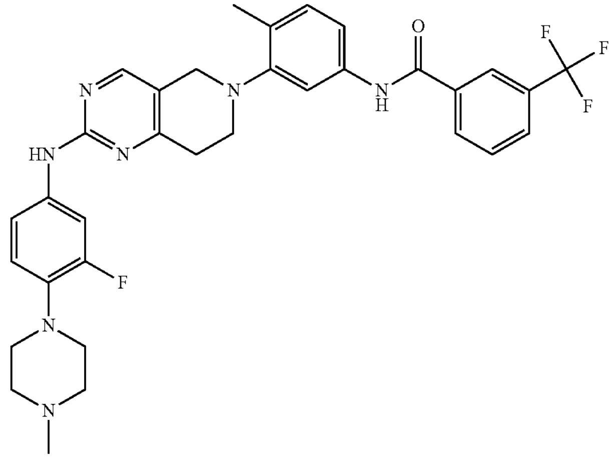 [SMILES: Cc1ccc(NC(=O)c2cccc(C(F)(F)F)c2)cc1N1CCc2nc(Nc3ccc(N4CCN(C)CC4)c(F)c3)ncc2C1] | ¹H NMR (300 MHz, CD₃OD) δ 8.3-8.16 (m, 3H), 7.93-7.86 (m, 1H), 7.82-7.7 (m, 2H), 7.68-7.62 (m, 1H), 7.38-7.2 (m, 3H), 7.05 (m, 1H), 4.06 (s, 2H), 3.67-3.48 (m, 4H), 3.2-2.9 (m, 8H), 2.34 (s, 3H) MS m/z 620.2 (M + 1), | N-(3-{2-[3-Fluoro-4-(4-methyl-piperazin-1-yl)-phenyl-amino]-7,8-dihydro-5H-pyrido[4,3-d]pyrimidin-6-yl}-4-methyl-phenyl)-3-trifluoromethyl-benzamide | 1 |
| 44 | 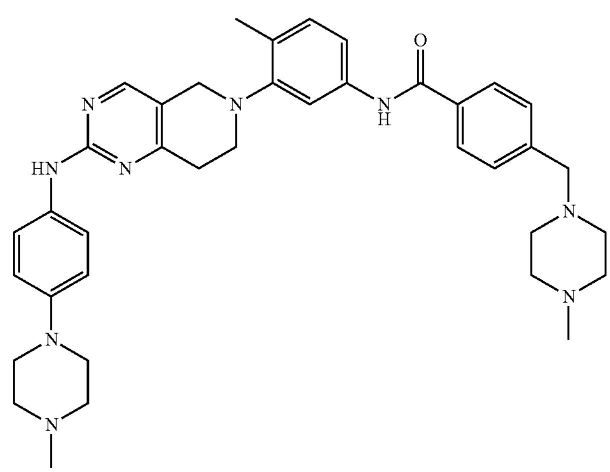 [SMILES: Cc1ccc(NC(=O)c2ccc(CN3CCN(C)CC3)cc2)cc1N1CCc2nc(Nc3ccc(N4CCN(C)CC4)cc3)ncc2C1] | ¹H NMR (300 MHz, DMSO-D₆) δ 10.15 (s, 1H), 9.25 (s, 1H), 8.24 (s, 1H), 7.9 (d, 2H), 7.68-7.55 (m, 3H), 7.5-7.4 (m, 3H), 7.15 (d, 1H), 6.88 (d, 2H), 3.95 (s, 2H), 3.52 (s, 3H), 3.22-3.16 (m, 4H), 2.92-2.86 (s, 2H), 2.45-2.32 (m, 9H), 2.26-2.20 (m, 6H), 2.14 (s, 3H), 1.86 (s, 10H) MS m/z 646.2 (M + 1), | N-(4-Methyl-3-{2-[4-(4-methyl-piperazin-1-yl)-phenylamino]-7,8-dihydro-5H-pyrido[4,3-d]pyrimidin-6-yl}-phenyl)-4-(4-methyl-piperazin-1-ylmethyl)-benzamide | 1 |

TABLE 1-continued

| No | Structure | Physical Data [¹HNMR and/or MS] | IUPAC NAME | Ex |
|----|-----------|-----------------------------------|------------|-----|
| 45 | 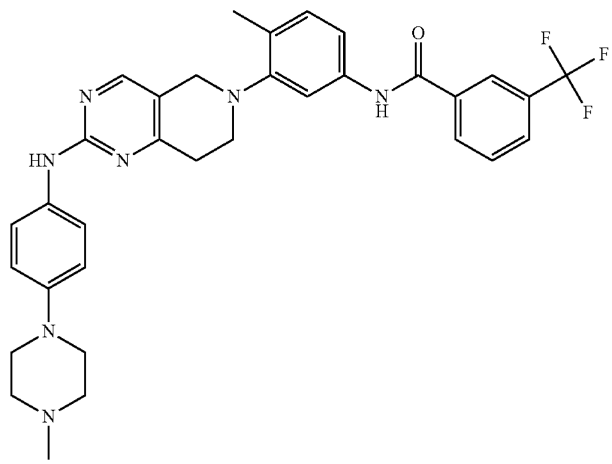 | ¹H NMR (300 MHz, CD₃OD) δ 8.84 (s, 1H), 8.3-8.14 (m, 2H), 7.9 (d, 1H), 7.83-7.61 (m, 4H), 7.61-7.52 (dd, 1H), 7.35 (d, 1H), 7.04 (d, 2H), 4.18-3.98 (m, 2H), 3.95-3.25 (m, 3H), 3.7-3.55 (m, 2H), 3.28-3.01 (m, 5H), 2.98 (s, 3H), 2.28 (s, 3H) MS m/z 616.2 (M + 1), | N-(4-Methyl-3-{2-[4-(4-methyl-piperazin-1-yl)-phenyl-amino]-5-oxo-7,8-dihydro-5H-pyrido[4,3-d]pyrimidin-6-yl}-phenyl)-3-trifluoromethyl-benzamide | 3 |
| 46 | 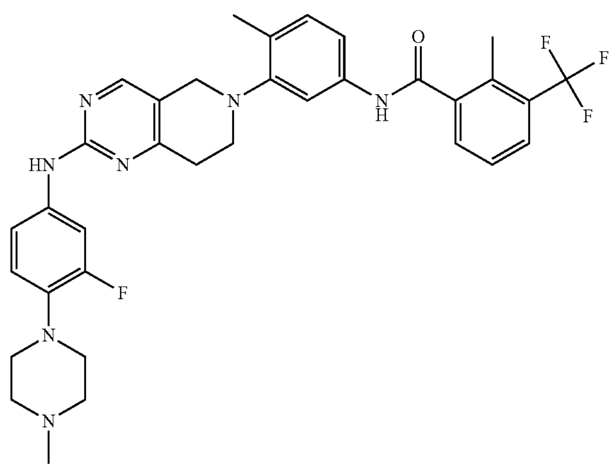 [SMILES: Cc1ccc(NC(=O)c2cccc(C(F)(F)F)c2C)cc1N1CCc2nc(Nc3ccc(N4CCN(C)CC4)c(F)c3)ncc2C1] | ¹H NMR (300 MHz, CDCl₃) δ 8.18 (s, 1H), 7.8-7.59 (m, 4H), 7.45-7.32 (m, 2H), 7.25-6.9 (m, 5H), 4.08 (s, 2H), 3.35-3.0 (m, 8H), 2.9-2.72 (br s, 4H), 2.6 (s, 3H), 2.5 (s, 3H), 2.34 (s, 3H) MS m/z 634.2 (M + 1), | N-(3-{2-[3-Fluoro-4-(4-methyl-piperazin-1-yl)-phenylamino]-7,8-dihydro-5H-pyrido[4,3-d]pyrimidin-6-yl}-4-methyl-phenyl)-2-methyl-3-trifluoromethyl-benzamide | 1 |
| 47 | 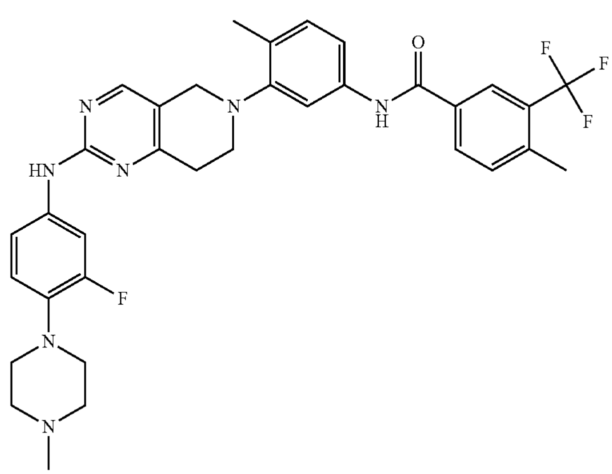 [SMILES: Cc1ccc(NC(=O)c2ccc(C)c(C(F)(F)F)c2)cc1N1CCc2nc(Nc3ccc(N4CCN(C)CC4)c(F)c3)ncc2C1] | ¹H NMR (300 MHz, CDCl₃) δ 8.15 (d, 2H), 7.95 (d, 1H), 7.81 (s, 1H), 7.7-7.6 (m, 2H), 7.45 (d, 1H), 7.25-7.1 (m, 3H), 7.03-6.9 (m, 2H), 4.06 (s, 2H), 3.5 (s, 1H), 3.3 (t, 2H), 3.35-3.25 (m, 6H), 2.7-2.56 (m, 7H), 2.38 (s, 3H), 2.33 (s, 3H) MS m/z 633.9 (M + 1), | N-(3-{2-[3-Fluoro-4-(4-methyl-piperazin-1-yl)-phenyl-amino]-7,8-dihydro-5H-pyrido[4,3-d]pyrimidin-6-yl}-4-methyl-phenyl)-4-methyl-3-trifluoromethyl-benzamide | 1 |

TABLE 1-continued

| No | Structure | Physical Data [¹HNMR and/or MS] | IUPAC NAME | Ex |
|---|---|---|---|---|
| 48 | 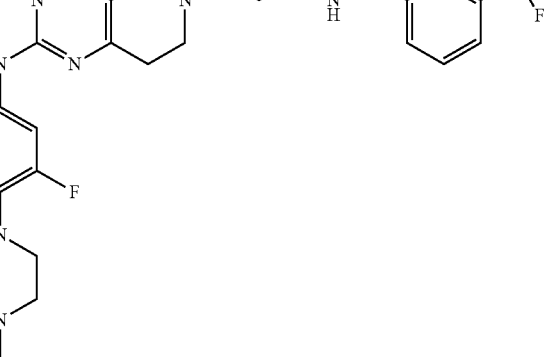 | ¹H NMR (300 MHz, DMSO-D₆) δ 10.6 (s, 1H), 10.32 (s, 1H), 9.9-9.7 (br s, 1H), 8.35 (s, 1H), 8.3-8.2 (m, 1H), 8.04-7.14 (m, 5H), 7.52-7.4 (m, 2H), 7.2-7.06 (m, 2H), 4.04 (t, 2H), 3.58-3.45 (m, 4H), 3.28-3.12 (m, 4H), 3.05-2.96 (m, 2H), 2.88 (s, 3H) MS m/z 620.1 (M + 1), | N-(3-{2-[3-Fluoro-4-(4-methyl-piperazin-1-yl)-phenyl-amino]-5-oxo-7,8-dihydro-5H-pyrido[4,3-d]pyrimidin-6-yl}-phenyl)-3-trilfuoromethyl-benzamide | 3 |
| 49 | 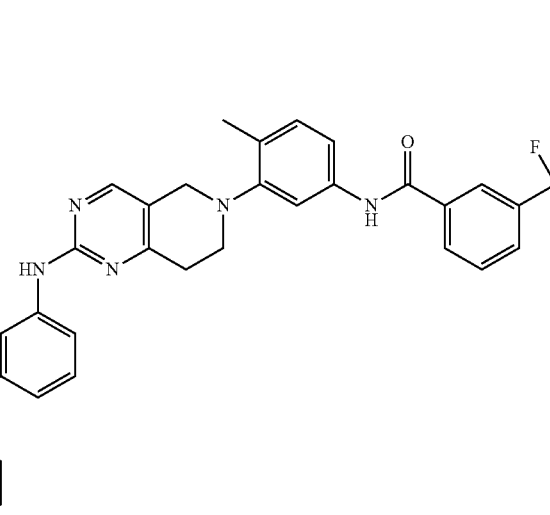 | ¹H NMR (300 MHz, CD₃OD) δ 8.36-8.2 (m, 3H), 7.98-7.66 (m, 5H), 7.45-7.35 (m, 2H), 7.28-7.12 (m, 2H), 4.12 (s, 4H), 3.54-3.46 (m, 4H), 3.41-3.36 (m, 5H), 3.31-3.21 (m, 4H), 3.1-3.02 (m, 2H), 2.95 (s, 3H), 2.36 (s, 3H) MS m/z 616.2 (M + 1), | N-(4-Methyl-3-{2-[3-(4-methyl-piperazin-1-ylmethyl)-phenylamino]-7,8-dihydro-5H-pyrido[4,3-d]pyrimidin-6-yl}-phenyl)-3-trifluoromethyl-benzamide | 1 |
| 50 | 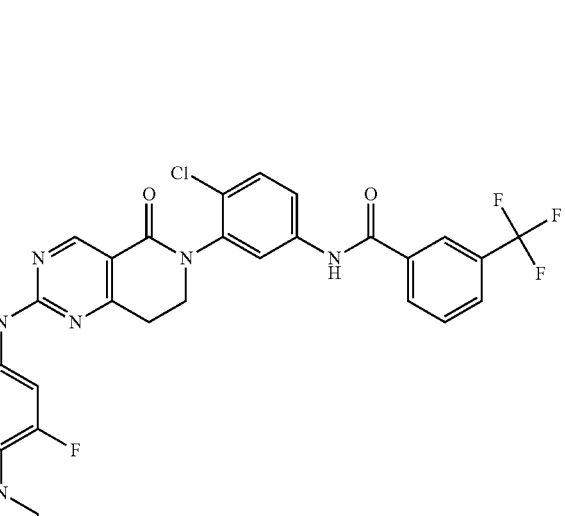 | ¹H NMR (300 MHz, CD₃OD) δ 8.9 (s, 1H), 8.3-8.2 (m, 2H), 8.0-7.9 (m, 2H), 7.82-7.72 (m, 3H), 7.62-7.58 (m, 1H), 7.42-7.36 (m, 1H), 7.1-7.0 (m, 1H), 4.1-3.9 (m, 4H), 3.2-3.0 (m, 4), 2.8-2.6 (m, 4H), 2.4 (s, 3H) MS m/z 653.9 (M + 1), | N-(4-Chloro-3-{2-[3-fluoro-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide | 3 |

TABLE 1-continued

| No | Structure | Physical Data [¹HNMR and/or MS] | IUPAC NAME | Ex |
|----|-----------|----------------------------------|------------|-----|
| 51 | 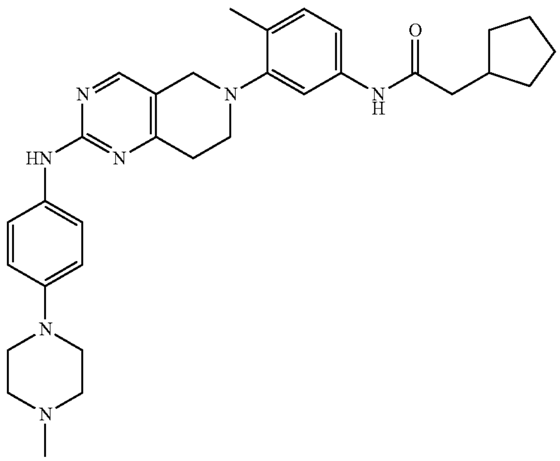 [SMILES: Cc1ccc(NC(=O)CC2CCCC2)cc1N1CCc2nc(Nc3ccc(N4CCN(C)CC4)cc3)ncc2C1] | ¹H NMR (300 MHz, CD₃OD) δ 9.77 (s, 1H), 9.26 (s, 1H), 8.22 (s, 1H), 7.6 (d, 2H), 7.46 (s, 1H), 7.3-7.04 (m, 2H), 6.49 (d, 2H), 3.92 (s, 2H), 3.2-3.02 (m, 7H), 2.95-2.65 (m, 7H), 2.35-2.12 (m, 6H), 1.91 (s, 2H), 1.85-1.45 (m, 6H), 1.03-1.01 (m, 2H) MS m/z 540.3 (M + 1), | 2-Cyclopentyl-N-(4-methyl-3-{2-[4-(4-methyl-piperazin-1-yl)-phenylamino]-7,8-dihydro-5H-pyrido[4,3-d]pyrimidin-6-yl}-phenyl)-acetamide | 1 |
| 52 | 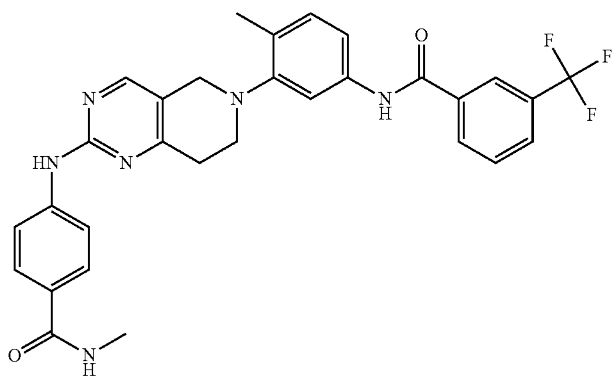 [SMILES: CNC(=O)c1ccc(Nc2ncc3c(n2)CCN(c2cc(NC(=O)c4cccc(C(F)(F)F)c4)ccc2C)C3)cc1] | ¹H NMR (300 MHz, DMSO-D₆) δ 10.4 (s, 1H), 9.84 (s, 1H), 8.4-8.2 (m, 3H), 8.02-7.7 (m, 6H), 7.63 (s, 1H), 7.52-7.44 (d, 1H), 7.25-7.16 (d, 1H), 4.05 (s, 2H), 3.2-3.1 (m, 2H), 3.0 (s, 2H), 2.76 (s, 3H), 2.3 (s, 3H), 1.88 (s, 1H) MS m/z 561.0 (M + 1), | N-{3-[2-(4-(Methylamino-carbonyl)-phenylamino)-7,8-dihydro-5H-pyrido[4,3-d]pyrimidin-6-yl]-4-methyl-phenyl}-3-trifluoromethyl-benzamide | 2 |
| 53 | 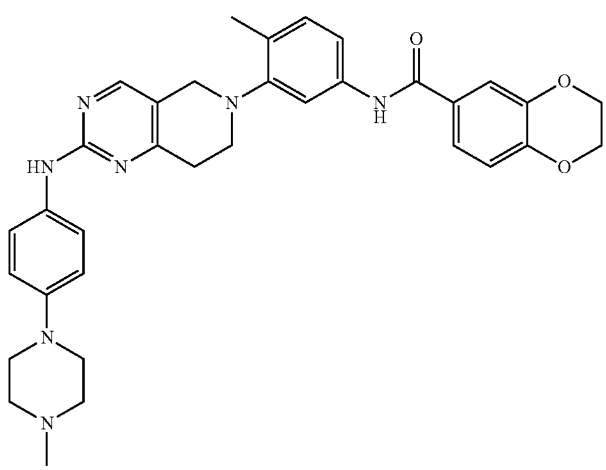 [SMILES: Cc1ccc(NC(=O)c2ccc3c(c2)OCCO3)cc1N1CCc2nc(Nc3ccc(N4CCN(C)CC4)cc3)ncc2C1] | ¹H NMR (300 MHz, DMSO-D₆) δ 10.2-9.6 (m, 2H), 9.35 (s, 1H), 8.4-8.2 (m, 2H), 7.75-7.4 (m, 6H), 7.2-7.1 (m, 1H), 7.02-6.9 (m, 3H), 4.3 (s, 4H), 3.98 (s, 2H), 3.28-3.1 (m, 5H), 3.0-2.8 (m, 7H), 2.25 (s, 3H) MS m/z 591.3 (M + 1), | 2,3-Dihydro-benzo[1,4]dioxine-6-carboxylic acid (4-methyl-3-{2-[4-(4-methyl-piperazin-1-yl)-phenylamino]-7,8-dihydro-5H-pyrido[4,3-d]pyrimidin-6-yl}-phenyl)-amide | 1 |

TABLE 1-continued

| No | Structure | Physical Data [¹HNMR and/or MS] | IUPAC NAME | Ex |
|---|---|---|---|---|
| 54 | 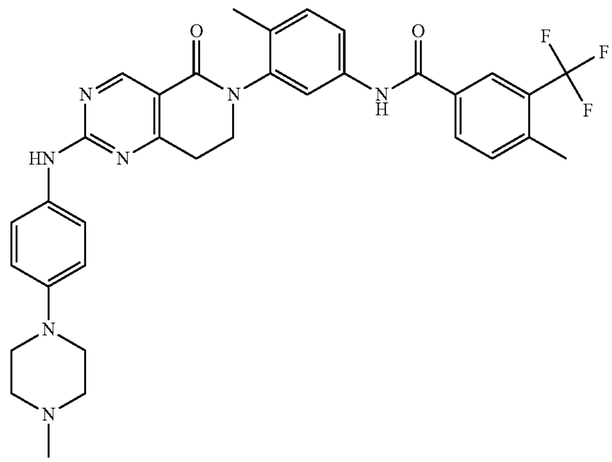 [SMILES: Cc1ccc(NC(=O)c2ccc(C)c(C(F)(F)F)c2)cc1N1CCc2nc(Nc3ccc(N4CCN(C)CC4)cc3)ncc2C1=O] | ¹H NMR (300 MHz, CD₃OD) δ 8.85 (s, 1H), 8.37 (s, 1H), 8.1 (d, 1H), 7.8-7.7 (m, 1H), 7.2-7.54 (m, 4H), 7.38 (d, 1H), 7.04 (d, 1H), 4.18-4.02 (m, 1H), 3.95-3.82 (m, 1H), 3.3-3.2 (m, 4H), 3.2-3.1 (m, 2H), 2.82-2.7 (m, 4H), 2.6 (s, 3H), 2.48 (s, 3H), 2.3 (s, 3H) MS m/z 630.1 (M + 1), | 4-Methyl-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-3-trifluoromethyl-benzamide | 3 |
| 55 | 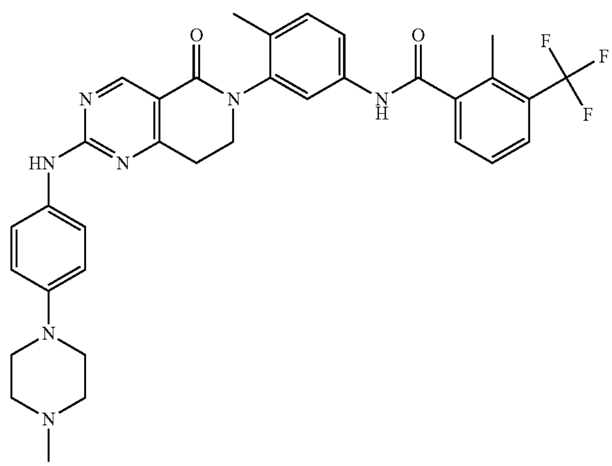 [SMILES: Cc1ccc(NC(=O)c2cccc(C(F)(F)F)c2C)cc1N1CCc2nc(Nc3ccc(N4CCN(C)CC4)cc3)ncc2C1=O] | ¹H NMR (300 MHz, CD₃OD) δ 8.82 (s, 1H), 7.85-7.42 (m, 7H), 7.4-7.28 (m, 1H), 7.02 (d, 2H), 4.1-3.95 (m, 1H), 3.9-3.7 (m, 3H), 3.7-3.5 (m, 2H), 3.3-2.9 (m, 9H), 2.5 (s, 3H), 2.2 (s, 3H) MS m/z 630.2 (M + 1) | 2-Methyl-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide | 3 |
| 56 | 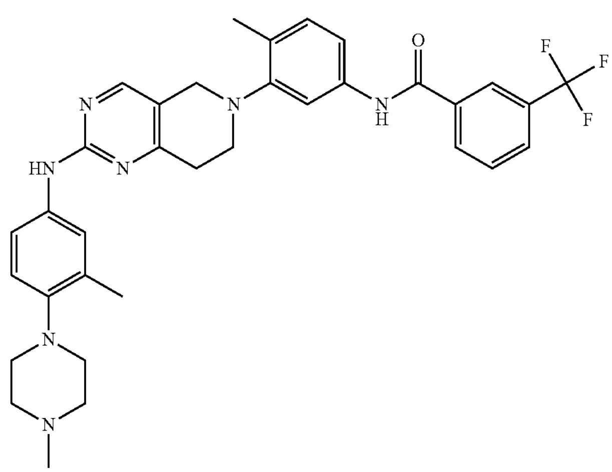 [SMILES: Cc1cc(Nc2ncc3c(n2)CCN(c2cc(NC(=O)c4cccc(C(F)(F)F)c4)ccc2C)C3)ccc1N1CCN(C)CC1] | ¹H NMR (300 MHz, CD₃OD) δ 8.35-8.12 (m, 3H), 7.96-7.83 (m, 1H), 7.78-7.61 (m, 2H), 7.58-7.42 (m, 2H), 7.38-7.29 (m, 1H), 7.26-7.19 (m, 1H), 7.14-7.04 (m, 1H), 4.07 (s, 2H), 3.6-3.55 (m, 2H), 3.4 (t, 2H), 3.12-2.95 (m, 8H), 2.95 (s, 3H), 2.35 (s, 6H) MS m/z 616.2 (M + 1), | N-(4-Methyl-3-{2-[3-methyl-4-(4-methyl-piperazin-1-yl)-phenylamino]-7,8-dihydro-5H-pyrido[4,3-d]pyrimidin-6-yl}-phenyl)-3-trifluoromethyl-benzamide | 1 |

TABLE 1-continued

| No | Structure | Physical Data [¹HNMR and/or MS] | IUPAC NAME | Ex |
|---|---|---|---|---|
| 57 | 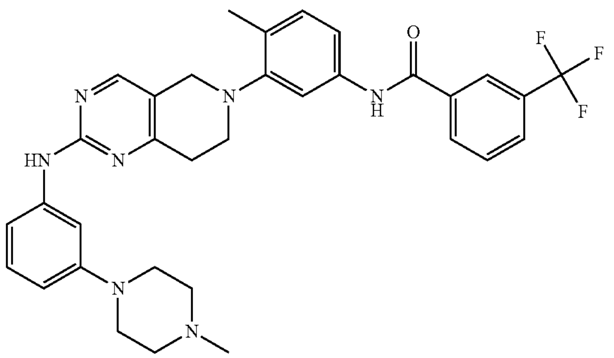 [SMILES: Cc1ccc(NC(=O)c2cccc(C(F)(F)F)c2)cc1N1CCc2nc(Nc3cccc(N4CCN(C)CC4)c3)ncc2C1] | ¹H NMR (300 MHz, CD₃OD) δ 8.3-8.15 (m, 3H), 7.9-7.8 (m, 1H), 7.75-7.65 (t, 1H), 7.6 (s, 1H), 7.45 (s, 1H), 7.4-7.3 (m, 1H), 7.25-7.1 (m, 3H), 6.7-6.55 (m, 1H), 4.1-4.05 (s, 2H), 3.35-3.2 (m, 6H), 3.05-2.95 (m, 2H), 2.7-2.6 (m, 4H), 2.4 (s, 3H), 2.3 (s, 3H) MS m/z 601.9 (M + 1), | N-(4-Methyl-3-{2-[3-(4-methyl-piperazin-1-yl)-phenylamino]-7,8-dihydro-5H-pyrido[4,3-d]pyrimidin-6-yl}-phenyl)-3-trifluoromethyl-benzamide | 1 |
| 58 | 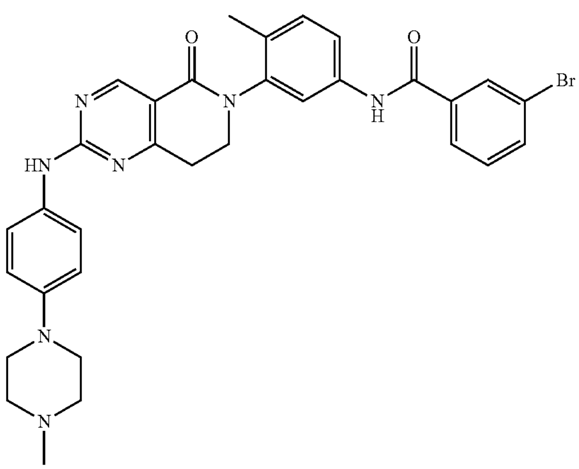 [SMILES: Cc1ccc(NC(=O)c2cccc(Br)c2)cc1N1CCc2nc(Nc3ccc(N4CCN(C)CC4)cc3)ncc2C1=O] | ¹H NMR (300 MHz, CD₃OD) δ 8.82 (s, 1H) 8.12-8.08 (t, 1H), 7.94-7.86 (m, 1H), 7.78-7.68 (m, 2H), 7.64-7.54 (m, 3H), 7.5-7.4 (m, 1H), 7.38-7.3 (m, 1H), 7.04-6.94 (m, 2H), 4.15-4.0 (m, 1H), 3.8-3.7 (m, 1H), 3.25-3.15 (m, 4H), 3.05-2.95 (m, 2H), 2.75-2.65 (m, 4H), 2.25 (s, 3H), 2.15 (s, 3H) MS m/z 625.8 (M + 1), | 3-Bromo-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide | 3 |
| 59 | 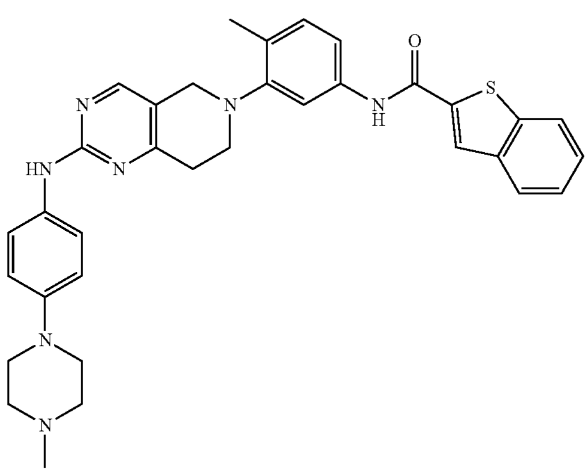 [SMILES: Cc1ccc(NC(=O)c2cc3ccccc3s2)cc1N1CCc2nc(Nc3ccc(N4CCN(C)CC4)cc3)ncc2C1] | ¹H NMR (300 MHz, DMSO-D₆) δ 10.43 (s, 1H), 9.28 (s, 1H), 8.36 (s, 1H), 8.25 (s, 1H), 8.12-7.98 (m, 2H), 7.69-7.44 (m, 6H), 7.25-7.15 (d, 1H), 6.86 (d, 2H), 4.12 (q, 1H), 4.0 (s, 2H), 3.25-3.15 (m, 5H), 3.1-3.02 (m, 4H), 2.96-2.88 (m, 2H), 2.28 (s, 3H), 2.22 (s, 3H) MS m/z 590.2 (M + 1), | Benzo[b]thiophene-2-carboxylic acid (4-methyl-3-{2-[4-(4-methyl-piperazin-1-yl)-phenylamino]-7,8-dihydro-5H-pyrido[4,3-d]pyrimidin-6-yl}-phenyl)-amide | 1 |

TABLE 1-continued

| No | Structure | Physical Data [¹HNMR and/or MS] | IUPAC NAME | Ex |
|---|---|---|---|---|
| 60 | 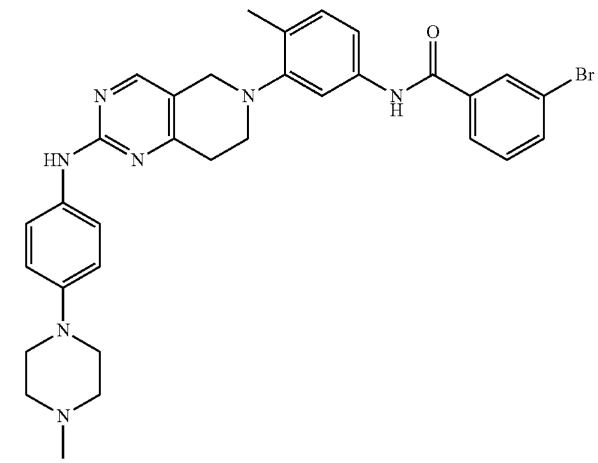 [SMILES: Cc1ccc(NC(=O)c2cccc(Br)c2)cc1N1CCc2nc(Nc3ccc(N4CCN(C)CC4)cc3)ncc2C1] | ¹H NMR (300 MHz, CDCl₃) δ 8.13 (s, 1H), 8.06-7.98 (br s, 1H), 7.92-7.78 (m, 2H), 7.72-7.48 (m, 4H), 7.44-7.32 (m, 2H), 7.24-7.06 (m, 3H), 7.0-6.9 (m, 2H), 4.02 (s, 2H), 3.36-3.16 (m, 6H), 3.06-2.95 (m, 3H), 2.76-2.62 (m, 4H), 2.5-2.25 (d, 7H) MS m/z 612.1 (M + 1), | 3-Bromo-N-(4-methyl-3-{2-[4-(4-methyl-piperazin-1-yl)-phenyl-amino]-7,8-dihydro-5H-pyrido[4,3-d]pyrimidin-6-yl}-phenyl)-benzamide | 1 |
| 61 | 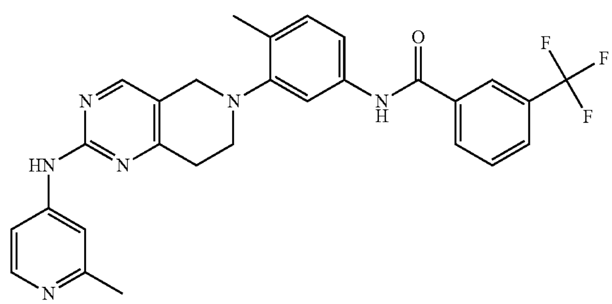 [SMILES: Cc1cc(Nc2ncc3c(n2)CCN(c2cc(NC(=O)c4cccc(C(F)(F)F)c4)ccc2C)C3)ccn1] | ¹H NMR (300 MHz, CDCl₃) δ 8.33 (d, 1H), 8.26-8.05 (m, 4H), 7.85-7.75 (m, 1H), 7.7-7.58 (m, 2H), 7.52-7.4 (m, 2H), 7.3-7.15 (m, 3H), 4.06 (s, 2H), 3.4-3.22 (m, 2H), 3.14-2.98 (m, 2H), 2.52 (s, 3H), 2.32 (s, 3H) MS m/z 518.8 (M + 1), | N-{4-Methyl-3-[2-(2-methyl-pyridin-4-ylamino)-7,8-dihydro-5H-pyrido[4,3-d]pyrimidin-6-yl]-phenyl}-3-trifluoromethyl-benzamide | 2 |
| 62 | 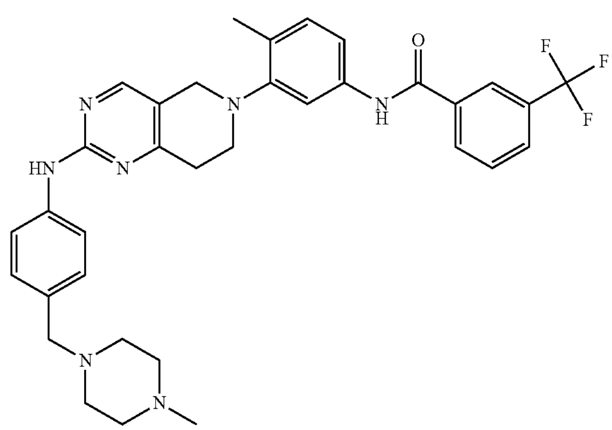 [SMILES: Cc1ccc(NC(=O)c2cccc(C(F)(F)F)c2)cc1N1CCc2nc(Nc3ccc(CN4CCN(C)CC4)cc3)ncc2C1] | ¹H NMR (300 MHz, CD₃OD) δ 8.38 (m, 3H), 7.94-7.62 (m, 5H), 7.42-7.3 (m, 2H), 7.28-7.2 (m, 1H), 7.14-7.05 (m, 1H), 4.05 (d, 4H), 3.2-3.0 (m, 7H), 2.9 (s, 3H), 2.34 (s, 3H) MS m/z 616.2 (M + 1), | N-(4-Methyl-3-{2-[4-(4-methyl-piperazin-1-ylmethyl)-phenylamino]-7,8-dihydro-5H-pyrido[4,3-d]pyrimidin-6-yl}-phenyl)-3-trifluoromethyl-benzamide | 1 |

TABLE 1-continued

| No | Structure | Physical Data [¹HNMR and/or MS] | IUPAC NAME | Ex |
|----|-----------|----------------------------------|------------|-----|
| 63 | 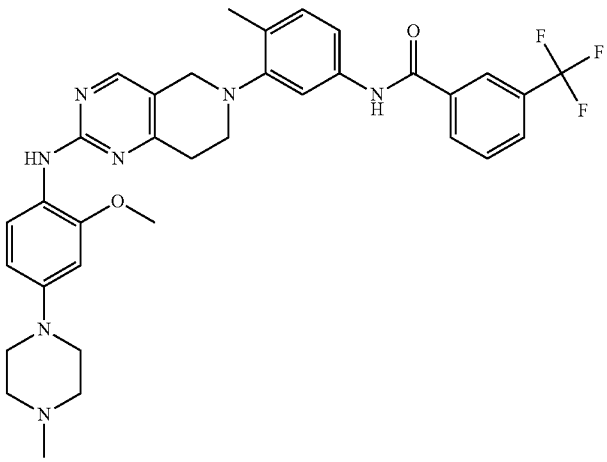 [SMILES: COc1cc(N2CCN(C)CC2)ccc1Nc1ncc2c(n1)CCN(c1cc(NC(=O)c3cccc(C(F)(F)F)c3)ccc1C)C2] | ¹H NMR (300 MHz, DMSO-D₆) δ 10.2 (s, 1H), 8.4-8.18 (m, 4H), 8.04-7.74 (m, 5H), 7.68-7.42 (m, 2H), 7.26-7.16 (m, 1H), 6.7-6.6 (m ,1H), 6.54-6.44 (m, 1H), 3.98 (s, 3H), 3.82 (s, 5H), 3.22-3.1 (m, 8H), 2.94-2.84 (m, 3H), 2.32-2.22 (m, 9H) MS m/z 632.0 (M + 1), | N-(3-{2-[2-Methoxy-4-(4-methyl-piperazin-1-yl)-phenylamino]-7,8-dihydro-5H-pyrido[4,3-d]pyrimidin-6-yl}-4-methyl-phenyl)-3-trifluoromethyl-benzamide | 1 |
| 64 | 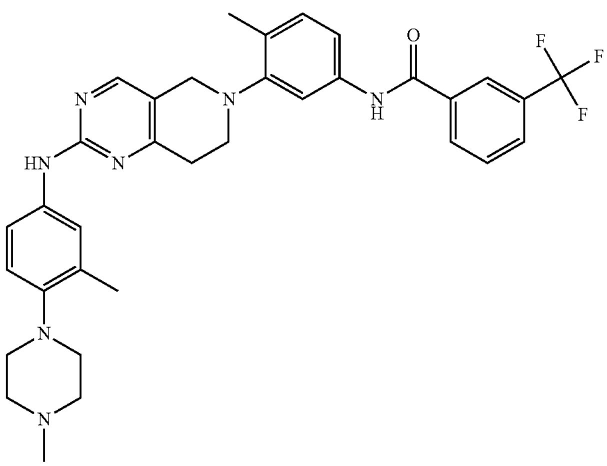 | ¹H NMR (300 MHz, CD₃OD) δ 8.76 (s, 1H), 8.23-8.06 (m, 3H), 7.84-7.59 (m, 3H), 7.56-7.41 (m, 3H), 7.3-7.2 (m, 1H), 6.98 (d, 1H), 4.04-3.92 (m, 1H), 3.8-3.7 (m, 1H), 3.11-2.94 (m, 9H), 2.64 (s, 3H), 2.26 (s, 3H), 2.18 (s, 3H) MS m/z 629.8 (M + 1), | N-(4-Methyl-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide | 3 |
| 65 | 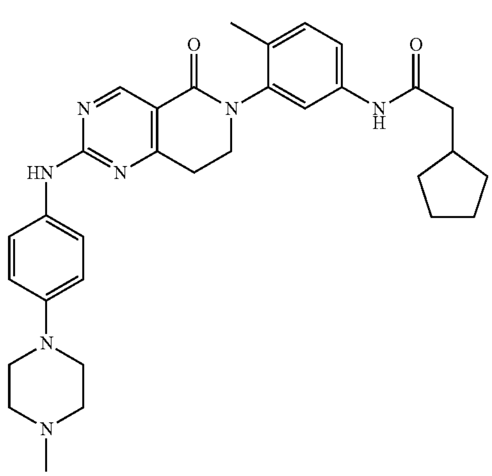 [SMILES: Cc1ccc(NC(=O)CC2CCCC2)cc1N1CCc2nc(Nc3ccc(N4CCN(C)CC4)cc3)ncc2C1=O] | ¹H NMR (300 MHz, DMSO-D₆) δ 10.15-10.0 (d, 2H), 8.75 (s, 1H), 7.7-7.55 (m, 3H), 7.5-7.4 (m, 1H), 7.25-7.15 (m, 1H), 7.05-6.95 (d, 2H), 4.0-3.9 (m, 1H), 3.75-3.65 (m, 1H), 3.2-3.1 (m, 4H), 3.3-3.1 (m, 4H), 3.1-2.95 (m, 2H), 2.75-2.65 (m, 4H), 2.3-2.2 (m, 2H), 2.1 (s, 3H), 1.8-1.4 (m, 9H), 1.3-1.1 (m, 4H) MS m/z 554.2 (M + 1), | 2-Cyclopentyl-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-acetamide | 3 |

TABLE 1-continued

| No | Structure | Physical Data [¹HNMR and/or MS] | IUPAC NAME | Ex |
|----|-----------|----------------------------------|------------|-----|
| 66 | 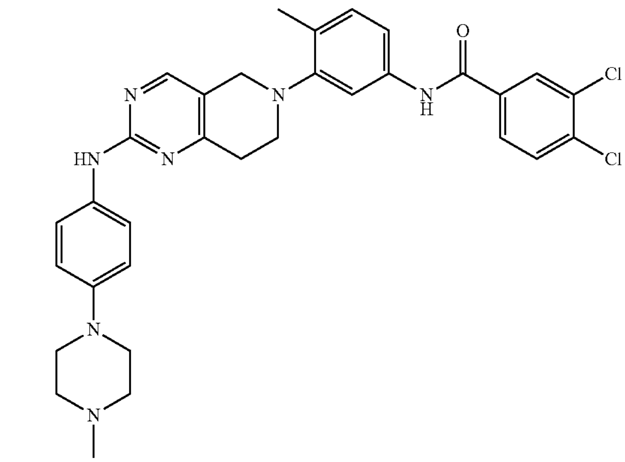 [SMILES: Cc1ccc(NC(=O)c2ccc(Cl)c(Cl)c2)cc1N1CCc2nc(Nc3ccc(N4CCN(C)CC4)cc3)ncc2C1] | ¹H NMR (300 MHz, DMSO-D₆) δ 10.32 (s, 1H), 9.28 (s, 1H), 8.3-8.2 (m, 2H), 8.0-7.78 (m, 2H), 7.65-7.4 (m, 4H), 7.18 (d, 1H), 6.88 (d, 2H), 3.98 (s, 2H), 3.24-3.18 (m, 2H), 3.14-3.06 (m, 4H), 2.94-2.86 (m, 3H), 2.38-2.22 (m, 8H) MS m/z 602.1 (M + 1), | 3,4-Dichloro-N-(4-methyl-3-{2-[4-(4-methyl-piperazin-1-yl)-phenylamino]-7,8-dihydro-5H-pyrido[4,3-d]pyrimidin-6-yl}-phenyl)-benzamide | 1 |
| 67 | 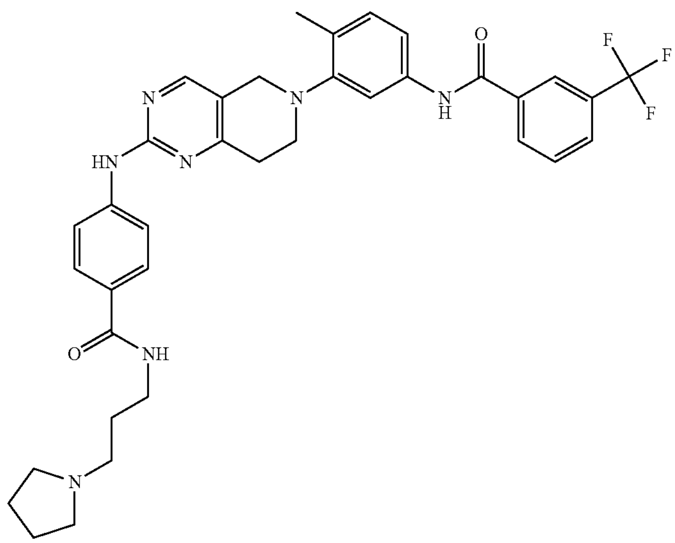 [SMILES: Cc1ccc(NC(=O)c2cccc(C(F)(F)F)c2)cc1N1CCc2nc(Nc3ccc(C(=O)NCCCN4CCCC4)cc3)ncc2C1] | ¹H NMR (300 MHz, DMSO-D₆) δ 10.46 (s, 1H), 9.9 (s, 1H), 8.5-8.2 (m, 3H), 8.05-7.7 (m, 5H), 7.68-7.42 (m, 2H), 7.25-7.15 (d, 1H), 4.05-4.0 (br s, 2H), 3.35-3.15 (m, 4H), 3.05-2.95 (br s, 2H), 2.28 (s, 2H), 2.0-1.6 (m, 13H) MS m/z 658.2 (M + 1), | N-{3-[2-(4-(3-Pyrrolidin-1-yl-propylamino-carbonyl)-phenylamino)-7,8-dihydro-5H-pyrido[4,3-d]pyrimidin-6-yl]-4-methyl-phenyl}-3-trifluoromethyl-benzamide | 2 |
| 68 | 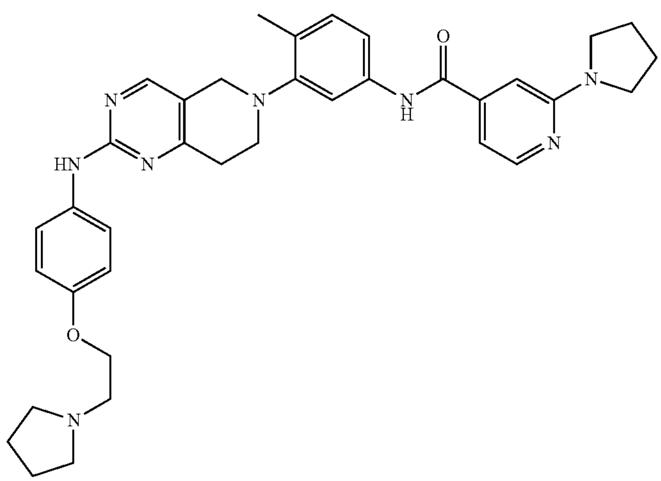 [SMILES: Cc1ccc(NC(=O)c2ccnc(N3CCCC3)c2)cc1N1CCc2nc(Nc3ccc(OCCN4CCCC4)cc3)ncc2C1] | 1H NMR (300 MHz, CD₃OD) δ 8.2-8.05 (m, 2H), 7.66-7.49 (m, 3H), 7.4-6.8 (m, 6H), 4.4-4.2 (m, 2H), 3.98 (s, 2H), 3.7-3.6 (m, 2H), 3.35-3.15 (m, 6H), 3.05-2.85 (m, 2H), 2.32 (s, 3H), 2.2-1.9 (m, 12H) MS m/z 619.2 (M + 1) | N-(4-Methyl-3-{2-[4-(2-pyrrolidin-1-yl-ethoxy)-phenylamino]-7,8-dihydro-5H-pyrido[4,3-d]pyrimidin-6-yl}-phenyl)-2-pyrrolidin-1-yl-isonicotinamide | 2 |

TABLE 1-continued

| No | Structure | Physical Data [¹HNMR and/or MS] | IUPAC NAME | Ex |
|---|---|---|---|---|
| 69 | 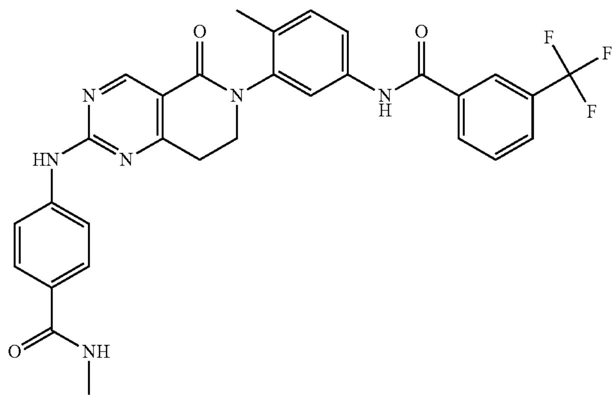 [SMILES: CNC(=O)c1ccc(Nc2ncc3c(n2)CCN(c2cc(NC(=O)c4cccc(C(F)(F)F)c4)ccc2C)C3=O)cc1] | ¹H NMR (300 MHz, DMSO-D$_6$) δ 10.5 (d, 2H), 8.4-8.2 (m, 3H), 8.0-7.6 (m, 9H), 7.4-7.2 (d, 1H), 4.1-3.9 (m, 1H), 3.9-3.7 (m, 1H), 3.2-3.1 (m, 1H), 2.8-2.7 (m, 4H), 2.2-2.1 (s, 3H) MS m/z 575.1 (M + 1), | N-[4-Methyl-3-(5-oxo-2-(4-Methyl-aminocarbonyl)-phenylamino-7,8-dihydro-5H-pyrido[4,3-d]pyrimidin-6-yl)-phenyl]-3-trifluoromethyl-benzamide | 4 |
| 70 | 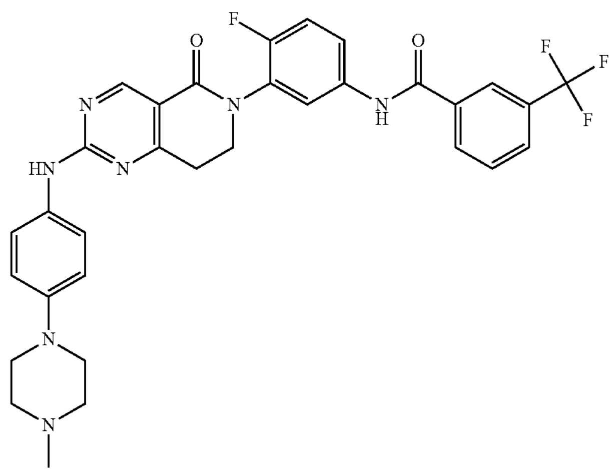 [SMILES: CN1CCN(c2ccc(Nc3ncc4c(n3)CCN(c3cc(NC(=O)c5cccc(C(F)(F)F)c5)ccc3F)C4=O)cc2)CC1] | ¹H NMR (300 MHz, CDCl$_3$) δ 9.2-8.8 (d, 2H), 8.3-7.9 (m, 2H), 7.9-7.3 (m, 7H), 7.2-6.8 (m, 3H), 4.1-3.8 (t, 2H), 3.4-3.2 (m, 4H), 3.2-3.0 (t, 2H), 2.9-2.6 (m, 4H), 2.4 (s, 3H) MS m/z 620.1 (M + 1), | N-(4-Fluoro-3-{2-[4-(4-methyl-piperazin-1-yl)-phenyl-amino]-5-oxo-7,8-dihydro-5H-pyrido[4,3-d]pyrimidin-6-yl}-phenyl)-3-trifluoromethyl-benzamide | 3 |
| 71 | 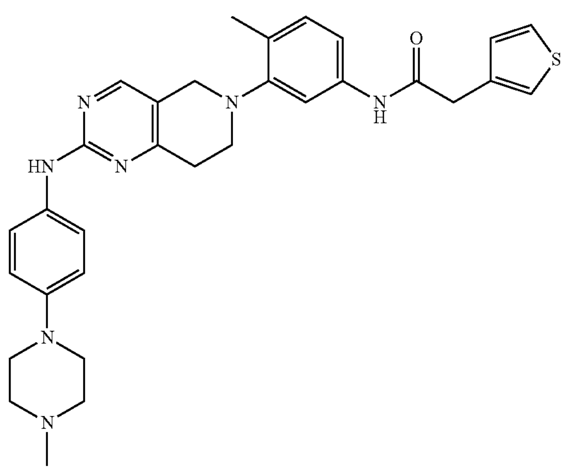 [SMILES: Cc1ccc(NC(=O)Cc2ccsc2)cc1N1CCc2nc(Nc3ccc(N4CCN(C)CC4)cc3)ncc2C1] | ¹H NMR (300 MHz, CD$_3$OD) δ 8.1 (s, 1H), 7.6-7.36 (m, 4H), 7.3-7.03 (m, 4H), 7.02-6.92 (d, 2H), 4.0 (s, 2H), 3.7 (s, 2H), 3.3-3.2 (m, 2H), 3.2-3.1 (m, 4H), 3.0-2.9 (m, 2H), 2.8-2.6 (m, 4H), 2.4 (s, 3H), 2.3 (s, 3H) MS m/z 554.2 (M + 1), | N-(4-Methyl-3-{2-[4-(4-methyl-piperazin-1-yl)-phenyl-amino]-7,8-dihydro-5H-pyrido[4,3-d]pyrimidin-6-yl}-phenyl)-2-thiophen-3-yl-acetamide | 1 |

TABLE 1-continued

| No | Structure | Physical Data [¹HNMR and/or MS] | IUPAC NAME | Ex |
|---|---|---|---|---|
| 72 | 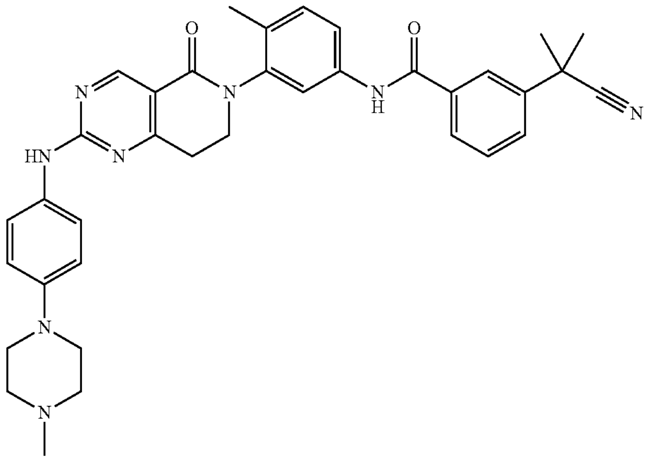 [SMILES: Cc1ccc(NC(=O)c2cccc(C(C)(C)C#N)c2)cc1N1CCc2nc(Nc3ccc(N4CCN(C)CC4)cc3)ncc2C1=O] | ¹H NMR (300 MHz, CD₃OD) δ 8.82 (s, 1H), 8.15-8.04 (m, 1H), 7.96-7.48 (m, 7H), 7.4-7.3 (m, 1H), 7.0 (d, 2H), 4.15-3.96 (m, 1H), 3.94-3.8 (m, 1H), 3.26-3.1 (m, 6H), 2.8-2.6 (m, 4H), 2.4 (s, 3H), 2.25 (s, 3H), 1.8 (s, 6H) MS m/z 615.3 (M + 1), | 3-(Cyano-dimethyl-methyl)-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-benzamide | 3 |
| 73 | 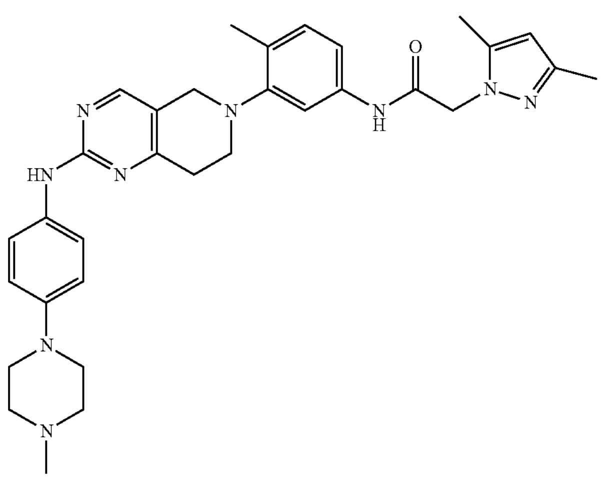 [SMILES: Cc1cc(C)n(CC(=O)Nc2ccc(C)c(N3CCc4nc(Nc5ccc(N6CCN(C)CC6)cc5)ncc4C3)c2)n1] | ¹H NMR (300 MHz, CDCl₃) δ 9.62 (s, 1H), 8.18 (s, 1H), 7.6 (d, 2H), 7.44 (s, 1H), 7.12 (s, 2H), 6.9 (d, 3H), 6.09 (s, 1H), 3.99 (s, 2H), 3.78-3.52 (m, 4H), 3.38-3.02 (m, 8H), 2.86 (s, 4H), 2.42 (d, 7H), 2.22 (s, 3H) MS m/z 566.1 (M + 1), | 2-(3,5-Dimethyl-pyrazol-1-yl)-N-(4-methyl-3-{2-[4-(4-methyl-piperazin-1-yl)-phenylamino]-7,8-dihydro-5H-pyrido[4,3-d]pyrimidin-6-yl}-phenyl)-acetamide | 1 |
| 75 | 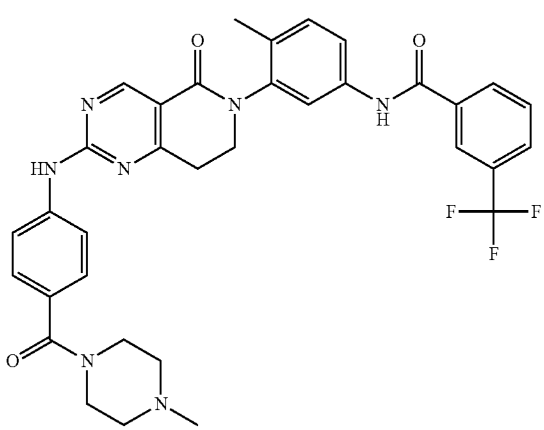 [SMILES: Cc1ccc(NC(=O)c2cccc(C(F)(F)F)c2)cc1N1CCc2nc(Nc3ccc(C(=O)N4CCN(C)CC4)cc3)ncc2C1=O] | ¹H NMR (300 MHz, CD3OD) δ 8.9 (s, 1H), 8.25-8.4 (m, 2H), 7.82-7.9 (m, 3H), 7.6-7.8 (m, 3H), 7.25-7.35 (dd, 3H), 4.05-4.15 (m, 2H), 3.6-3.92 (m, 6H), 2.5 (m, 4H), 2.2-2.4 (m, 6H) MS m/z 644.1 (M + 1), | N-(4-Methyl-3-{2-[4-(4-methyl-piperazine-1-carbonyl)-phenyl-amino]-5-oxo-7,8-dihydro-5H-pyrido[4,3-d]pyrimidin-6-yl}-phenyl)-3-trifluoromethyl-benzamide | 4 |

TABLE 1-continued

| No | Structure | Physical Data [¹HNMR and/or MS] | IUPAC NAME | Ex |
|---|---|---|---|---|
| 76 | 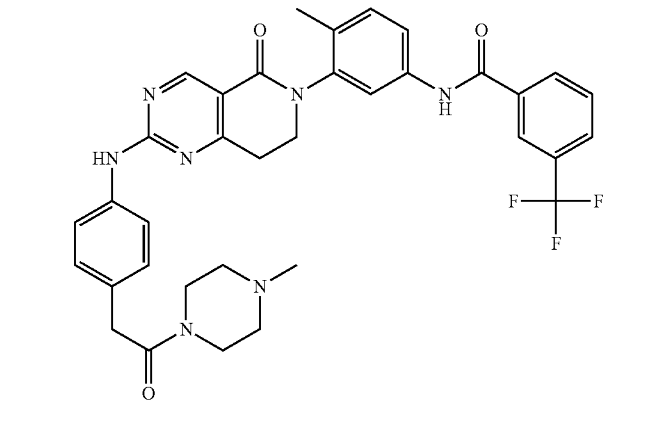 [SMILES: Cc1ccc(NC(=O)c2cccc(C(F)(F)F)c2)cc1N1CCc2nc(Nc3ccc(CC(=O)N4CCN(C)CC4)cc3)ncc2C1=O] | ¹H NMR (300 MHz, CDCl₃) δ 9.1 (d, 2H), 8.1-8.3 (m, 2H), 7.5-7.9 (m, 5H), 7.0-7.5 (m, 5H), 3.3-4.2 (m, 6H), 3.0-3.3 (d, 2H), 2.1-2.45 (m, 7H), 1.7-1.8 (s, 4H), MS m/z 658.0 (M + 1), | N-[4-Methyl-3-(2-{4-[2-(4-methyl-piperazin-1-yl)-2-oxo-ethyl]-phenyl-amino}-5-oxo-7,8-dihydro-5H-pyrido[4,3-d]pyrimidin-6-yl)-phenyl]-3-trilfuoromethyl-benzamide | 4 |
| 77 | 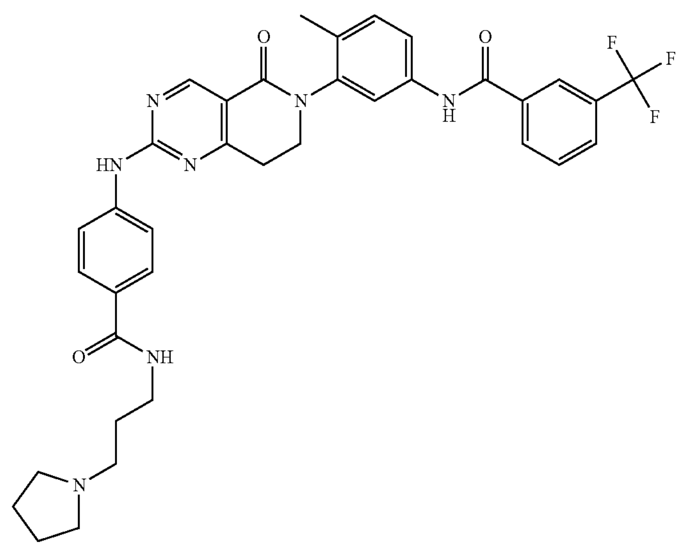 [SMILES: Cc1ccc(NC(=O)c2cccc(C(F)(F)F)c2)cc1N1CCc2nc(Nc3ccc(C(=O)NCCCN4CCCC4)cc3)ncc2C1=O] | MS m/z 672.1 (M + 1), 1H NMR (300 MHz, CD₃OD) δ 8.92 (s, 1H), 8.36-8.12 (m, 2H), 8.05-7.66 (m, 9H), 7.66-7.50 (m, 1H), 7.45-7.22 (m, 1H), 4.1-4.0 (m, 3H), 3.6-3.4 (br s, 3H), 2.4-2.2 (s, 4H), 2.2-1.8 (m, 11H) | N-(4-methyl-3-(5-oxo-2-(4-(3-(pyrrolidin-1-yl) propylcarbamoyl) phenylamino)-7,8-dihydropyrido[4,3-d]pyrimidin-6(5H)-yl)phenyl)-3-(trifluoromethyl) benzamide | 4 |
| 78 | 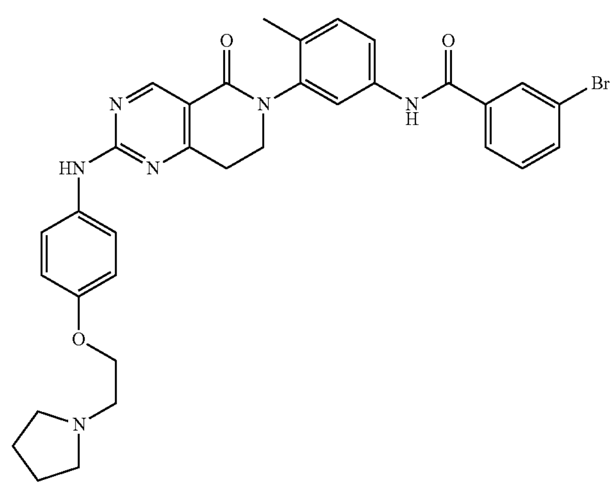 [SMILES: Cc1ccc(NC(=O)c2cccc(Br)c2)cc1N1CCc2nc(Nc3ccc(OCCN4CCCC4)cc3)ncc2C1=O] | 1H NMR (300 MHz, CD₃OD) δ 9.02-8.70 (br s, 1H), 8.26-8.02 (m, 1H), 8.02-7.18 (m, 8H), 7.18-6.80 (m, 2H), 4.4-4.2 (br s, 2H), 4.1-4.0 (br s, 2H), 3.62-3.42 (br s, 3H), 2.25 (s, 3H), 2.1-1.9 (m, 9H) MS m/z 642.9 (M + 2) | 3-Bromo-N-(4-methyl-3-{5-oxo-2-[4-(2-pyrrolidin-1-yl-ethoxy)-phenylamino]-7,8-dihydro-5H-pyrido[4,3-d]pyrimidin-6-yl}-phenyl)-benzamide | 3 |

TABLE 1-continued

| No | Structure | Physical Data [¹HNMR and/or MS] | IUPAC NAME | Ex |
|----|-----------|----------------------------------|------------|-----|
| 79 | 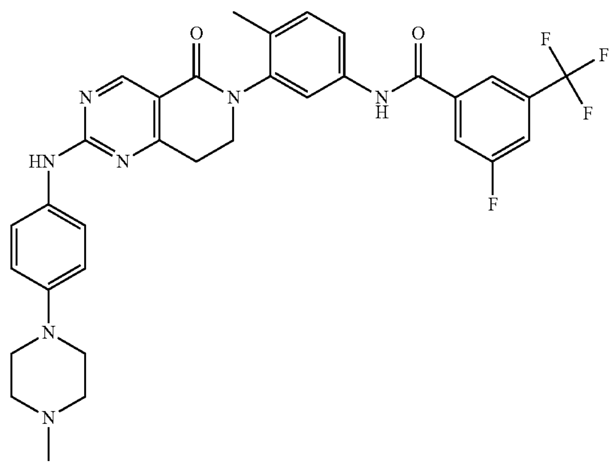 [SMILES: Cc1ccc(NC(=O)c2cc(F)cc(C(F)(F)F)c2)cc1N1CCc2nc(Nc3ccc(N4CCN(C)CC4)cc3)ncc2C1=O] | 1H NMR (300 MHz, CD₃OD) δ 8.95-8.65 (br s, 1H), 8.2-7.9 (m, 2H), 7.8-7.5 (m, 5H), 7.45-7.25 (d, 1H), 7.15-6.90 (d, 2H), 4.2-3.8 (m, 2H), 3.3-3.1 (m, 6H), 2.75-2.6 (m, 4H), 2.4 (s, 3H), 2.2 (s, 3H) MS m/z 634.1 (M + 1) | 3-Fluoro-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-5-trifluoromethyl-benzamide | 3 |
| 80 | 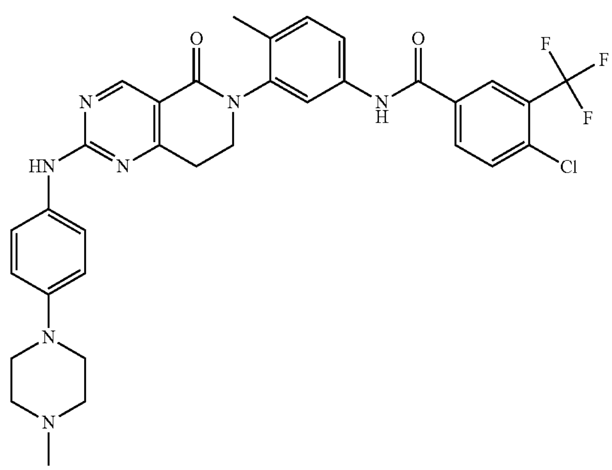 | 1H NMR (300 MHz, CDCl₃) δ 9.28 (s, 1H), 9.0 (s, 1H), 8.25 (s, 1H), 8.15-7.95 (m 1H), 7.65-7.45 (m, 4H), 7.45-7.36 (m, 2H), 7.1-6.9 (m, 3H), 4.00-3.82 (m, 1H), 3.82-3.65 (m, 1H), 3.4-3.0 (m, 6H), 2.7-2.5 (m, 4H), 2.36 (s, 3H), 1.76 (s, 3H) MS m/z 650.1 (M + 1) | 4-Chloro-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-3-trifluoromethyl-benzamide | 3 |
| 81 | 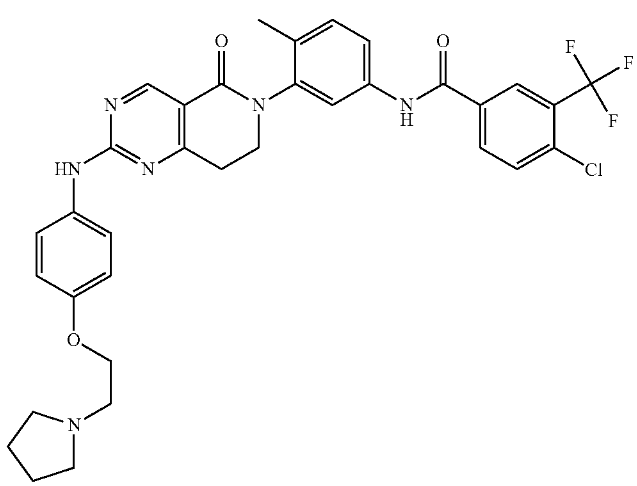 [SMILES: Cc1ccc(NC(=O)c2ccc(Cl)c(C(F)(F)F)c2)cc1N1CCc2nc(Nc3ccc(OCCN4CCCC4)cc3)ncc2C1=O] | 1H NMR (300 MHz, CDCl₃) δ 9.30-8.82 (m, 2H), 8.2 (s, 1H), 8.10-7.88 (m, 1H), 7.7-7.3 (m, 6H), 7.08-6.74 (m, 3H), 4.25-3.99 (m, 2H), 3.99-3.52 (m, 2H), 3.3-2.8 (m, 4H), 2.80-2.2 (br s, 3H), 1.85-1.7 (m, 8H) MS m/z 664.9 (M + 1) | 4-Chloro-N-(4-methyl-3-{5-oxo-2-[4-(2-pyrrolidin-1-yl-ethoxy)-phenylamino]-7,8-dihydro-5H-pyrido[4,3-d]pyrimidin-6-yl}-phenyl)-3-trifluoromethyl-benzamide | 3 |

TABLE 1-continued

| No | Structure | Physical Data [¹HNMR and/or MS] | IUPAC NAME | Ex |
|---|---|---|---|---|
| 82 | 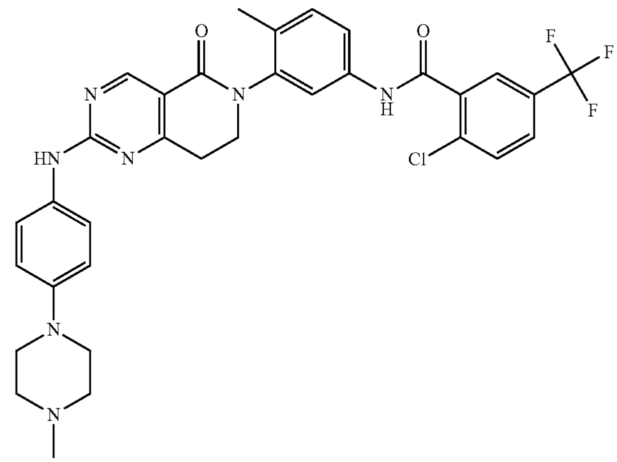 [SMILES: Cc1ccc(NC(=O)c2cc(C(F)(F)F)ccc2Cl)cc1N1CCc2nc(Nc3ccc(N4CCN(C)CC4)cc3)ncc2C1=O] | 1H NMR (300 MHz, CDCl₃) δ 8.85 (s, 1H), 8.6-8.4 (m, 1H), 8.0 (s, 1H), 7.78-7.48 (m, 4H), 7.38-7.18 (m, 4H), 7.18-6.88 (m, 2H), 4.08-3.90 (m, 1H), 3.86-3.70 (m, 1H), 3.35-3.05 (m, 6H), 2.72-2.52 (m, 4H), 2.36 (s, 3H), 2.12 (s, 3H) MS m/z 650.1 (M + 1) | 2-Chloro-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-5-trifluoromethyl-benzamide | 3 |
| 83 | 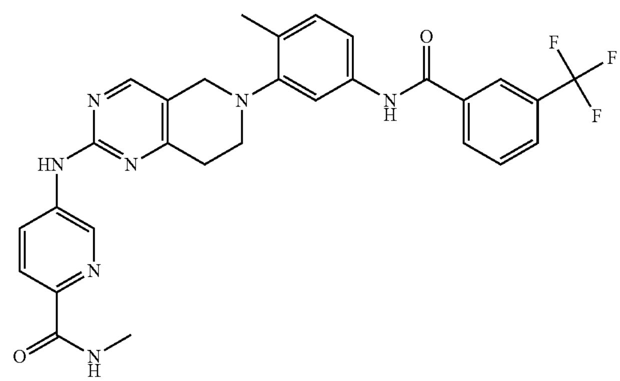 [SMILES: CNC(=O)c1ccc(Nc2ncc3c(n2)CCN(c2cc(NC(=O)c4cccc(C(F)(F)F)c4)ccc2C)C3)cn1] | 1H NMR (300 MHz, CDCl₃) δ 8.72 (s, 1H), 8.48-8.32 (m, 1H), 8.3-8.02 (m, 3H), 8.0-7.54 (m, 5H), 7.4-7.05 (s, 4H), 4.1 (s, 2H), 3.43-3.21 (m, 2H), 3.18-2.95 (m, 5H), 2.32 (s, 3H) MS m/z 562.1 (M + 1) | 5-{6-[2-Methyl-5-(3-trifluoromethyl-benozylamino)-phenyl]-5,6,7,8-tetrahydro-pyrido[4,3-d]pyrimidin-2-ylamino}-pyridine-2-carboxylic acid methylamide | 2 |
| 84 | 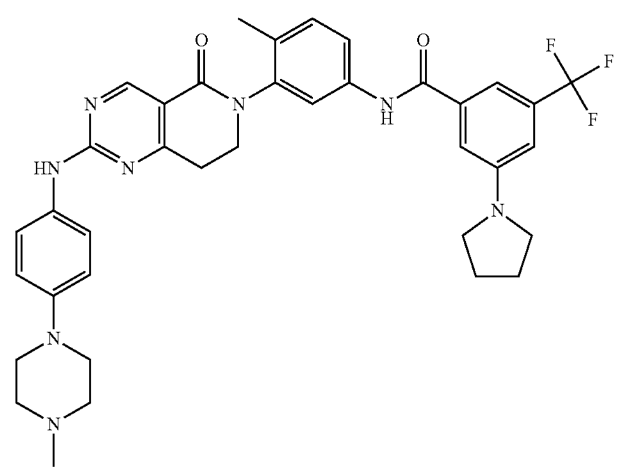 [SMILES: Cc1ccc(NC(=O)c2cc(N3CCCC3)cc(C(F)(F)F)c2)cc1N1CCc2nc(Nc3ccc(N4CCN(C)CC4)cc3)ncc2C1=O] | 1H NMR (300 MHz, CDCl₃) δ 9.0 (s, 1H), 8.49 (s, 1H), 7.68 (s, 1H), 7.53 (d, 2H), 7.45-7.09 (m, 5H), 6.96 (d, 2H), 6.82 (s, 1H), 4.1-3.82 (m, 1H), 3.82-3.68 (m, 1H), 3.42-3.0 (m, 8H), 2.6 (s, 3H), 2.35 (s, 3H), 2.12 (s, 3H), 2.1-1.89 (m, 7H) MS m/z 685.2 (M + 1) | N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-pyrrolidin-1-yl-5-trifluoromethyl-benzamide | 3 |

TABLE 1-continued

| No | Structure | Physical Data [¹HNMR and/or MS] | IUPAC NAME | Ex |
|---|---|---|---|---|
| 85 | 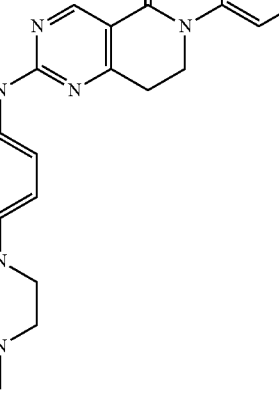 | 1H NMR (300 MHz, DMSO) δ 10.59 (s, 1H), 9.99 (s, 1H), 8.79 (s, 1H), 8.48 (s, 1H), 8.25 (d, 2H), 7.79-7.51 (m, 4H), 7.3 (d, 1H), 6.9 (d, 2H), 4.1-3.9 (s, 2H), 3.8-3.6 (m, 2H), 3.2-2.9 (m, 8H), 2.24-2.0 (m, 6H) MS m/z 693.9 (M + 1) | 3-Bromo-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-5-trifluoromethyl-benzamide | 3 |
| 86 | 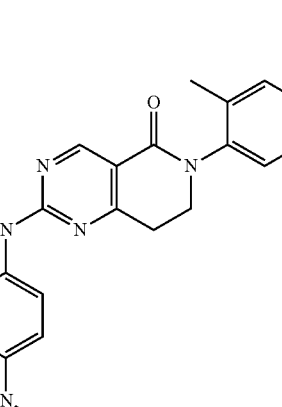 | 1H NMR (300 MHz, DMSO-D₆) δ 10.21 (s, 1H), 9.9 (s, 1H), 8.76 (s, 1H), 7.94 (s, 1H), 7.9-7.1 (m, 8H), 7.1-6.76 (m, 2H), 4.82-4.12 (m, 2H), 4.05-3.6 (m, 2H), 3.2-2.9 (s, 6H), 2.2 (d, 8H), 1.7-1.1 (s, 9H) MS m/z 604.2 (M + 1) | tert-Butyl-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide | 3 |
| 87 | 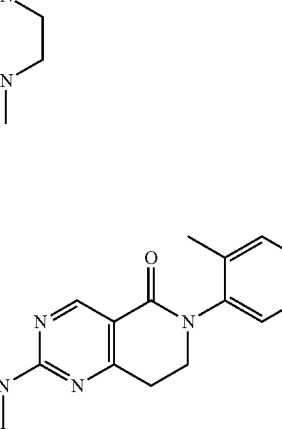 | 1H NMR (300 MHz, CDCl₃) δ 10.00-9.65 (br s, 1H), 9.25-8.85 (br s, 1H), 8.7-8.3 (br s, 2H), 8.1-7.8 (br s, 1H), 7.7-7.3 (m, 5H), 7.15-6.85 (m, 3H), 4.0-3.4 (m, 2H), 3.4-3.0 (m, 6H), 2.8-2.6 (m, 4H), 2.4 (s, 3H), 1.5 (s, 3H) MS m/z 684.1 (M + 1) | N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3,5-bis-trifluoromethyl-benzamide | 3 |

TABLE 1-continued

| No | Structure | Physical Data [¹HNMR and/or MS] | IUPAC NAME | Ex |
|---|---|---|---|---|
| 88 | 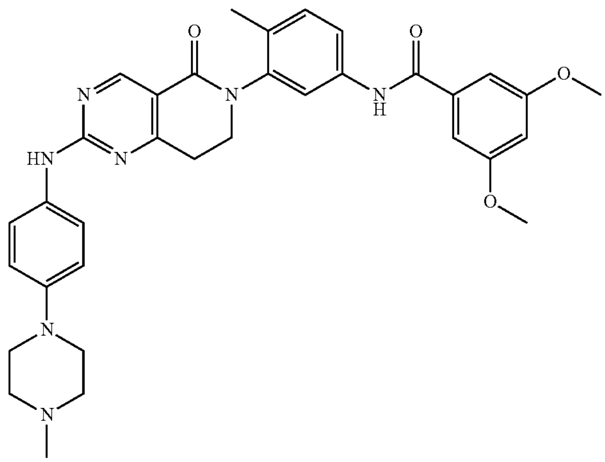 [SMILES: COc1cc(OC)cc(C(=O)Nc2ccc(C)c(N3CCc4nc(Nc5ccc(N6CCN(C)CC6)cc5)ncc4C3=O)c2)c1] | 1H NMR (300 MHz, CDCl₃) δ 8.99 (s, 1H), 8.28 (s, 1H), 7.8-6.8 (m, 10H), 6.6 (s, 1H), 4.08-3.90 (m, 1H), 3.9-3.6 (m, 7H), 3.35-3.05 (m, 6H), 2.92-2.75 (m, 4H), 2.36 (s, 3H), 2.17 (s, 3H) MS m/z 608.2 (M + 1), | 3,5-Dimethoxy-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide | 3 |
| 89 | 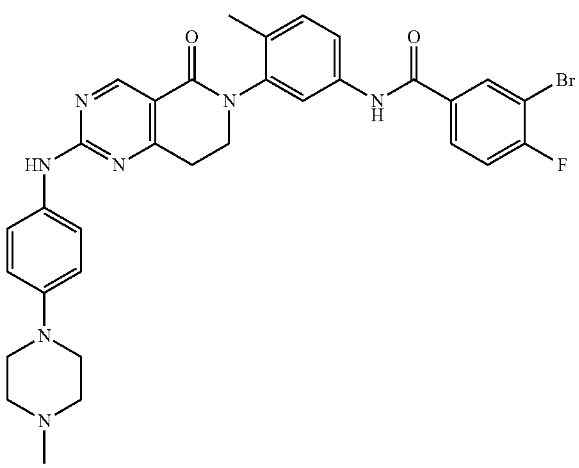 [SMILES: Cc1ccc(NC(=O)c2ccc(F)c(Br)c2)cc1N1CCc2nc(Nc3ccc(N4CCN(C)CC4)cc3)ncc2C1=O] | 1H NMR (300 MHz, DMSO) δ 8.75 (s, 1H), 8.49-8.2 (m, 1H), 8.19-7.82 (m, 1H), 7.81-7.4 (m, 5H), 7.4-7.19 (m, 1H), 7.1-6.8 (m, 2H), 4.08-3.90 (m, 1H), 3.86-3.70 (m, 1H), 3.35-3.05 (m, 6H), 2.92-2.75 (m, 4H), 2.36 (s, 3H), 2.17 (s, 3H) MS m/z 646.0 (M + 3) | 3-Bromo-4-fluoro-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-benzamide | 3 |
| 90 | 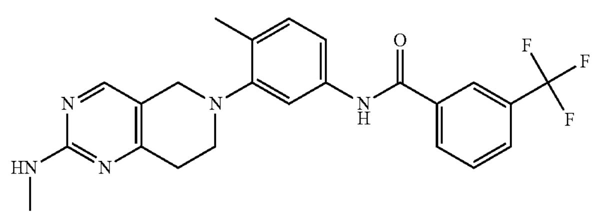 [SMILES: CNc1ncc2c(n1)CCN(c1cc(NC(=O)c3cccc(C(F)(F)F)c3)ccc1C)C2] | 1H NMR (300 MHz, CDCl₃) δ 8.30-7.05 (m, 9H), 5.0 (s, 1H), 4.0 (s, 2H), 3.4-3.15 (m, 2H), 3.15-2.80 (m, 5H), 2.3 (s, 3H) MS m/z 442.4 (M + 1) | N-[4-Methyl-3-(2-methylamino-7,8-dihydro-5H-pyrido[4,3-d]pyrimidin-6-yl)-phenyl]-3-trifluoromethyl-benzamide | 1 |
| 91 | 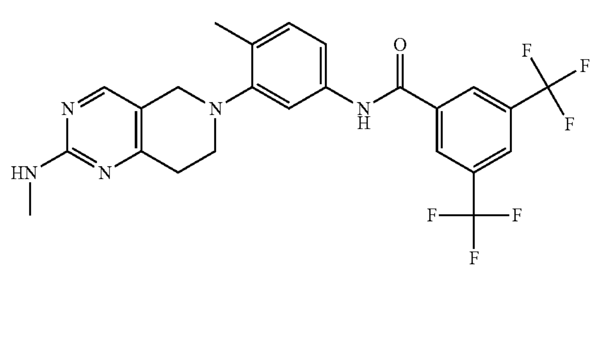 [SMILES: CNc1ncc2c(n1)CCN(c1cc(NC(=O)c3cc(C(F)(F)F)cc(C(F)(F)F)c3)ccc1C)C2] | 1H NMR (300 MHz, CD₃OD) δ 8.56 (s, 2H), 8.4-7.94 (m, 2H), 7.6 (s, 1H), 7.5-7.04 (m, 2H), 4.0 (s, 2H), 3.3-3.2 (m, 2H), 2.92 (s, 5H), 2.32 (s, 3H) MS m/z 510.0 (M + 1) | N-[4-Methyl-3-(2-methylamino-7,8-dihydro-5H-pyrido[4,3-d]pyrimidin-6-yl)-phenyl]-3,5-bis-trifluoromethyl-benzamide | 1 |

TABLE 1-continued

| No | Structure | Physical Data [¹HNMR and/or MS] | IUPAC NAME | Ex |
|---|---|---|---|---|
| 92 | 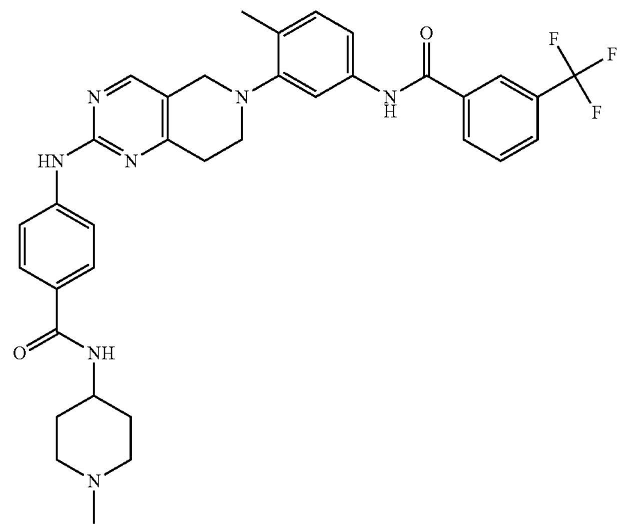 [SMILES: Cc1ccc(NC(=O)c2cccc(C(F)(F)F)c2)cc1N1CCc2nc(Nc3ccc(C(=O)NC4CCN(C)CC4)cc3)ncc2C1] | 1H NMR (300 MHz, CD₃OD) δ 8.4-7.56 (m, 10H), 7.4-7.1 (m, 2H), 4.0 (s, 2H), 3.1-3.0 (m, 2H), 2.8-2.5 (m, 5H), 2.3 (s, 3H), 2.2-2.0 (m, 3H), 1.9-1.6 (m, 2H), 1.5-1.1 (m, 4H) MS m/z 644.0 (M + 1) | 3-(2-Amino-7,8-dihydro-5H-pyrido[4,3-d]pyrimidin-6-yl)-4-methyl-N-phenyl-benzamide | 2 |
| 93 | 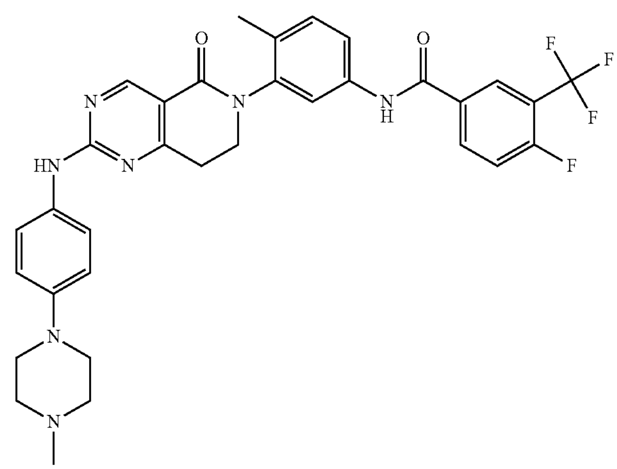 [SMILES: Cc1ccc(NC(=O)c2ccc(F)c(C(F)(F)F)c2)cc1N1CCc2nc(Nc3ccc(N4CCN(C)CC4)cc3)ncc2C1=O] | 1H NMR (300 MHz, DMSO) δ 10.5 (s, 1H), 9.98 (s, 1H), 8.75 (s, 1H), 8.5-8.25 (m, 2H), 7.8-7.5 (m, 5H), 7.32 (d, 1H), 6.9 (d, 2H), 4.10-3.82 (m, 1H), 3.8-3.6 (m, 1H), 3.15-2.98 (m, 6H), 2.4-2.5 (m, 4H), 2.35 (s, 3H), 2.2 (s, 3H) MS m/z 634.0 (M + 1) | 4-Fluoro-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide | 3 |
| 94 | 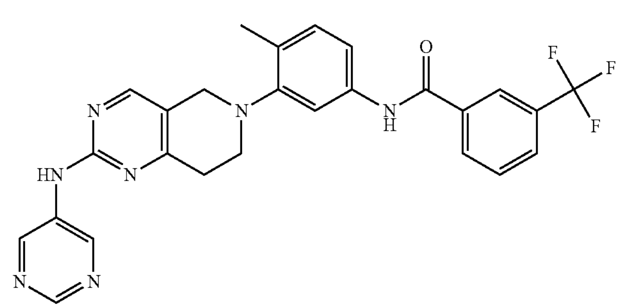 [SMILES: Cc1ccc(NC(=O)c2cccc(C(F)(F)F)c2)cc1N1CCc2nc(Nc3cncnc3)ncc2C1] | 1H NMR (300 MHz, CDCl₃) δ 9.12 (s, 2H), 8.88 (s, 1H), 8.30-8.02 (m, 2H), 7.97-7.55 (m, 4H), 7.33-7.00 (m, 4H), 4.09 (s, 2H), 3.3 (t, 2H), 3.02 (t, 2H), 2.31 (s, 3H) MS m/z 506.1 (M + 1) | N-{4-Methyl-3-[2-(pyrimidin-5-ylamino)-7,8-dihydro-5H-pyrido-5H-pyrido[4,3-d]pyrimidin-6-yl]-phenyl}-3-trifluoromethyl-benzamide | 2 |

TABLE 1-continued

| No | Structure | Physical Data [¹HNMR and/or MS] | IUPAC NAME | Ex |
|---|---|---|---|---|
| 95 | 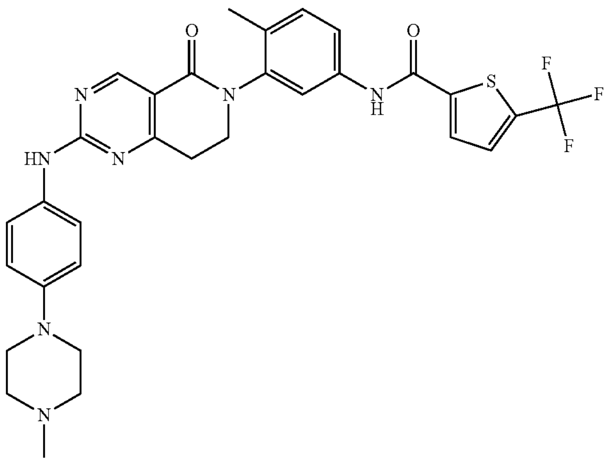 [SMILES: Cc1ccc(NC(=O)c2ccc(C(F)(F)F)s2)cc1N1CCc2nc(Nc3ccc(N4CCN(C)CC4)cc3)ncc2C1=O] | 1H NMR (300 MHz, CD₃OD) δ 8.8 (s, 1H), 8.05-7.4 (m, 6H), 7.3 (d, 1H), 6.95 (d, 2H), 4.12-3.7 (m, 2H), 3.4-3.0 (m, 6H), 2.8-2.5 (m, 4H), 2.4 (s, 3H), 2.25 (s, 3H) MS m/z 622.1 (M + 1) | 5-Trifluoromethyl-thiophene-2-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |
| 96 | 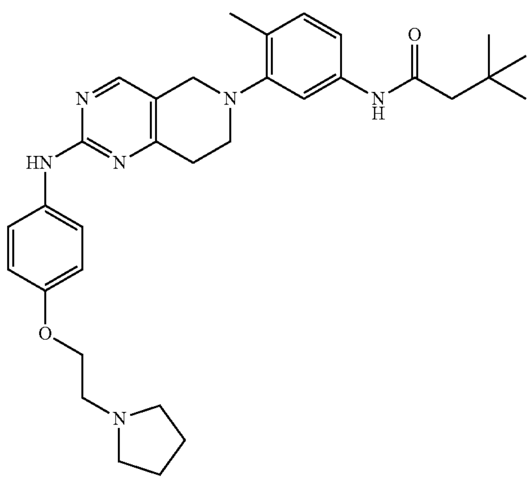 [SMILES: Cc1ccc(NC(=O)CC(C)(C)C)cc1N1CCc2nc(Nc3ccc(OCCN4CCCC4)cc3)ncc2C1] | 1H NMR (300 MHz, CDCl₃) δ 11.4 (s, 1H), 8.15 (s, 1H), 7.8-7.5 (m, 3H), 7.45-6.70 (m, 4H), 4.32 (s, 2H), 4.18-3.80 (m, 4H), 3.72-2.90 (m, 9H), 2.49-2.00 (m, 8H), 1.4-1.0 (m, 9H) MS m/z 543.2 (M + 1) | 3,3-Dimethyl-N-(4-methyl-3-{2-[4-(2-pyrrolidin-1-yl-ethoxy)-phenylamino]-7,8-dihydro-5H-pyrido[4,3-d]pyrimidin-6-yl}-phenyl)-butyramide | 1 |
| 97 | 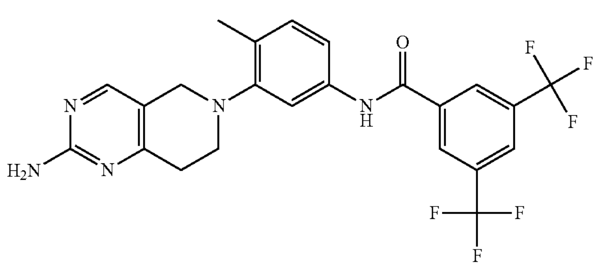 [SMILES: Cc1ccc(NC(=O)c2cc(C(F)(F)F)cc(C(F)(F)F)c2)cc1N1CCc2nc(N)ncc2C1] | 1H NMR (300 MHz, CD₃OD) δ 8.54 (s, 2H), 8.3-7.96 (m, 2H), 7.6 (s, 1H), 7.6-7.16 (m, 2H), 3.98 (s, 2H), 3.2-3.1 (t, 2H), 2.9 (t, 2H), 2.3 (s, 3H) MS m/z 496.0 (M + 1) | N-[3-(2-Amino-7,8-dihydro-5H-pyrido[4,3-d]pyrimidin-6-yl)-4-methyl-phenyl]-3,5-bis-trifluoromethyl-benzamide | 1 |

TABLE 1-continued

| No | Structure | Physical Data [¹HNMR and/or MS] | IUPAC NAME | Ex |
|---|---|---|---|---|
| 98 | 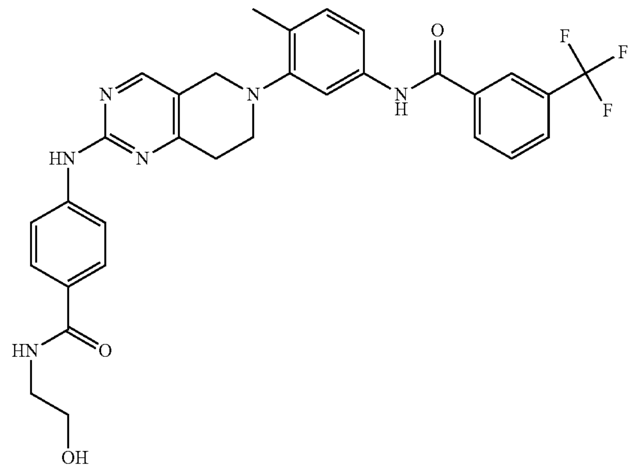 [SMILES: Cc1ccc(NC(=O)c2cccc(C(F)(F)F)c2)cc1N1CCc2nc(Nc3ccc(C(=O)NCCO)cc3)ncc2C1] | 1H NMR (300 MHz, CD₃OD) δ 8.4-8.08 (m, 3H), 8.0-7.66 (m, 6H), 7.5-7.06 (m, 3H), 4.03 (s, 2H), 3.7 (t, 2H), 3.5 (t, 2H), 3.3-3.2 (t, 2H), 3.12-2.9 (m, 2H), 2.32 (s, 3H) MS m/z 591.1 (M + 1), | N-(2-Aminol-3-{2-[4-(hydroxyphenyl amino]-5-oxo-7,8-dihydro-5H-pyrido[4,3-d]pyrimidin-6-yl}-phenyl)-3-trifluoromethyl-benzamide | 2 |
| 99 | 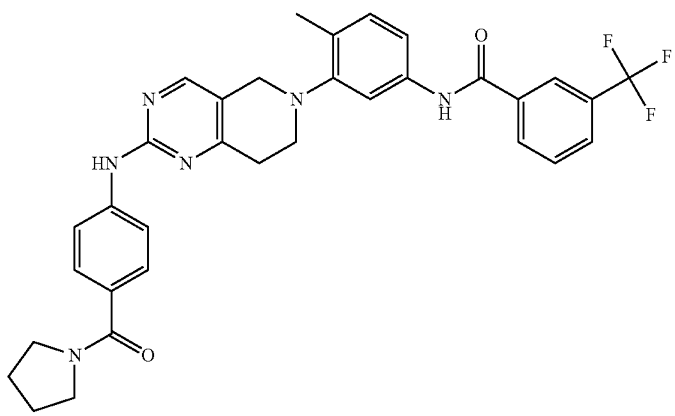 [SMILES: Cc1ccc(NC(=O)c2cccc(C(F)(F)F)c2)cc1N1CCc2nc(Nc3ccc(C(=O)N4CCCC4)cc3)ncc2C1] | 1H NMR (300 MHz, CDCl₃) δ 8.5 (s, 1H), 8.4-7.00 (m, 13H), 3.9 (s, 2H), 3.7-3.4 (br s, 4H), 3.4-2.9 (m, 4H), 2.3 (s, 3H), 2.0-1.8 (br s, 4H) MS m/z 601.1 (M + 1) | N-(4-Methyl-3-{2-[4-pyrrolidine-1-carbonyl)-phenylamino]-7,8-dihydro-5H-pyrido[4,3-d]pyrimidin-6-yl}-phenyl)-3-trilfuoromethyl-benzamide | 2 |
| 100 | 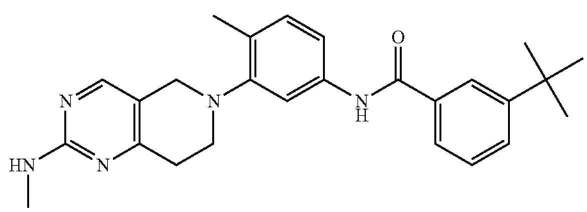 [SMILES: CNc1ncc2c(n1)CCN(c1cc(NC(=O)c3cccc(C(C)(C)C)c3)ccc1C)C2] | 1H NMR (300 MHz, CDCl₃) δ 8.08 (s, 1H), 7.96 (s, 1H), 7.86-7.56 (m, 4H), 7.48-7.38 (m, 1H), 7.24-7.06 (m, 2H), 5.0 (s, 1H), 4.0 (s, 2H), 3.35-3.30 (m, 2H), 3.1-2.9 (m, 5H), 2.3 (s, 3H), 1.4 (s, 9H) MS m/z 430.1 (M + 1) | 3-tert-Butyl-N-[4-methyl-3-(2-methylamino-7,8-dihydro-5H-pyrido[4,3-d]pyrimidin-6-yl)-phenyl]-benzamide | 1 |
| 101 | 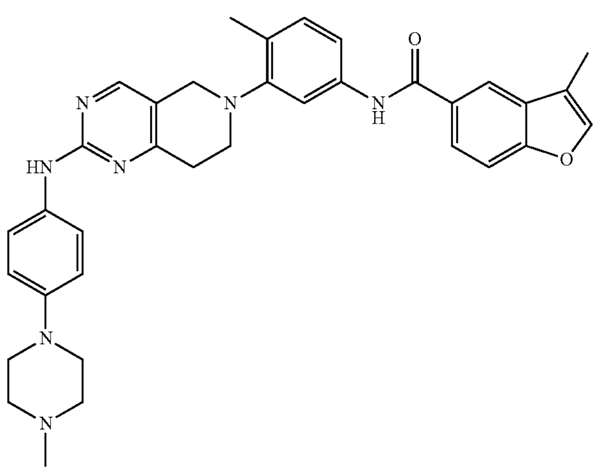 | 1H NMR (300 MHz, CDCl₃) δ 9.0 (s, 1H), 8.55 (s, 1H), 8.1 (s, 1H), 7.82 (d, 1H), 7.69 (s, 1H), 7.62-7.40 (m, 6H), 7.12 (d, 1H), 6.94 (d, 2H), 4.05-3.9 (m, 1H), 3.80-3.69 (m, 1H), 3.3-3.0 (m, 6H), 2.75-2.55 (m, 4H), 2.4 (s, 3H), 2.25 (s, 3H), 2.0 (s, 3H) MS m/z 602.2 (M + 1) | 3-Methyl-benzofuran-5-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |

TABLE 1-continued

| No | Structure | Physical Data [¹HNMR and/or MS] | IUPAC NAME | Ex |
|---|---|---|---|---|
| 102 | 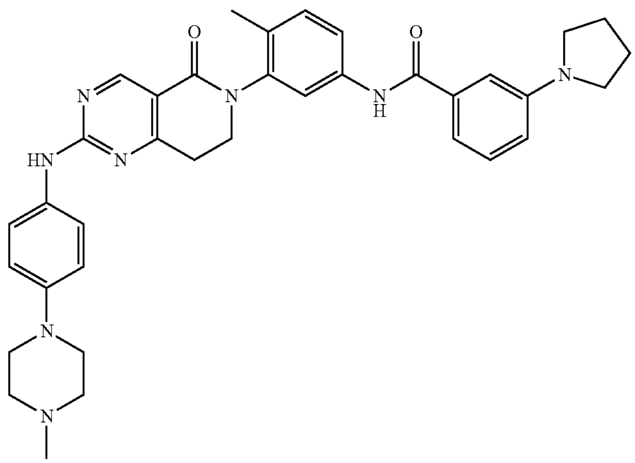 [SMILES: Cc1ccc(NC(=O)c2cccc(N3CCCC3)c2)cc1N1CCc2nc(Nc3ccc(N4CCN(C)CC4)cc3)ncc2C1=O] | 1H NMR (300 MHz, CDCl₃) δ 8.95 (s, 1H), 8.28 (s, 1H), 7.72-7.44 (m, 4H), 7.38-7.10 (m, 3H), 7.09-6.90 (m, 4H), 6.7-6.6 (m, 1H), 4.05-3.84 (m, 1H), 3.80-3.62 (m, 1H), 3.36-3.28 (m, 9H), 3.15-2.96 (m, 2H), 2.78-2.56 (m, 4H), 2.36 (s, 3H), 2.13 (s, 3H), 2.05-1.95 (m, 3H) MS m/z 617.2 (M + 1) | N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-pyrrolidin-1-yl-benzamide | 3 |
| 103 | 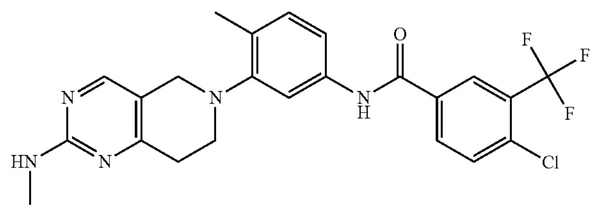 [SMILES: CNc1ncc2c(n1)CCN(c1cc(NC(=O)c3ccc(Cl)c(C(F)(F)F)c3)ccc1C)C2] | 1H NMR (300 MHz, CDCl₃) δ 8.34-7.84 (m, 3H), 7.54-7.40 (m, 2H), 7.39-7.04 (m, 3H), 5.2-4.9 (br s, 1H), 4.10-3.82 (s, 2H), 3.22-3.10 (m, 2H), 3.09-2.80 (m, 5H), 2.47-2.12 (s, 3H) MS m/z 476.0 (M + 1) | 4-Chloro-N-[4-methyl-3-(2-methylamino-7,8-dihydro-5H-pyrido[4,3-d]pyrimidin-6-yl}-phenyl]-3-trifluoromethyl-benzamide | 1 |
| 104 | 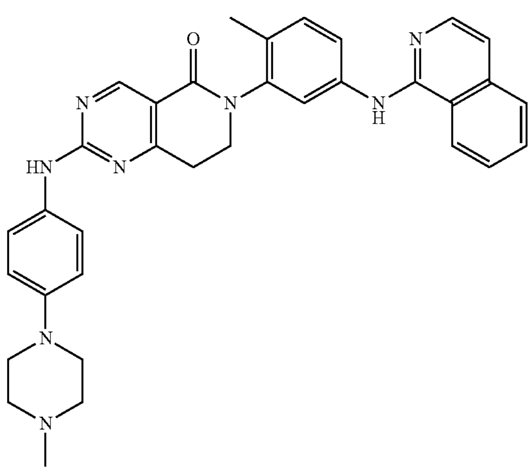 [SMILES: Cc1ccc(Nc2nccc3ccccc23)cc1N1CCc2nc(Nc3ccc(N4CCN(C)CC4)cc3)ncc2C1=O] | 1H NMR (300 MHz, CDCl₃) δ 8.99 (s, 1H), 8.12-6.82 (m, 15H), 4.12-3.66 (m, 2H), 3.42-3.00 (m, 6H), 2.75-2.48 (m, 4H), 2.35 (s, 3H), 2.2 (s, 3H) MS m/z 571.2 (M + 1) | 6-[5-(Isoquinolin-1-ylamino)-2-methyl-phenyl]-2-[4-(4-methyl-piperazin-1-yl)-phenyl-amino]-7,8-dihydro-6H-pyrido[4,3-d]pyrimidin-5-one | 11 |

TABLE 1-continued

| No | Structure | Physical Data [¹HNMR and/or MS] | IUPAC NAME | Ex |
|---|---|---|---|---|
| 105 | 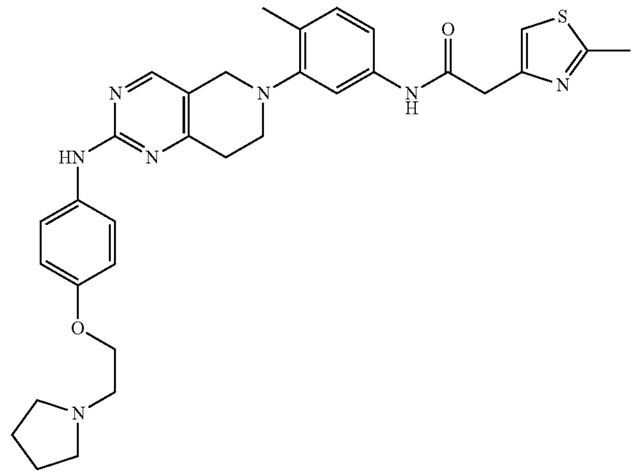 [SMILES: Cc1nc(CC(=O)Nc2ccc(C)c(N3CCc4nc(Nc5ccc(OCCN6CCCC6)cc5)ncc4C3)c2)cs1] | 1H NMR (300 MHz, CDCl₃) δ 9.0 (s, 1H), 8.1 (s, 1H), 7.6-7.4 (m, 3H), 7.15-7.05 (d, 1H), 7.0-6.85 (m, 5H), 4.20-4.05 (m, 2H), 4.0 (s, 2H), 3.8 (s, 2H), 3.30-3.15 (m, 2H), 3.00-2.85 (m, 4H), 2.75 (s, 3H), 2.72-2.60 (br s, 4H), 2.25 (s, 3H), 1.85-1.75 (br s, 4H) MS m/z 584.1 (M + 1) | N-(4-Methyl-3-{2-[4-(2-pyrrolidin-1-yl-ethoxy)-phenylamino]-7,8-dihydro-5H-pyrido[4,3-d]pyrimidin-6-yl}-phenyl)-2-(2-methyl-thiazol-4-yl)-acetamide | 1 |
| 106 | 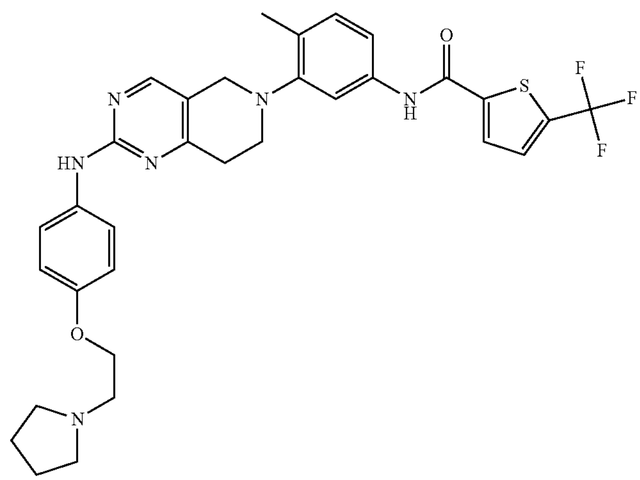 [SMILES: Cc1ccc(NC(=O)c2ccc(C(F)(F)F)s2)cc1N1CCc2nc(Nc3ccc(OCCN4CCCC4)cc3)ncc2C1] | 1H NMR (300 MHz, CDCl₃) δ 8.12 (s, 1H), 7.8 (s, 1H), 7.60-7.42 (m, 5H), 7.2 (d, 1H), 7.1 (d, 1H), 6.96-6.84 (m, 3H), 4.15-3.95 (m ,4H), 3.26 (t, 2H), 3.05-2.85 (m, 4H), 2.7-2.6 (m, 4H), 2.3 (s, 3H), 2.0-1.65 (m, 4H) MS m/z 622.8 (M + 1) | 5-Trifluoromethyl-thiophene-2-carboxylic acid (4-methyl-3-{2-[4-(2-pyrrolidin-1-yl-ethoxy)-phenylamino]-7,8-dihydro-5H-pyrido[4,3-d]pyrimidin-6-yl}-phenyl)-amide | 1 |
| 107 | 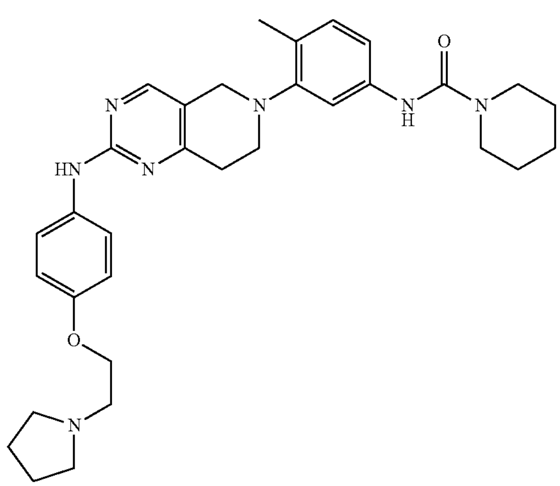 [SMILES: Cc1ccc(NC(=O)N2CCCCC2)cc1N1CCc2nc(Nc3ccc(OCCN4CCCC4)cc3)ncc2C1] | 1H NMR (300 MHz, CDCl₃) δ 8.11 (s, 1H), 7.60-7.32 (m, 3H), 7.28-7.02 (m, 1H), 7.00-6.72 (m, 4H), 6.31 (s, 1H), 4.28-3.85 (m, 4H), 3.56-2.82 (m, 10H), 2.75-2.50 (m, 4H), 2.26 (s, 3H), 1.90-1.75 (m, 4H), 1.7-1.6 (m, 4H), 1.25 (s, 2H) MS m/z 556.2 (M + 1) | Piperidine-1-carboxylic acid (4-methyl-3-{2-[4-(2-pyrrolidin-1-yl-ethoxy)-phenylamino]-7,8-dihydro-5H-pyrido[4,3-d]pyrimidin-6-yl}-phenyl)-amide | 1 |

TABLE 1-continued

| No | Structure | Physical Data [¹HNMR and/or MS] | IUPAC NAME | Ex |
|---|---|---|---|---|
| 108 | 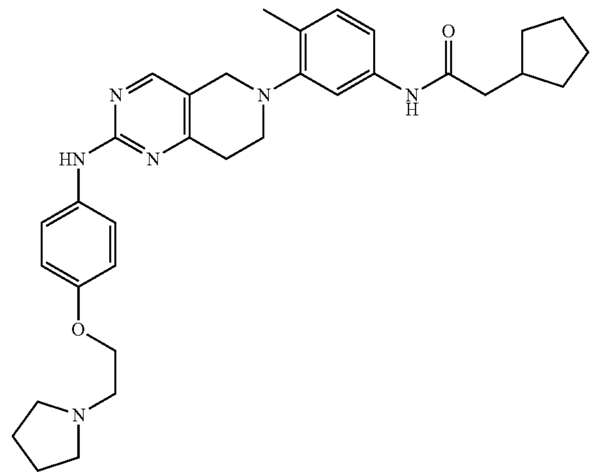 [SMILES: Cc1ccc(NC(=O)CC2CCCC2)cc1N1CCc2nc(Nc3ccc(OCCN4CCCC4)cc3)ncc2C1] | 1H NMR (300 MHz, CD₃OD) δ 8.1 (s, 1H), 7.6-7.4 (m, 3H), 7.25-7.05 (m, 2H), 6.95-6.80 (d, 2H), 4.2-4.1 (t, 2H), 3.95 (s, 2H), 3.3-3.2 (t, 2H), 3.05-2.85 (m, 5H), 2.85-2.65 (m, 4H), 2.4-2.2 (m, 6H), 1.95-1.50 (m, 11H) MS m/z 555.2 (M + 1) | 2-Cyclopentyl-N-(4-methyl-3-{2-[4-(2-pyrrolidin-1-yl-ethoxy)-phenylamino]-7,8-dihydro-5H-pyrido[4,3-d]pyrimidin-6-yl}-phenyl)-acetamide | 1 |
| 109 | 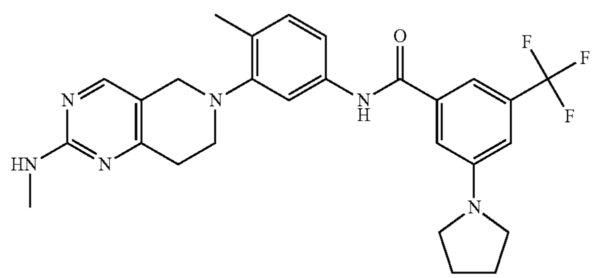 [SMILES: CNc1ncc2c(n1)CCN(c1cc(NC(=O)c3cc(N4CCCC4)cc(C(F)(F)F)c3)ccc1C)C2] | 1H NMR (300 MHz, CDCl₃) δ 8.45 (s, 1H), 7.84 (s, 1H), 7.63 (s, 1H), 7.42-7.02 (m, 4H), 6.85 (s, 1H), 5.1-4.83 (br s, 1H), 4.0 (s, 2H), 3.59-3.16 (m, 4H), 3.15-2.82 (m, 3H), 2.3 (s, 3H), 2.23-2.12 (m, 4H), 2.11-1.98 (m, 4H) MS m/z 510.9 (M + 1) | N-[4-Methyl-3-(2-methylamino-7,8-dihydro-5H-pyrido[4,3-d]pyrimidin-6-yl)-phenyl]-3-pyrrolidin-1-yl-5-trifluoromethyl-benzamide | 1 |
| 110 | 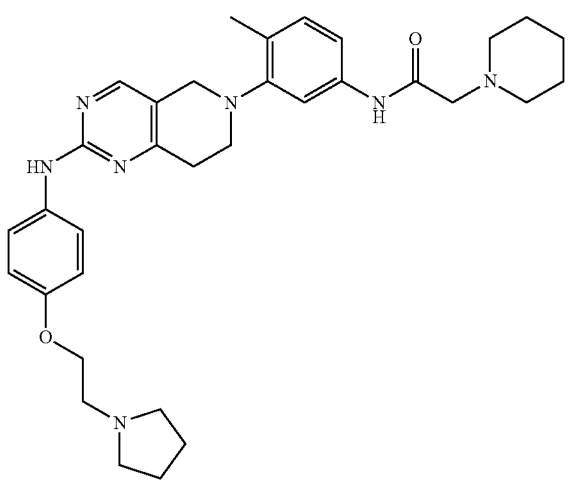 [SMILES: Cc1ccc(NC(=O)CN2CCCCC2)cc1N1CCc2nc(Nc3ccc(OCCN4CCCC4)cc3)ncc2C1] | 1H NMR (300 MHz, CDCl₃) δ 9.21 (s, 1H), 8.12 (s, 1H), 7.68-7.44 (m, 2H), 7.21-7.10 (m, 1H), 7.08-6.82 (m, 4H), 4.23-4.08 (t, 2H), 4.0 (s, 2H), 3.3 (t, 2H), 3.1 (s, 2H), 3.0-2.9 (m, 4H), 2.8-2.7 (br s, 4H), 2.5-2.6 (m, 4H), 2.3 (s, 3H), 1.9-1.8 (m, 6H), 1.7-1.6 (m, 4H) MS m/z 570.2 (M + 1) | N-(4-Methyl-3-{2-[4-(2-pyrrolidin-1-yl-ethoxy)-phenylamino]-7,8-dihydro-5H-pyrido[4,3-d]pyrimidin-6-yl}-phenyl)-2-piperidin-1-yl-acetamide | 1 |

| No | Structure | Physical Data [¹HNMR and/or MS] | IUPAC NAME | Ex |
|---|---|---|---|---|
| 111 | 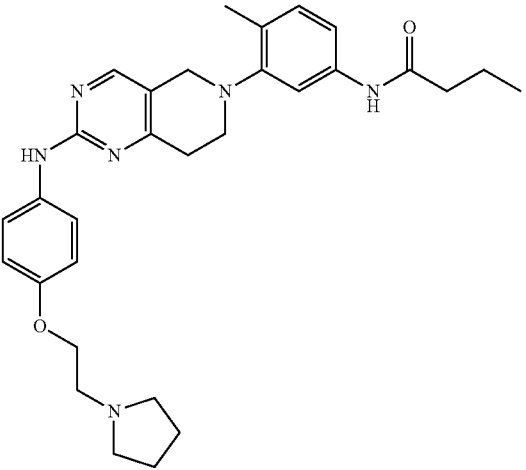 [SMILES: CCCC(=O)Nc1ccc(C)c(N2CCc3nc(Nc4ccc(OCCN5CCCC5)cc4)ncc3C2)c1] | 1H NMR (300 MHz, CDCl₃) δ 8.1 (s, 1H), 7.65-6.80 (m, 9H), 4.12 (t, 2H), 3.98 (s, 2H), 3.45 (s, 3H), 3.2 (t, 1H), 3.1-2.9 (m, 4H), 2.89-2.70 (br s, 3H), 2.40-2.22 (m, 5H), 1.97-1.70 (m, 5H), 1.10-0.92 (t, 3H) MS m/z 515.2 (M + 1) | N-(4-Methyl-3-{2-[4-(2-pyrrolidin-1-yl-ethoxy)-phenylamino]-7,8-dihydro-5H-pyrido[4,3-d]pyrimidin-6-yl}-phenyl)-butyramide | 1 |
| 112 | 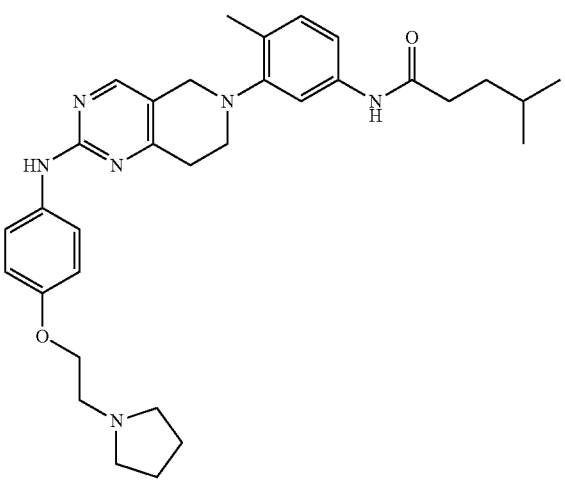 [SMILES: Cc1ccc(NC(=O)CCC(C)C)cc1N1CCc2nc(Nc3ccc(OCCN4CCCC4)cc3)ncc2C1] | 1H NMR (300 MHz, CD₃OD) δ 8.15 (s, 1H), 7.65-7.45 (m, 3H), 7.15 (s, 2H), 7.05-6.90 (d, 2H), 4.3-4.2 (d, 2H), 4.0 (s, 2H), 3.60-3.45 (d, 2H), 3.4-3.3 (m, 2H), 3.3-3.2 (t, 2H), 3.3-2.9 (t, 2H), 2.50-2.25 (m, 5H), 2.15-2.00 (m ,4H), 1.7-1.5 (m, 3H), 1.4-1.3 (m, 2H), 1.05-0.90 (d, 6H) MS m/z 543.2 (M + 1), | 4-Methyl-pentanoic acid (4-methyl-3-{2-[4-(2-pyrrolidin-1-yl-ethoxy)-phenylamino]-7,8-dihydro-5H-pyrido[4,3-d]pyrimidin-6-yl}-phenyl)-amide | 1 |
| 113 | 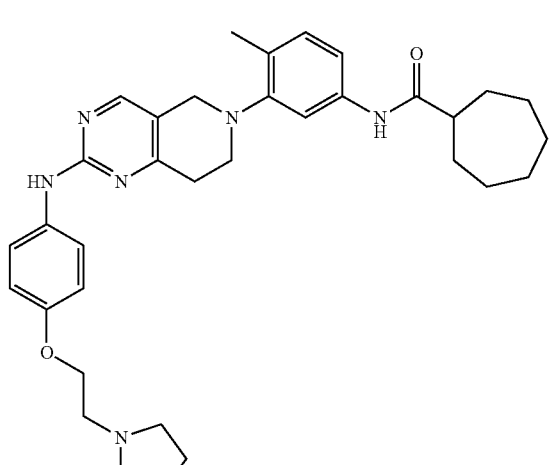 | 1H NMR (300 MHz, CD₃OD) δ 8.15 (s, 1H), 7.65-7.45 (m, 3H), 7.1 (s, 2H), 7.05-6.90 (d, 2H), 4.3-4.2 (t, 2H), 4.0 (s, 2H), 3.4-3.3 (t, 2H), 3.3-3.1 (m, 4H), 3.0-2.9 (t, 2H), 2.60-2.45 (m, 1H), 2.3 (s, 3H), 2.1-1.5 (m, 18H) MS m/z 569.3 (M + 1), | Cycloheptanecarboxylic acid (4-methyl-3-{2-[4-(2-pyrrolidin-1-yl-ethoxy)-phenylamino]-7,8-dihydro-5H-pyrido[4,3-d]pyrimidin-6-yl}-phenyl)-amide | 1 |

TABLE 1-continued

| No | Structure | Physical Data [¹HNMR and/or MS] | IUPAC NAME | Ex |
|---|---|---|---|---|
| 114 | 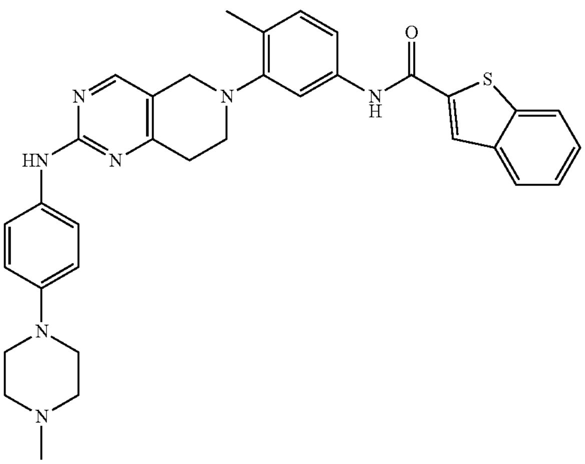 | , 1H NMR (300 MHz, CDCl₃) δ 9.2 (s, 2H), 7.96 (s, 1H), 7.85 (d, 1H), 7.8-7.6 (m, 2H), 7.60-7.45 (m, 3H), 7.45-7.30 (m, 2H), 7.3-7.15 (m, 1H), 7.1 (d, 1H), 7.05-6.90 (m, 2H), 4.0-3.8 (m, 1H), 3.80-3.65 (m, 1H), 3.3-3.0 (m, 6H), 2.7-2.5 (m, 4H), 2.34 (s, 3H), 1.9 (s, 3H) MS m/z 604.1 (M + 1) | Benzo[b]thiophene-2-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |
| 115 | 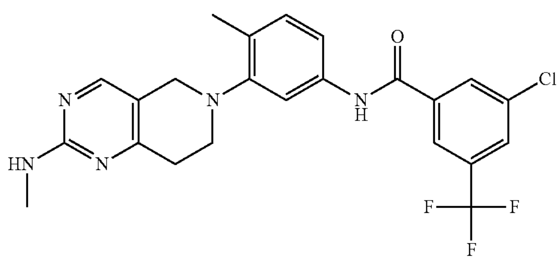 [SMILES: CNc1ncc2c(n1)CCN(c1cc(NC(=O)c3cc(Cl)cc(C(F)(F)F)c3)ccc1C)C2] | 1H NMR (300 MHz, CDCl₃) δ 8.18-7.97 (m, 3H), 7.81 (d, 2H), 7.54 (s, 1H), 7.38-7.05 (m, 2H), 5.1-4.9 (br s, 1H), 4.15-3.90 (m, 2H), 3.40-3.15 (m, 2H), 3.15-2.75 (m, 5H), 2.3 (s, 3) MS m/z 476.1 (M + 1), | 3-Chloro-N-[4-methyl-3-(2-methylamino-7,8-dihydro-5H-pyrido[4,3-d]pyrimidin-6-yl)-phenyl]-5-trifluoromethyl-benzamide | 1 |
| 116 | 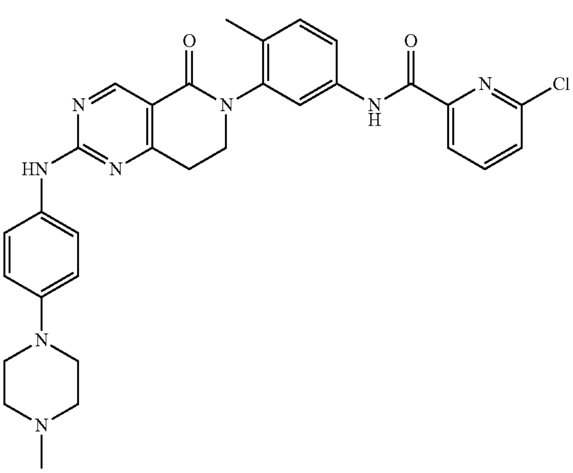 [SMILES: Cc1ccc(NC(=O)c2cccc(Cl)n2)cc1N1CCc2nc(Nc3ccc(N4CCN(C)CC4)cc3)ncc2C1=O] | 1H NMR (300 MHz, CDCl₃) δ 9.85 (s, 1H), 9.0 (s, 1H), 8.2 (d, 1H), 7.86 (t, 1H), 7.82-7.76 (m, 1H), 7.65-7.46 (m, 4H), 7.43-7.30 (m, 2H), 6.95 (d, 2H), 4.19-3.95 (m, 1H), 3.89-3.70 (m, 1H), 3.34-3.00 (m, 6H), 2.68-2.55 (m, 4H), 2.36 (s, 3H), 2.25 (s, 3H) MS m/z 583.2 (M + 1), | 6-Chloro-pyridine-2-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |

TABLE 1-continued

| No | Structure | Physical Data [¹HNMR and/or MS] | IUPAC NAME | Ex |
|---|---|---|---|---|
| 117 | 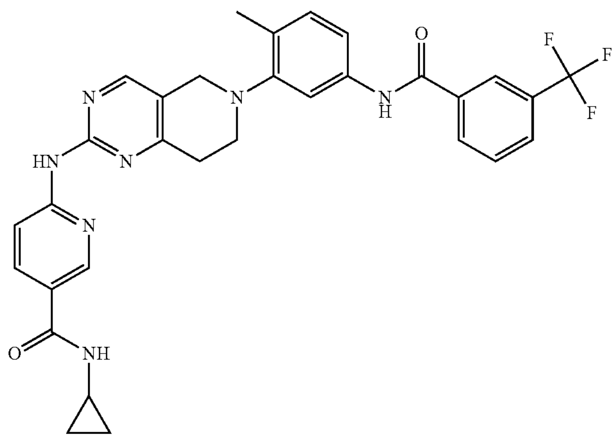 [SMILES: Cc1ccc(NC(=O)c2cccc(C(F)(F)F)c2)cc1N1CCc2nc(Nc3ccc(C(=O)NC4CC4)cn3)ncc2C1] | 1H NMR (300 MHz, CDCl₃) δ 8.7 (d, 1H), 8.42-8.3 (m, 1H), 8.3-8.02 (m, 4H), 8.00-7.76 (m, 3H), 7.74-7.54 (m, 2H), 7.40-7.02 (m, 4H), 4.1 (s, 2H), 3.4-3.2 (m, 2H), 3.15-3.00 (m, 2H), 3.0-2.9 (m, 1H), 2.35 (s, 3H), 0.9-0.8 (m, 2H), 0.7-0.6 (m, 2H) MS m/z 588.0 (M + 1), | 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide | 2 |
| 118 | 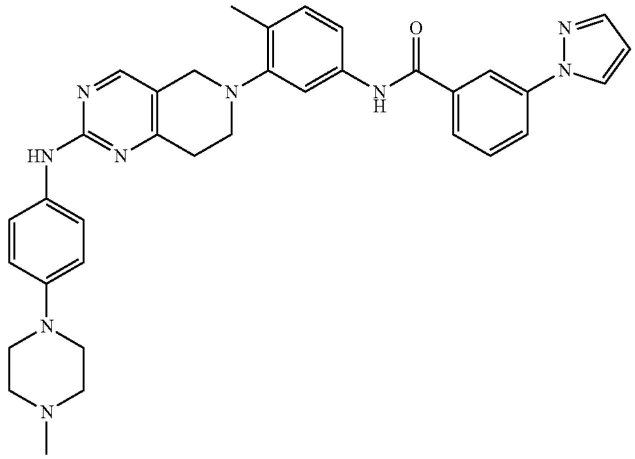 | 1H NMR (300 MHz, CDCl₃) δ 8.97 (d, 2H), 8.2 (s, 1H), 8.08-7.32 (m, 11H), 7.2-6.8 (m, 3H), 6.42 (s, 1H), 4.10-3.52 (m, 2H), 3.40-2.88 (m, 6H), 2.8-2.5 (m, 4H), 2.38 (s, 3H), 1.9 (s, 3H) MS m/z 614.0 (M + 1), | N-(4-Methyl-3-{2-[4-(4-methyl-piperazin-1-yl)-phenyl-amino]-5-oxo-7,8-dihydro-5H-pyrido[4,3-d]pyrimidin-6-yl}-phenyl)-3-pyrazol-1-yl-benzamide | 3 |
| 119 | 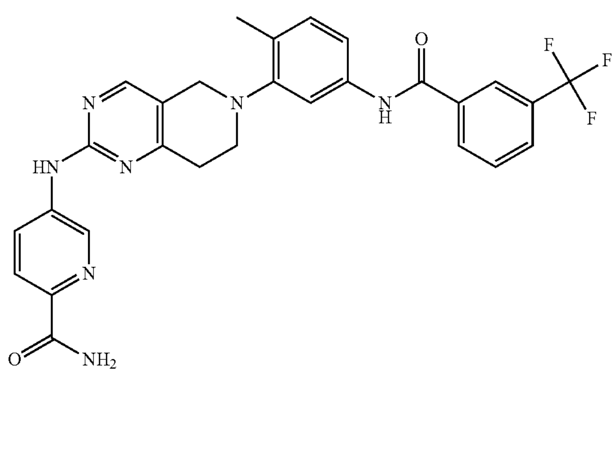 [SMILES: Cc1ccc(NC(=O)c2cccc(C(F)(F)F)c2)cc1N1CCc2nc(Nc3ccc(C(N)=O)nc3)ncc2C1] | 1H NMR (300 MHz, DMSO-D₆) δ 10.42 (s, 1H), 10.15 (s, 1H), 9.0 (s, 1H), 8.51-8.12 (m, 4H), 8.20-7.61 (m, 4H), 7.61 (s, 1H), 7.60-7.32 (m, 2H), 7.2 (d, 1H), 4.05 (s, 2H), 3.08-2.93 (m, 2H), 2.61-2.52 (m, 2H), 2.28 (s, 3H) MS m/z 548.1 (M + 1), | 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid amide | 2 |

TABLE 1-continued

| No | Structure | Physical Data [¹HNMR and/or MS] | IUPAC NAME | Ex |
|---|---|---|---|---|
| 120 | 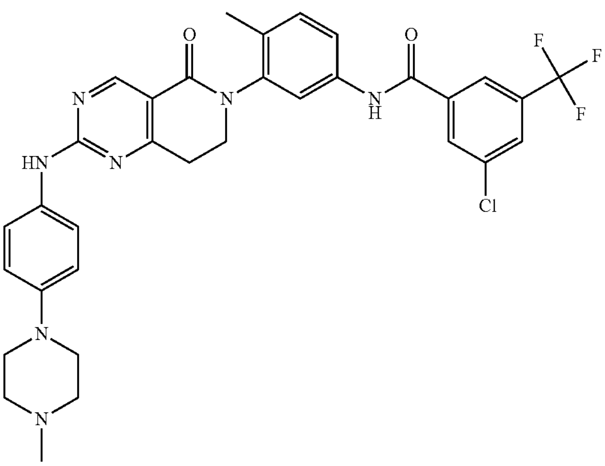 [SMILES: Cc1ccc(NC(=O)c2cc(Cl)cc(C(F)(F)F)c2)cc1N1CCc2nc(Nc3ccc(N4CCN(C)CC4)cc3)ncc2C1=O] | 1H NMR (300 MHz, CDCl₃) δ 9.39 (s, 1H), 9.11-9.00 (m, 1H), 8.13 (d, 2H), 7.7 (s, 1H), 7.65-7.30 (m, 5H), 7.1-6.86 (m, 3H), 4.10-3.52 (m, 2H), 3.40-2.88 (m, 6H), 2.8-2.5 (m, 4H), 2.38 (s, 3H), 1.9 (s, 3H) MS m/z 650.1 (M + 1), | 3-Chloro-N-(4-methyl-3-{2-[4-(4-methyl-piperazin-1-yl)-phenyl-amino]-5-oxo-7,8-dihydro-5H-pyrido[4,3-d]pyrimidin-6-yl}-phenyl)-5-trifluoromethyl-benzamide | 3 |
| 121 | 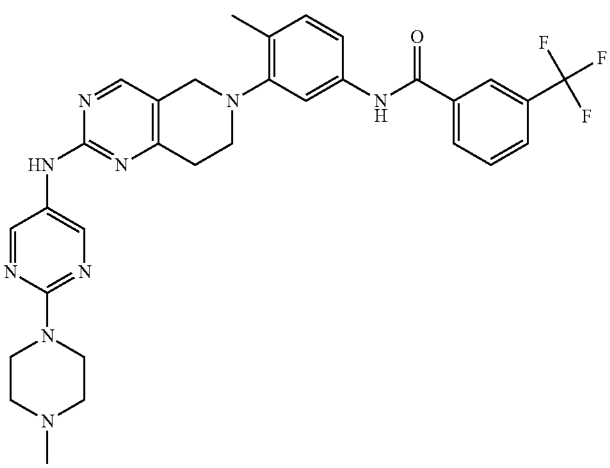 [SMILES: Cc1ccc(NC(=O)c2cccc(C(F)(F)F)c2)cc1N1CCc2nc(Nc3cnc(N4CCN(C)CC4)nc3)ncc2C1] | 1H NMR (300 MHz, CDCl₃) δ 8.58 (s, 1H), 8.28-8.0 (m, 3H), 7.88-7.78 (m, 2H), 7.72-7.58 (m, 2H), 7.26-7.08 (m, 3H), 6.61 (s, 1H), 4.02 (s, 2H), 3.92-3.72 (m, 4H), 3.36-3.21 (m, 2H), 3.05-2.88 (m, 2H), 2.60-2.48 (m, 4H), 2.36 (s, 3H), 2.32 (s, 3H) MS m/z 604.2 (M + 1), | N-(4-Methyl-3-{2-[2-(4-methyl-piperazin-1-yl)-pyrimidin-5-ylamino]-7,8-dihydro-5H-pyrido[4,3-d]pyrimidin-6-yl}-phenyl)-3-trifluoromethyl-benzamide | 2 |
| 122 | 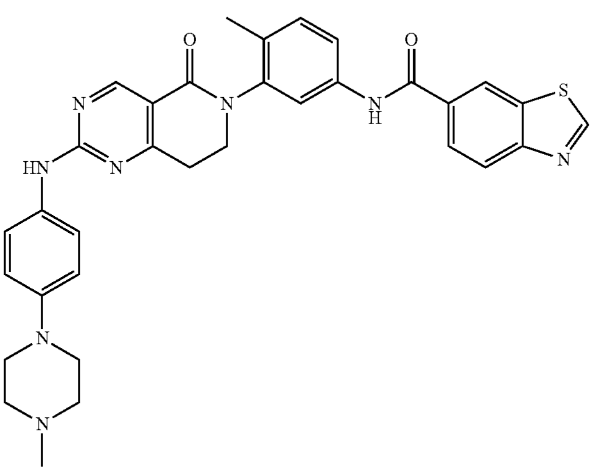 [SMILES: Cc1ccc(NC(=O)c2ccc3ncsc3c2)cc1N1CCc2nc(Nc3ccc(N4CCN(C)CC4)cc3)ncc2C1=O] | 1H NMR (300 MHz, CDCl₃) δ 9.1 (s, 1H), 9.0 (s, 1H), 8.85 (s, 1H), 8.6 (s, 1H), 8.25-8.1 (d, 1H), 8.1-8.0 (m, 1H), 7.8-7.65 (m, 1H), 7.6-7.5 (m, 2H), 7.45-7.30 (m, 2H), 7.20-7.05 (m, 2H), 7.05-6.90 (m, 2H), 4.00-3.85 (m, 1H), 3.80-3.65 (m, 1H), 3.5 (s, 1H), 3.3-3.0 (m, 6H), 2.70-2.55 (m, 4H), 2.4 (s, 3H), 1.9 (s, 3H) MS m/z 604.9 (M + 1), | Benzothiazole-6-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |

TABLE 1-continued

| No | Structure | Physical Data [¹HNMR and/or MS] | IUPAC NAME | Ex |
|---|---|---|---|---|
| 123 | 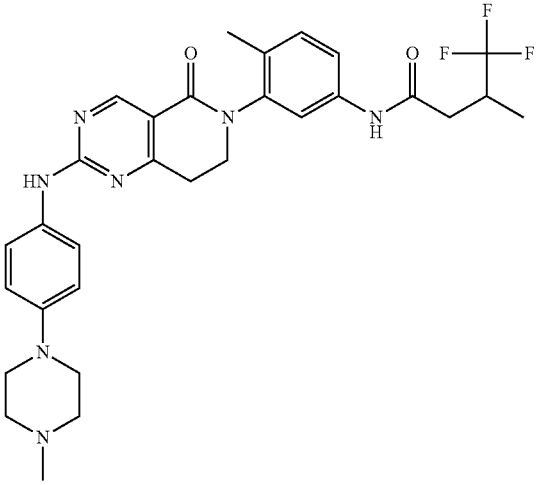 | 1H NMR (300 MHz, CDCl₃) δ 8.12 (s, 1H), 7.56-7.46 (m, 2H), 7.32-7.12 (m, 3H), 7.06-6.89 (m, 4H), 4.0 (s, 2H), 3.3-3.1 (m, 6H), 3.05-2.90 (m, 3H), 2.85-2.70 (m, 1H), 2.65-2.60 (m, 4H), 2.4 (s, 3H), 2.3 (s, 3H), 1.3 (s, 3H) MS m/z 568.2 (M + 1), | 4,4,4-Trifluoro-3-methyl-N-(4-methyl-3-{2-[4-(4-methyl-piperazin-1-yl)-phenylamino]-7,8-dihydro-5H-pyrido[4,3-d]pyrimidin-6-yl}-phenyl)-butyramide | 1 |
| 124 | 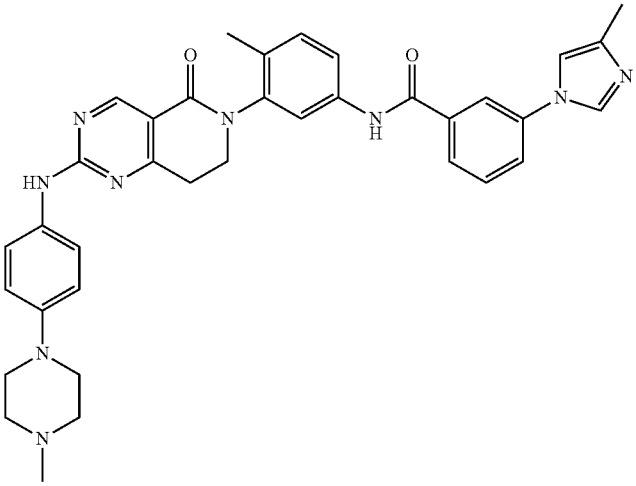 [SMILES: Cc1cn(-c2cccc(C(=O)Nc3ccc(C)c(N4CCc5nc(Nc6ccc(N7CCN(C)CC7)cc6)ncc5C4=O)c3)c2)cn1] | 1H NMR (300 MHz, CDCl₃) δ 9.2 (s, 1H), 8.95 (s, 1H), 7.95 (s, 1H), 7.9-7.8 (m, 2H), 7.65-7.34 (m, 7H), 7.10-7.01 (m, 2H), 7.00-6.89 (m, 2H), 4.0-3.8 (m, 1H), 3.8-3.6 (m ,1H), 3.3-2.9 (m, 6H), 2.7-2.5 (m, 4H), 2.4 (s, 3H), 2.25 (s, 3H), 1.85 (s, 3H) MS m/z 628.1 (M + 1), | 3-(4-Methyl-imidazol-1-yl)-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide | 3 |
| 125 | 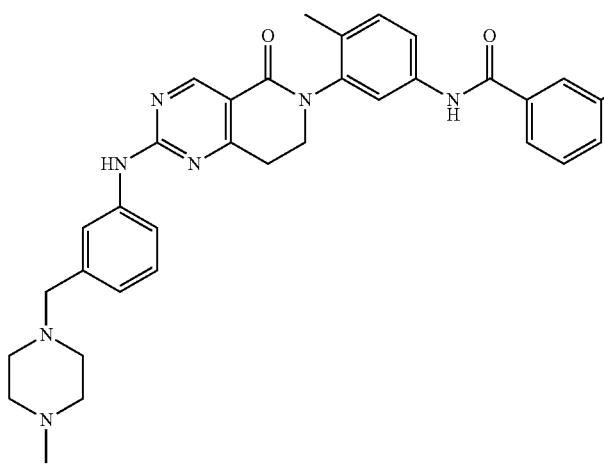 | 1H NMR (300 MHz, CD₃OD) δ 8.88 (s, 1H), 8.38-8.08 (m, 3H), 7.92-7.80 (m, 1H), 7.80-7.50 (m, 6H), 7.43-7.20 (m, 2H), 7.15-6.95 (d, 1H), 4.3-3.7 (m, 4H), 3.6 (s, 2H), 3.0-2.6 (m, 8H), 2.45 (s, 3H), 2.25 (s, 3H) MS m/z 630.0 (M + 1), | N-(4-Methyl-3-{2-[3-(4-methyl-piperazin-ylmethyl)-phenylamino]-5-oxo-7,8-dihydro-5H-pyrido[4,3-d]pyrimidin-6-yl}-phenyl)-3-trifluoromethyl-benzamide | 3 |

| No | Structure | Physical Data [¹HNMR and/or MS] | IUPAC NAME | Ex |
|---|---|---|---|---|
| 126 | 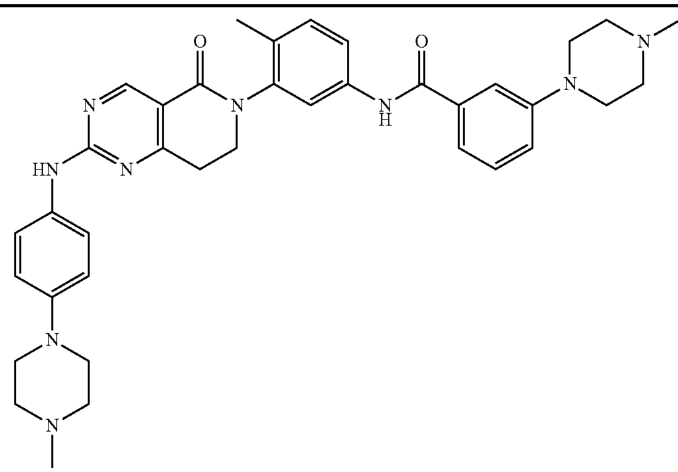 | 1H NMR (300 MHz, CDCl₃) δ 9.0 (s, 1H), 8.2 (s, 1H), 7.65 (d, 1H), 7.6-7.4 (m, 6H), 7.3-7.15 (m, 2H), 7.1-6.9 (m, 3H), 4.1-3.9 (m, 1H), 3.85-3.65 (m, 1H), 3.3-3.0 (m, 10H), 2.7-2.5 (m, 8H), 2.4-2.3 (m, 6H), 2.15 (s, 3H) MS m/z 646.0 (M + 1), | N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-(4-methyl-piperazin-1-yl)-benzamide | 3 |
| 127 | 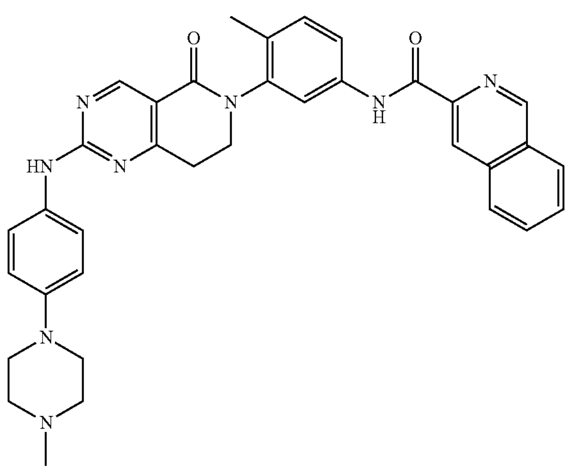 | 1H NMR (300 MHz, DMSO-D₆) δ 10.7 (s, 1H), 9.48 (s, 1H), 9.29 (s, 1H), 8.7 (s, 1H), 8.4-8.2 (m, 3H), 8.0-7.5 (m, 6H), 7.2 (d, 1H), 6.89 (d, 2H), 4.0 (s, 2H), 3.25 (t, 2H), 3.1-3.0 (m, 4H), 2.9 (t, 2H), 2.5-2.4 (m, 4H), 2.3 (s, 3H), 2.2 (s, 3H) MS m/z 585.1 (M + 1), | Isoquinoline-3-carboxylic acid (4-methyl-3-{2-[4-(4-methyl-piperazin-1-yl)-phenyl-amino]-7,8-dihydro-5H-pyrido[4,3-d]pyrimidin-6-yl}-phenyl)-amide | 1 |
| 128 | 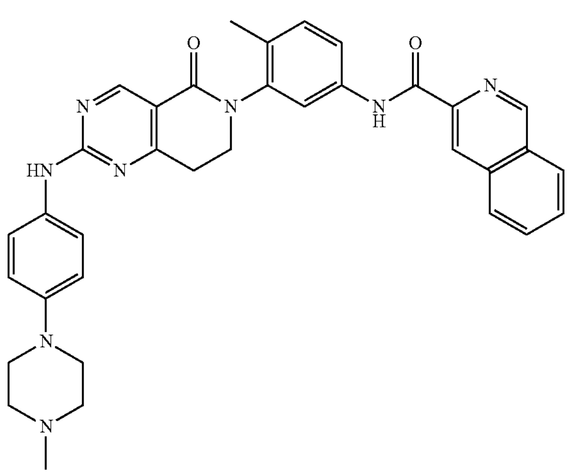 [SMILES: Cc1ccc(NC(=O)c2cc3ccccc3cn2)cc1N1CCc2nc(Nc3ccc(N4CCN(C)CC4)cc3)ncc2C1=O] | 1H NMR (300 MHz, CD₃OD) δ 9.37 (s, 1H), 8.83 (s, 1H), 8.66 (s, 1H), 8.22 (d, 1H), 8.12 (d, 1H), 7.96-7.69 (m, 4H), 7.6 (d, 2H), 7.45-7.32 (m, 1H), 7.0 (d, 2H), 4.25-4.0 (m, 1H), 3.95-3.75 (m, 1H), 3.25-3.1 (m, 6H), 2.8-2.65 (m, 4H), 2.4 (s, 3H), 2.25 (s, 3H) MS m/z 599.1 (M + 1), | Isoquinoline-3-carboxylic acid (4-methyl-3-{2-[4-(4-methyl-piperazin-1-yl)-phenylamino]-5-oxo-7,8-dihydro-5H-pyrido[4,3-d]pyrimidin--6-yl}-phenyl)-amide | 3 |
| 129 | 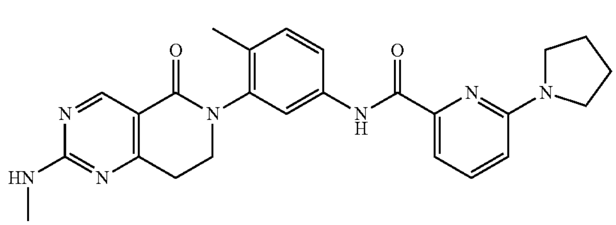 | 1H NMR (300 MHz, CDCl₃) δ 8.05 (s, 1H), 7.76-7.60 (m, 2H), 7.44-6.88 (m, 6H), 6.82-6.58 (m, 1H), 5.12-4.82 (m, 1H), 4.01 (s, 2H), 3.49-2.82 (m, 10H), 2.31 (s, 3H), 2.05 (s, 3H) MS m/z 442.9 (M + 1), | N-[4-Methyl-3-(2-methylamino-7,8-dihydro-5H-pyrido[4,3-d]pyrimidin-6-yl)-phenyl]-3-pyrrolidin-1-yl-benzamide | 1 |

TABLE 1-continued

| No | Structure | Physical Data [¹HNMR and/or MS] | IUPAC NAME | Ex |
|---|---|---|---|---|
| 131 | 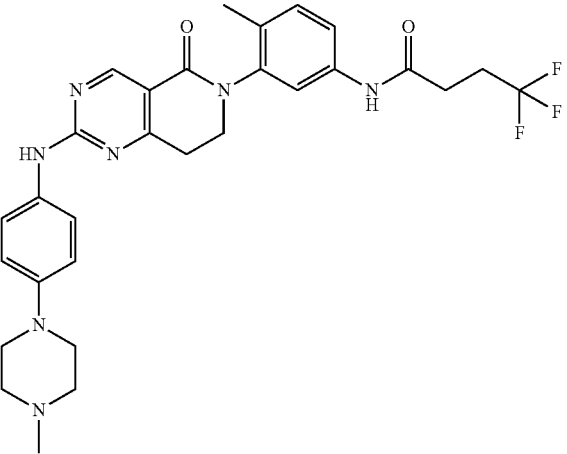 | 1H NMR (300 MHz, CDCl₃) δ 8.11 (s, 1H), 7.54-7.42 (m, 3H), 7.24-7.12 (m, 2H), 7.04-6.86 (m, 4H), 4.0 (s, 2H), 3.3-3.1 (m, 6H), 3.02-2.90 (m, 2H), 2.7-2.5 (m, 8H), 2.35 (s, 3H), 2.3 (s, 3H) MS m/z 554.2 (M + 1), | 4,4,4-Trifluoro-N-(4-methyl-3-{2-[4-(4-methyl-piperazin-1-yl)-phenylamino]-7,8-dihydro-5H-pyrido[4,3-d]pyrimidin-6-yl}-phenyl)-butyramide | 1 |
| 132 | 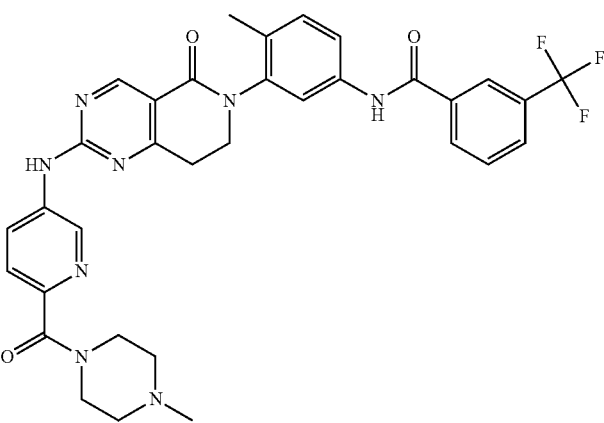 | 1H NMR (300 MHz, CDCl₃) δ 8.85-8.64 (m, 1H), 8.40-7.96 (m, 5H), 7.90-7.50 (m, 4H), 7.48-7.00 (m, 3H), 4.05 (s, 2H), 3.94-3.60 (m, 4H), 3.4-3.1 (m, 2H), 3.1-2.9 (m, 2H), 2.60-2.15 (m, 10H) MS m/z 631.2 (M + 1), | N-(4-Methyl-3-{2-[6-(4-methyl-piperazine-1-carbonyl)-pyridin-3-ylamino]-7,8-dihydro-5H-pyrido[4,3-d]pyrimidin-6-yl}-phenyl)-3-trifluoromethyl-benzamide | 2 |
| 133 | 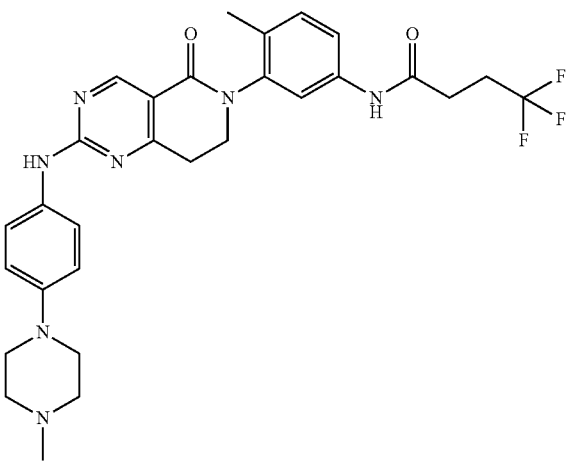 [SMILES: Cc1ccc(NC(=O)CCC(F)(F)F)cc1N1CCc2nc(Nc3ccc(N4CCN(C)CC4)cc3)ncc2C1=O] | 1H NMR (300 MHz, CDCl₃) δ 8.95 (s, 1H), 8.35 (s, 1H), 7.55-7.45 (m, 2H), 7.4-7.3 (m, 2H), 7.20-7.15 (m, 2H), 7.0-6.9 (m, 2H), 4.05-3.90 (m, 1H), 3.85-3.70 (m, 1H), 3.7-3.1 (m, 6H), 2.7-2.6 (m, 4H), 2.55-2.45 (m, 4H), 2.4 (s, 3H), 2.25 (s, 3) MS m/z 568.1 (M + 1), | 4,4,4-Trifluoro-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-butyramide | 3 |

TABLE 1-continued

| No | Structure | Physical Data [¹HNMR and/or MS] | IUPAC NAME | Ex |
|---|---|---|---|---|
| 134 | 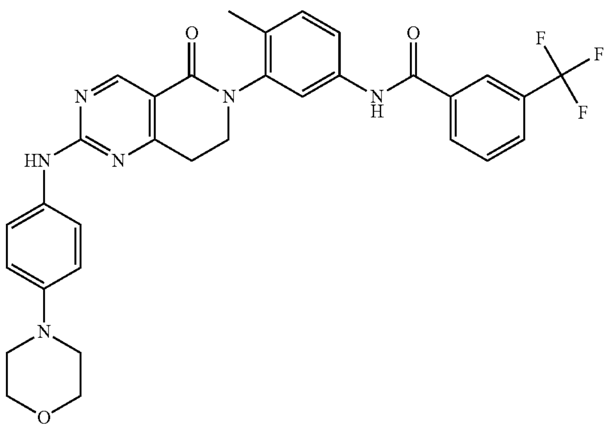 [SMILES: Cc1ccc(NC(=O)c2cccc(C(F)(F)F)c2)cc1N1CCc2nc(Nc3ccc(N4CCOCC4)cc3)ncc2C1=O] | 1H NMR (300 MHz, CDCl₃) δ 9.05 (s, 1H), 8.85-8.75 (br s, 1H), 8.2 (s, 1H), 8.15-8.05 (m, 1H), 7.7-7.5 (m, 5H), 7.45-7.35 (m, 2H), 7.2-7.1 (m, 1H), 7.0-6.9 (m, 2H), 4.05-3.85 (m, 5H), 3.80-3.65 (m, 1H), 3.20-3.05 (m, 6H), 2.15 (s, 3H) MS m/z 602.9 (M + 1), | N-{4-Methyl-3-[2-(4-morpholin-4-yl-phenylamino)-5-oxo-7,8-dihydro-5H-pyrido[4,3-d]pyrimidin-6-yl]-phenyl}-3-trifluoromethyl-benzamide | 3 |
| 135 | 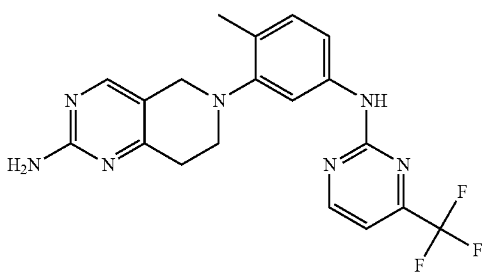 [SMILES: Cc1ccc(Nc2nccc(C(F)(F)F)n2)cc1N1CCc2nc(N)ncc2C1] | ¹H NMR (300 MHz, DMSO-D₆) δ 10.1 (s, 1H), 8.8-8.74 (m, 1H), 8.06-8.0 (br s, 1H), 7.68-7.6 (br s, 1H), 7.4-7.08 (m, 3H), 6.5-6.38 (br s, 2H), 3.9 (s, 2H), 3.2-3.1 (m, 2H), 2.84-2.7 (m, 2H), 2.2 (s, 3H) MS m/z 402.1 (M + 1) | 6-[2-Methyl-5-(4-trifluoromethyl-pyrimidin-2-ylamino)-phenyl]-5,6,7,8-tetrahydro-pyrido[4,3-d]pyrimidin-2-ylamine | 6 |
| 136 | 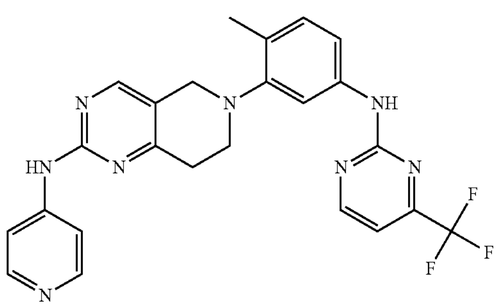 [SMILES: Cc1ccc(Nc2nccc(C(F)(F)F)n2)cc1N1CCc2nc(Nc3ccncc3)ncc2C1] | ¹H NMR (300 MHz, CDCl₃) δ 8.65-8.55 (m, 3H), 8.5-8.4 (br s, 1H), 8.35 (s, 1H), 8.2-8.1 (m, 2H), 7.85-7.75 (br s, 1H), 7.4 (s, 1H), 7.25-7.15 (m, 1H), 7.1-7.0 (m, 2H), 4.2 (s, 2H), 3.35 (t, 2H), 3.15 (t, 2H), 2.3 (s, 3H) MS m/z 478.9 (M + 1) | {6-[2-Methyl-5-(4-trifluoromethyl-pyrimidin-2-ylamino)-phenyl]-5,6,7,8-tetra-hydro-pyrido[4,3-d]pyrimidin-2-yl}-pyridin-4-yl-amine | 6 |
| 137 | 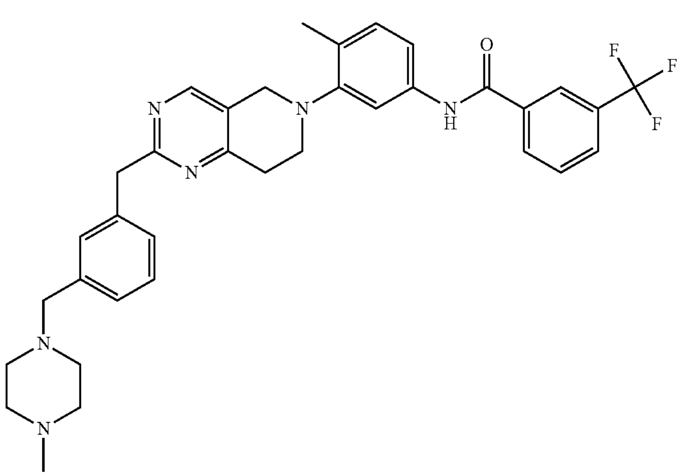 [SMILES: Cc1ccc(NC(=O)c2cccc(C(F)(F)F)c2)cc1N1CCc2nc(Cc3cccc(CN4CCN(C)CC4)c3)ncc2C1] | ¹H NMR (300 MHz, CD₃OD) δ 8.36-8.2 (m, 3H), 7.98-7.66 (m, 5H), 7.45-7.35 (m, 2H), 7.28-7.12 (m, 2H), 4.12 (s, 2H), 3.54-3.46 (m, 2H), 3.41-3.36 (m, 5H), 3.31-3.21 (m, 4H), 3.1-3.02 (m, 2H), 2.95 (s, 3H), 2.36 (s, 3H) MS m/z 616.2 (M + 1) | N-(4-Methyl-3-{2-[3-(4-methyl-piperazin-1-ylmethyl)-phenylamino]-7,8-dihydro-5H-pyrido[4,3-d]pyrimidin-6-yl}-phenyl)-3-trifluoromethyl-benzamide | 1 |

TABLE 1-continued

| No | Structure | Physical Data [¹HNMR and/or MS] | IUPAC NAME | Ex |
|----|-----------|----------------------------------|------------|-----|
| 138 | 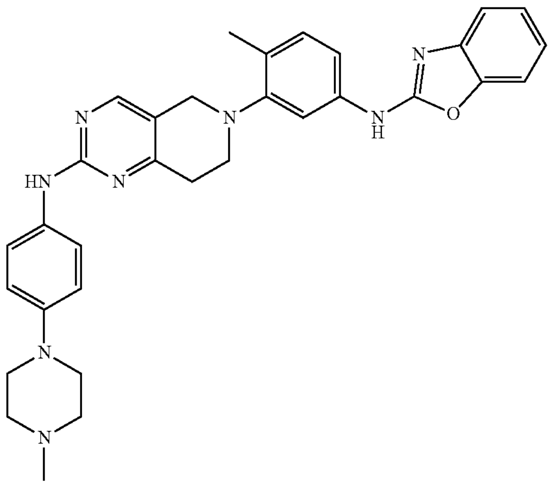 | ¹H NMR (300 MHz, DMSO-D$_6$) δ 10.7 (s, 1H), 8.8 (s, 1H), 7.7-7.0 (m, 10H), 6.95-6.85 (d, 2H), 4.1-3.95 (m, 1H), 3.85-8.7 (m, 1H), 3.3-3.0 (m, 6H), 2.5-2.4 (m, 4H), 2.24 (s, 3H), 2.15 (s, 3H) MS m/z 561.2 (M + 1) | 6-{5-(Benzooxazol-2-ylamino)-2-methyl-phenyl]-2-[4-(4-methyl-piperazin-1-yl)-phenylamino]-7,8-dihydro-6H-pyrido[4,3-d]pyrimidin-5-one | 10 |
| 139 | 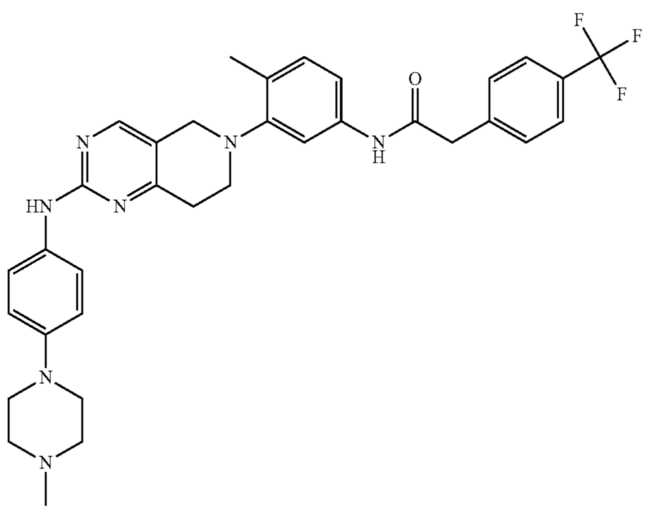 [SMILES: Cc1ccc(NC(=O)Cc2ccc(C(F)(F)F)cc2)cc1N1CCc2nc(Nc3ccc(N4CCN(C)CC4)cc3)ncc2C1] | ¹H NMR (300 MHz, CD$_3$OD) δ 8.12 (s, 1H), 7.7-7.45 (m, 7H), 7.15 (s, 2H), 6.96 (d, 2H), 3.98 (s, 2H), 3.77 (s, 2H), 3.25-3.15 (m, 6H), 2.99-2.75 (m, 6H), 2.5 (s, 3H), 2.28 (s, 3H) MS m/z 615.9 (M + 1) | N-(4-Methyl-3-{2-[4-(4-methyl-piperazin-1-yl)-phenylamino]-7,8-dihydro-5H-pyrido[4,3-d]pyrimidin-6-yl}-phenyl)-2-(4-trifluoromethyl-phenyl)-acetamide | 1 |
| 140 | 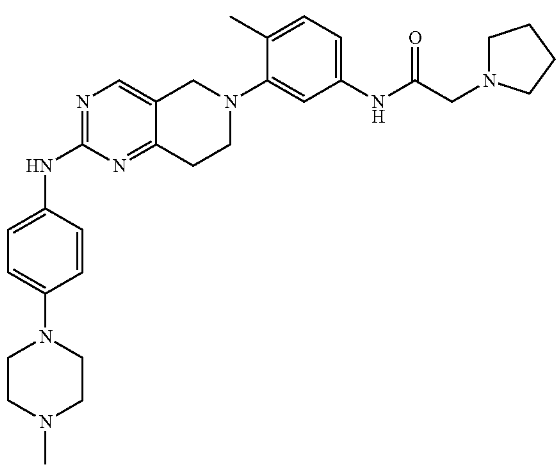 [SMILES: Cc1ccc(NC(=O)CN2CCCC2)cc1N1CCc2nc(Nc3ccc(N4CCN(C)CC4)cc3)ncc2C1] | ¹H NMR (300 MHz, CDCl$_3$) δ 9.16 (s, 1H), 8.12 (s, 1H), 7.84 (s, 1H), 7.7-7.4 (m, 3H), 7.25-6.8 (m, 4H), 4.02 (s, 2H), 3.4-3.14 (m, 7H), 3.08-2.92 (m, 2H), 2.85-2.65 (br s, 7H), 2.52-2.2 (d, 6H), 2.06 (s, 3H), 1.95-1.8 (br s, 3H) MS m/z 541.2 (M + 1) | N-(4-Methyl-3-{2-[4-(4-methyl-piperazin-1-yl)-phenylamino]-7,8-dihydro-5H-pyrido[4,3-d]pyrimidin-6-yl}-phenyl)-2-pyrrolidin-1-yl-acetamide | 1 |

TABLE 1-continued

| No | Structure | Physical Data [¹HNMR and/or MS] | IUPAC NAME | Ex |
|---|---|---|---|---|
| 141 | 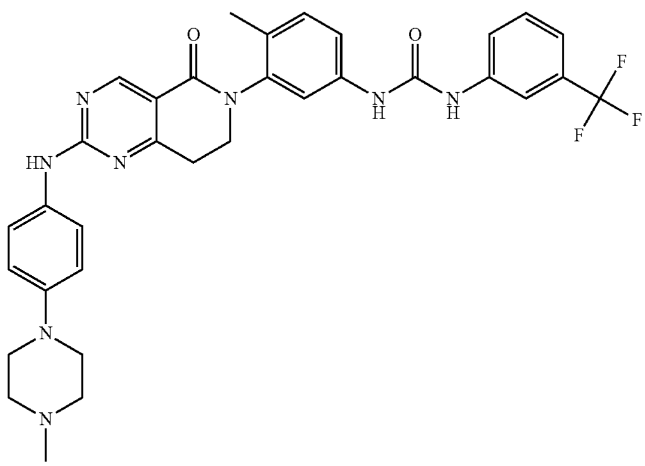 [SMILES: Cc1ccc(NC(=O)Nc2cccc(C(F)(F)F)c2)cc1N1CCc2nc(Nc3ccc(N4CCN(C)CC4)cc3)ncc2C1=O] | ¹H NMR (300 MHz, CDCl₃) δ 9.0 (s, 1H), 7.7-6.6 (m, 11H), 8.2-7.7 (m, 3H), 4.2-3.7 (m, 2H), 3.5-2.8 (m, 10H), 2.2-1.9 (m, 6H) MS m/z 631.2 (M + 1) | 1-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-(3-trifluoromethyl-phenyl)-urea | 8 |
| 145 | 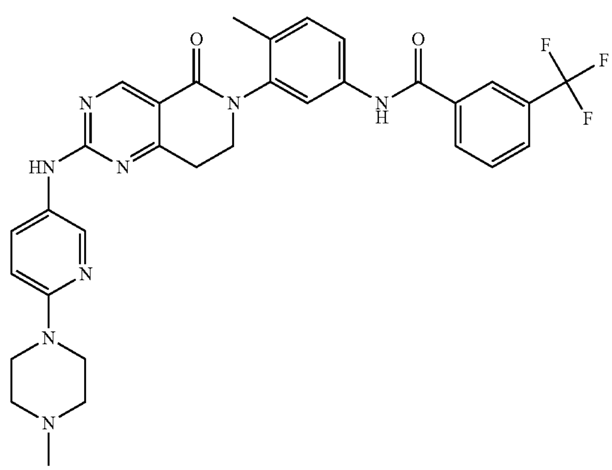 [SMILES: Cc1ccc(NC(=O)c2cccc(C(F)(F)F)c2)cc1N1CCc2nc(Nc3ccc(N4CCN(C)CC4)nc3)ncc2C1=O] | ¹H NMR (300 MHz, CDCl₃) δ 9.15 (s, 1H), 9.02 (s, 1H), 8.45-8.37 (br s, 1H), 8.23-8.08 (m, 2H), 7.85 (dd, 1H), 7.74 (d, 1H), 7.66-7.52 (m, 2H), 7.40-7.30 (m, 2H), 7.06 (d, 1H), 6.72 (d, 1H), 4.00-3.88 (m, 1H), 3.70-3.67 (m, 1H), 3.55 (t, 4H), 3.15-3.05 (m, 2H), 2.55 (t, 4H), 2.36 (s, 3H), 1.75 (s, 3H) MS m/z 617.1 (M + 1) | N-(4-Methyl-3-{2-[6-(4-methyl-piperazin-1-yl)-pyridin-3-ylamino]-5-oxo-7,8-dihydro-5H-pyrido[4,3-d]pyrimidin-6-yl}-phenyl)-3-trifluoromethyl-benzamide | 3 |
| 146 | 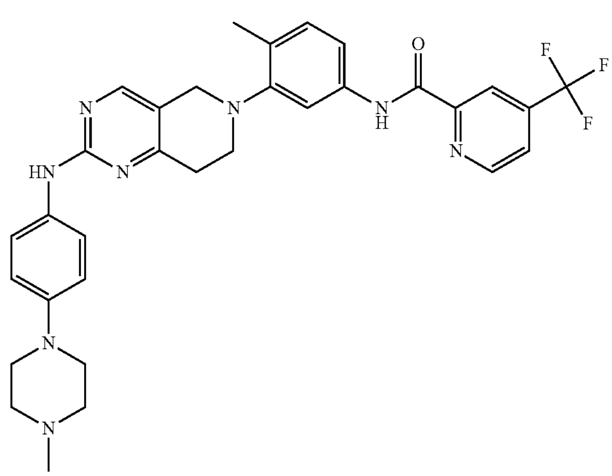 [SMILES: Cc1ccc(NC(=O)c2cc(C(F)(F)F)ccn2)cc1N1CCc2nc(Nc3ccc(N4CCN(C)CC4)cc3)ncc2C1] | ¹H NMR (300 MHz, CDCl₃) δ 9.9 (s, 1H), 8.83 (d, 1H), 8.56 (s, 1H), 8.15 (s, 1H), 7.8-7.7 (m, 2H), 7.50 (d, 2H), 7.0-6.9 (m, 5H), 4.08 (s, 2H), 3.37-2.98 (m, 8H), 2.65-2.58 (m, 4H), 2.36 (s, 3H), 2.32 (s, 3H) MS m/z 603.1 (M + 1) | 4-Trifluoromethyl-pyridine-2-carboxylic acid (4-methyl-3-{2-[4-(4-methyl-piperazin-1-yl)-phenylamino]-7,8-dihydro-5H-pyrido[4,3-d]pyrimidin-6-yl}-phenyl)-amide | 1 |

| No | Structure | Physical Data [¹HNMR and/or MS] | IUPAC NAME | Ex |
|---|---|---|---|---|
| 147 | 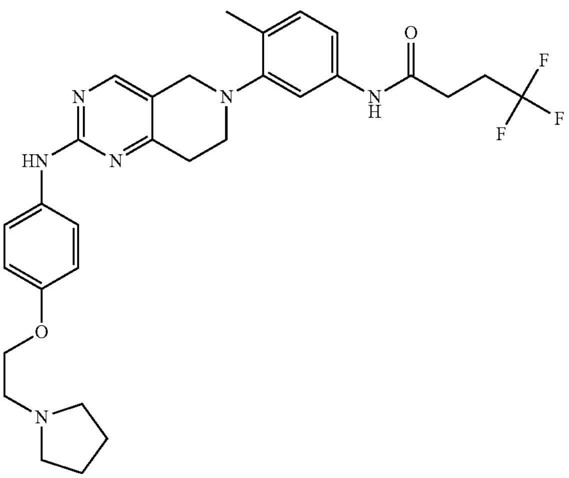 [SMILES: Cc1ccc(NC(=O)CCC(F)(F)F)cc1N1CCc2nc(Nc3ccc(OCCN4CCCC4)cc3)ncc2C1] | ¹H NMR (300 MHz, CDCl$_3$) δ 8.13 (s, 1H), 7.55-7.45 (m, 3H), 7.22-7.13 (m, 2H), 7.00-6.90 (m, 4H), 4.14 (t, 2H), 4.00 (s, 2H), 3.25 (t, 2H), 3.00-2.90 (m, 4H), 2.70-2.60 (m, 8H), 2.30 (s, 3H), 1.90-1.80 (m, 4H) MS m/z 569.2 (M + 1) | 4,4,4-Trifluoro-N-(4-methyl-3-{2-[4-(2-pyrrolidin-1-yl-ethoxy)-phenyl-amino]-7,8-dihydro-5H-pyrido[4,3-d]pyrimidin-6-yl}-phenyl)-butyramide | 1 |
| 148 | 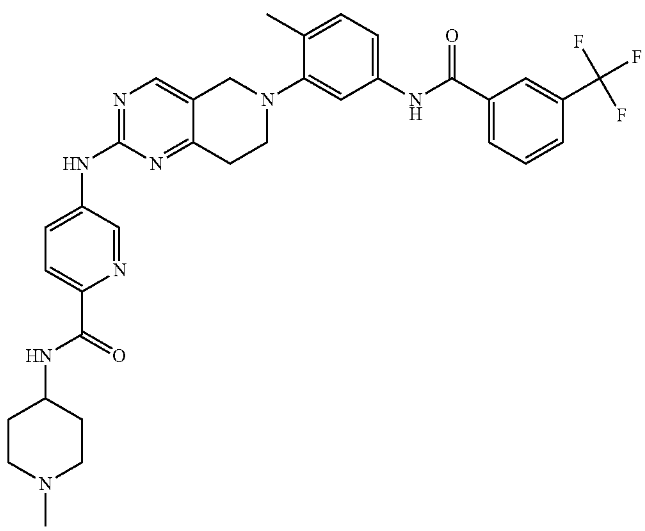 [SMILES: Cc1ccc(NC(=O)c2cccc(C(F)(F)F)c2)cc1N1CCc2nc(Nc3ccc(C(=O)NC4CCN(C)CC4)nc3)ncc2C1] | ¹H NMR (300 MHz, CDCl$_3$) δ 8.75 (s, 1H), 8.40-7.95 (m, 6H), 7.90-7.50 (m, 4H), 7.40-7.10 (m, 3H), 4.12-3.90 (m, 3H), 3.35-3.25 (m, 2H), 3.15-3.00 (m, 2H), 2.90-2.76 (m, 2H), 2.40-1.95 (m, 12H) MS m/z 645.2 (M + 1) | 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid (1-methyl-piperidin-4-yl)-amide | 2 |
| 149 | 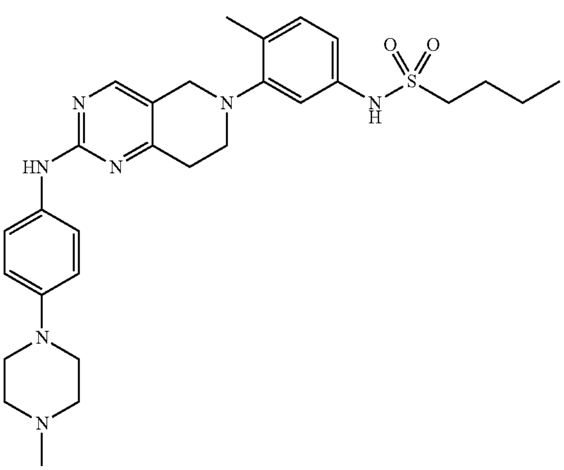 [SMILES: CCCCS(=O)(=O)Nc1ccc(C)c(N2CCc3nc(Nc4ccc(N5CCN(C)CC5)cc4)ncc3C2)c1] | ¹H NMR (300 MHz, CDCl$_3$) δ 8.15 (s, 1H), 7.50 (d, 2H), 7.19 (d, 1H), 7.00-6.80 (m, 5H), 6.60-6.40 (m, 1H), 4.00 (s, 2H), 3.30-2.95 (m, 10H), 2.60 (t, 4H), 2.38 (s, 3H), 2.30 (s, 3H), 1.85-1.75 (m, 2H), 1.50-1.36 (m, 2H), 1.25 (s, 2H), MS m/z 550.2 (M + 1) | Butane-1-sulfonic acid (4-methyl-3-{2-[4-(4-methyl-piperazin-1-yl)-phenylamino]-7,8-dihydro-5H-pyrido[4,3-d]pyrimidin-6-yl}-phenyl)-amide | 9 |

TABLE 1-continued

| No | Structure | Physical Data [¹HNMR and/or MS] | IUPAC NAME | Ex |
|---|---|---|---|---|
| 150 | 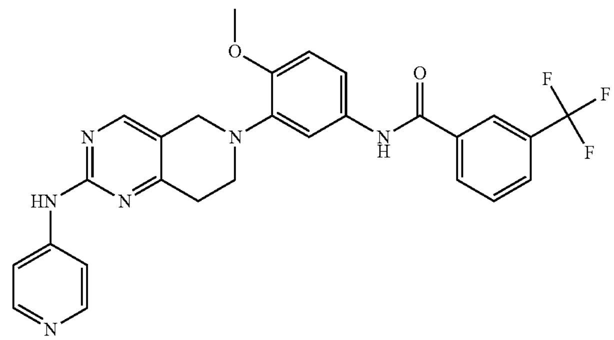 [SMILES: COc1ccc(NC(=O)c2cccc(C(F)(F)F)c2)cc1N1CCc2nc(Nc3ccncc3)ncc2C1] | 1H NMR (300 MHz, CD₃OD) δ 8.5-8.4 (t, 3H), 8.35-8.25 (br s, 1H), 7.7-7.3 (m, 5H), 7.2-7.1 (d, 1H), 6.95-6.8 (m, 2H), 3.9 (s, 2H), 3.7 (s, 3H), 3.15-3.05 (m, 2H), 3.05-2.95 (m, 2H), . MS m/z 521.5 (M + 1) | N-{4-Methoxy-3-[2-(pyridin-4-ylamino)-7,8-dihydro-5H-pyrido [4,3-d] pyrimidin-6-yl]-phenyl}-3-trifluoromethyl-benzamide | 2 |
| 153 | 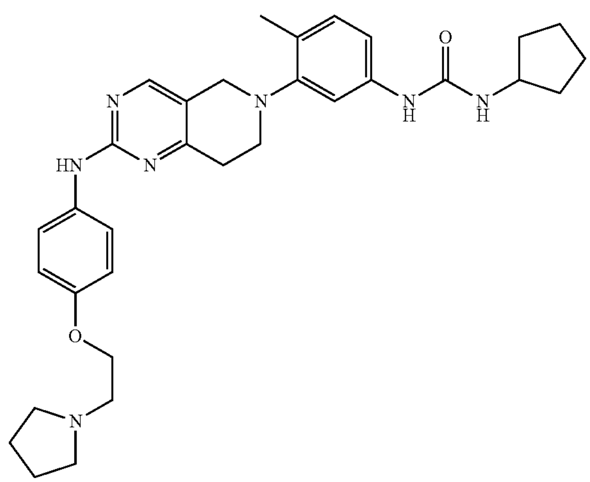 [SMILES: Cc1ccc(NC(=O)NC2CCCC2)cc1N1CCc2nc(Nc3ccc(OCCN4CCCC4)cc3)ncc2C1] | ¹H NMR (400 MHz, CDCl₃) δ 8.11 (s, 1H), 7.50 (d, 2H), 7.23 (d, 1H), 7.13 (d, 1H), 6.98-6.88 (m, 3H), 6.82 (dd, 1H), 6.54 (s, 1H), 4.73 (d, 1H), 4.20-4.10 (m, 2H), 3.99 (s, 2H), 3.24 (t, 2H), 2.98 (t, 2H), 2.75-2.67 (br s, 4H), 2.29 (s, 3H), 2.06-1.95 (m, 2H), 1.90-1.80 (m, 4H), 1.8-1.5 (m, 10H) | 1-Cyclopentyl-3-(4-methyl-3-{2-[4-(2-pyrrolidin-1-yl-ethoxy)-phenyl amino]-7,8-dihydro-5H-pyrido[4,3-d]pyrimidin-6-yl}-phenyl)-urea | 7 |
| 154 | 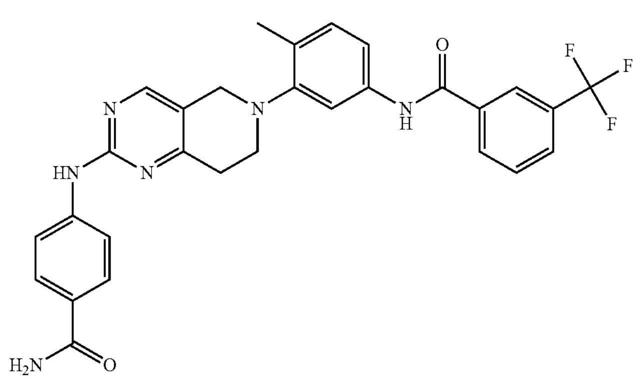 [SMILES: Cc1ccc(NC(=O)c2cccc(C(F)(F)F)c2)cc1N1CCc2nc(Nc3ccc(C(N)=O)cc3)ncc2C1] | ¹H NMR (300 MHz, DMSO-D₆) δ 10.4 (s, 1H), 9.84 (s, 1H), 8.42-8.24 (m, 3H), 8.02-7.72 (m, 5H), 7.62 (s, 1H), 7.52-7.44 (m, 1H), 7.28-7.10 (m, 4H), 4.0 (s, 2H), 3.3-3.2 (t, 2H), 3.05-2.95 (t, 2H), 2.4 (s, 3H) MS m/z 547.1 (M + 1) | 4-{6-[2-Methyl-5-(3-trifluoromethyl-benozylamino)-phenyl]-5,6,7,8-tetrahydro-pyrido [4,3-d]pyrimidin-2-ylamino}-benzamide | 2 |

TABLE 1-continued

| No | Structure | Physical Data [¹HNMR and/or MS] | IUPAC NAME | Ex |
|---|---|---|---|---|
| 155 | 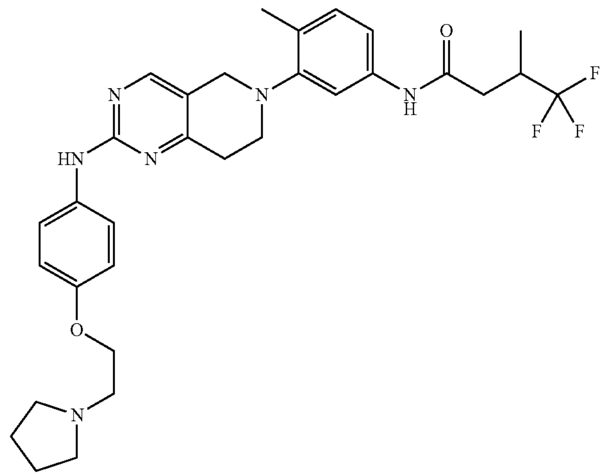 [SMILES: Cc1ccc(NC(=O)CC(C)C(F)(F)F)cc1N1CCc2nc(Nc3ccc(OCCN4CCCC4)cc3)ncc2C1] | ¹H NMR (300 MHz, CDCl₃) δ 8.13 (s, 1H), 7.52-7.46 (m, 3H), 7.20-7.12 (m, 2H), 7.04-6.86 (m, 4H), 4.12 (t, 2H), 4.0 (s, 2H), 3.27 (t, 2H), 3.05-2.89 (m, 4H), 2.7-2.6 (m, 3H), 2.32-2.28 (m, 4H), 1.85-1.80 (m, 3H), 1.3-1.2 (m, 6H). MS m/z 583.2 (M + 1) | 4,4,4-Trifluoro-3-methyl-N-(4-methyl-3-{2-[4-(2-pyrrolidin-1-yl-ethoxy)-phenylamino]-7,8-dihydro-5H-pyrido[4,3-d]pyrimidin-6-yl}-phenyl)-butyramide | 1 |
| 156 | 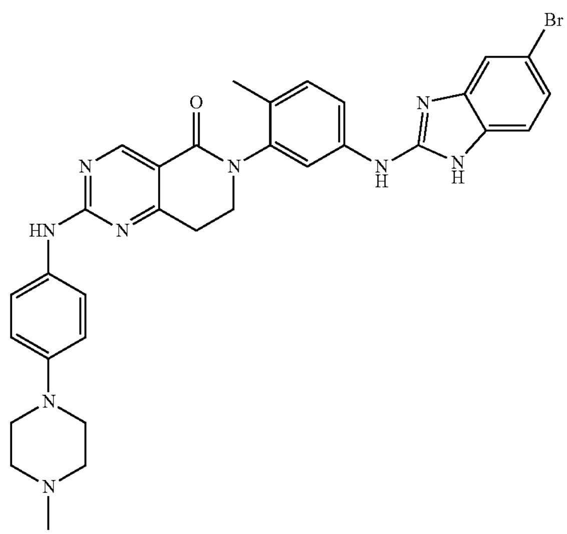 [SMILES: Cc1ccc(Nc2nc3cc(Br)ccc3[nH]2)cc1N1CCc2nc(Nc3ccc(N4CCN(C)CC4)cc3)ncc2C1=O] | ¹H NMR (400 MHz, CD₃OD) δ 8.5-8.3 (bs, 1H), 7.8-7.6 (m, 3H), 7.5-6.94 (m, 7H), 3.9-3.5 (m, 8H), 3.3-3.2 (m, 4H), 3.1 (s, 3H), 2.3 (s, 3H), | 6-{5-(5-Bromo-1H-benzoimidazol-2-ylamino)-2-methyl-phenyl]-2-{4-(4-methyl-piperazin-1-yl)-phenylamino]-7,8-dihydro-6H-pyrido[4,3-d]pyrimidin-5-one | 10 |
| 157 | 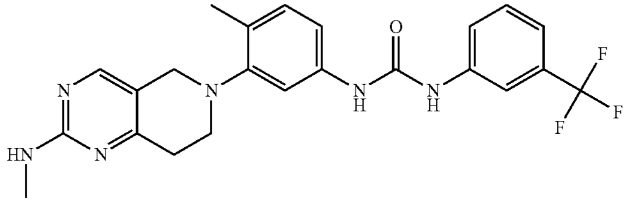 [SMILES: CNc1ncc2c(n1)CCN(c1cc(NC(=O)Nc3cccc(C(F)(F)F)c3)ccc1C)C2] | ¹H NMR (300 MHz, CDCl₃) δ 7.98 (s, 1H), 7.6-7.06 (m, 8H), 6.84 (d, 1H), 5.1-5.0 (m, 1H), 3.85 (s, 2H), 3.2-2.8 (m, 7H), 2.22 (s, 3H) MS m/z 457.1 (M + 1) | 1-{4-Methyl-3-(2-methylamino-7,8-dihydro-5H-pyrido[4,3-d]pyrimidin-6-yl)-phenyl]-3-(3-trifluoromethyl-phenyl)-urea | 7 |

TABLE 1-continued

| No | Structure | Physical Data [¹HNMR and/or MS] | IUPAC NAME | Ex |
|---|---|---|---|---|
| 158 | 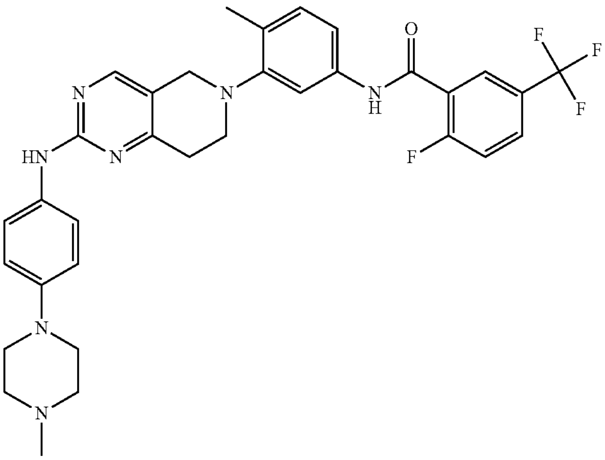 [SMILES: Cc1ccc(NC(=O)c2cc(C(F)(F)F)ccc2F)cc1N1CCc2nc(Nc3ccc(N4CCN(C)CC4)cc3)ncc2C1] | ¹H NMR (300 MHz, DMSO-D₆) δ 11 (s, 1H), 10.0 (s, 1H), 8.70 (s, 1H), 8.00 (s, 2H), 8.04 (s, 1H), 7.82 (t, 2H), 7.72-7.55 (m, 2H), 7.3 (d, 1H), 6.92 (d, 2H), 4.05-3.90 (m, 1H), 3.80-3.69 (m, 1H), 3.3-3.0 (m, 6H), 2.5-2.4 (m, 4H), 2.23 (s, 3H), 2.17 (s, 3H) | 2-Fluoro-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-5-trifluoromethyl-benzamide | 3 |
| 159 | 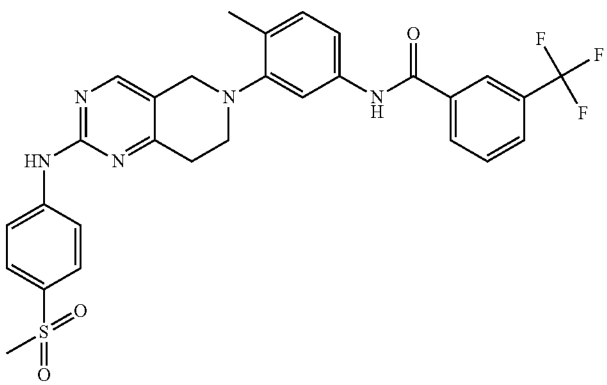 [SMILES: Cc1ccc(NC(=O)c2cccc(C(F)(F)F)c2)cc1N1CCc2nc(Nc3ccc(S(C)(=O)=O)cc3)ncc2C1] | ¹H NMR (400 MHz, DMSO-D₆) δ 10.43 (s, 1H), 10.2 (s, 1H), 8.42 (s, 1H), 8.32-8.24 (m, 2H), 8.06-7.94 (m, 3H), 7.82-7.76 (m, 3H), 7.66-7.62 (m, 1H), 7.48 (dd, 1H), 7.21 (d, 1H), 4.05 (s, 2H), 3.26 (t, 2H), 3.14 (s, 3H), 3.00 (t, 2H), 2.27 (s, 3H) | N-{3-[2-(4-Methanesulfonyl-phenylamino)-7,8-dihydro-5H-pyrido[4,3-d]pyrimidin-6-yl]-4-methyl-phenyl}-3-trifluoromethyl-benzamide | 2 |
| 160 | 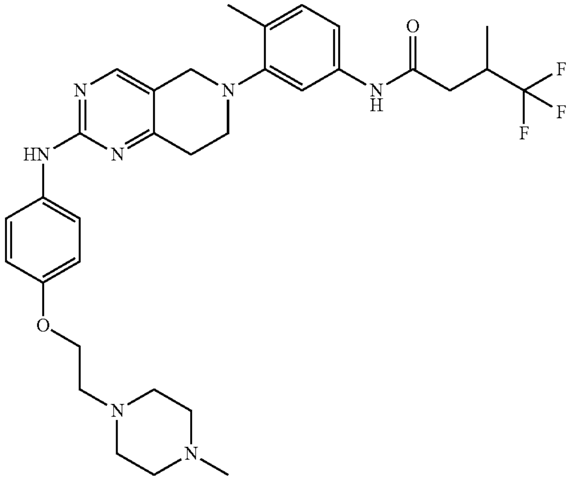 [SMILES: Cc1ccc(NC(=O)CC(C)C(F)(F)F)cc1N1CCc2nc(Nc3ccc(OCCN4CCN(C)CC4)cc3)ncc2C1] | ¹H NMR (400 MHz, CD₃OD) δ 8.16 (s, 1H), 7.58-7.52 (m, 2H), 7.46 (s, 1H), 7.20-7.14 (m, 2H), 6.94-6.89 (m, 2H), 4.15 (t, 2H), 4.00 (s, 2H), 3.29 (t, 2H), 2.96 (t, 2H), 2.84 (t, 2H), 2.72 (dd, 2H), 2.7-2.5 (m, 8H), 2.45-2.35 (m, 1H), 2.32 (s, 3H), 2.29 (s, 3H), 1.2 (d, 3H) | 4,4,4-Trifluoro-3-methyl-N-[4-methyl-3-(2-{4-[2-(4-methyl-piperazin-1-yl)-ethoxy]-phenyl-amino}-7,8-dihydro-5H-pyrido[4,3-d]pyrimidin-6-yl)-phenyl]-butyramide | 1 |

TABLE 1-continued

| No | Structure | Physical Data [¹HNMR and/or MS] | IUPAC NAME | Ex |
|---|---|---|---|---|
| 161 | 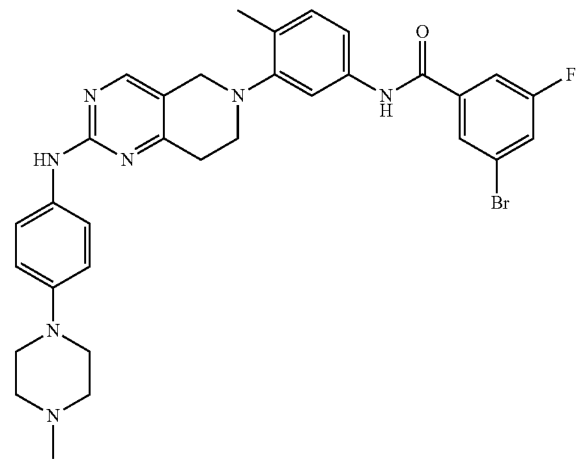 | ¹H NMR (300 MHz, DMSO-D$_6$) δ 10.45 (s, 1H), 10.0 (s, 1H), 8.77 (s, 1H), 8.32 (s, 2H), 8.04 (s, 1H), 7.82 (t, 2H), 7.72-7.55 (m, 3H), 7.3 (d, 1H), 6.92 (d, 2H), 4.05-3.92 (m, 1H), 3.80-3.69 (m, 1H), 3.3-3.0 (m, 6H), 2.5-2.4 (m, 4H), 2.23 (s, 3H), 2.17 (s, 3H) MS m/z 644.0 (M + 1) | 3-Bromo-5-fluoro-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide | 3 |
| 162 | 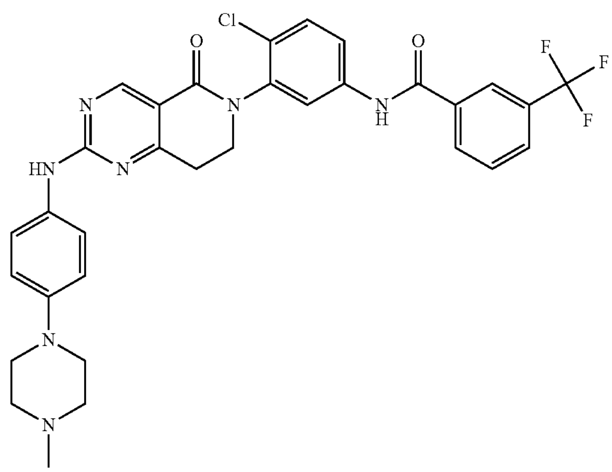 [SMILES: CN1CCN(c2ccc(Nc3ncc4c(n3)CCN(c3cc(NC(=O)c5cccc(C(F)(F)F)c5)ccc3Cl)C4=O)cc2)CC1] | ¹H NMR (300 MHz, DMSO-D$_6$) δ 10.7 (s, 1H), 10.09 (s, 1H), 8.76 (s, 1H), 8.34-8.24 (m, 2H), 8.04-7.93 (m, 2H), 7.86-7.76 (m, 2H), 7.66-7.56 (m, 3H), 6.92 (d, 2H), 4.00-3.78 (m, 2H), 3.15-3.00 (m, 6H), 2.5-2.4 (m, 4H), 2.2 (s, 3H) MS m/z 635.7 (M + 1) | N-(4-Chloro-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide | 3 |
| 163 | 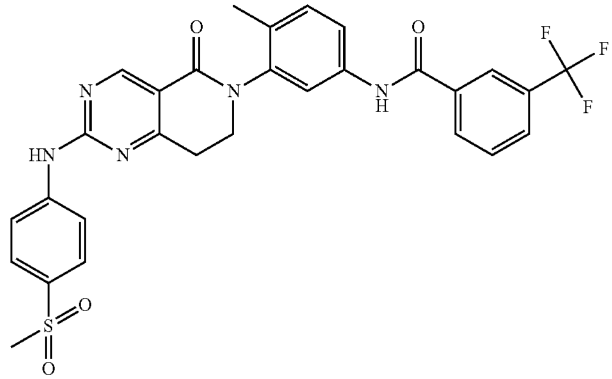 [SMILES: Cc1ccc(NC(=O)c2cccc(C(F)(F)F)c2)cc1N1CCc2nc(Nc3ccc(S(C)(=O)=O)cc3)ncc2C1=O] | ¹H NMR (300 MHz, DMSO-D$_6$) δ 10.75 (s, 1H), 10.55 (s, 1H), 8.92 (s, 1H), 8.35-8.25 (m, 2H), 8.1 (d, 2H), 8.05-7.63 (m, 6H), 7.35 (d, 1H), 4.14-4.00 (m, 1H), 3.88-3.76 (m, 1H), 3.2-3.1 (m, 5H), 2.2 (s, 3H) MS m/z 596.0 (M + 1) | N-{3-[2-(4-Methanesulfonyl-phenylamino)-5-oxo-7,8-dihydro-5H-pyrido[4,3-d]pyrimidin-6-yl]-4-methyl-phenyl}-3-trifluoromethyl-benzamide | 4 |

| No | Structure | Physical Data [¹HNMR and/or MS] | IUPAC NAME | Ex |
|---|---|---|---|---|
| 164 | 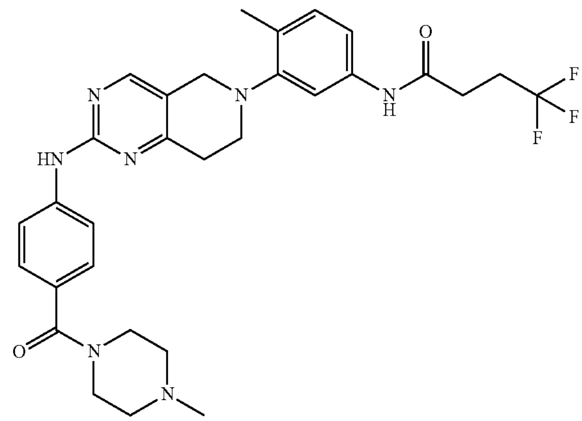 [SMILES: Cc1ccc(NC(=O)CCC(F)(F)F)cc1N1CCc2nc(Nc3ccc(C(=O)N4CCN(C)CC4)cc3)ncc2C1] | ¹H NMR (300 MHz, CDCl₃) δ 8.16 (s, 1H), 7.76-7.64 (m, 3H), 7.46-7.32 (m, 3H), 7.22-7.08 (m, 3H), 3.92 (s, 2H), 3.7-3.6 (m, 5H), 3.2 (t, 2H), 3.0 (t, 2H), 2.75-2.55 (m, 4H), 2.54-2.13 (m, 10H) MS m/z 582.2 (M + 1) | 4,4,4-Trifluoro-N-(4-methyl-3-{2-[4-(4-methyl-piperazine-1-carbonyl)-phenylamino]-7,8-dihydro-5H-pyrido[4,3-d]pyrimidin-6-yl}-phenyl)-butyramide | 2 |
| 165 | 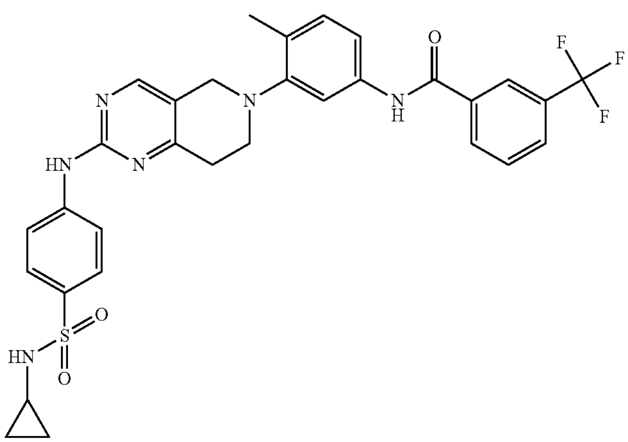 [SMILES: Cc1ccc(NC(=O)c2cccc(C(F)(F)F)c2)cc1N1CCc2nc(Nc3ccc(S(=O)(=O)NC4CC4)cc3)ncc2C1] | ¹H NMR (300 MHz, CDCl₃) δ 8.25 (s, 1H), 8.15 (s, 1H), 8.1 (d, 1H), 7.95-7.80 (m, 7H), 7.75-7.60 (m, 2H), 7.45 (s, 1H), 7.28-7.12 (m, 2H), 4.88 (s, 1H), 4.1 (s, 2H), 3.3 (t, 2H), 3.08 (t, 2H), 2.32 (s, 3H), 0.70-0.55 (m, 4H) MS m/z 623.1 (M + 1) | N-{3-[2-(4-Cyclopropylsulfamoyl-phenylamino)-7,8-dihydro-5H-pyrido[4,3-d]pyrimidin-6-yl]-4-methyl-phenyl}-3-trifluoromethyl-benzamide | 1 |
| 166 | 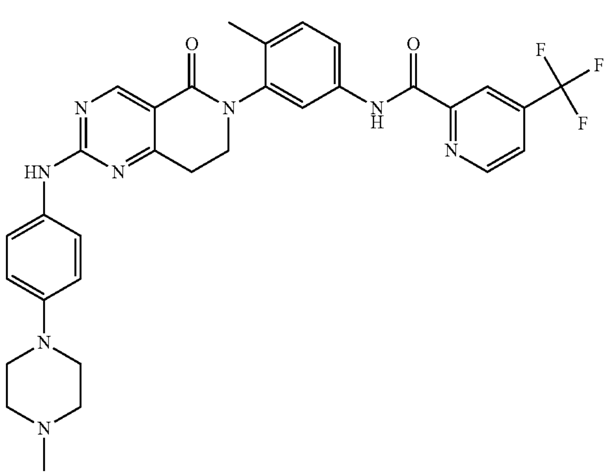 [SMILES: Cc1ccc(NC(=O)c2cc(C(F)(F)F)ccn2)cc1N1CCc2nc(Nc3ccc(N4CCN(C)CC4)cc3)ncc2C1=O] | ¹H NMR (300 MHz, CDCl₃) δ 9.1 (s, 1H), 9 (s, 1H), 8.45-8.35 (s, 1H), 8.2 (s, 1H), 8.15-8.05 (d, 1H), 7.9-7.5 (m, 4H), 7.45-7.25 (m, 2H), 7.15-7.0 (d, 1H), 6.75-6.65 (d, 1H), 4.1-3.85 (m, 1H), 3.8-3.65 (m, 1H), 3.15-3 (m, 2H), 2.6-2.5 (t, 4H), 2.35 (s, 3H), 1.75 (s, 3H). MS m/z 617.4 (M + 1) | 4-Trifluoromethyl-pyridine-2-carboxylic acid (4-methyl-3-{2-[4-(4-methyl-piperazin-1-yl)-phenylamino]-5-oxo-7,8-dihydro-5H-pyrido[4,3-d]pyrimidin-6-yl}-phenyl)-amide | 3 |

| No | Structure | Physical Data [¹HNMR and/or MS] | IUPAC NAME | Ex |
|---|---|---|---|---|
| 167 | 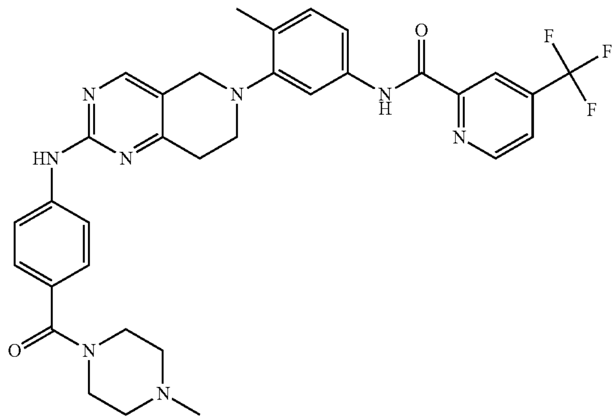 [SMILES: Cc1ccc(NC(=O)c2cc(C(F)(F)F)ccn2)cc1N1CCc2nc(Nc3ccc(C(=O)N4CCN(C)CC4)cc3)ncc2C1] | ¹H NMR (300 MHz, CDCl₃) δ 9.9 (s, 1H), 8.82 (d, 1H), 8.55 (s, 1H), 8.22 (s, 1H), 7.81 (s, 1H), 7.75-7.68 (m, 3H), 7.46-7.38 (m, 2H), 7.32-7.20 (m, 3H), 4.11 (s, 2H), 3.85-3.50 (m, 4H), 3.34 (t, 2H), 3.06 (t, 2H), 2.52-2.20 (m, 10H) MS m/z 631.3 (M + 1) | 4-Trifluoromethyl-pyridine-2-carboxylic acid (4-methyl-3-{2-[4-(4-methyl-piperazine-1-carbonyl)-phenylamino]-7,8-dihydro-5H-pyrido[4,3-d]pyrimidin-6-yl}-phenyl)-amide | 2 |
| 168 | 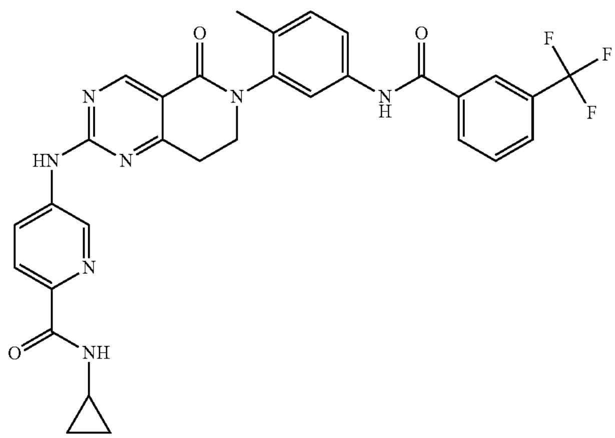 [SMILES: Cc1ccc(NC(=O)c2cccc(C(F)(F)F)c2)cc1N1CCc2nc(Nc3ccc(C(=O)NC4CC4)nc3)ncc2C1=O] | ¹H NMR( 300 MHz, DMSO-D₆) δ 10.7 (s, 1H), 10.58 (s, 1H), 9.06 (d, 1H), 8.91 (s, 1H), 8.6 (d, 1H), 8.42 (dd, 1H), 8.15 (d, 2H), 8.04-7.9 (m, 3H), 7.79-7.75 (m, 1H), 7.54 (dd, 1H), 7.32 (d, 1H), 4.11-3.98 (m, 1H), 3.85-3.72 (m, 1H), 3.22-3.10 (m, 1H), 2.95-2.82 (m, 1H), 2.18 (s, 3H), 0.25-0.10 (m, 5H) MS m/z 602.2 (M + 1) | 5-{6-[2-Methyl-5-(3-trifluoromethyl-benzoylamino)-phenyl]-5-oxo-5,6,7,8-tetrahydro-pyrido[4,3-d]pyrimidin-2-yl-amino}-pyridine-2-carboxylic acid cyclopropylamide | 4 |
| 169 | 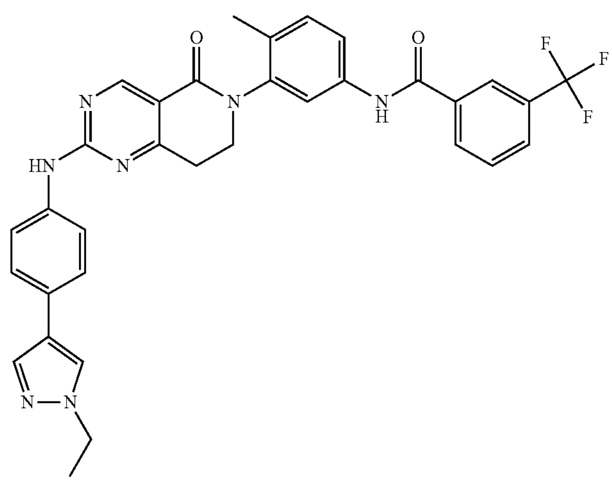 [SMILES: CCn1cc(-c2ccc(Nc3ncc4c(n3)CCN(c3cc(NC(=O)c5cccc(C(F)(F)F)c5)ccc3C)C4=O)cc2)cn1] | ¹H NMR (400 MHz, CD₃OD) δ 8.9 (s, 1H), 8.30-8.20 (m, 2H), 7.99 (s, 1H), 7.91 (d, 1H), 7.84-7.72 (m, 5H), 7.62 (dd, 1H), 7.54 (d, 2H), 7.36 (d, 1H), 4.23 (q, 2H), 4.15-4.05 (m, 1H), 3.93-3.85 (m, 1H), 3.23-3.13 (m, 2H), 2.30 (s, 3H), 1.50 (t, 3H) | N-(3-{2-[4-(1-Ethyl-1H-pyrazol-4-yl)-phenylamino]-5-oxo-7,8-dihydro-5H-pyrido[4,3-d]pyrimidin-6-yl}-4-methyl-phenyl)-3-trifluoromethyl-benzamide | 4 |

| No | Structure | Physical Data [¹HNMR and/or MS] | IUPAC NAME | Ex |
|----|-----------|--------------------------------|------------|-----|
| 170 | 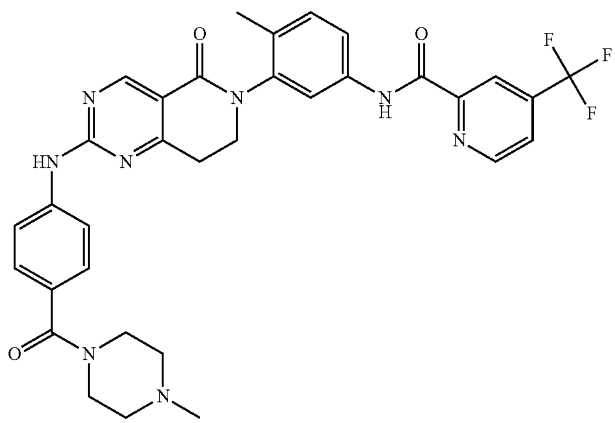 [SMILES: Cc1ccc(NC(=O)c2cc(C(F)(F)F)ccn2)cc1N1CCc2nc(Nc3ccc(C(=O)N4CCN(C)CC4)cc3)ncc2C1=O] | ¹H NMR (300 MHz, CDCl₃) δ 9.99 (s, 1H), 9.07 (s, 1H), 8.82 (d, 1H), 8.52 (s, 1H), 7.84 (d, 1H), 7.79-7.70 (m, 3H), 7.64-7.54 (m, 2H), 7.45 (d, 2H), 7.34 (d, 1H), 4.15-4.04 (m, 1H), 3.90-3.80 (m, 5H), 3.35-3.10 (m, 2H), 2.50-2.25 (m, 10H) MS m/z 645.2 (M + 1) | 4-Trifluoromethyl-pyridine-2-carboxylic acid (4-methyl-3-{2-[4-(4-methyl-piperazine-1-carbonyl)-phenyl-amino]-5-oxo-7,8-dihydro-5H-pyrido[4,3-d]pyrimidin-6-yl}-phenyl)-amide | 4 |
| 171 | 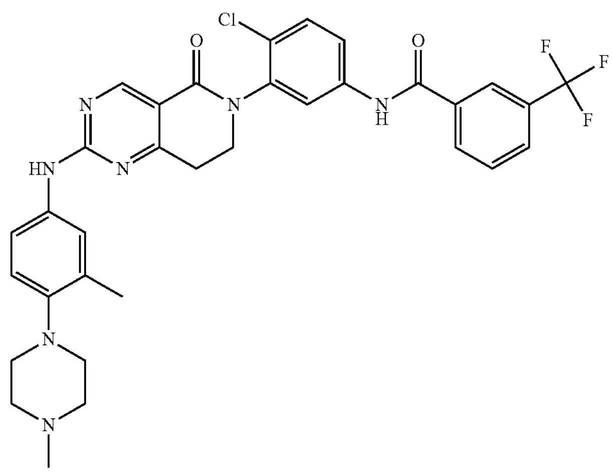 [SMILES: Cc1cc(Nc2ncc3c(n2)CCN(c2cc(NC(=O)c4cccc(C(F)(F)F)c4)ccc2Cl)C3=O)ccc1N1CCN(C)CC1] | ¹H NMR (300 MHz, CDCl₃) δ 9.65 (s, 1H), 9.08 (s, 1H), 8.26-8.10 (m, 2H), 7.9-7.7 (m, 2H), 7.65-7.45 (m, 3H), 7.23 (d, 1H), 7.1 (d, 1H), 4.0-3.8 (m, 2H), 3.40-3.05 (m, 10H), 2.9 (s, 3H), 2.34 (s, 3H) MS m/z 650.3 (M + 1) | N-(4-Chloro-3-{2-[3-methyl-4-(4-methyl-piperazin-1-yl)-phenyl-amino]-5-oxo-7,8-dihydro-5H-pyrido[4,3-d]pyrimidin-6-yl}-phenyl)-3-trifluoromethyl-benzamide | 3 |
| 172 | 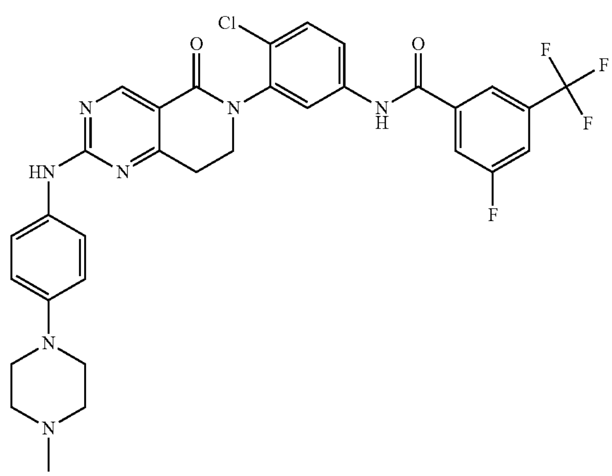 [SMILES: CN1CCN(c2ccc(Nc3ncc4c(n3)CCN(c3cc(NC(=O)c5cc(F)cc(C(F)(F)F)c5)ccc3Cl)C4=O)cc2)CC1] | ¹H NMR (300 MHz, CDCl₃) δ 9.7 (s, 1H), 9.1 (s, 1H), 8.26-8.10 (m, 2H), 7.9-7.7 (m, 3H), 7.65-7.45 (m, 3H), 7.23 (d, 1H), 7.1 (d, 1H), 4.0-3.8 (m, 2H), 3.40-3.05 (m, 10H), 2.34 (s, 3H) MS m/z 655.2 (M + 1) | N-(4-Chloro-3-{2-[4-(4-methyl-piperazin-1-yl)-phenylamino]-5-oxo-7,8-dihydro-5H-pyrido[4,3-d]pyrimidin-6-yl}-phenyl)-3-fluoro-5-trifluoromethyl-benzamide | 3 |

TABLE 1-continued

| No | Structure | Physical Data [¹HNMR and/or MS] | IUPAC NAME | Ex |
|---|---|---|---|---|
| 173 | 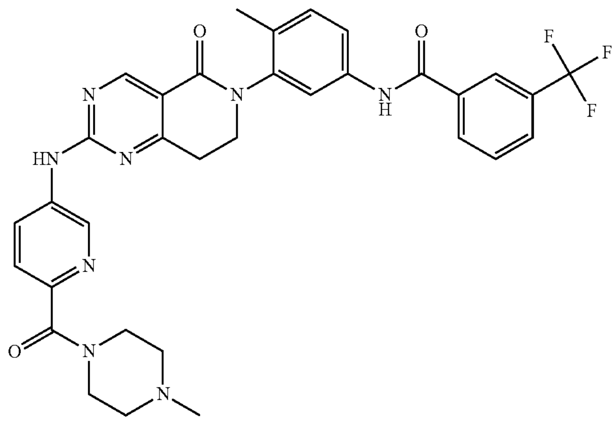 [SMILES: Cc1ccc(NC(=O)c2cccc(C(F)(F)F)c2)cc1N1CCc2nc(Nc3ccc(C(=O)N4CCN(C)CC4)nc3)ncc2C1=O] | ¹H NMR (300 MHz, CDCl₃) δ 10.1 (s, 1H), 9.5 (s, 1H), 8.9 (d, 1H), 8.52 (s, 1H), 7.84 (d, 1H), 7.79-7.70 (m, 3H), 7.64-7.54 (m, 2H), 7.45 (d, 2H), 7.34 (d, 1H), 4.15-4.04 (m, 1H), 3.90-3.80 (m, 5H), 3.35-3.10 (m, 2H), 2.50-2.25 (m, 10H) | N-(4-Methyl-3-{2-[6-(4-methyl-piperazine-1-carbonyl)-pyridin-3-ylamino]-5-oxo-7,8-dihydro-5H-pyrido[4,3-d]pyrimidin-6-yl}-phenyl)-3-trifluoromethyl-benzamide | 4 |
| 174 | 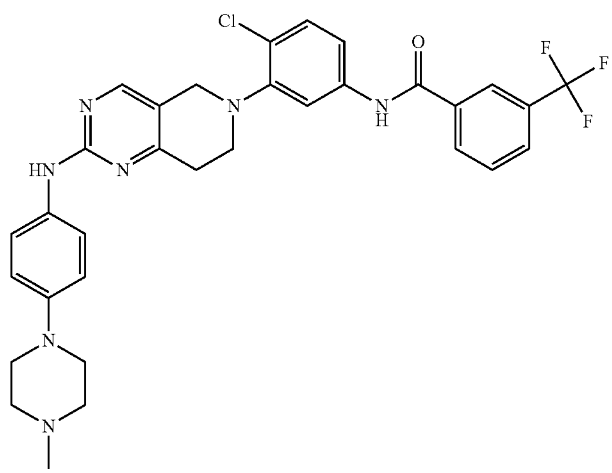 [SMILES: CN1CCN(c2ccc(Nc3ncc4c(n3)CCN(c3cc(NC(=O)c5cccc(C(F)(F)F)c5)ccc3Cl)C4)cc2)CC1] | ¹H NMR (400 Mhz, CD3OD) 8.3-8.18 (m, 3H), 8.0-7.88 (d, 1H), 7.8-7.7 (m, 2H), 7.6-7.4 (m, 4H), 7.1-6.9 (m, 2H), 4.18 (s, 2H), 3.5-3.4 (t, 2H), 3.2-3.14 (t, 4H), 3.05-2.95 (t, 2H), 2.7-2.6 (t, 4H), 2.38 (s, 3H). MS m/z 623.2 (M + 1) | N-(4-Chloro-3-{2-[4-(4-methyl-piperazin-1-yl)-phenylamino]-7,8-dihydro-5H-pyrido[4,3-d]pyrimidin-6-yl}-phenyl)-3-trifluoromethyl-benzamide | 1 |
| 175 | 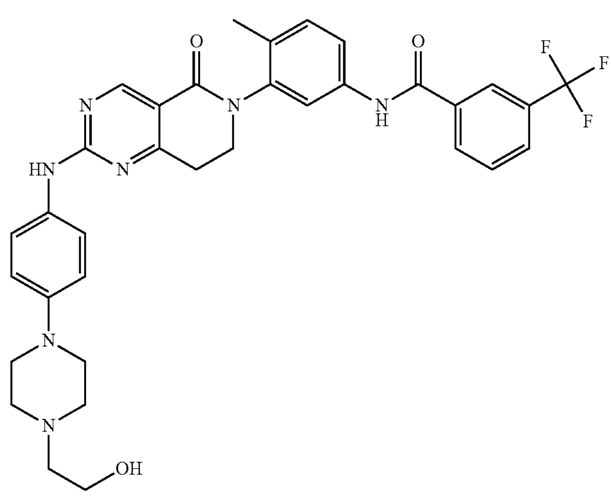 [SMILES: Cc1ccc(NC(=O)c2cccc(C(F)(F)F)c2)cc1N1CCc2nc(Nc3ccc(N4CCN(CCO)CC4)cc3)ncc2C1=O] | ¹H NMR (300 MHz, DMSO-D₆) δ 8.75 (s, 1H), 8.34-8.24 (m, 2H), 8.0 (d, 1H), 7.83-7.56 (m, 5H), 7.32 (d, 1H), 6.92 (d, 2H), 4.45 (t, 2H), 4.05-3.92 (m, 1H), 3.8-3.7 (m, 1H), 3.53 (q, 2H), 3.12-3.04 (m, 6H), 2.5-2.4 (m, 4H), 2.2 (s, 3H) MS m/z 646.1 (M + 1) | N-[3-(2-{4-[4-(2-Hydroxy-ethyl)-piperazin-1-yl]-phenylamino}-5-oxo-7,8-dihydro-5H-pyrido[4,3-d]pyrimidin-6-yl)-4-methyl-phenyl]-3-trifluoromethyl-benzamide | 3 |

| No | Structure | Physical Data [¹HNMR and/or MS] | IUPAC NAME | Ex |
|---|---|---|---|---|
| 176 | 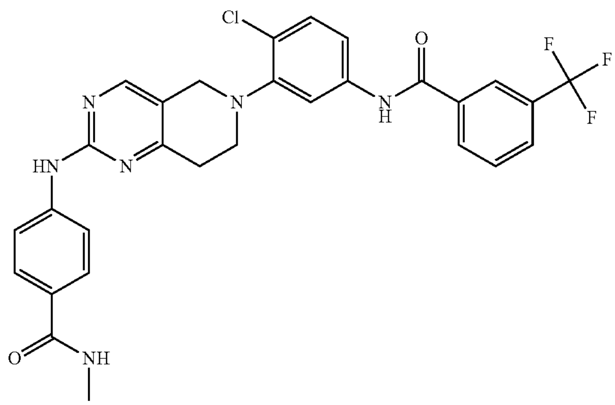 | ¹H NMR (300 MHz, CD3OD) δ 8.4-8.18 (m, 3H), 7.94-7.7 (m, 7H), 7.5-7.4 (m, 2H), 4.22 (s, 2H), 3.5 (t, 2H), 3.12-3.04 (t, 2H), 2.92 (s, 3H) MS m/z 581.2 (M + 1) | N-{4-Chloro-3-[2-(4-methyl-carbamoyl-phenylamino)-7,8-dihydro-5H-pyrido[4,3-d]pyrimidin-6-yl]-phenyl}- -5-trifluoromethyl-benzamide | 2 |
| 177 | 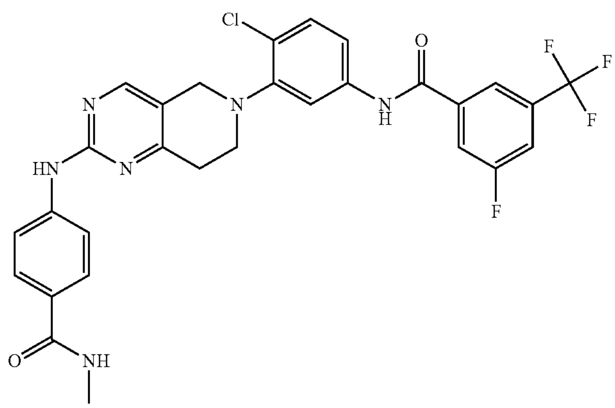 [SMILES: CNC(=O)c1ccc(Nc2ncc3c(n2)CCN(c2cc(NC(=O)c4cc(F)cc(C(F)(F)F)c4)ccc2Cl)C3)cc1] | ¹H NMR (300 MHz, CD3OD δ 10.6 (s, 1H), 9.9 (s, 1H), 8.4 (s, 1H), 8.3-7.94 (m, 4H), 7.9-7.7 (m, 5H), 7.6-7.4 (m, 2H) 4.22 (s, 2H), 3.4 (t, 2H), 3.0 (t, 2H), 2.8-2.7 (d, 3H) MS m/z 599.1 (M + 1) | N-{4-Chloro-3-[2-(4-methyl-carbamoyl-phenylamino)-7,8-dihydro-5H-pyrido[4,3-d]pyrimidin-6-yl]-phenyl}-3-fluoro-5-trifluoromethyl-benzamide | 2 |
| 178 | 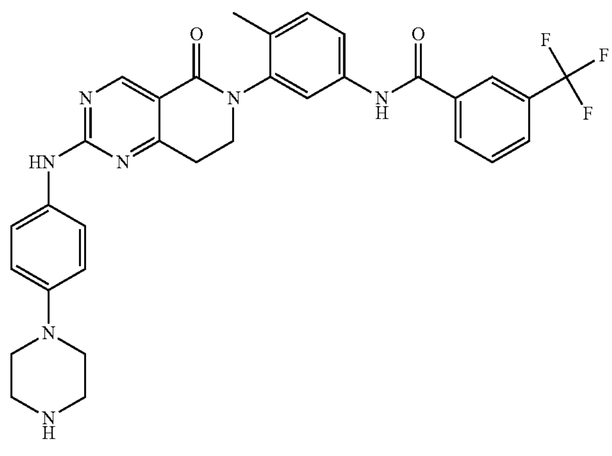 [SMILES: Cc1ccc(NC(=O)c2cccc(C(F)(F)F)c2)cc1N1CCc2nc(Nc3ccc(N4CCNCC4)cc3)ncc2C1=O] | ¹H NMR (300 MHz, CDCl₃) δ 9.15 (s, 1H), 9.04 (s, 1H), 8.25-8.10 (m, 2H) ,7.73 (d, 1H), 7.65-7.50 (m, 4H), 7.42-7.33 (m, 2H), 7.0 (dd, 3H), 4.00-3.87 (m, 1H), 3.80-3.67 (m, 1H), 3.2-3.0 (m, 11H), 1.75 (s, 3H) MS m/z 602.2 (M + 1) | N-{4-Methyl-3-[5-oxo-2-(4-piperazin-1-yl-phenylamino)-7,8-dihydro-5H-pyrido[4,3-d]pyrimidin-6-yl]-phenyl}-3-trifluoromethyl-benzamide | 3 |

TABLE 1-continued

| No | Structure | Physical Data [¹HNMR and/or MS] | IUPAC NAME | Ex |
|---|---|---|---|---|
| 179 | 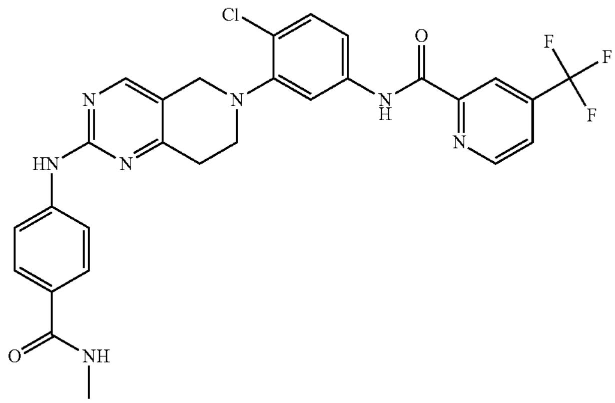 [SMILES: CNC(=O)c1ccc(Nc2ncc3c(n2)CCN(c2cc(NC(=O)c4cc(C(F)(F)F)ccn4)ccc2Cl)C3)cc1] | ¹H NMR (300 MHz, DMSO-D₆) δ 11.0 (s, 1H), 8.9 (s, 1H), 9.05 (d, 1H), 8.42-8.36 (m, 2H), 8.25 (d, 1H), 8.15-8.10 (m, 1H), 7.98 (d, 1H), 7.90-7.82 (m, 2H), 7.80-7.72 (m, 3H), 7.48 (d, 1H), 4.17 (s, 2H), 3.04-2.96 (m, 2H), 2.76 (d, 3H), 2.5 (s, 3H) MS m/z 582.0 (M + 1) | 4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide | 2 |
| 180 | 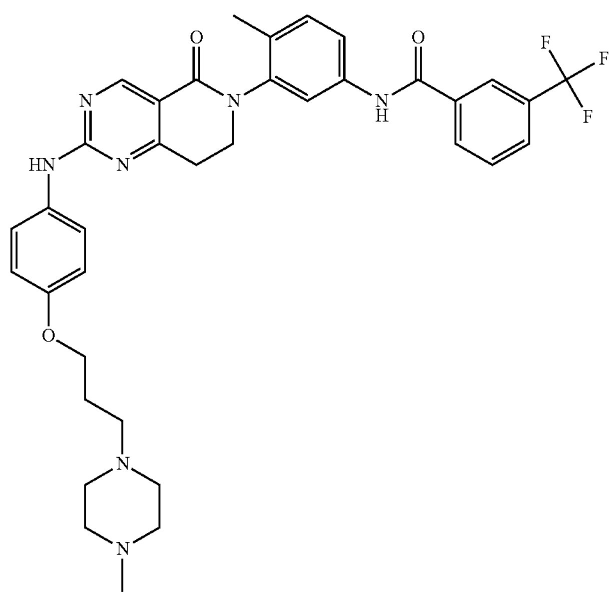 [SMILES: Cc1ccc(NC(=O)c2cccc(C(F)(F)F)c2)cc1N1CCc2nc(Nc3ccc(OCCCN4CCN(C)CC4)cc3)ncc2C1=O] | ¹H NMR (300 MHz, CDCl₃) δ 9.13-9.00 (m, 2H), 8.22-8.10 (m, 2H), 7.75 (d, 1H), 7.65-7.50 (m, 4H), 7.42-7.35 (m, 2H), 7.08 (d, 1H), 6.94 (d, 2H), 4.04 (t, 3H), 3.80-3.68 (m, 1H), 3.16-3.10 (m, 2H), 2.6-2.4 (m, 10H), 2.3 (s, 3H), 2.05-1.92 (m, 2H), 1.8 (s, 3H). MS m/z 674.3 (M + 1) | N-[4-Methyl-3-(2-{4-[3-(4-methyl-piperazin-1-yl)-propoxy]-phenylamino}-5-oxo-7,8-dihydro-5H-pyrido[4,3-d]pyrimidin-6-yl)-phenyl]-3-trifluoromethyl-benzamide | 3 |
| 181 | 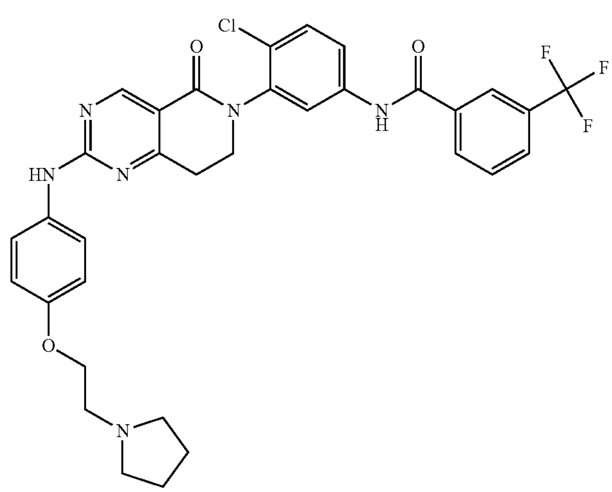 [SMILES: O=C(Nc1ccc(Cl)c(N2CCc3nc(Nc4ccc(OCCN5CCCC5)cc4)ncc3C2=O)c1)c1cccc(C(F)(F)F)c1] | ¹H NMR (400 MHz, CD₃OD) δ 8.9 (s, 1H), 8.30-8.20 (m, 2H), 8.05-7.95 (d, 2H), 7.95-7.9 (m, 1H), 7.8-7.65 (m, 4H), 7.65-7.55 (m, 1H), 7.1-7.00 (m, 2H), 4.35 (t, 2H), 4.1-3.9 (s, 2H), 3.7-3.6 (t, 2H), 3.5-3.4 (bs, 4H), 3.3-3.1 (m, 2H), 2.2-2.1 (m, 4H). | N-(4-Chloro-3-{5-oxo-2-[4-(2-pyrrolidin-1-yl-ethoxy)-phenylamino]-7,8-dihydro-5H-pyrido[4,3-d]pyrimidin-6-yl}-phenyl)-3-trifluoromethyl-benzamide | 3 |

TABLE 1-continued

| No | Structure | Physical Data [¹HNMR and/or MS] | IUPAC NAME | Ex |
|---|---|---|---|---|
| 182 | 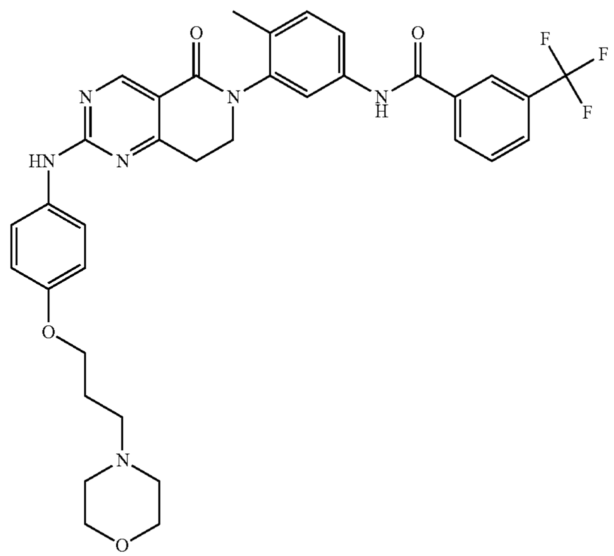 [SMILES: Cc1ccc(NC(=O)c2cccc(C(F)(F)F)c2)cc1N1CCc2nc(Nc3ccc(OCCCN4CCOCC4)cc3)ncc2C1=O] | ¹H NMR (300 MHz, CDCl₃) δ 9.1-9.00 (m, 2H), 8.3-8.10 (m, 2H), 7.75 (d, 1H), 7.65-7.50 (m, 4H), 7.42-7.35 (m, 2H), 7.08 (d, 1H), 6.94 (d, 2H), 4.04 (t, 3H), 3.80-3.68 (m, 1H), 3.16-3.10 (m, 2H), 2.6-2.4 (m, 6H), 2.3 (s, 3H), 2.05-1.92 (m, 2H) MS m/z 661.2 (M + 1) | N-(4-Methyl-3-{2-[4-(3-morpholin-4-yl-propoxy)-phenyl-amino]-5-oxo-7,8-dihydro-5H-pyrido[4,3-d]pyrimidin-6-yl}-phenyl)-3-trifluoromethyl-benzamide | 3 |
| 183 | 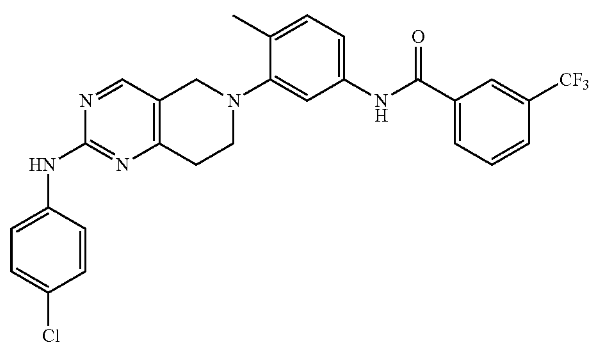 [SMILES: Cc1ccc(NC(=O)c2cccc(C(F)(F)F)c2)cc1N1CCc2nc(Nc3ccc(Cl)cc3)ncc2C1] | ¹H NMR (300 MHz, CD₃OD) δ: 8.26 (s, 1H), 8.19-8.12 (m, 1H), 7.98-7.92 (m, 1H), 7.79-7.74 (m, 1H), 7.72-7.61 (m, 3H), 7.55 (t, 1H), 7.45-7.36 (m, 2H), 7.34-7.25 (m, 2H), 4.11 (s, 2H), 3.4-3.32 (m, 2H), 3.05 (t, 2H), 2.42 (s, 3H) MS: Calculated: m/z 538.1 (M + 1)⁺. | 3-[2-(4-Chloro-phenylamino)-7,8-dihydro-5H-pyrido[4,3-d]pyrimidin-6-yl]-4-methyl-N-(3-trifluoromethyl-phenyl)-benzamide | 5 |
| 184 | 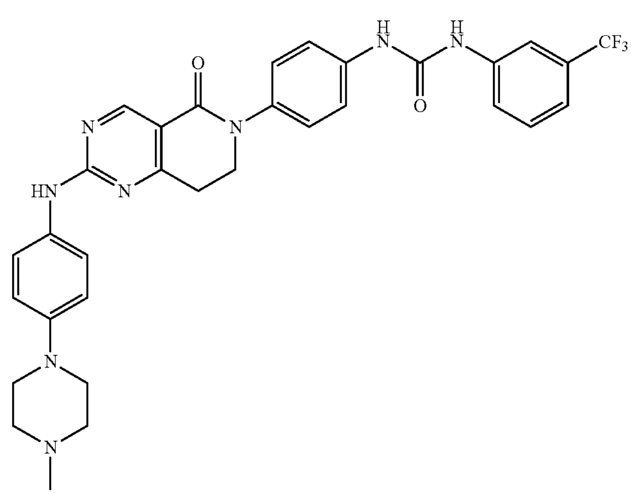 [SMILES: CN1CCN(c2ccc(Nc3ncc4c(n3)CCN(c3ccc(NC(=O)Nc5cccc(C(F)(F)F)c5)cc3)C4=O)cc2)CC1] | ¹H NMR (400 MHz, DMSO-d₆) δ 10.0 (s, 1H), 9.1 (s, 1H), 8.8 (s, 1H), 8.75 (s, 1H), 8.05 (s, 1H), 7.7-7.45 (m, 6H), 7.35-7.25 (m, 3H), 6.95-6.85 (d, 2H), 4-3.9 (t, 2H), 3.22-3.0 (m, 6H), 2.6-2.5 (m, 4H), 2.25 (s, 3H), MS: m/z 617.2.0 (M + 1), | 1-(4-{2-[4-(4-Methyl-piperazin-1-yl)-phenylamino]-5-oxo-7,8-dihydro-5H-pyrido[4,3-d]pyrimidin-6-yl}-phenyl)-3-(3-trifluoromethyl-phenyl)-urea | 8 |

| No | Structure | Physical Data [¹HNMR and/or MS] | IUPAC NAME | Ex |
|---|---|---|---|---|
| 185 | 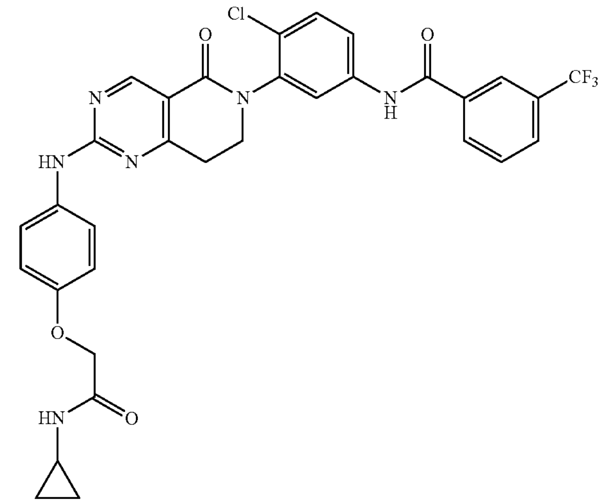 [SMILES: O=C(COc1ccc(Nc2ncc3c(n2)CCN(c2cc(NC(=O)c4cccc(C(F)(F)F)c4)ccc2Cl)C3=O)cc1)NC1CC1] | ¹HNMR: [CDCl₃, 400 MHz] 9.6-9.4 (s, 1H), 9.2-9.0 (s, 1H), 8.3-8.04 (m, 2H), 7.96-7.84 (bs, 1H), 7.84-7.7 (d, 1H), 7.7-7.5 (m, 3H), 7.5-7.38 (m, 2H), 7.28-7.2 (d, 1H), 7.04-6.88 (d, 2H), 6.74-6.6 (bs, 1H) 4.5 (s, 2H), 4-3.75 (m, 2H), 3.35-3 (m, 2H), 2.9-2.7 (m, 1H), 0.95-0.8 (m, 2H), 0.7-0.55 (m, 2H). Mass: 651.00 = [M + 1]⁺ | N-{4-Chloro-3-[2-(4-(cyclopropyl-carbamoylmethoxy)phenylamino)-5-oxo-7,8-dihydro-5H-pyrido[4,3-d]pyrimidin-6-yl]-phenyl}-3-trifluoromethyl-benzamide | 3 |
| 186 | 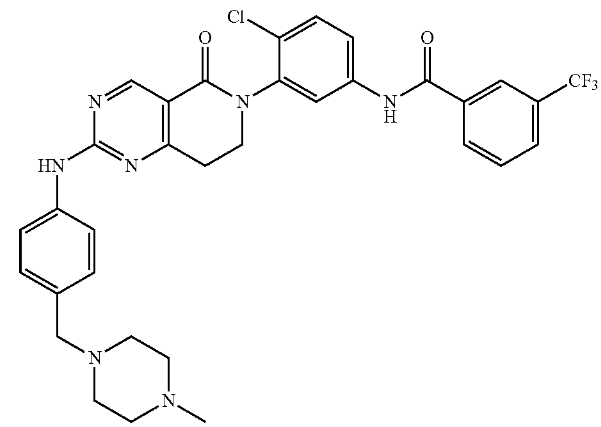 [SMILES: CN1CCN(Cc2ccc(Nc3ncc4c(n3)CCN(c3cc(NC(=O)c5cccc(C(F)(F)F)c5)ccc3Cl)C4=O)cc2)CC1] | ¹H NMR: [DMSO-d₆, 400 MHz] δ 10.7 (s, 1H), 10.2 (s, 1H), 8.82 (s, 1H), 8.38-8.24 (m, 2H), 8.04-7.92 (m, 2H), 7.88-7.78 (m, 2H), 7.78-7.7 (m, 2H), 7.68-7.58 (d, 1H), 7.3-7.2 (d, 2H), 4.05-3.8 (m, 2H), 3.4 (s, 2H), 3.25-3.05 (m, 2H), 2.45-2.1 (m, 11H), Mass: 650.00 = [M + 1]⁺ | N-(4-Chloro-3-{2-[4-(4-methyl-piperazin-1-ylmethyl)-phenylamino]-5-oxo-7,8-dihydro-5H-pyrido[4,3-d]pyrimidin-6-yl}-phenyl)-3-trifluoromethyl-benzamide | 3 |

According to the present invention, pharmaceutically acceptable salts are produced from acidic inorganic or organic compounds, or alkaline inorganic or organic compounds. As used herein, the phrase "pharmaceutically acceptable salt" refers to a salt that retains the biological effectiveness of the free acids and bases of a specified compound and that is not biologically or otherwise undesirable.

A desired salt may be prepared by any suitable method known in the art, including treatment of the free base with an inorganic acid, such as hydrochloric acid, hydrobromic acid, sulphuric acid, nitric acid, phosphoric acid, and the like, or with an organic acid, such as formic acid, acetic acid, maleic acid, succinic acid, mandelic acid, maleic acid, fumaric acid, malonic acid, pyruvic acid, oxalic acid, glycolic acid, salicylic acid; a pyranosidyl acid, such as glucuronic acid or galacturonic acid; an alpha-hydroxy acid, such as citric acid or tartaric acid; an amino acid, such as aspartic acid or glutamic acid; an aromatic acid, such as benzoic acid or cinnamic acid; a sulfonic acid, such as methanesulfonic acid, p-toluenesulfonic acid or ethanesulfonic acid; or the like.

Generally, the salts are prepared by reacting the free base with stoichiometric amounts or with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, symmetrical or asymmetrical ethers containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt from the mixture, or it can be precipitated by the addition of a solvent in which the salt is insoluble and recovered there from.

Examples of suitable inorganic and organic solvents for performing the various reactions include any inorganic or organic solvent that does not adversely affect the reactants or the resulting product, including halogenated solvents such as methylene chloride, chloroform, ether solvents such as diethyl ether, and other solvents such as tetrahydrofuran, dioxane, diglyme, cyclooctane, benzene or toluene, heptane, cyclohexane, aliphatic as well as cycloaliphatic and aromatic hydrocarbon solvents, water, acidified aqueous solutions, mixed organic and inorganic solutions, ethyl acetate, propyl acetate and mixtures thereof.

Also encompassed by the present invention are salts formed from acidic prodrugs, such as phosphates, and alkaline inorganic or organic compounds. Preferred inorganic cations comprised in the salts are lithium, sodium, potassium, rubidium, ammonium, calcium, magnesium, zinc and manganese. Production of phosphate salts are described in e.g. G. R. Pettit et al. *Anti-Cancer Drug Design* 16 (2001) 185-193.

Salts of the present invention also include those formed from acidic prodrugs and organic amines, including, but not limited to, imidazole and morpholine. Alkaline amino acid salts may also be used. The term "amino acids" designates, according to the invention, in particular the [alpha]-amino acids occurring in nature, but moreover also includes their homologues, isomers and derivatives. Enantiomers can be mentioned as an example of isomers. Derivatives can be, for example, amino acids provided with protective groups. Preferred alkaline amino acid are arginine, ornithine, diaminobutyric acid, lysine or hydroxy lysine and especially L-arginine, L-lysine or L-hydroxy lysine; an alkaline dipeptide or a pharmaceutically acceptable alkaline amino acid derivate.

The compounds of the present invention contain at least one chiral centre and therefore may exist in different enantiomeric forms. Although particularly preferred compounds are enantiomerically pure the scope of the present invention is intended to cover both enantiomers per se, as well as mixtures of them in any ratio, such as racemic mixtures.

Enantiomerically pure compounds of the present invention may also be obtained from their racemates by crystallization of their addition salts with chiral acids (D. L. Minor et al. *J. Med. Chem.* 37 (1994) 4317-4328; U.S. Pat. No. 4,349,472), or alternatively, may be isolated by preparative HPLC using commercially available chiral phases. Other routes to the pure enantiomers of compounds of the present invention are the use of asymmetric synthesis (M. J. Munchhof et al. *J. Org. Chem.* 60 (1995) 7086-7087; R. P. Polniaszek et al. *Tetrahedron Letters* 28 (1987) 4511-4514), by asymmetric transfer hydrogenation of the intermediate imines (II) or iminium salts (III) (N. Uematsu et al. *J. Am. Chem. Soc.* 118 (1996) 4916-4917; G. Meuzelaar et al. *Eur. J. Org. Chem.* 1999, 2315-2321), or by resolution of chiral diastereometric derivatives thereof, as known by those skilled in the art.

The invention also encompasses prodrugs of the compounds of the invention. "Prodrug" means a compound which is convertible in vivo by metabolic means (e.g. by hydrolysis, reduction or oxidation) to a compound of formula (I). For example an ester prodrug of a compound of formula I containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula I containing a carboxy group may be convertible by hydrolysis in vivo to the parent molecule. (Examples of ester prodrugs are those described by F. J. Leinweber, Drug Metab. Res., 18:379, 1987).

The invention also encompasses chemical modifications of the parent compounds to prolong their circulating lifetimes. Examples of suitable poly(ethylene glycol) derivatives that possess this property are described in e.g. US 2005171328 (NEKTAR THERAPEUTICS AL CORP) or U.S. Pat. No. 6,713,454 (NOBEX CORP).

The present invention also provides a pharmaceutical composition comprising the compound of the present invention and at least one pharmaceutically acceptable excipient, carrier or diluent.

A pharmaceutical composition of the invention is formulated to be compatible with its intended route of administration, which is preferably the oral administration. For example the pharmaceutical compositions of the invention may be formulated for administration by inhalation, such as aerosols or dry powders; for oral administration, such in the form of tablets, capsules, gels, syrups, suspensions, solutions, powders or granules; for rectal or vaginal administration, such as suppositories; or for parenteral injection (including in-travenous, subcutaneous, intramuscular, intravascular, or infusion) such as a sterile solution, suspension or emulsion.

The compounds of the present invention and their pharmaceutically acceptable salts, where applicable, may be administered in the form of a pharmaceutical composition in which they are in association with a pharmaceutically acceptable excipient, carrier or diluent, in order to treat any STAT3 induced disorders. As to the appropriate excipients, carriers or diluents, reference may be made to the standard literature describing these, for example to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002 (in German).

The compounds of the present invention may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the compounds of the present invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions of the invention will preferably comprise from 0.001 to 50% by weight of compound of the present invention.

The daily dose of the compounds of the present invention will necessarily be varied depending upon the host treated, the particular route of administration, and the severity and kind of the illness being treated. Accordingly the optimum dosage may be determined by the practitioner who is treating any particular patient.

The pharmaceutical compositions can be included in a container, pack, or dispenser together with instructions for administration.

The compounds of the present invention have the unexpected advantage to present either:
  an inhibition for efficient STAT3 blockade following the inhibition of c-Src and JAK2;
  an inhibition of STAT3 phosphorylation by in-cell Western preferably having an $IC_{50} \leq 500$ nM, more preferably $\leq 400$ nM, and even more preferably $\leq 300$ nM, in an established xenograft models using A431 and A549 (STAT3 positive cell lines) an inhibition of growth (>60%) of established tumors at a dose below MTD with a clear dose-response (highest dose close to MTD) and an inhibition of STAT3 phosphorylation in tumors.

The compounds of the invention represent compounds showing a surprisingly good compromise between these 3 criteria. Preferred compounds of the invention are compounds that fulfill at least one, preferably at least two and ideally the three above-listed criteria.

Another advantage of the compounds of the present invention is their low selectivity and inhibition towards JAK3 and/or TYK2. Preferably the inhibition of JAK3 and/or TYK2 is 200 fold less compared to the inhibition towards c-SRC, JAK2 and/or JAK1.

The Src family of kinases ("SFKs") has multiple substrates that lead to diverse biologic effects including changes in proliferation, motility, invasion, survival and angiogenesis. The role of SFKs in the initiation and/or progression of cancer has been demonstrated in colon cancer, pancreatic cancer, breast cancer, non-small cell lung cancer (NSCLC), head and neck squamous cell carcinoma (HNSCC), prostate cancer, other solid tumors, several hematologic malignancies, hepatic cancer, certain B-cell leukemias and lymphomas. Talamonti et al., J. Clin. Invest., 91, 53 (1993); Lutz et al., Biochem. Biophys. Res. 243, 503 (1998); Rosen et al., J. Biol. Chem., 261, 13754 (1986); Bolen et al., Proc. Natl. Acad. Sci. USA, 84, 2251 (1987); Masaki et al., Hepatology, 27, 1257 (1998); Biscardi et al., Adv. Cancer Res., 76, 61 (1999); and Lynch et al., Leukemia, 7, 1416 (1993). The methods and compositions described herein may be used in any one or more cancers or carcinoma disorders.

A "tyrosine kinase" is an enzyme that transfers a phosphate group from ATP to a tyrosine residue in a protein. Tyrosine kinases are a subgroup of the larger class of protein kinases. Fundamentally, a protein kinase is an enzyme that modifies a protein by chemically adding phosphate groups to a hydroxyl or phenolic functional group. Such modification often results in a functional change to the target protein or substrate by altering the enzyme structure, activity, cellular location or association with other proteins. Chemically, the kinase removes a phosphate group from ATP and covalently attaches it to one of three amino acids (serine, threonine or tyrosine) that have a free hydroxyl group. Many kinases act on both serine and threonine, and certain others, tyrosine. There are also a number of kinases that act on all three of these amino acids.

Tyrosine kinases are divided into two groups: cytoplasmic proteins and transmembrane receptor kinases. In humans, there are 32 cytoplasmic protein tyrosine kinases and 48 receptor-linked protein-tyrosine kinases.

Generally, tyrosine kinases play critical roles in signaling between cells. Basically, the activation of cell surface receptors (e.g., the epidermal growth factor (EGF) receptor) by extracellular ligands results in the activation of tyrosine kinases. Then, the tyrosine kinase generates phosphotyrosine residues in the cell. The phosphotyrosine residue acts as a "beacon" and attracts signaling proteins to the receptor via SH2 domains. Hence, one important aspect of the signaling mechanism of a tyrosine kinase is the recognition of the phosphotyrosine by SH2 domains (also referred to herein as Src homology domain 2 or Src homology-2).

Generally, kinases are enzymes known to regulate the majority of cellular pathways, especially pathways involved in signal transduction or the transmission of signals within a cell. Because protein kinases have profound effect on a cell, kinase activity is highly regulated. Kinases can be turned on or off by phosphorylation (sometimes by the kinase itself—cis-phosphorylation/autophosphorylation) and by binding to activator proteins, inhibitor proteins or small molecules.

Deregulated kinase activity is a frequent cause of disease, particularly cancer where kinases regulate many aspect that control cell growth, movement and death. For example, neoplastic transformation in which multiple genetic defects such as translocation, mutations within oncogenes and the like, have been implicated in the development of leukemia. Many of these genetic defects have been identified as key components of signaling pathways responsible for proliferation and differentiation. The Src family of kinases, "SFKs," are also referred to as the transforming (sarcoma inducing) gene of Rous sarcoma virus. SFKs are cytoplasmic proteins with tyrosine-specific protein kinase activity that associates with the cytoplasmic face of the plasma membrane. Silverman L., Sigal C. T., Resh M. D., Binding of pp[delta]Ov-src to Membranes: Evidence for Multiple Membrane Interactions, Biochem Cell Biol 1992 70(10-11):1187-92. There are 9 Src kinases in the human genome: v-Src, c-Src, Fyn, Yes, Fgr, Lyn, Hck, Lck, and Blk. These proteins are all closely related to each other and share the same regulatory mechanism. Brickell, P. M, The p60c-src Family of Protein-Tyrosine Kinases: Structure, Regulation, and Function, Crit. Rev Oncog. 1992; 3(4):401-46. More specifically, Src kinases are 52-62 kD proteins having six distinct functional domains: SH4 (src homology 4), a unique domain, SH3, SH2, SH1 and a C-terminal regulatory region. Brown, M. T., Cooper, J. A., Regulations, Substrates, and Functions of Src, Biochim. Biophys. Acta. 1996, 1287(2-3): 121-49.

The "Src kinases" (herein also referred to as: "Src family of kinases" "Src proteins" and "SFKs") are normally kept off by an autoinhibitory interaction between the phosphotyrosine-binding module (SH2) that is located within the protein before the catalytic kinase domain, and its C-terminal phosphotyrosine (Tyr 527).

Of the various STAT pathways, STAT3 has been identified as a mediator cell proliferation. Inhibition of SFKs does not durably inhibit STAT3. While the SFK inhibitor may initially inhibit STAT3, within a short period of time, STAT3 subsequently re-activates and is expressed. Johnson, F. M., Saigal, B, Talpaz, M. and Donate, N. J., Dasatin[iota]b (BMS-354825) Tyrosine Kinase Inhibitor Suppresses Invasion and Induces Cell Cycle Arrest and Apoptosis of Head and Neck Squamous Cell Carcinoma and Non-Small Cell Lung Cancer Cells, Clin. Cancer Res. 11:6924-6932, 2005.

The STAT (Signal Transducers and Activators of Transcription) proteins are transcription factors specifically activated to regulate gene transcription when cells encounter cytokines and growth factors. STAT proteins act as signal transducers in the cytoplasm and transcription activators in the nucleus. Kisseleva T., Bhattacharya S., Braunstein J., Schindler C. W., Signaling Through the JAKJSTAT Pathway, Recent Advances and Future Challenges, Gene 285: 1-24 (2002). STAT proteins regulate many aspects of cell growth, survival and differentiation. Quadros, M. R., Peruzzi, F., Kari, C, and Rodeck, U., Complex Regulation of Signal Transducers and Activators of Transcription 3 Activation in Normal and Malignant Keratinocytes, Cancer Res, 64: 3934-3939, 2004. The seven mammalian STAT family members identified are: STAT1, STAT2, STAT3, STAT4, STAT5a, STAT5b and STAT6.

STAT3 can be activated by growth factor receptors, cytokine receptors and non-receptor tyrosine kinases (Src or JAK family kinases). As reported, STAT3 activation mediated by EGFR, EPO-R, and IL-6 R via c-Src or JAK2.

The JAK-STAT pathway is negatively regulated on multiple levels. Protein tyrosine phosphatases remove phosphates from cytokine receptors as well as activated STATs Hebenstreit D. et al. (2005) Drug News Perspect. Vol. 18 (4), pages 243-249. More recently, identified Suppressors of Cytokine Signaling (SOCS) inhibit STAT phosphorylation by binding and inhibiting JAKs or competing with STATs for phosphotyrosine binding sites on cytokine receptors. Krebs, L. et al. (2001) Stem Cells Vol. 19, pages 378-387. STATs are also negatively regulated by Protein Inhibitors of Activated STATs (PIAS), which act in the nucleus through several mechanisms. Shuai, K. (2006) Vol. 16 (2), pages 196-202. For example, PIAS1 and PIAS3 inhibit transcriptional activation by STAT1 and STAT3 respectively by binding and blocking access to the DNA sequences they recognize.

The JAK-STAT signaling pathway takes part in the regulation of cellular responses to cytokines and growth factors. Employing Janus kinases (JAKs) and Signal Transducers and Activators of Transcription (STATs), the pathway transduces the signal carried by these extracellular polypeptides to the cell nucleus, where activated STAT proteins modify gene expression. Although STATs were originally discovered as targets of Janus kinases, it is now reported that certain stimuli can activate them independent of JAKs. D W Leaman, S Pisharody, T W Flickinger, M A Commane, J Schlessinger, I M Kerr, D E Levy, and G R Stark Roles of JAKs in Activation of STATs and Stimulation of c-fos Gene Expression by Epidermal Growth Factor, Mol Cell Biol. 1996 16(1): 369-375. This pathway plays a central role in principal cell fate decisions, regulating the processes of cell proliferation, differentiation and apoptosis.

Without being bound to theory, the compounds of the present invention were found to block STAT3 signalling pathway by inhibiting the upstream activators c-SRC and JAK2 involved in the activation of STAT3 by phosphorylation of the residue Tyrosine 705 of STAT3. The compounds of the present invention are also found to be efficient JAK1 inhibitors.

Thus the present invention provides compounds which simultaneously inhibit c-SRC, JAK2 and JAK1. The compounds of the present invention are multi-target inhibitors of c-SRC, JAK2 and JAK1, and more preferably dual inhibitors c-SRC and JAK2.

STAT3 pathway is suggested to have a crucial role in selectively inducing and maintaining a procarcinogenic inflammatory microenvironment, both at the initiation of malignant transformation and during cancer progression. Persistent activation of STAT3 mediates the propagation of tumor-promoting inflammation and increases tumor cell proliferation, survival and invasion while suppressing anti-tumor immunity (Hua Yu et al.; Nature Reviews, Cancer, Volume 9, November 2009, p. 798).

The compounds of the invention for use in therapy are encompassed herein. Preferably the compounds of the invention are used in a method for treating diseases associated with activation of STAT3 pathway, through multi-target inhibition of c-SRC, JAK2 and JAK1, preferably through multi-target inhibition of c-SRC and JAK2.

Another object of the invention is the use of the compound or the pharmaceutical composition of the invention in the manufacture of a medicament for treating or preventing diseases associated with activation of STAT3 pathway, through multi-target inhibition of c-SRC, JAK2 and JAK1, preferably through multi-target inhibition of c-SRC and JAK2.

The present invention further provides a method of treating diseases associated with activation of STAT3 pathway, through multi-target inhibition of c-SRC, JAK2 and JAK1, preferably through multi-target inhibition of c-SRC and JAK2, comprising administering to a subject in need thereof a therapeutically effective amount of the compound of the invention and/or the pharmaceutical composition of the invention.

Preferably the administration is oral, transdermal or parenteral.

Preferably diseases associated with activation of STAT3 pathway are cancer, auto-immune, bone related and hematological diseases.

The cancer is either related to blood tumours or solid tumours. Blood tumours are multiple myeloma, leukaemias (HTLV-1-dependent, Erythroleukaemia, acute myelogenous leukaemia (AML), chronic myelogenous leukaemia (CML), large granular lymphocyte leukaemia (LGL)), myeloproliferative neoplasms and lymphomas (EBV-related/Burkitt's, mycosis fungoides, cutaneous T-cell lymphoma, non-Hodgkins lymphoma (NHL), anaplastic large-cell lymphoma (ALCL)). Solid tumours are breast cancer, head and neck cancer, melanoma, ovarian cancer, lung cancer, pancreatic cancer, colon cancer, uterine cancer, gastric cancer, renal cancer, bladder cancer, liver cancer and prostate cancer.

Alternatively diseases are associated with activation of c-SRC and/or activation of JAK1 and/or JAK2.

According to another particular embodiment of the present invention, when cancer is breast cancer, head and neck cancer, melanoma, ovarian cancer, lung cancer, pancreatic cancer, colon cancer, uterine cancer, gastric cancer, renal cancer, bladder cancer, liver cancer and prostate cancer, the preferred compound used in the method for treating said diseases is selected from the group comprising:

N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide 4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide or a pharmaceutically acceptable salts thereof.

According to a particular embodiment of the present invention, when cancer is multiple myeloma, leukaemias, myeloproliferative neoplasms and lymphomas, the preferred compound used in the method for treating said diseases is selected from the group comprising:

N-(4-Chloro-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide N-{4-Chloro-3-[2-(4-cyclopropylcarbamoylmethoxy-phenylamino)-5-oxo-7,8-dihydro-5H-pyrido[4,3-d]pyrimidin-6-yl]-phenyl}-3-trifluoromethyl-benzamide or a pharmaceutically acceptable salts thereof.

The above listed compounds have a very low distribution volume (Vd in ml/kg) and therefore are more suitable for treating blood tumours since said compounds do not penetrate or weakly penetrate into organs and tissues.

"Treatment" or "treating" refers to both therapeutic treatment and prophylactic or preventative measures. Those in need of treatment include those already with the disorder as well as those in which the disorder is to be prevented. Hence, the subject to be treated herein may have been diagnosed as having the disorder or may be predisposed or susceptible to the disorder.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject or subject who has already undergone a standard cancer therapy, such as standard chemotherapy, standard radiotherapy, targeted therapy or surgery. The term does not denote a particular age or sex. Thus, adult and newborn subjects, whether male or female, are intended to be covered.

The term "therapeutically effective amount" refers to an amount of a drug effective to treat a disease or disorder in a subject. In the case of cancer, the therapeutically effective amount of the drug may reduce the number of cancer cells; reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; inhibit, to some extent, tumour angiogenesis; inhibit, to some extent, in the case of a tumour of epithelial origin (carcinoma) the epithelial to mesenchymal transition; inhibit, to some extent, cancer stem cells growth; increase, to some extent, the immune response against the tumour; and/or relieve to some extent one or more of the symptoms associated with the cancer. To the extent the drug may prevent growth and/or kill existing cancer cells, it may be cytostatic and/or cytotoxic. The phrase "therapeutically effective amount" is used herein to mean an amount sufficient to prevent, or preferably reduce by at least about 30 percent, preferably by at least 50 percent, preferably by at least 70 percent, preferably by at least 80 percent, preferably by at least 90 percent, a clinically significant change in the growth or progression or mitotic activity of a target cellular mass, group of cancer cells or tumour, or other feature of pathology.

Optionally the compounds of the present invention may be used against cell proliferating diseases in combination with conventional treatments such as irradiation and/or one or more chemotherapeutic agents such as Actinomycin, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taxol, Temozolomide, Thiotepa, Tioguanine/Thioguanine, Topotecan, Treosulfan, Vinblastine, Vincristine, Vindesine or Vinorelbine.

Optionally the compounds of the present invention may be used against cell proliferating diseases in combination with other targeted therapies, including other kinase inhibitors.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

The foregoing description will be more fully understood with reference to the following Examples. Such Examples, are, however, exemplary of methods of practicing the present invention and are not intended to limit the scope of the invention.

EXAMPLES

The present invention is further exemplified, but not limited, by the following examples that illustrate the preparation of compounds according to the invention.

The following compounds serve as common building blocks for the general synthetic schemes:

1)

3-Dimethylaminomethylene-1-(2-methyl-5-nitrophenyl)piperidin-4-one [4]

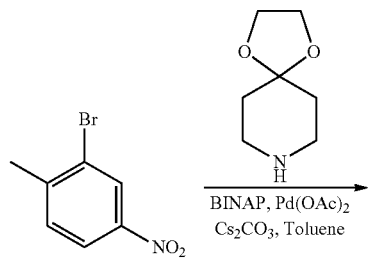

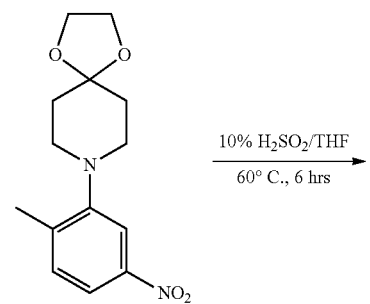

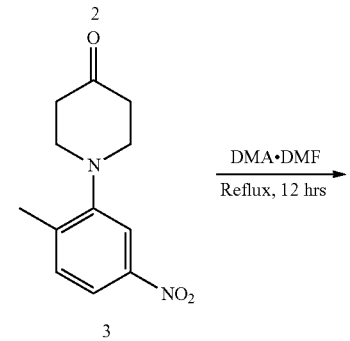

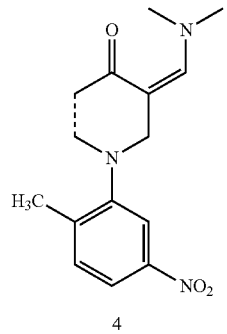

A mixture of 2,2'-Bis(diphenylphosphino)1,1'-binaphthyl [BINAP] (54.35 mg, 0.085 mmol) and Palladium(II)acetate

[Pd(OAc)₂] (6.95 mg, 0.028 mmol) in dry toluene (3 ml) was stirred vigorously and nitrogen was bubbled through the suspension for 30 minutes. To this, 14-Dioxa-8-aza-spiro[4.5]-decane (100 mg, 0.699 mmol), 2-Bromo-1-methyl-4-nitrobenzene (181.29 mg, 0.839 mmol) and dry cesium carbonate (683.5 mg, 2.097 mmol) was added. Nitrogen was bubbled through for another 30 minutes; the mixture was allowed to reflux overnight. The mixture was cooled, diluted with ethyl acetate, water was added and the layers separated. The aqueous layer was extracted with ethyl acetate and the two organic extracts were combined. The organics were washed with brine, then dried (sodium sulfate), filtered and concentrated. Further purification by silica gel chromatography using 5-10% ethyl acetate/hexane as eluent provided 8-(2-Methyl-5-nitro-phenyl)-1,4-dioxa-8-aza-spiro[4.5]decane [2] as a yellow solid [Yield:—193 mg, 82.7%].

To a solution of Methyl-5-nitro-phenyl)-1,4-dioxa-8-aza-spiro[4.5]decane [50 mg, 0.179 mmol] in THF (1 ml) was added, 1 ml of 10% H₂SO₄ (aq). The reaction mixture was heated at 60° C. for 6 hours, and then partitioned between ethyl acetate and water. The aqueous layer was extracted twice further with ethyl acetate and combined organic fractions were washed with water, brine then dried (sodium sulfate), filtered. The filtrate was concentrated to give desired compound i.e., 1-(2-Methyl-5-nitro-phenyl)-piperidin-4-one [3] as brown viscous liquid. [Yield: 37.5 mg, 89.2%] The compound obtained was used in next step without further purification.

A solution of 1-(2-Methyl-5-nitro-phenyl)-piperidin-4-one [100 mg, 0.426 mmol] in N,N-Dimethylformamide dimethyl acetal (DMA.DMF) [1 ml] was heated to reflux for 12 hrs. After cooling to room temperature, reaction mixture was concentrated under vacuum. The dark brown crude product obtained was further purified by silica gel chromatography using 30-60% ethyl acetate/hexane as eluent to obtain pure desired product i.e., 3-Dimethylaminomethylene-1-(2-methyl-5-nitro-phenyl)-piperidin-4-one [4] as orange solid [Yield: 76.2 mg, 62.02%]

¹H NMR (300 MHz, CDCl₃): δ 7.9 (m, 1H), 7.8 (d, 1H), 7.6 (s, 1H), 7.3 (s, 1H), 4.2 (s, 2H), 3.2 (t, 2H), 3.1 (s, 6H), 2.6 (t, 2H), 2.4 (s, 3H)

2)

3-Dimethylaminomethylene-1-(2-methyl-5-nitro-phenyl)-piperidine-2,4-dione [9]

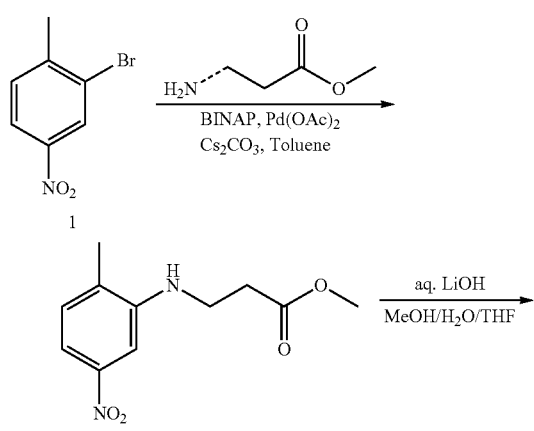

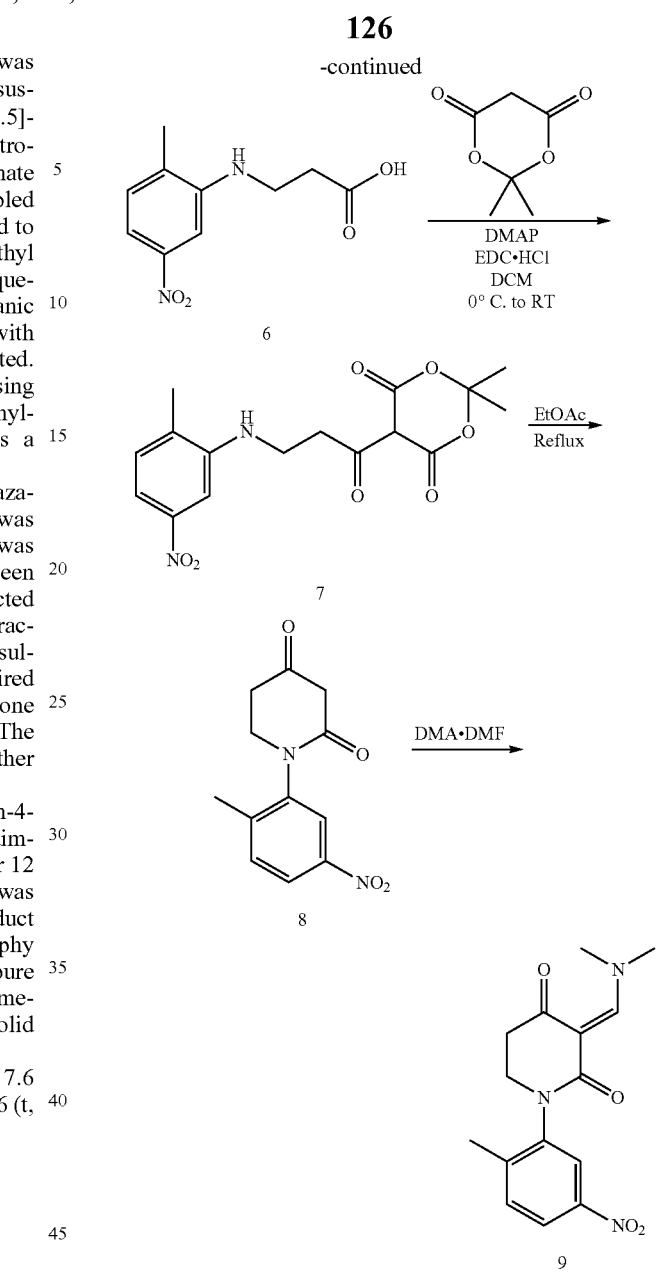

A mixture of 2,2'-Bis(diphenylphosphino)1,1'-binaphthyl [BINAP] (54.35 mg, 0.085 mmol) and Palladium(II)acetate [Pd(OAc)₂] (6.95 mg, 0.028 mmol) in dry toluene (3 ml) was stirred vigorously and nitrogen was bubbled through the suspension for 30 minutes. To this, 3-Amino-propionic acid methyl ester (72.00 mg, 0.699 mmol), 2-Bromo-1-methyl-4-nitrobenzene (181.29 mg, 0.839 mmol) and dry Cesium Carbonate (683.5 mg, 2.097 mmol) were added. Nitrogen was bubbled through for another 30 minutes; the mixture was allowed to reflux overnight. The mixture was cooled, diluted with ethylacetate, water was added and the layers separated. The aqueous layer was extracted with ethyl acetate and the two organic extracts were combined. The organics were washed with brine, then dried (sodium sulfate), filtered and concentrated. Further purification by silica gel chromatography using 5-10% ethyl acetate/hexane as eluent provided 3-(2-Methyl-5-nitro-phenylamino)propionic acid methyl ester [5] as a yellow solid [Yield: 149.00 mg, 74.7%]

A solution of 3-(2-Methyl-5-nitro-phenylamino)propionic acid methyl ester (100 mg, 0.419 mmol] in 3 ml of mixed solvent [1:0.3:0.5 THF/water/methanol] was treated with lithium hydroxide [15.00 mg, 0.628 mmol]. The mixture was stirred at room temperature for 6 hours, concentrated and acidified [pH=2] with 2M HCl. The precipitate obtained was filtered, washed with water and dried under vacuum. The crude material was washed with ether, air dried overnight to give desired product i.e., 3-(2-Methyl-5-nitro-phenyl amino)-propionic acid [6] as yellow colored solid. On the basis of mass recovery (91.2 mg) the yield was assumed to be quantitative.

To a solution of 3-(2-Methyl-5-nitro-phenylamino)-propionic acid [2.95 gm, 13.2 mmol], 2,2-dimethyl-1,3-dioxane-4,6-dione (Meldrum's acid (2.08 gm, 14.5 mmol), and 4-dimethylaminopyridine (DMAP) [2.42 gm, 198 mmol) in anhy. dichloromethane (70 ml) at 0° C. was added 1-(3-dimethylaminopropyl)-3-ethylcarboiimide hydrochloride (EDC.HCl) [3.04 gm, 158 mmol), and the resulting solution was stirred overnight at room temperature. The reaction mixture was washed (50 ml×4) with 5% potassium bisulfate (aq). The organic layer was dried over anhydrous sodium sulfate, filtered and concentrated under vacuum, thereby affording crude 2,2-Dimethyl-5-[3-(2-methyl-5-nitro-phenylamino) propionyl]-[1,3]dioxane-4,6-dione (7), that was dissolved in 60 ml of ethyl acetate and refluxed for 4 hrs, The reaction mixture was cooled to room temperature and concentrated under vacuum. The crude product obtained was further purified by silica gel chromatography (eluent: 2% methanol in chloroform) to give desired produced i.e., 1-(2-Methyl-5-nitro-phenyl)-piperidine-2,4-dione [8] as yellow solid [Yield: 1.91 gm, 58.6%]

A solution of 1-(2-Methyl-5-nitro-phenyl)-piperidine-2,4-dione [100 mg, 0.402 mmol] in N,N-Dimethylformamide dimethyl acetal (DMA.DMF) [1 ml] was heated to reflux for 3 hrs. After cooling to room temperature, reaction mixture was concentrated under vacuum. The crude product obtained was further purified by silica gel chromatography using 30-60% ethylacetate/hexane as eluent to obtain pure desired product i.e., 3-Dimethylaminomethylene-1-(2-methyl-5-nitro-phenyl)-piperidine-2,4-dione [9] as dark red solid [Yield: 79.02 mg, 65.02%]

$^1$H NMR (300 MHz, CD$_3$OD) δ 8.2-7.9 (m, 3H), 7.5-7.34 (d, 1H), 4.0-3.8 (m, 1H), 3.7-3.5 (m, 1H), 3.35 (s, 3H), 3.2 (s, 3H), 2.85-2.65 (m, 2H), 2.35 (s, 3H)

3)

3-(1,4-Dioxa-8-aza-spiro[4.5]dec-8-yl)-4-methyl-benzoic acid [12]

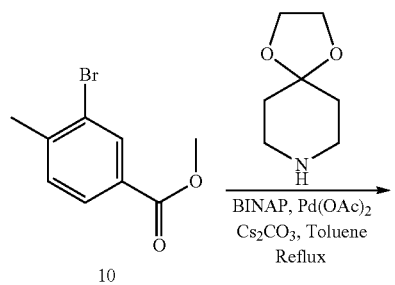

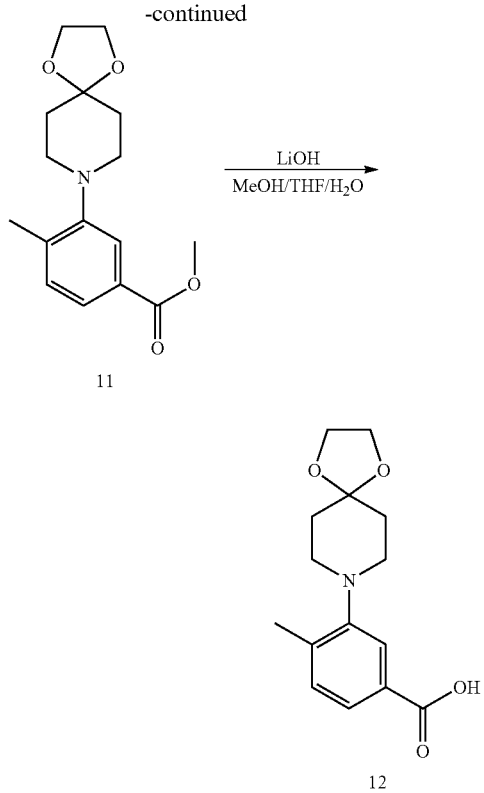

A mixture of 2,2'-Bis(diphenylphosphino)1,1'-binaphthyl [BINAP] (54.35 mg, 0.085 mmol) and Palladium(II)acetate [Pd(OAc)$_2$] (6.95 mg, 0.028 mmol) in dry toluene (3 ml) was stirred vigorously and nitrogen was bubbled through the suspension for 30 minutes. To this, 1,4-Dioxa-8-aza-spiro[4.5]-decane (100 mg, 0.699 mmol), 3-Bromo-4-methyl-benzoic acid methyl ester (192.1 mg, 0.839 mmol) and dry Cesium Carbonate (683.5 mg, 2.09 mmol) was added. Nitrogen was bubbled through for another 30 minutes; the mixture was allowed to reflux overnight. The mixture was cooled, diluted with ethylacetate, water was added and the layers separated. The aqueous layer was extracted with ethyl acetate) and the two organic extracts were combined. The organics were washed with brine, then dried (sodium sulfate), filtered and concentrated. Further purification by silica gel chromatography using 5-10% ethyl acetate/Hexane as eluent provided 3-(1,4-Dioxa-8-aza-spiro[4.5]dec-8-yl)-4-methyl-benzoic acid methyl ester [11] as a yellow solid [150.5 mg, 61.7%]

A solution of 3-(1,4-Dioxa-8-aza-spiro[4.5]dec-8-yl)-4-methyl-benzoic acid methyl ester (100 mg, 0.343 mmol] in 3 ml of mixed solvent [1:0.3:0.5 THF/water/methanol] was treated with lithium hydroxide (12.25 mg, 0.514 mmol]. The reaction mixture was stirred at room temperature for 6 hours, concentrated and acidified [pH=4] with 2M HCl. The precipitate obtained was filtered, washed with water and dried under vacuum. The crude material was washed with ether, air dried overnight to give desired product. i.e., 3-(1,4-Dioxa-8-aza-spiro[4.5]dec-8-yl)-4-methyl-benzoic acid [12] as yellow colored solid. On the basis of mass recovery (93.2 mg) the yield was assumed to be quantitative.

$^1$H NMR (300 MHz, DMSO-d$_6$) δ 12.8 (s, 1H), 7.58-7.50 (m, 2H), 7.3-7.24 (m, 1H), 3.92 (s, 4H), 2.96-2.86 (t, 4H), 2.3 (s, 3H), 1.82-1.74 (m, 2H),

The compounds in the present invention were prepared by general synthetic routes typified by examples 1-10. In Table 1, each compound bears an example number corresponding to the particular synthetic route by which it was prepared.

Example 1

N-{3-[2-(4-Chloro-phenylamino)-7,8-dihydro-5H-pyrido[4,3-d]pyrimidin-6-yl]-4-methyl-phenyl}-3-trifluoromethyl benzamide [13]

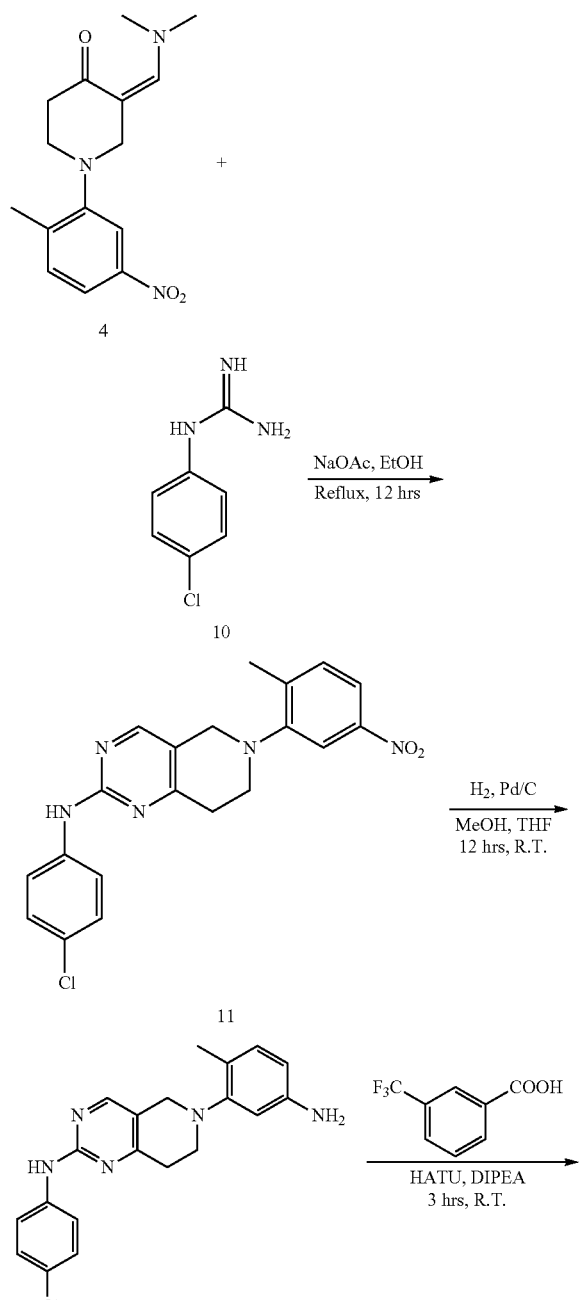

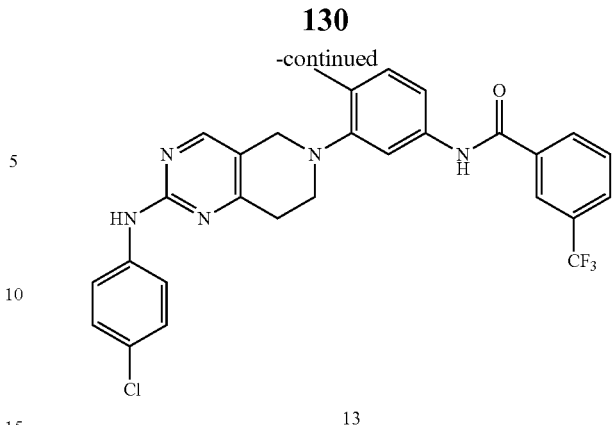

To a solution of 3-Dimethylaminomethylene-1-(2-methyl-5-nitro-phenyl)-piperidin-4-one (12.06 gm, 41.7 mmol)[as prepared in reference 1] in Ethanol (250 ml) were added N-(4-Chloro-phenyl)-guanidine (28.32 gm, 167 mmol) and sodium acetate (27.32 gm, 334 mmol) and solution was heated under reflux for 12 hours. After cooling to room temperature, the reaction mixture was diluted with water, extracted with ethyl acetate. The organic layer was washed with brine, dried [sodium sulfate] and concentrated under vacuum. The crude product obtained was further purified by silica gel chromatography using 5-10% Methanol/Chloroform as eluent to give pure desired product [11]i.e., (4-Chloro-phenyl)-[6-(2-methyl-5-nitro-phenyl)-5,6,7,8-tetrahydro-pyrido[4,3-d]pyrimidin-2-yl]-amine as yellow solid. (Yield: 2.50 gm, 15.2%)

To a solution of (4-Chloro-phenyl)-[6-(2-methyl-5-nitro-phenyl)-5,6,7,8-tetrahydro-pyrido[4,3-d]pyrimidin-2-yl] amine (100 mg, 0.25 mmol) in the mixed solvent of THF (5 ml) and methanol (5 ml) was added 10% Pd/C, and the reaction mixture was stirred for 12 hours at room temperature under a hydrogen balloon. The reaction mixture was filtered and the filtrate was concentrated under vacuum to give [6-(5-Amino-2-methyl-phenyl)-5,6,7,8-tetrahydro-pyrido[4,3-d]pyrimidin-2-yl]-(4-chloro-phenyl)amine [12]as a off white solid [Yield: 81.5 mg, 88.2%]

To a solution of [6-(5-Amino-2-methyl-phenyl)-5,6,7,8-tetrahydro-pyrido[4,3-d]pyrimidin-2-yl]-(4-chloro-phenyl) amine (54.87 mg, 0.15 mmol), 3-Trifluoromethylbenzoic acid (28.51 mg, 0.15 mmol), and Diisipropylethylamine (DIPEA)(78 µl, 0.45 mmol) in DMF (7.5 ml) was added 2-(7-Aza-1H-benzotriazole-1-yl)-1,1,3,3-tetramethyluronium hexafluorophosphate (HATU) (59 mg, 0.15 mmol) and the reaction mixture is stirred for 3 hour at room temperature. The reaction mixture was diluted with ethyl acetate and washed with 5% aqueous sodium bisulphate solution, saturated aqueous sodium bicarbonate solution and brine. The organic layer is dried over sodium sulphate and concentrated under reduced pressure. The crude product obtained was purified by column chromatography (SiO$_2$, 2-10% methanol in chloroform to give of N-{3-[2-(4-chlorophenylamino)-7,8-dihydro-5H-pyrido[4,3-d]pyrimidin-6-yl]-4-methyl-phenyl}-3-trifluoromethylbenzamide [13] as a pale yellow solid. [Yield: 60.6 mg, 75.2%]

$^1$H NMR (300 MHz, CDCl$_3$) δ 8.22 (s, 1H), 8.13 (s, 1H), 8.06 (d, 1H), 7.84-7.78 (m, 1H), 7.75-7.7 (br s, 1H), 7.68-7.6 (m, 3H), 7.34-7.27 (m, 2H), 7.24-7.19 (m, 1H), 7.15-7.08 (m, 1H), 4.06 (s, 2H), 3.35-3.26 (m, 2H), 3.18-3.09 (m, 2H), 2.3 (s, 3H)

MS: m/z 538.1 (M+1)$^+$

Example 2

N-{4-Methyl-3-[2-(pyrimidin-5-ylamino)-7,8-dihydro-5H-pyrido[4,3-d]pyrimidin-6-yl]-phenyl}-3-trifluoromethylbenzamide [17]

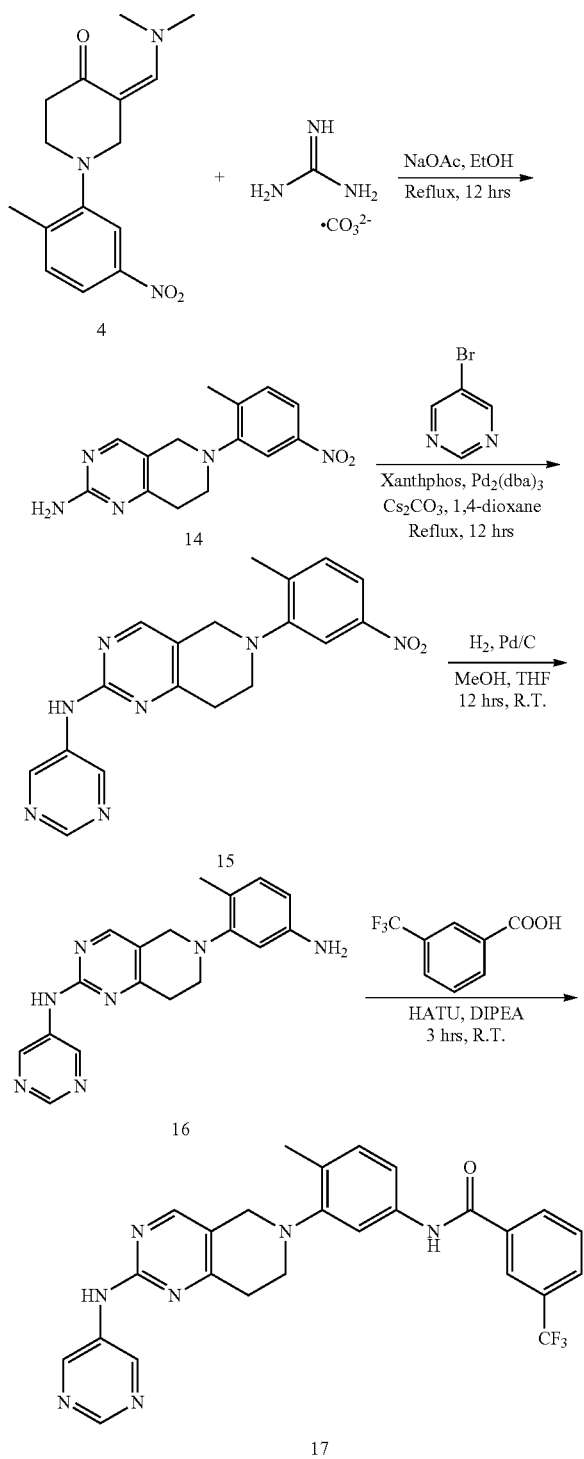

To a solution of 3-Dimethylaminomethylene-1-(2-methyl-5-nitro-phenyl)-piperidin-4-one (12.06 gm, 41.7 mmol)[as prepared in reference 1] in Ethanol (250 ml) were added guanidine carbonate (30.17 gm, 167 mmol) and sodium acetate (27.40 gm, 334 mmol). The reaction mixture was heated under reflux for 12 hours. After cooling to room temperature, the reaction mixture was diluted with water, extracted with ethyl acetate. The organic layer was washed with brine, dried [sodium sulfate] and evaporated. The crude product obtained was purified by silica gel chromatography using 2-5% Methanol/Chloroform as eluent to give pure desired product i.e., 6-(2-Methyl-5-nitro-phenyl)-5,6,7,8-tetrahydro pyrido[4,3-d]pyrimidin-2-ylamine [14]as yellow solid. (Yield: 3.00 gm, 25.2%)

A mixture of 4,5 Bis(diphenyl-phosphino)-9,9-dimethylxanthene [xanthopos](8.6 mg, 0.01488 mmol) and Tris(dibenzylideneacetone)di-palladium(0)[$Pd_2(dba)_3$](6.81 mg, 0.00744 mmol) in dry 1,4-dioxane (5 ml) was stirred vigorously and nitrogen was bubbled through the suspension for 30 minutes. 5-Bromo pyrimidine (19.7 mg, 0.1247 mmol), 6-(2-Methyl-5-nitro-phenyl)-5,6,7,8-tetrahydro-pyrido[4,3-d]pyrimidin-2-ylamine (35.57 mg, 0.1247 mmol) and dry cesium carbonate (100 mg, 0.31 mmol) was added. Nitrogen was bubbled through for another 30 minutes; the mixture was allowed to reflux overnight. The mixture was cooled, diluted with ethylacetate, water was added and the layers were separated. The aqueous layer was extracted with ethyl acetate and the two organic extracts were combined. The organics were washed with brine, then dried (sodium sulfate), filtered and concentrated under vacuum. Further purification by silica gel chromatography using 5-10% ethyl acetate/hexane as eluent provided [6-(2-Methyl-5-nitro-phenyl)-5,6,7,8-tetrahydro-pyrido[4,3-d]pyrimidin-2-yl]-pyrimidin-5-yl-amine [15] as a yellow solid [Yield: 9.75 mg, 21.7%]

To a solution of [6-(2-Methyl-5-nitro-phenyl)-5,6,7,8-tetrahydro-pyrido[4,3-d]pyrimidin-2-yl]-pyrimidin-5-yl-amine (100 mg, 0.275 mmol] in the mixed solvent of THF (3 ml) and methanol (3 ml) was added 10% Pd/C, and the reaction mixture was stirred for 12 hours at room temperature under a hydrogen balloon. The reaction mixture is filtered and the filtrate was concentrated under vacuum to give [6-(5-Amino-2-methyl-phenyl)-5,6,7,8-tetrahydro-pyrido[4,3-d]pyrimidin-2-yl]-pyrimidin-5-yl-amine [16] (Yield: 84.2 mg 92.2%) as a off white solid.

To a solution of [6-(5-Amino-2-methyl-phenyl)-5,6,7,8-tetrahydro-pyrido[4,3-d]pyrimidin-2-yl]-pyrimidin-5-yl-amine (50.0 mg, 0.15 mmol), 3-Trifluoromethylbenzoic acid (28.5 mg, 0.15 mmol), and DIPEA (78 µl, 0.45 mmol) in DMF was added HATU (59 mg, 0.15 mmol), and the reaction mixture was stirred for 3 hour at room temperature. The reaction mixture is diluted with ethyl acetate and washed with 5% aqueous sodium bisulphate solution, saturated aqueous sodium bicarbonate solution and brine. The organic layer is dried over sodium sulphate and concentrated under reduced pressure. The crude product obtained was purified by column chromatography ($SiO_2$, 2-10% methanol in chloroform) to give 49.75 mg (65.6%) of N-{4-Methyl-3-[2-(pyrimidin-5-ylamino)-7,8-dihydro-5H-pyrido[4,3-d]pyrimidin-6-yl]-phenyl}-3-trifluoromethyl benzamide [17] as a pale yellow solid.

$^1$H NMR (300 MHz, $CDCl_3$) δ 9.2-9.0 (m, 2H), 8.9 (s, 1H), 8.3-8 (m, 2H), 7.95-7.5 (m, 4H), 7.3-77 (m, 4H), 4.1 (s, 2H), 3.4-3.2 (t, 2H), 3.15-2.95 (t, 2H), 2.3 (s, 3H).

MS: m/z 506.4 $(M+1)^+$

Example 3

N-(4-Methyl-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide. [20]

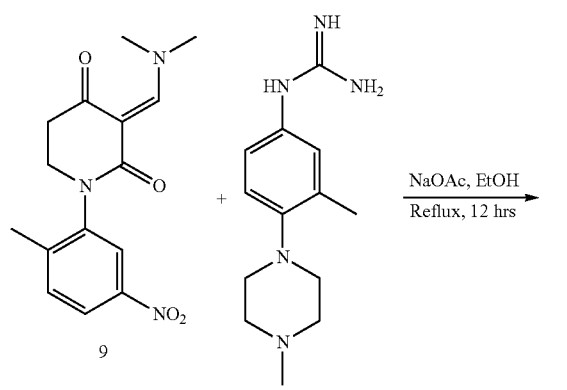

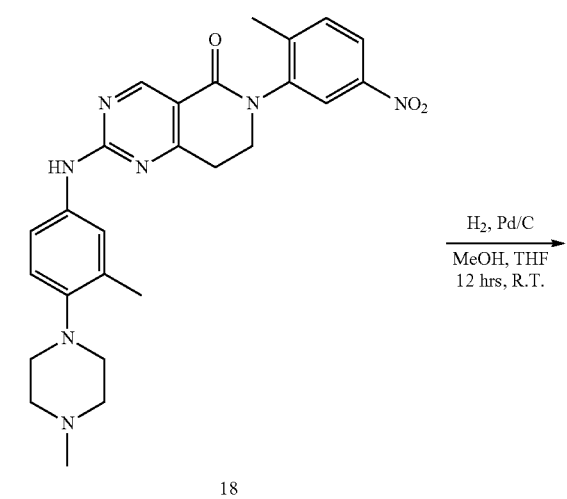

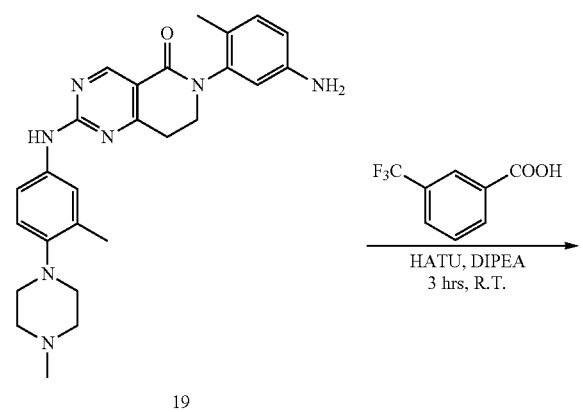

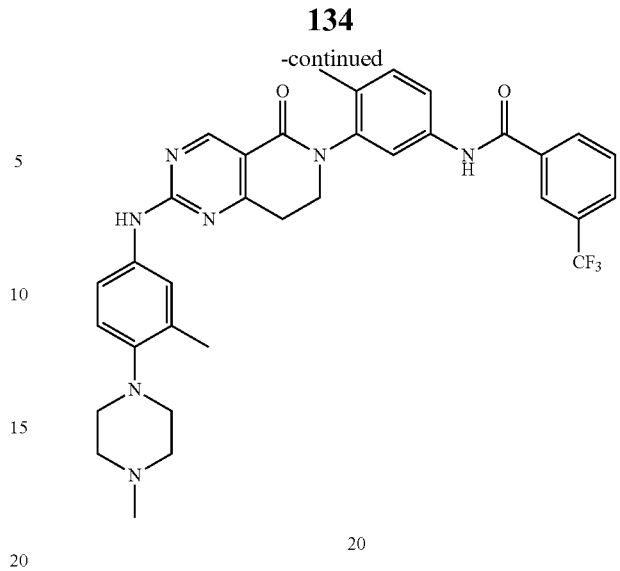

To a solution of 3-Dimethylaminomethylene-1-(2-methyl-5-nitro-phenyl)-piperidine-2,4-dione [9], (12.6 gm, 41.7 mmol)[as prepared in reference 2] in Ethanol (250 ml) were N-[3-Methyl-4-(4-methyl-piperazin-1-yl)-phenyl]-guanidine (43.9 gm 167 mmol) and sodium acetate (27.38 gm, 334 mmol) and solution was heated under reflux for 12 hours. After cooling to room temperature, the reaction mixture was diluted with water, extracted with ethyl acetate. The organic layer was washed with brine and dried over sodium sulfate and evaporated. The crude product obtained was purified by silica gel chromatography using 5-10% Methanol/Chloroform as eluent to give pure desired product i.e., 2-[3-methyl-4-(4-methyl-piperazin-1-yl)-phenylamino]-6-(2-methyl-5-nitro-phenyl)-7,8-dihydro-6H-pyrido[4,3-d]pyrimidin-5-one [18] as solid. (Yield: 3.09 gm, 14.8%)

To a solution of 2-[3-Methyl-4-(4-methyl-piperazin-1-yl)-phenylamino]-6-(2-methyl-5-nitro-phenyl)-7,8-dihydro-6H-pyrido[4,3-d]pyrimidin-5-one (100 mg, 0.198 mmol) in the mixed solvent of THF (5 ml) and methanol (5 ml) was added 10% Pd/C, and the reaction mixture was stirred for 12 hours at room temperature under a hydrogen balloon. The reaction mixture was filtered and the filtrate was concentrated under vacuum to give 6-(5-Amino-2-methyl-phenyl)-2-[3-methyl-4-(4-methyl-piperazin-1-yl)-phenylamino]-7,8-dihydro-6H-pyrido[4,3-d]pyrimidin-5-one [19] (Yield: 81.72 mg, 86.9%) as a off white solid.

To a solution of 6-(5-Amino-2-methyl-phenyl)-2-[3-methyl-4-(4-methyl-piperazin-1-yl)-phenylamino]-7,8-dihydro-6H-pyrido[4,3-d]pyrimidin-5-one (71.0 mg, 0.15 mmol), 3-Trifluoro-methylbenzoic acid (28.5 mg, 0.15 mmol), and DIPEA (78 µl, 0.45 mmol) in DMF was added HATU (59 mg, 0.15 mmol), and the reaction mixture was stirred for 3 hour at room temperature. The reaction mixture was diluted with ethyl acetate and washed with 5% aqueous sodium bisulphate solution, saturated aqueous sodium bicarbonate solution and brine. The organic layer was dried over sodium sulphate and concentrated under reduced pressure. The crude product obtained was purified by column chromatography (SiO$_2$, 2-10% methanol in chloroform) to give 71.7 mg (74.2%) N-(3-{2-[4-(2-Methoxy-4-methyl-piperazin-1-yl)-phenylamino]-5-oxo-7,8-dihydro-5H-pyrido[4,3-d]pyrimidin-6-yl}-4-methyl-phenyl)-3-trifluoromethyl-benzamide [20] as a pale yellow solid.

$^1$H NMR (300 MHz, CD$_3$OD) δ 8.76 (s, 1H), 8.25-8.04 (m, 3H), 8.06 (d, 1H), 7.82-7.6 (m, 3H), 7.56-7.4 (m, 3H), 7.2-7.35 (d, 1H), 7.05-6.92 (d, 1H), 4.1-3.92 (m, 1H), 3.1-2.9 (m, 6H), 2.6 (s, 3H), 2.25 (s, 3H), 2.15 (s, 3H)

MS: m/z 630.5 (M+1)$^+$,

Example 4
N-(4-Methyl-3-{2-[4-(4-methyl-piperazine-1-carbonyl)-phenylamino]-5-oxo-7,8-dihydro-5H-pyrido[4,3-d]pyrimidin-6-yl}-phenyl)-3-trifluoromethylbenzamide [24]
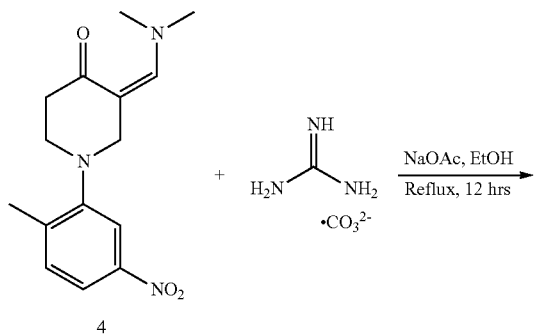
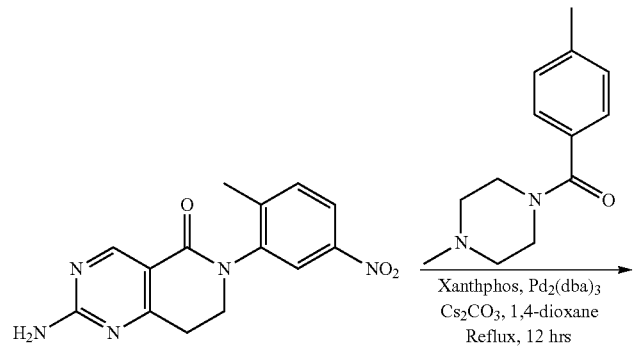
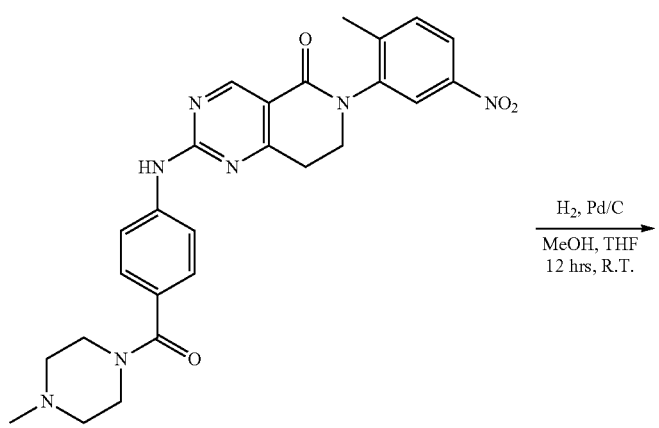

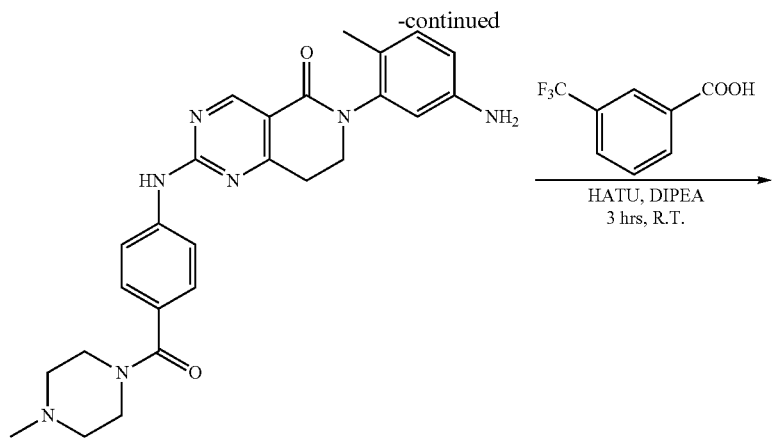

23

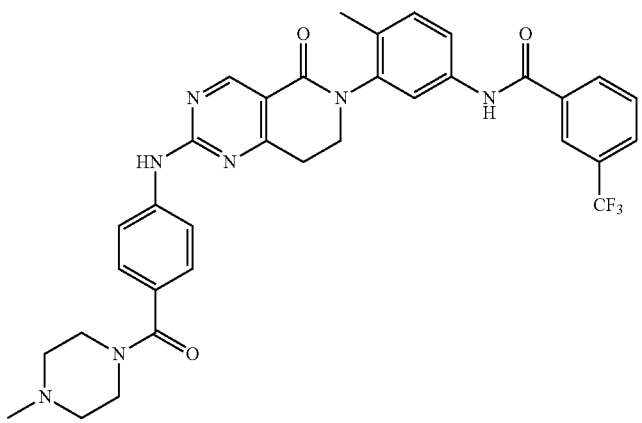

24

To a solution of 3-Dimethylaminomethylene-1-(2-methyl-5-nitro-phenyl)-piperidine-2,4-dione, (12.6 gm, 41.7 mmol) [as prepared in reference 2] in Ethanol (250 ml) were added guanidine carbonate (30.17 gm, 167 mmol) and sodium acetate (27.40 gm, 334 mmol) and solution was heated under reflux for 12 hours. After cooling to room temperature, the reaction mixture was diluted with water, extracted with ethyl acetate. The organic layer was washed with brine, dried [sodium sulfate] and evaporated. The crude product obtained was purified by silica gel chromatography using 2-5% methanol/chloroform as eluent to give pure desired product i.e., 2-Amino-6-(2-methyl-5-nitro-phenyl)-7,8-dihydro-6H-pyrido[4,3-d]pyrimidin-5-one [21] as solid. [yield: 2.63 gm, 21.2%]

A mixture of 4,5-Bis(diphenylphos-phino)-9,9-dimethylxanthene (xanthopos) (8.6 mg, 0.0148 mmol) and Tris(dibenzylideneacetone)dipalladium(0)[Pd$_2$(dba)$_3$] (6.81 mg, 0.0074 mmol) in dry 1,4-dioxane (5 ml) was stirred vigorously and nitrogen was bubbled through the suspension for 30 minutes. (4-Iodo-phenyl)-(4-methyl-piperazin-1-yl)-methanone (41.1 mg, 0.1247 mmol), 2-Amino-6-(2-methyl-5-nitro-phenyl)-7,8-dihydro-6H-pyrido[4,3-d]pyrimidin-5-one (37.3 mg, 0.1247 mmol) and dry cesium carbonate (100 mg, 0.31 mmol) was added. Nitrogen was bubbled through for another 30 minutes; the mixture was allowed to reflux overnight. The mixture was cooled, diluted with ethylacetate, water was added and the layers were separated. The aqueous layer was extracted with ethyl acetate and the two organic extracts were combined. The organics were washed with brine, then dried (sodium sulfate), filtered and concentrated. Silica gel chromatography using 5-10% ethyl acetate/hexane as eluent provided 6-(2-Methyl-5-nitro-phenyl)-2-[4-(4-methyl-piperazine-1-carbonyl)phenylamino]-7,8-dihydro-6H-pyrido[4,3-d]pyrimidin-5-one [22] as a yellow solid [Yield: 12.3 mg, 19.7%]

To a solution of 6-(2-Methyl-5-nitro-phenyl)-2-[4-(4-methyl-piperazine-1-carbonyl)phenylamino]-7,8-dihydro-6H-pyrido[4,3-d]pyrimidin-5-one (100 mg, 0.199 mmol) in the mixed solvent of THF (3 ml) and methanol (3 ml) was added 10% Pd/C, and the reaction mixture was stirred for 12 hours at room temperature under a hydrogen balloon. The reaction mixture was filtered and the filtrate was concentrated under vacuum to give 6-(5-Amino-2-methyl-phenyl)-2-[4-(4-methyl-piperazine-1-carbonyl)-phenylamino]-7,8-dihydro-6H-pyrido[4,3-d]pyrimidin-5-one [23] as a offwhite solid [Yield: 83.0 mg, 88.3%]

To a solution of 6-(5-Amino-2-methyl-phenyl)-2-[4-(4-methyl-piperazine-1-carbonyl)phenylamino]-7,8-dihydro-6H-pyrido[4,3-d]pyrimidin-5-one (70.7 mg, 0.15 mmol), 3-Trifluoromethyl benzoic acid (28.5 mg, 0.15 mmol), and DIPEA (78 µl, 0.45 mmol) in DMF was added HATU (59 mg, 0.15 mmol), and the reaction mixture was stirred for 3 hour at room temperature. The reaction mixture was diluted with ethylacetate and washed with 5% aqueous sodium bisulphate solution, saturated aqueous sodium bicarbonate solution and brine. The organic layer was dried over sodium sulphate and concentrated under reduced pressure. The crude product obtained was purified by column chromatography (SiO$_2$, 2-10% methanol in chloroform) to give 69.8 mg (72.3%) of N-(4-Methyl-3-{2-[4-(4-methyl-piperazine-1-carbonyl)phenylamino]-5-oxo-7,8-dihydro-5H-pyrido[4,3-d]pyrimidin-6-yl}-phenyl)-3-trifluoromethyl-benzamide [24] as a pale yellow solid.

$^1$H NMR (300 MHz, CD$_3$OD) δ 8.9 (s, 1H), 8.25-8.4 (m, 2H), 8.06 (d, 1H), 7.82-7.9 (m, 3H), 7.6-7.8 (m, 3H), 7.25-7.35 (dd, 3H), 4.05-4.15 (m, 2H), 3.6-3.92 (m, 6H), 2.5 (m, 4H), 2.2-2.4 (m, 6H).

MS: m/z 644.30 (M+1)$^+$,

Example 5

3-[2-(4-Chloro-phenylamino)-7,8-dihydro-5H-pyrido[4,3-d]pyrimidin-6-yl]-4-methyl-N-(3-trifluoromethylphenyl)benzamide. [28]

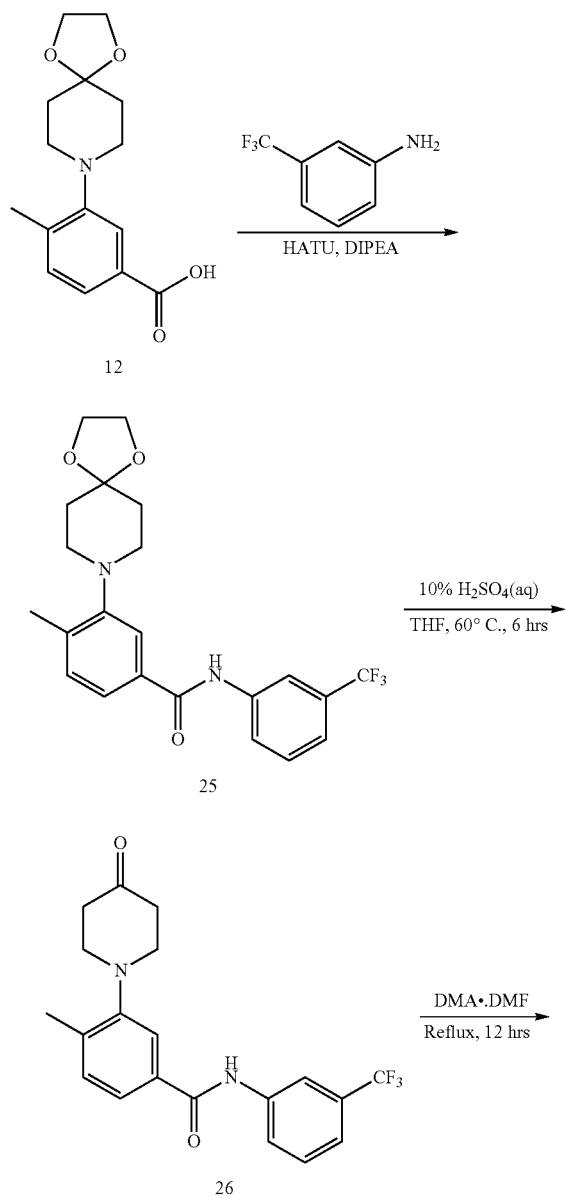

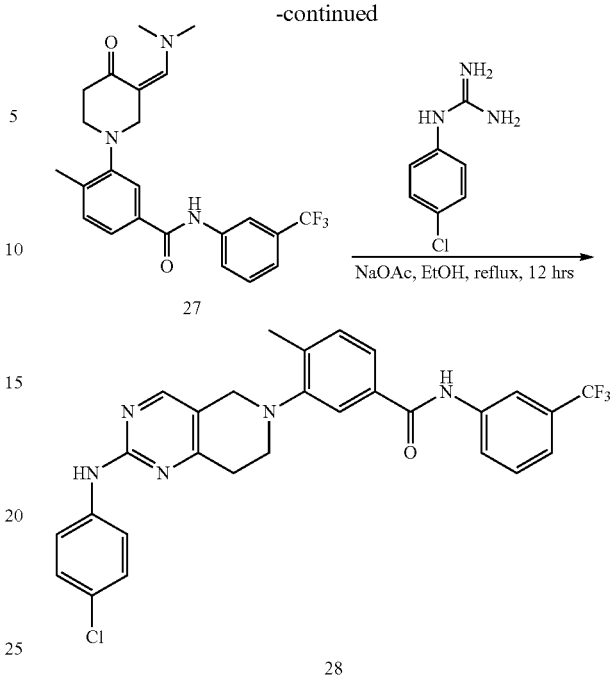

To a solution of 3-Trifluoromethyl-phenylamine (24.1 mg, 0.15 mmol), 3-(1,4-Dioxa-8-aza-spiro[4.5]dec-8-yl)-4-methyl-benzoic acid [as prepared in reference 3] (41.5 mg, 0.15, and DIPEA (78 μl, 0.45 mmol) in DMF was added HATU (59 mg, 0.15 mmol), and the reaction mixture was stirred for 3 hour at room temperature. The reaction mixture was diluted with ethyl acetate and washed with 5% aqueous sodium bisulphate solution, saturated aqueous sodium bicarbonate solution and brine. The organic layer was dried over sodium sulphate and concentrated under reduced pressure. The crude product obtained was purified by column chromatography (SiO$_2$, 2-10% methanol in chloroform) to give 43.1 mg (68.6%) of 3-(1,4-Dioxa-8-aza-spiro[4.5]dec-8-yl)-4-methyl-N-(3-trifluoromethyl-phenyl)-benzamide [25] as a pale yellow solid.

To a solution 3-(1,4-Dioxa-8-aza-spiro[4.5]dec-8-yl)-4-methyl-N-(3-trifluoromethyl-phenyl)-benzamide [100 mg, 0.237 mmol] in THF (2 ml) was added, 3 ml of 10% aqueous H$_2$SO$_4$. The reaction mixture was heated at 60° C. for 6 hours, then partitioned between ethylacetate and water. The aqueous layer was extracted twice further with ethyl acetate and combined organic fractions were washed with water, brine then dried (sodium sulfate), filtered and concentrated to give desired compound i.e., 4-Methyl-3-(4-oxo-piperidin-1-yl)-N-(3-trifluoromethyl-phenyl)-benzamide [26] as brown viscous liquid. [Yield: 76.6 mg, 85.6%]. The compound obtained was used in next step without further purification A solution of 4-Methyl-3-(4-oxo-piperidin-1-yl)-N-(3-trifluoromethyl-phenyl)-benzamide [100 mg, 0.2656 mmol] in DMA.DMF [1 ml] was heated to reflux for 3 hrs. After cooling to room temperature, reaction mixture was concentrated under vacuum to give crude product. The crude product obtained was further purified by silica gel chromatography using 30-60% ethylacetate/hexane as eluent to obtain pure desired product i.e., 3-(3-Dimethylaminomethylene-4-oxo-piperidin-1-yl)-4-methyl-N-(3-trifluoromethyl-phenyl)-benzamide [27]_as brown solid [Yield: 13.7 mg, 12.02%]

To a solution of 3-(3-Dimethylamino-methylene-4-oxo-piperidin-1-yl)-4-methyl-N-(3-trifluoromethyl-phenyl)benzamide (17.9 gm, 41.7 mmol) in Ethanol (250 ml) were added N-(4-Chloro-phenyl)-guanidine (28.32 gm, 167 mmol) and sodium acetate (27.32 gm, 334 mmol) and solution was heated under reflux for 12 hours. After cooling to room temperature, the reaction mixture was diluted with water, extracted with ethyl acetate. The organic layer was washed with brine and dried [sodium sulfate] and evaporated. The crude product obtained was purified by silica gel chromatography using 5-10% methanol/chloroform as eluent to give pure desired product i.e., 3-[2-(4-Chloro-phenylamino)-7,8-dihydro-5H-pyrido[4,3-d]pyrimidin-6-yl]-4-methyl-N-(3-trifluoromethyl phenyl)benzamide [28] as off white solid. [yield: 1.83 gm, 8.2%]

$^1$H NMR (300 MHz, CD$_3$OD) δ: 8.26 (s, 1H), 8.19-8.12 (m, 1H), 7.98-7.92 (m, 1H), 7.79-7.74 (m, 1H), 7.72-7.61 (m, 3H), 7.55 (t, 1H), 7.45-7.36 (m, 2H), 7.34-7.25 (m, 2H), 4.11 (s, 2H), 3.4-3.32 (m, 2H), 3.05 (t, 2H), 2.42 (s, 3H)

MS: Calculated: m/z 538.1 (M+1)$^+$.

Example 6

{6-[2-Methyl-5-(4-trifluoromethyl pyrimidin-2-ylamino)-phenyl]-5,6,7,8-tetrahydropyrido[4,3-d]pyrimidin-2-yl}-pyridin-4-amine [34]

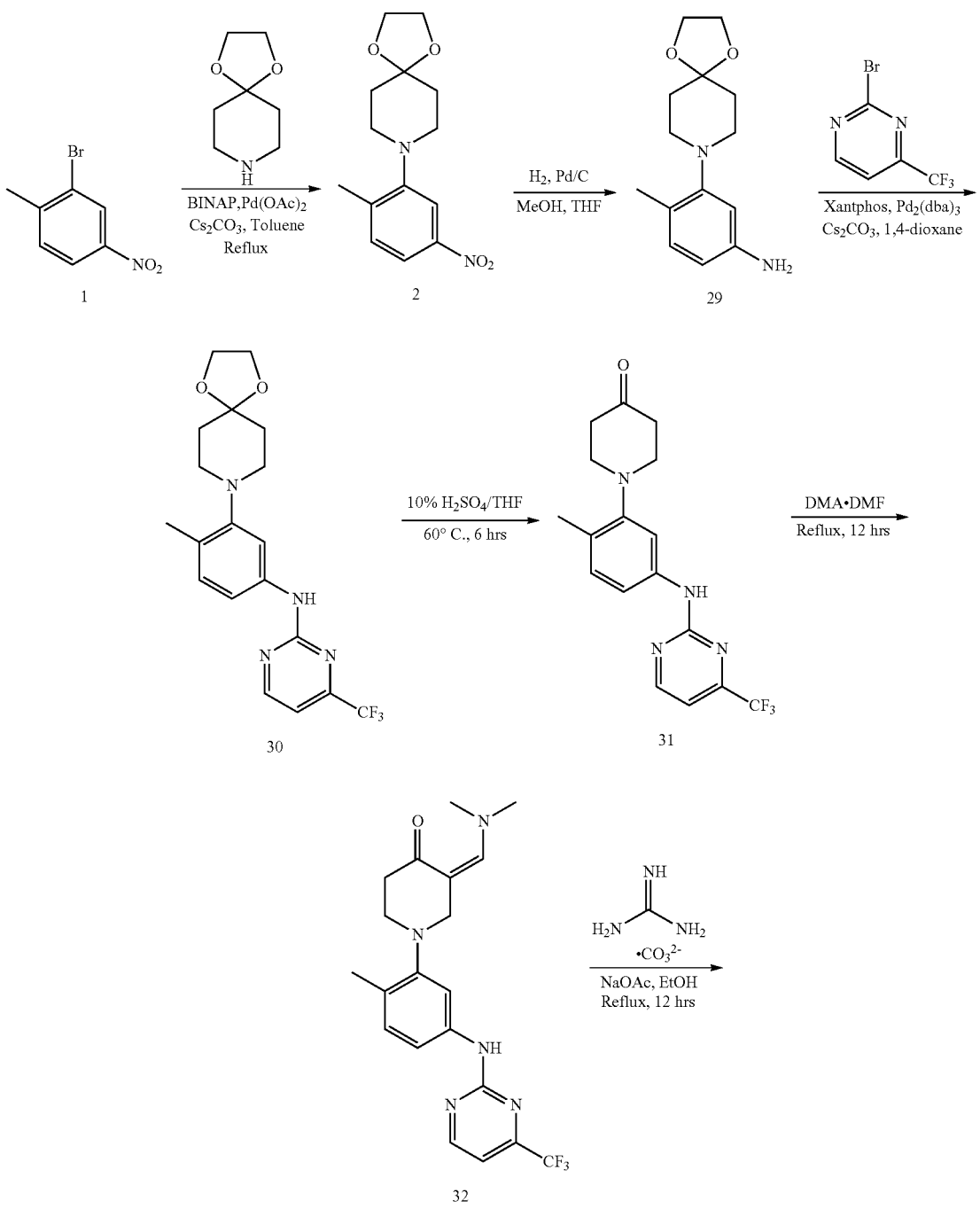

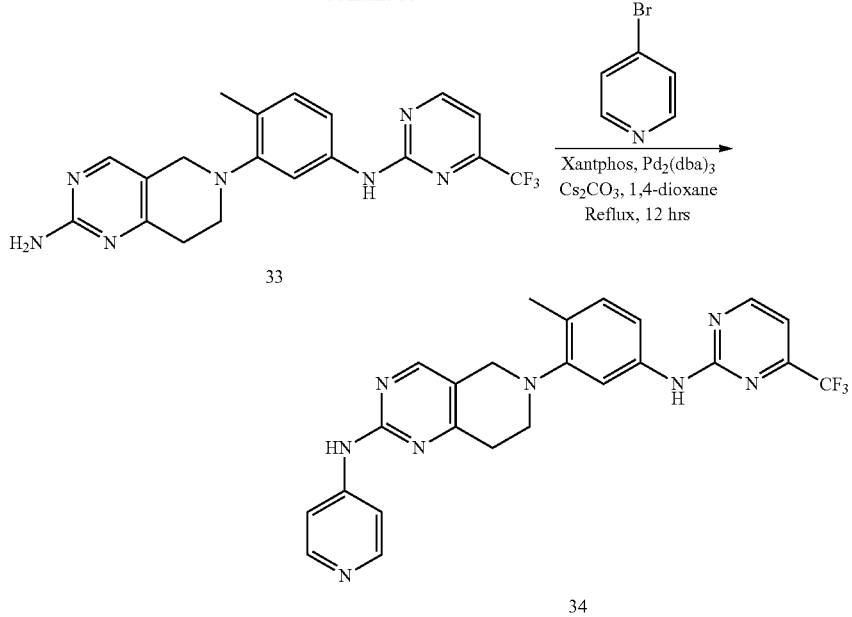

A mixture of 2,2'-Bis(diphenylphosphino)1,1'-binaphthyl [BINAP] (54.35 mg, 0.085 mmol) and Palladium(II)acetate [Pd(OAc)₂] (6.95 mg, 0.028 mmol) in dry toluene (3 ml) was stirred vigorously and nitrogen was bubbled through the suspension for 30 minutes. To this, 14-Dioxa-8-aza-spiro[4.5]-decane (100 mg, 0.699 mmol), 2-Bromo-1-methyl-4-nitro-benzene (181.29 mg, 0.839 mmol) and dry cesium carbonate (683.5 mg, 2.097 mmol) was added. Nitrogen was bubbled through for another 30 minutes; the mixture was allowed to reflux overnight. The mixture was cooled, diluted with ethyl acetate, water was added and the layers separated. The aqueous layer was extracted with ethyl acetate and the two organic extracts were combined. The organics were washed with brine, then dried (sodium sulfate), filtered and concentrated. Further purification by silica gel chromatography using 5-10% ethyl acetate/hexane as eluent provided 8-(2-Methyl-5-nitro-phenyl)-1,4-dioxa-8-aza-spiro[4.5]decane [2] as a yellow solid [Yield:—193 mg, 82.7%].

To a solution of 8-(2-Methyl-5-nitro-phenyl)-1,4-dioxa-8-aza-spiro[4.5]decane (100 mg, 0.278 mmol) in the mixed solvent of THF (3 ml) and methanol (3 ml) was added 10% Pd/C, and the reaction mixture was stirred for 12 hours at room temperature under a hydrogen balloon. The reaction mixture is filtered and the filtrate was concentrated under vacuum to give 3-(1,4-Dioxa-8-aza-spiro[4.5]dec-8-yl)-4-methyl-phenylamine [29] (Yield: 84.9 mg, 95.2%) as a off white solid.

A mixture of 4,5 Bis(diphenyl-phosphino)-9,9-dimethylx-anthene [xanthopos](8.6 mg, 0.01488 mmol) and Tris(dibenzylideneacetone)di-palladium(0)[Pd₂(dba)₃](6.81 mg, 0.00744 mmol) in dry 1,4-dioxane (5 ml) was stirred vigorously and nitrogen was bubbled through the suspension for 30 minutes. 5-Bromo pyrimidine (19.7 mg, 0.1247 mmol), 3-(1, 4-Dioxa-8-aza-spiro[4.5]dec-8-yl)-4-methyl-phenylamine (30.96 mg, 0.1247 mmol) and dry cesium carbonate (100 mg, 0.31 mmol) was added. Nitrogen was bubbled through for another 30 minutes; the mixture was allowed to reflux overnight. The mixture was cooled, diluted with ethylacetate, water was added and the layers were separated. The aqueous layer was extracted with ethyl acetate and the two organic extracts were combined. The organics were washed with brine, then dried (sodium sulfate), filtered and concentrated under vacuum. Further purification by silica gel chromatography using 5-10% ethyl acetate/hexane as eluent [3-(1,4-Dioxa-8-aza-spiro[4.5]dec-8-yl)-4-methyl-phenyl]-(4-trifluoromethyl-pyrimidin-2-yl)-amine [30] as a pale yellow solid [Yield: 4.05 mg, 29.8%]

To a solution of [3-(1,4-Dioxa-8-aza-spiro[4.5]dec-8-yl)-4-methyl-phenyl]-(4-trifluoromethyl-pyrimidin-2-yl)-amine [50 mg, 0.126 mmol] in THF (1 ml) was added, 1 ml of 10% H₂SO₄ (aq). The reaction mixture was heated at 60° C. for 6 hours, and then partitioned between ethyl acetate and water. The aqueous layer was extracted twice further with ethyl acetate and combined organic fractions were washed with water, brine then dried (sodium sulfate), filtered. The filtrate was concentrated to give desired compound i.e., 1-[2-Methyl-5-(4-trifluoromethyl-pyrimidin-2-ylamino)-phenyl]-piperidin-4-one [31] as viscous liquid. [Yield: 40.9 mg, 92.2%] The compound obtained was used in next step without further purification.

A solution of 1-[2-Methyl-5-(4-trifluoromethyl-pyrimidin-2-ylamino)-phenyl]-piperidin-4-one [100 mg, 0.285 mmol] in N,N-Dimethylformamide dimethyl acetal (DMA.DMF) [1 ml] was heated to reflux for 12 hrs. After cooling to room temperature, reaction mixture was concentrated under vacuum. The dark brown crude product obtained was further purified by silica gel chromatography using 30-60% ethyl acetate/hexane as eluent to obtain pure desired product i.e., 3-Dimethyl-aminomethylene-1-[2-methyl-5-(4-trifluoromethyl-pyrimidin-2-ylamino)-phenyl]-piperidin-4-one [32] as orange solid [Yield: 78.2 mg, 68.02%]

To a solution of 3-Dimethyl-aminomethylene-1-[2-methyl-5-(4-trifluoromethyl-pyrimidin-2-ylamino)-phenyl]-piperidin-4-one (16.90 gm, 41.7 mmol) in Ethanol (250 ml) were added guanidine carbonate (30.17 gm, 167 mmol) and sodium acetate (27.40 gm, 334 mmol). The reaction mixture was heated under reflux for 12 hours. After cooling to room temperature, the reaction mixture was diluted with water, extracted with ethyl acetate. The organic layer was washed with brine, dried [sodium sulfate] and evaporated. The crude product obtained was purified by silica gel chromatography using 2-5% Methanol/Chloroform as eluent to give pure desired product i.e., 6-[2-Methyl-5-(4-trifluoromethyl-pyrimidin-2-ylamino)-phenyl]-5,6,7,8-tetrahydro-pyrido[4,3-d]pyrimidin-2-ylamine [33]as pale yellow solid. (Yield: 5.00 gm, 30.6%)

A mixture of 4,5 Bis(diphenyl-phosphino)-9,9-dimethylxanthene [xanthopos](8.6 mg, 0.01488 mmol) and Tris(dibenzylideneacetone)di palladium(0)[Pd₂(dba)₃](6.81 mg, 0.00744 mmol) in dry 1,4-dioxane (5 ml) was stirred vigorously and nitrogen was bubbled through the suspension for 30 minutes. 5-Bromo pyridine (19.7 mg, 0.1247 mmol), 6-[2-Methyl-5-(4-trifluoromethyl-pyrimidin-2-ylamino)-phenyl]-5,6,7,8-tetrahydro-pyrido[4,3-d]pyrimidin-2-ylamine (50.02 mg, 0.1247 mmol) and dry cesium carbonate (100 mg, 0.31 mmol) was added. Nitrogen was bubbled through for another 30 minutes; the mixture was allowed to reflux overnight. The mixture was cooled, diluted with ethylacetate, water was added and the layers were separated. The aqueous layer was extracted with ethyl acetate and the two organic extracts were combined. The organics were washed with brine, then dried (sodium sulfate), filtered and concentrated under vacuum. Further purification by silica gel chromatography using 5-10% ethyl acetate/hexane as eluent {6-[2-Methyl-5-(4-trifluoromethyl-pyrimidin-2-ylamino)-phenyl]-5,6,7,8-tetrahydro-pyrido[4,3-d]pyrimidin-2-yl}-pyridin-4-ylamine [34] as a pale yellow solid [Yield: 17.75 mg, 29.8%]

¹H NMR (300 MHz, CDCl₃) δ 8.65-8.55 (m, 3H), 8.5-8.4 (br s, 1H), 8.35 (s, 1H), 8.2-8.1 (m, 2H), 7.85-7.75 (br s, 1H), 7.4 (s, 1H), 7.25-7.15 (m, 1H), 7.1-7.0 (m, 2H), 4.2 (s, 2H), 3.35 (t, 2H), 3.15 (t, 2H), 2.3 (s, 3H)

MS m/z 478.9 (M+1)

Example 7

1-[4-Methyl-3-(2-methylamino-7,8-dihydro-5H-pyrido[4,3-d]pyrimidin-6-yl)-phenyl]-3-(3-trifluoromethyl-phenyl)-urea [43]

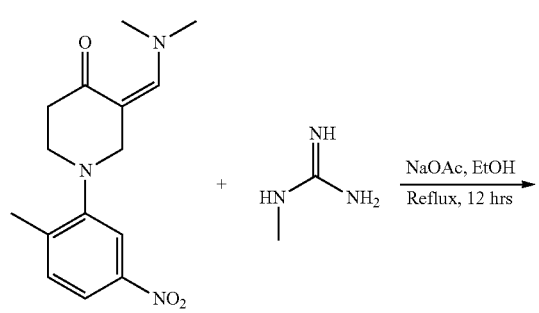

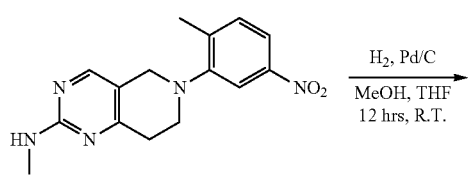

41

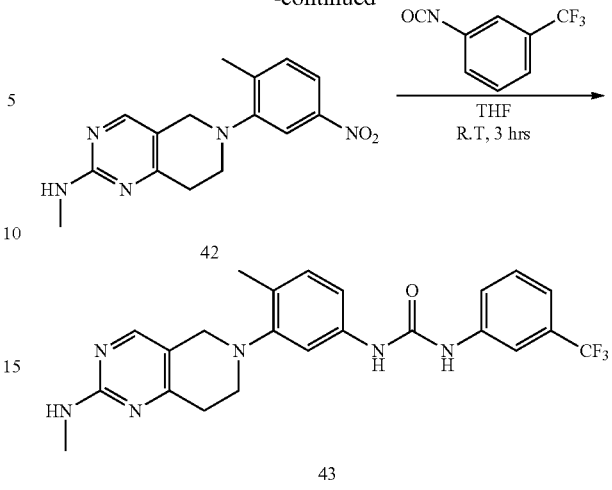

To a solution of 3-Dimethylaminomethylene-1-(2-methyl-5-nitrophenyl)piperidin-4-one (12.06 gm, 41.7 mmol)[as prepared in reference 1] in Ethanol (250 ml) were added N-Methyl guanidine (12.20 gm, 167 mmol) and sodium acetate (27.32 gm, 334 mmol) and solution was heated under reflux for 12 hours. After cooling to room temperature, the reaction mixture was diluted with water, extracted with ethyl acetate. The organic layer was washed with brine, dried [sodium sulfate] and concentrated under vacuum. The crude product obtained was further purified by silica gel chromatography using 5-10% Methanol/Chloroform as eluent to give pure desired product [41]i.e., Methyl-[6-(2-methyl-5-nitrophenyl)-5,6,7,8-tetrahydro-pyrido[4,3-d]pyrimidin-2-yl]-amine as yellow solid. (Yield: 2.47 gm, 19.8%).

To a solution of Methyl-[6-(2-methyl-5-nitro-phenyl)-5,6,7,8-tetrahydro-pyrido[4,3-d]pyrimidin-2-yl]-amine (100 mg, 0.33 mmol) in the mixed solvent of THF (5 ml) and methanol (5 ml) was added 10% Pd/C, and the reaction mixture was stirred for 12 hours at room temperature under a hydrogen balloon. The reaction mixture was filtered and the filtrate was concentrated under vacuum to [6-(5-Amino-2-methyl-phenyl)-5,6,7,8-tetrahydro-pyrido[4,3-d]pyrimidin-2-yl]-methyl-amine [42]as a off white solid [Yield: 84.0 mg, 93.4%].

To a clear stirred solution of [6-(5-Amino-2-methyl-phenyl)-5,6,7,8-tetrahydro-pyrido[4,3-d]pyrimidin-2-yl]-methyl-amine (75 mg, 0.278 mmol) in the THF (1.5 ml) was added 1-Isocyanato-3-trifluoromethylbenzene (57.3 mg, 0.306 mmol) all at once, and the reaction mixture was allowed to stirred for 3 hours at room temperature. After 3 hours, the reaction mixture was diluted with water, extracted with ethyl acetate. The organic layer was given a brine wash, dried over sodium sulphate and concentrated to dryness to get sticky mass which was given a hexane wash to get 83.4 mg of 1-[4-Methyl-3-(2-methylamino-7,8-dihydro-5H-pyrido[4,3-d]pyrimidin-6-yl)-phenyl]-3-(3-trifluoromethyl-phenyl)-urea [43] [Yield 65.6%] as light brown colored solid.

¹H NMR (300 MHz, CDCl₃) δ 7.98 (s, 1H), 7.6-7.06 (m, 8H), 6.84 (d, 1H), 5.1-5.0 (m, 1H), 3.85 (s, 2H), 3.2-2.8 (m, 7H), 2.22 (s, 3H)

MS m/z 457.1 (M+1)

Example 8

1-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-(3-trifluoromethyl phenyl)urea [46]

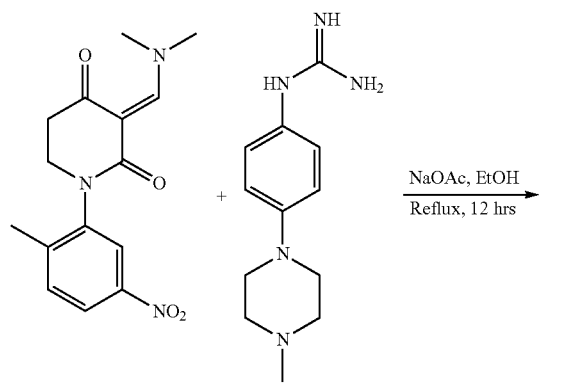

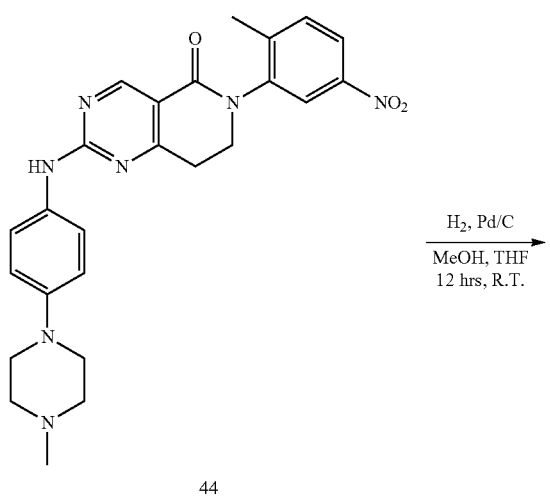

44

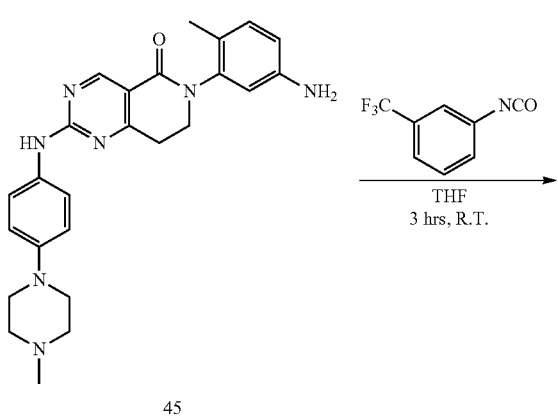

45

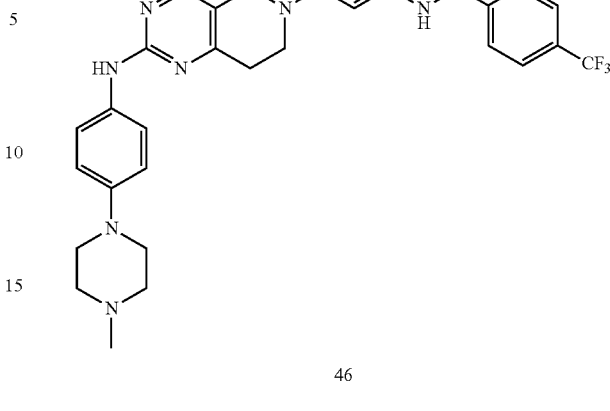

46

To a solution of 3-Dimethylaminomethylene-1-(2-methyl-5-nitro-phenyl)-piperidine-2,4-dione (12.6 gm, 41.7 mmol) [as prepared in reference 2] in Ethanol (250 ml) were N-[4-(4-Methyl-piperazin-1-yl)-phenyl]-guanidine (38.9 gm, 167 mmol) and sodium acetate (27.38 gm, 334 mmol) and solution was heated under reflux for 12 hours. After cooling to room temperature, the reaction mixture was diluted with water, extracted with ethyl acetate. The organic layer was washed with brine and dried over sodium sulfate and evaporated. The crude product obtained was purified by silica gel chromatography using 5-10% Methanol/Chloroform as eluent to give pure desired product i.e., 6-(2-Methyl-5-nitro-phenyl)-2-[4-(4-methyl-piperazin-1-yl)-phenylamino]-7,8-dihydro-6H-pyrido[4,3-d]pyrimidin-5-one [44] as solid. (Yield: 4.30 gm, 21.9%).

To a solution of 6-(2-Methyl-5-nitro-phenyl)-2-[4-(4-methyl-piperazin-1-yl)-phenylamino]-7,8-dihydro-6H-pyrido[4,3-d]pyrimidin-5-one (100 mg, 0.211 mmol) in the mixed solvent of THF (5 ml) and methanol (5 ml) was added 10% Pd/C, and the reaction mixture was stirred for 12 hours at room temperature under a hydrogen balloon. The reaction mixture was filtered and the filtrate was concentrated under vacuum to give 6-(5-Amino-2-methyl-phenyl)-2-[4-(4-methyl-piperazin-1-yl)-phenylamino]-7,8-dihydro-6H-pyrido[4,3-d]pyrimidin-5-one [45] (Yield: 86.45 mg, 92.3%) as a white solid.

To a clear stirred solution of 6-(5-Amino-2-methyl-phenyl)-2-[4-(4-methyl-piperazin-1-yl)-phenylamino]-7,8-dihydro-6H-pyrido[4,3-d]pyrimidin-5-one (75 mg, 0.169 mmol) in the THF (1.5 ml) was added 1-Isocyanato-3-trifluoro-methyl-benzene (34.7 mg, 0.186 mmol) all at once, and the reaction mixture was allowed to stirred for 3 hours at room temperature. After 3 hours, the reaction mixture was diluted with water, extracted with ethyl acetate. The organic layer was given a brine wash, dried over sodium sulphate and concentrated to dryness to get sticky mass which was given a hexane wash to get 56.7 mg of 1-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-(3-trifluoromethyl-phenyl)-urea [Yield 53.2%] as light brown colored solid.

$^1$H NMR (300 MHz, CDCl$_3$) δ 9.0 (s, 1H), 7.7-6.6 (m, 11H), 8.2-7.7 (m, 3H), 4.2-3.7 (m, 2H), 3.5-2.8 (m, 10H), 2.2-1.9 (m, 6H)

MS m/z 631.2 (M+1)

Example 9

Butane-1-sulfonic acid (4-methyl-3-{2-[4-(4-methyl-piperazin-1-yl)-phenylamino]-7,8-dihydro-5H-pyrido[4,3-d]pyrimidin-6-yl}phenyl)amide [49]

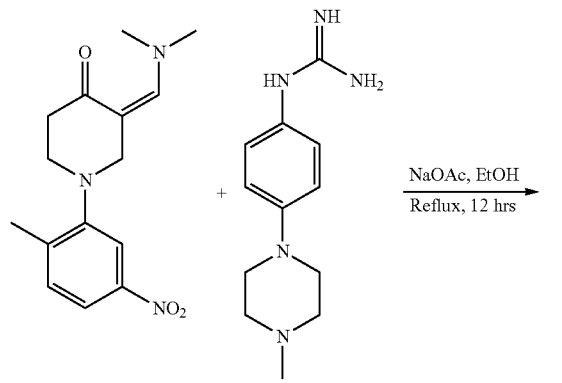

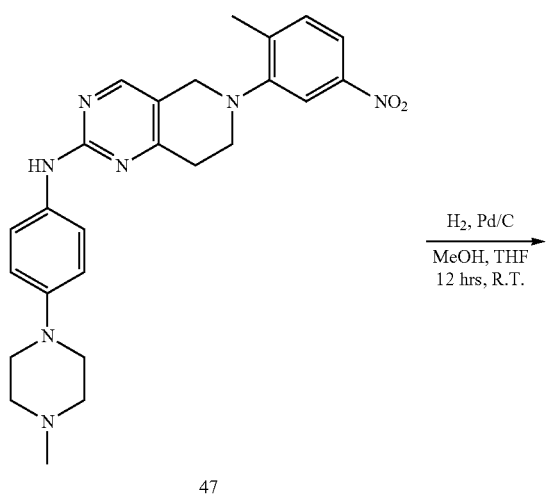

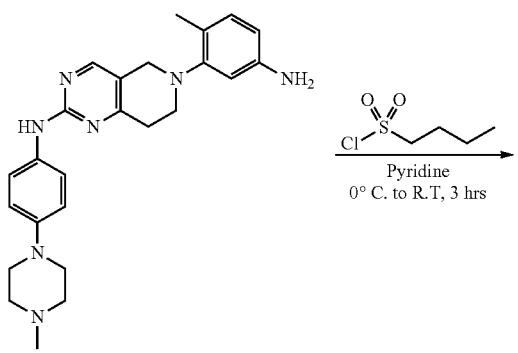

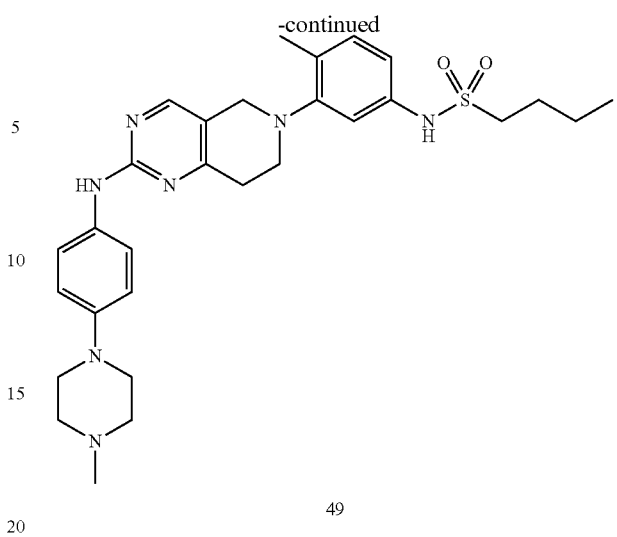

49

To a solution of 3-Dimethylaminomethylene-1-(2-methyl-5-nitrophenyl)-piperidin-4-one (12.06 gm, 41.7 mmol)[as prepared in reference 1] in Ethanol (250 ml) were added N-[4-(4-Methyl-piperazin-1-yl)-phenyl]-guanidine (38.9 gm, 167 mmol) and sodium acetate (27.32 gm, 334 mmol) and solution was heated under reflux for 12 hours. After cooling to room temperature, the reaction mixture was diluted with water, extracted with ethyl acetate. The organic layer was washed with brine, dried [sodium sulfate] and concentrated under vacuum. The crude product obtained was further purified by silica gel chromatography using 5-10% Methanol/Chloroform as eluent to give pure desired product [47]i.e., [6-(2-Methyl-5-nitro-phenyl)-5,6,7,8-tetrahydro-pyrido[4,3-d]pyrimidin-2-yl]-[4-(4-methyl-piperazin-1-yl)-phenyl]-amine as yellow solid. (Yield: 3.65 gm, 19.0%).

To a solution of [6-(2-Methyl-5-nitro-phenyl)-5,6,7,8-tetrahydro-pyrido[4,3-d]pyrimidin-2-yl]-[4-(4-methyl-piperazin-1-yl)-phenyl]-amine (100 mg, 0.217 mmol) in the mixed solvent of THF (5 ml) and methanol (5 ml) was added 10% Pd/C, and the reaction mixture was stirred for 12 hours at room temperature under a hydrogen balloon. The reaction mixture was filtered and the filtrate was concentrated under vacuum to [6-(5-Amino-2-methyl-phenyl)-5,6,7,8-tetrahydro-pyrido[4,3-d]pyrimidin-2-yl]-[4-(4-methyl-piperazin-1-yl)-phenyl]-amine [48] as a off white solid [Yield: 83.7 mg, 89.6%].

To a solution [6-(5-Amino-2-methyl-phenyl)-5,6,7,8-tetrahydro-pyrido[4,3-d]pyrimidin-2-yl]-[4-(4-methyl-piperazin-1-yl)-phenyl]-amine (50.0 mg, 0.116 mmol) in Pyridine (1 ml) at 0° C. was added Butane-1-sulfonyl chloride (21.3 mg, 0.139 mmol) dropwise The reaction mixture was stirred for 15 minutes at 0° C. and then allowed to attain room temperature. It was then further stirred for 3 hours at room temperature. The reaction mixture was concentrated under vacuum. The reaction mass was then, diluted with water and extracted with dichloromethane. The dichloromethane layer was washed with water, then with brine solution. The organic layer is dried over sodium sulphate and concentrated under reduced pressure. The crude product obtained was purified by column chromatography (SiO$_2$, 2-10% methanol in chloroform) to give 50.4 mg (78.9%) Butane-1-sulfonic acid (4-methyl-3-{2-[4-(4-methyl-piperazin-1-yl)-phenylamino]-7,8-dihydro-5H-pyrido[4,3-d]pyrimidin-6-yl}-phenyl)-amide [49] as off white solid.

$^1$H NMR (300 MHz, CDCl$_3$) δ 8.15 (s, 1H), 7.50 (d, 2H), 7.19 (d, 1H), 7.00-6.80 (m, 5H), 6.60-6.40 (m, 1H), 4.00 (s, 2H), 3.30-2.95 (m, 10H), 2.60 (t, 4H), 2.38 (s, 3H), 2.30 (s, 3H), 1.85-1.75 (m, 2H), 1.50-1.36 (m, 2H), 1.25 (s, 2H), MS m/z 550.2 (M+1)

Example 10
6-[5-(Benzooxazol-2-ylamino)-2-methylphenyl]-2-[4-(4-methyl-piperazin-1-yl)-phenylamino]-7,8-dihydro-6H-pyrido[4,3-d]pyrimidin-5-one [54]
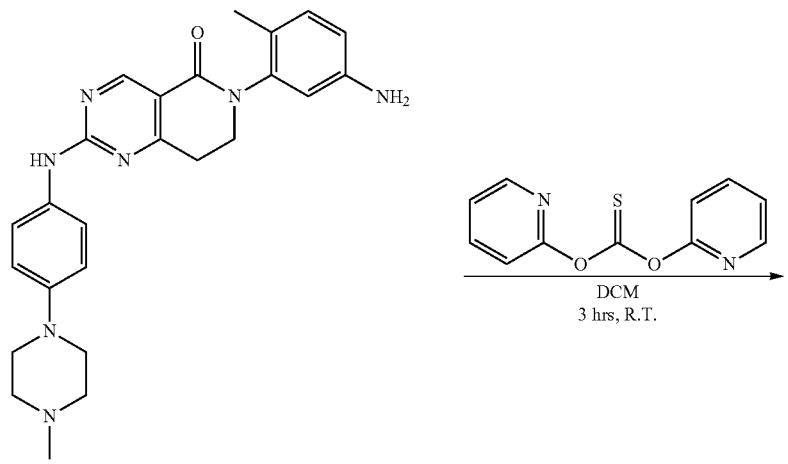
45
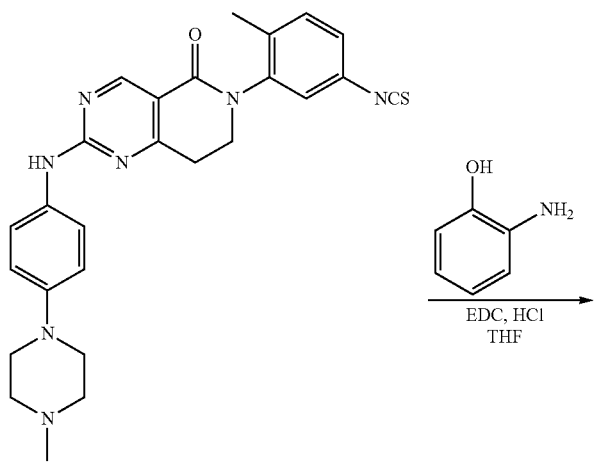
53
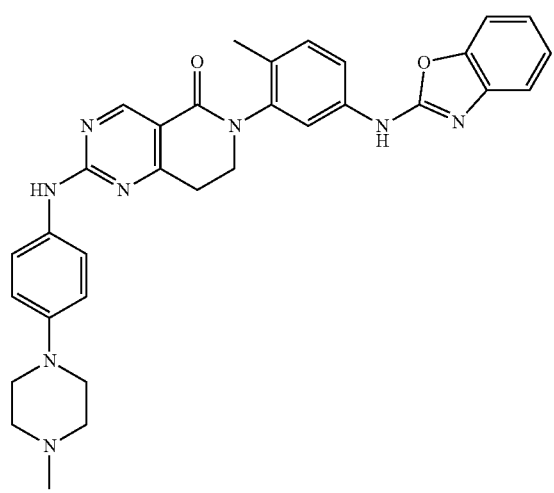
54

153

To a clear solution of 6-(5-Amino-2-methyl-phenyl)-2-[4-(4-methyl-piperazin-1-yl)-phenylamino]-7,8-dihydro-6H-pyrido[4,3-d]pyrimidin-5-one (75 mg, 0.169 mmol) in the DCM (5 ml) was added Di(2-pyridyl)thionocarbonate (47 mg, 0.203 mmol) all at once, and the reaction mixture was allowed to stirred for 3 hours at room temperature. After 3 hours, the reaction mixture was diluted with water, extracted with ethyl acetate. The organic layer was given a brine wash, dried over sodium sulphate and concentrated to dryness to get sticky mass which was given a hexane wash to get 70.3 mg of 6-(5-Isothiocyanato-2-methyl-phenyl)-2-[4-(4-methyl-piperazin-1-yl)-phenylamino]-7,8-dihydro-6H-pyrido[4,3-d]pyrimidin-5-one [53][Yield: 85.6%] as light brown coloured.

To a solution of 6-(5-Isothiocyanato-2-methyl-phenyl)-2-[4-(4-methyl-piperazin-1-yl)-phenylamino]-7,8-dihydro-6H-pyrido[4,3-d]pyrimidin-5-one (50.0 mg, 0.089 mmol), and 2-Amino-phenol (9.73 mg, 0.089 mmol) in THF (5 ml) was added EDC.HCl (25.6 mg, 0.133 mmol), and the reaction mixture was refluxed for 12 hour under nitrogen atmosphere. After 12 hrs, the reaction mass was concentrated to dryness to get crude compound. The crude obtained was subjected to preparative HPLC. The desired compound i.e., 6-[5-(Benzooxazol-2-ylamino)-2-methyl-phenyl]-2-[4-(4-methyl-piperazin-1-yl)-phenylamino]-7,8-dihydro-6H-pyrido[4,3-d]pyrimidin-5-one was obtained as brown solid [54][Yield: 57.7 mg, 63.2%]

$^1$H NMR (300 MHz, DMSO-D$_6$) δ 10.7 (s, 1H), 8.8 (s, 1H), 7.7-7.0 (m, 10H), 6.95-6.85 (d, 2H), 4.1-3.95 (m, 1H), 3.85-8.7 (m, 1H), 3.3-3.0 (m, 6H), 2.5-2.4 (m, 4H), 2.24 (s, 3H), 2.15 (s, 3H)

MS m/z 561.2 (M+1)

Example 11

6-(5-(isoquinolin-1-ylamino)-2-methylphenyl)-2-(4-(4-methylpiperazin-1-yl)phenylamino)-7,8-dihydropyrido[4,3-d]pyrimidin-5(6H)-one

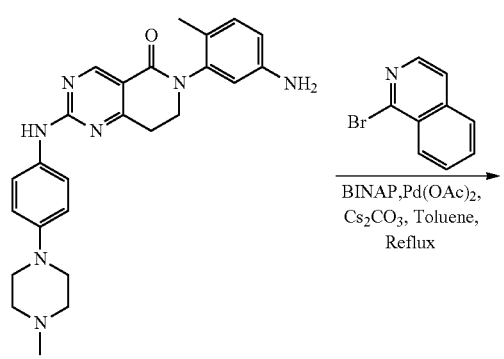

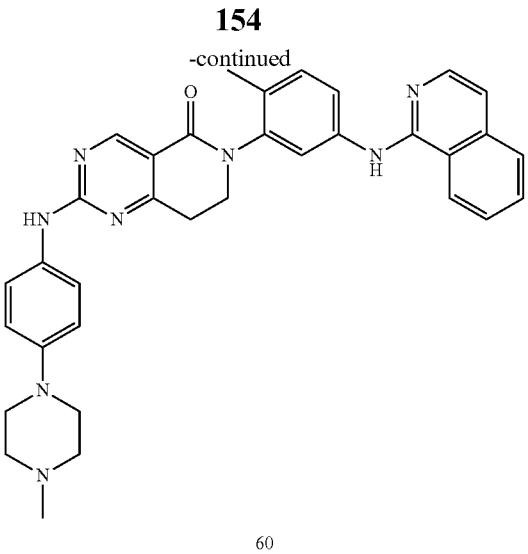

A mixture of 2,2'-Bis(diphenylphosphino)1,1'-binaphthyl [BINAP] (28.00 mg, 0.0451 mmol) and Palladium(II)acetate [Pd(OAc)2] (5.00 mg, 0.022 mmol) in dry toluene (3 ml) was stirred vigorously and nitrogen was bubbled through the suspension for 30 minutes. To this, 6-(5-amino-2-methylphenyl)-2-(4-(4-methylpiperazin-1-yl)phenylamino)-7,8-dihydropyrido[4,3-d]pyrimidin-5(6H)-one [45](200 mg, 0.451 mmol), 1-bromoisoquinoline (112.60 mg, 0.541 mmol) and dry cesium carbonate (443.0 mg, 1.352 mmol) was added. Nitrogen was bubbled through for another 30 minutes; the mixture was allowed to 15 reflux overnight. The mixture was cooled, diluted with ethyl acetate, water was added and the layers separated. The aqueous layer was extracted with ethyl acetate and the two organic extracts were combined. The organics were washed with brine, then dried (sodiumsulfate), filtered and concentrated. Further purification by silica gel chromatography using 5-10% ethyl acetate/hexane as eluent provided 6-(5-(isoquinolin-1-ylamino)-2-methylphenyl)-2-(4-(4-methylpiperazin-1-yl)phenylamino)-7,8-dihydropyrido[4,3-d]pyrimidin-5(6H)-one [60] as a yellow solid [Yield:—223 mg, 87.0%].

Example 12

Pharmacological Data c-Src and Jak 2 Kinase Assays:

Compounds were screened in the TR-FRET assay for JAK2 and c-Src kinase inhibition. Ultra light poly GT (Perkin Elmer) was used as the substrate for JAK2 and c-Src with the ATP concentration of 10 µM and 50 µM, respectively. The Eu-labelled anti-phospho tyrosine antibody (Perkin Elmer) was added at 1 nM and the fluorescence emission at 615 nm and 665 nm was measured with an excitation wavelength of 340 nm. The ratio of 665 to 615 nm is proportional to substrate phosphorylation and kinase activity. The dose-response curve fitting was done using GraphPad Prism software.

In-Cell-Western Blot Assay for pStat3 (ICW):

A431 cells were seeded onto a 96-well micro plate. After overnight serum starvation cells were incubated with compounds for 2 hrs. Cells were fixed with 4% paraformaldehyde in PBS and then permeabilized with 0.1% Triton X-100 in PBS (PBST). Cells were blocked with 5% BSA in PBST for 2 hrs, followed by overnight incubation with phospho Stat3 antibody. Cells were washed and incubated with europium-labeled anti-rabbit secondary antibody for 2 hrs. After washing enhancement solution was added to the wells. The micro-plate was read on the Victor instrument at the Europium setting. The Hoechst readings were used to normalize for cell number. $IC_{50}$ values were calculated with the normalized europium values using Graphpad Prism.

Cell Viability Assay (XTT Assay):

Mda-Mb-231 or A549 cells were seeded onto a 96-well micro plate. Next day compounds were added to cells and incubated for 72 hrs. Compound treatment was done in triplicates. After 72 hrs cell culture media was aspirated from the wells and XTT working solution was added and plates were incubated for 2-5 hrs. The absorbance of the samples was measured with a spectrophotometer at a wavelength of 465 nM. $EC_{50}$ values were calculated using Graphpad Prism. Tumor cell lines used in the examples of the present invention were procured from ATCC. Description of the cell lines is included in the following table:

| Cell line | Origin | Source and hyperlink to details |
|---|---|---|
| B16F10 | Mouse melanoma | ATCC |
| A549 | Human lung carcinoma | ATCC |
| A431 | Human epidermoid carcinoma | ATCC |
| Mda-Mb-231 | Human breast carcinoma | ATCC |

Abbreviations:

| IP | Intraperitoneal(ly) |
|---|---|
| IV | Intravenous(ly) |
| MTV | Mean Tumor Volume |
| No | Number of |
| NS | Not Significant |
| S | Significant |
| SA | Sacrificed |
| SC | Subcutaneous(ly) |
| V | Volume |
| Vs | Versus |
| HPC | Hydroxypropylcyclodextrine |
| PBS | Phosphate buffered saline |
| MPK | mg per Kg body weight |
| MTD | Maximum Tolerated Dose |
| TGI | Tumor growth inhibition |
| PD | Pharmaco Dynamic |
| ATD | Acute Toxicity Dose |
| N/D | Not determined |

Results

Table 2 and 4 evidence that the compounds of the present invention present a dual inhibition activity against c-SRC and JAK kinases (JAK2 and JAK1) and therefore comply with the requirements of the present invention. Table 2 also shows the in vitro inhibition activity of cell growth in A431, A549 and MDA-MB-231 cancer cell lines as well as an inhibition activity of STAT3 phosphorylation in A431 cancer cell line.

Table 3 shows the activity of Dasatinib (a c-SRC inhibitor) and TG101348 (a highly selective JAK2 inhibitor). It can be concluded that these compounds are not dual inhibitors. In addition, the inhibitory activity of STAT3 phosphorylation is less efficient with these compounds compared to the compounds according to the present invention.

TABLE 2

| Compound No | JAK2 % inhibition at 100 nM | JAK2 % inhibition at 1 µM | JAK2 IC50 (nM) | c-SRC % inhibition at 100 nM | c-SRC % inhibition at 1 µM | c-SRC IC50 (nM) | MDA-MB-231 EC50 (µM) | A549 EC50 (µM) | A431 EC50 (µM) | pSTAT3 inhibition (nM) |
|---|---|---|---|---|---|---|---|---|---|---|
| 83 | | | 32 | | | 4 | 0.305 | — | 0.240 | 240 |
| 76 | | | 61 | | | 30 | 2.15 | — | 0.135 | 130 |
| 86 | | | 45 | | | 28 | 0.53 | 0.078 | 0.57 | 580 |
| 92 | | | 7 | | | 2 | 0.005 | — | 0.026 | 26 |
| 94 | | | 19 | | | 2 | 0.05 | — | 0.180 | 160 |
| 98 | | | 7 | | | 1 | 0.05 | — | 0.061 | 60 |
| 99 | | | 14 | | | 6 | 0.12 | — | 0.29 | 300 |
| 106 | 85 | 98 | 18 | 99 | 100 | 2 | 0.31 | — | 0.22 | 220 |
| 107 | 72 | 94 | 40 | 93 | 98 | 1 | 0.61 | — | 0.12 | 120 |
| 108 | 89 | 98 | 12 | 98 | 100 | 1 | 2.6 | — | — | |
| 75 | 83 | 97 | | | | 19 | 4.67 | | 1.06 | |
| 117 | | | 18 | 80 | 96 | | 0.66 | 0.025 | 0.33 | 340 |
| 119 | | | 8 | 95 | 98 | | 0.38 | | | 280 |
| 120 | | | 36 | 94 | 95 | | 2.5 | | | |
| 123 | | | 9 | | | 3 | 0.83 | | | 190 |
| 131 | | | 40 | 74 | 90 | | 0.88 | | | |
| 132 | | | 3 | | | 5 | 0.041 | 0.047 | — | 480 |
| 146 | | | 5 | | | 6 | 0.37 | | | 350 |
| 147 | 88 | 93 | 21 | 67 | 90 | — | 0.72 | — | — | |
| 148 | 94 | 96 | 5 | 99 | 99 | 2.4 | 0.034 | — | — | 270 |
| 155 | | | 18 | | | 2 | 1.2 | — | — | |
| 162 | 92 | 97 | 6 | 73 | 81 | 27 | 1.38 | 1.14 | 0.60 | 350 |
| 164 | 68 | 91 | 46 | 70 | 79 | 26 | | | | |
| 165 | 74 | 93 | 54 | 93 | 98 | 16 | 0.44 | — | 0.32 | 257 |
| 166 | 74 | 93 | 48 | 60 | 87 | 27 | | | | |
| 167 | 95 | 97 | 5.3 | 97 | 98 | 27 | | | | 283 |
| 170 | 64 | 93 | 70 | 26 | 58 | — | | | | |
| 171 | 92 | 97 | 19 | 74 | 87 | 20 | 1.30 | 2.10 | — | 471 |
| 172 | 94 | 97 | 9 | 66 | 72 | | 1.84 | — | — | |
| 174 | 94 | 97 | 8.8 | 95 | 98 | — | | | | 161 |
| 176 | 89 | 94 | 15 | 87 | 96 | 13 | 0.33 | — | — | |
| 177 | 84 | 94 | 10 | 86 | 96 | 20 | 0.12 | — | — | 290 |
| 178 | 91 | 92 | 7 | 77 | 90 | 17 | 1.75 | — | — | 150 |
| 179 | 81 | 92 | 6.4 | 79 | 93 | 15 | 0.90 | — | — | 280 |

TABLE 2-continued

| Compound No | JAK2 % inhibition at 100 nM | JAK2 % inhibition at 1 µM | JAK2 IC50 (nM) | c-SRC % inhibition at 100 nM | c-SRC % inhibition at 1 µM | c-SRC IC50 (nM) | MDA-MB-231 EC50 (µM) | A549 EC50 (µM) | A431 EC50 (µM) | pSTAT3 inhibition (nM) |
|---|---|---|---|---|---|---|---|---|---|---|
| 180 | 67 | 91 | | 66 | 87 | | 1.62 | 1.48 | 1.07 | 140 |
| 181 | 85 | 93 | | 53 | 77 | | 3.34 | 2.54 | 1.3 | |
| 182 | 55 | 85 | | 51 | 80 | | 2.76 | 1.08 | 5.07 | |
| 7 | | | 83 | | | 16 | 3.60 | 3.40 | 1.45 | 450 |
| 17 | | | 3 | | | 2 | 0.044 | 0.01 | 0.092 | 150 |
| 45 | | | 15 | | | 10 | 1.83 | 1.07 | 1.4 | 220 |
| 137 | | | 28 | | | 7 | 0.074 | 0.426 | 0.67 | 670 |
| 58 | | | 44 | | | 19 | 3.82 | — | — | |
| 77 | 80 | 96 | | | | 17 | 4.92 | — | 0.512 | 510 |
| 153 | | | 4 | 98 | 99 | | 0.61 | | | |
| 160 | | | 15 | | | 66 | | | | |

TABLE 3

| Compound | JAK2 % inhibition at 100 nM | JAK2 % inhibition at 1 µM | JAK2 IC50 (nM) | c-SRC % inhibition at 100 nM | c-SRC % inhibition at 1 µM | c-SRC IC50 (nM) | MDA-MB-231 EC50 (µM) | A549 EC50 (µM) | A431 IC50 (µM) | pSTAT3 inhibition (nM) |
|---|---|---|---|---|---|---|---|---|---|---|
| Dasatinib | | 55 | | | | 5 | 0.044 | >10 | | 1057 |
| TG101348 | | | 2 | | | 77 | 0.68 | 1.2 | | >10000 |

TABLE 4

| Compound No. | JAK1 % inhibition at 100 nM | JAK1 % inhibition at 1 µM | JAK1 IC50 (nM) |
|---|---|---|---|
| 179 | | | 12 |
| 171 | 61 | 84 | |
| 117 | | | 24 |
| 45 | 56 | 82 | 116 |
| 17 | 85 | 89 | |
| 15 | 49 | 73 | |
| 18 | 82 | 89 | |
| 23 | 84 | 88 | |
| 25 | 58 | 96 | |
| 26 | 57 | 79 | |
| 28 | 66 | 79 | |
| 9 | 58 | 85 | |

Anti-Tumour Activity in B16F10 Metastasis and Survival Model:

IV injection of $0.1 \times 10^6$ B16F10 tumor cells in the tail vain of 60 male C57B16 mice. Randomization of mice one day after tumor cell injection into 4 groups of 15 mice. Out of 15, 6 mice were sacrificed on $14^{th}$ day for counting metastatic foci on lungs. Rest 9 mice were dosed continuously till morbidity/mortality for recording survival.
Formulation: 20% HPC, 2% ethanol solution in PBS for the compound No. 45
  Normal saline for Taxol®
Dosing route: Oral for the compound No. 45 and i.p. for Taxol®
Dose Volume: 10 mL/Kg body weight
Dosing schedule: Once daily for 14 consecutive days (Q1D×14) for metastasis study and once daily continuously till mortality/morbidity for survival study
Dosage:
  Group1: Vehicle Control-0 MPK (mg/kg) of the compound No. 45
  Group2: 5 MPK of Taxol®
  Group3: 30 MPK of the compound No. 45
  Group4: 100 MPK of the compound No. 45

Figure 2:
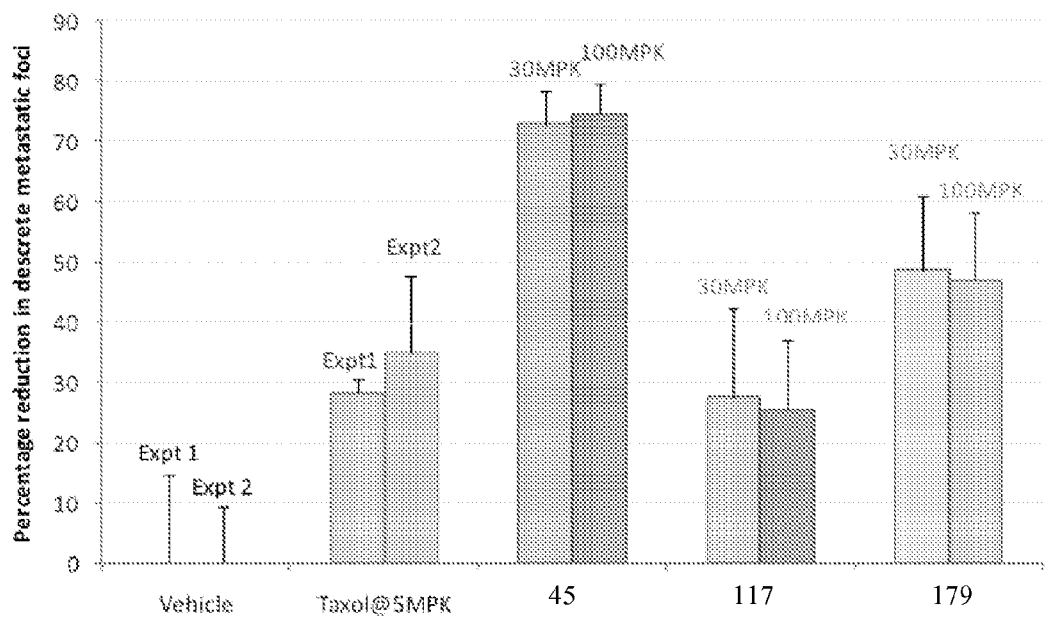
FIG. 2 shows inhibition activity of the compounds of the invention compared to Taxol®

Recording of body weight of animals everyday
Observation for clinical signs, morbidity and mortality—twice everyday
Termination of mice at $T_{max}$ (0.75 hrs) on the day of last dose
Metastatic foci on the lungs were counted
Observations during necropsy: Gross pathology in internal organs such as lung, liver, kidney, spleen and intestines, histopathology of these organs in case gross pathology is observed. Plasma collected for drug concentration estimation and whole blood was collected to isolate PBMCs to determine pStat3 inhibition by flow cytometry as PD readout.
Similar study was done with the compounds No. 117 ad No. 179.
Results:
FIGS. 1 and 2 show a better inhibition activity of the compounds of the present invention compared to Taxol® (paclitaxel; a standard drug used in the B16-F10 model)). Although paclitaxel does not have c-SRC or JAK kinases inhibition activity, paclitaxel modulates STAT3 activity through loss of STAT3 phosphorylation (paclitaxel disrupts the interaction of STAT3 with tubulin).
Anti-Tumour Activity in A549 Xenograft Model:
Expt. 1
Sub-cutaneous (SC) injection of $5 \times 10^6$ A549 tumor cells on the left flank of 48 female athymic nude mice. Randomization of mice 14 days after tumor cell injection into 6 groups of 8 mice each with a mean tumor volume of 134±5 mm3.
Formulation: 20% HPC, 2% ethanol solution in PBS for the compounds No. 45, 117 and 179.
  Normal saline for Erlotinib®
Dosing route: Oral for the compounds No. 45, 117 and 179, and Erlotinib®
Dose Volume: 10 mL/Kg body weight
Dosing schedule: Once daily for 14 consecutive days (Q1D×14)
Dosage:
  Group1. Vehicle control
  Group2. Erlotinib®—100 MPK
  Group3. Compound No. 45—10 MPK
  Group4. Compound No. 45—30 MPK
  Group5. Compound No. 45—100 MPK Group6. Compound No. 117—30 MPK
Group7. Compound No. 117—100 MPK
Group8. Compound No. 179—10 MPK
Group9. Compound No. 179—30 MPK Recording of body weight of animals everyday
Tumor volumes recorded three times every week
Observation for clinical signs, morbidity and mortality—twice everyday
Termination of mice at $T_{max}$ (0.75 hrs) on the day of last dose
Observations during necropsy: Gross pathology in internal organs such as lung, liver, kidney, spleen and intestines, histopathology of these organs in case gross pathology is observed. Plasma collected for drug concentration estimation and whole blood was collected to isolate PBMCs (peripheral blood monocytes) to determine pStat3 inhibition by flow cytometry as PD readout. Tumors were snap frozen in liquid nitrogen and stored at −80° C. to estimate pStat3 by flow cytometry as PD readout Expt. 2

SC injection of $5 \times 10^6$ A549 tumor cells on the left flank of 24 female athymic nude mice. Randomization of mice 14 days after tumor cell injection into 3 groups of 8 mice each with a mean tumor volume of 75±7 mm3.

Formulation: 20% HPC, 2% ethanol solution in PBS for the compound No. 45

Normal saline for Erlotinib®

Figure 3:
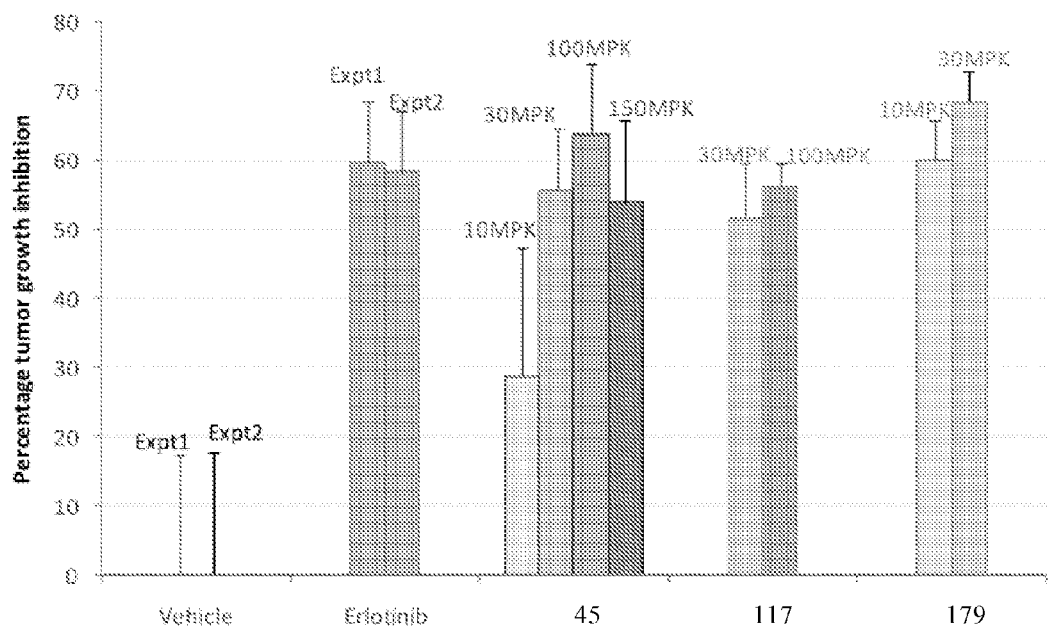
FIG. 3 shows the inhibition of tumour growth of the compounds of the invention compared to Erlotinib

Dosing route: Oral for compound No. 45 and Erlotinib®
Dose Volume: 10 mL/Kg body weight
Dosing schedule: Once daily for 14 consecutive days (Q1D× 14)
Dosage:
Group1. Vehicle control
Group2. Compound No. 45—150 MPK
Group3. Erlotinib®-100 MPK Recording of body weight of animals everyday
Tumor volumes recorded three times every week
Observation for clinical signs, morbidity and mortality—twice everyday
Termination of mice at $T_{max}$ (0.75 hrs) on the day of last dose
Observations during necropsy: Gross pathology in internal organs such as lung, liver, kidney, spleen and intestines, histopathology of these organs in case gross pathology is observed. Plasma collected for drug concentration estimation and whole blood was collected to isolate PBMCs to determine pStat3 inhibition by flow cytometry as PD readout. Tumors were snap frozen in liquid nitrogen and stored at −80° C. to estimate pStat3 by flow cytometry as PD readout Results:

FIG. 3 shows that the compounds of the present invention have equal or better inhibition of tumour growth compared to Erlotinib, a specific EGFR tyrosine kinase inhibitor, suggesting that the combination of the compounds with a strong EGFR tyrosine kinase inhibitor might lead to synergistic effects by combined inhibition of the STAT3 and EGFR pathways.

Anti-Tumour Activity in A431 Xenograft Model:

SC injection of $5 \times 10^6$ A431 tumor cells with Matrigel® on the left flank of 24 female athymic nude mice. Randomization of mice 14 days after tumor cell injection into 3 groups of 8 mice each with a mean tumor volume of 90±1 mm3.

Formulation: 20% HPC, 2% ethanol solution in PBS for the compound No. 45

Normal saline for Gefitinib®

Dosing route: Oral for the compound No. 45 and Gefitinib®
Dose Volume: 10 mL/Kg body weight
Dosing schedule: Once daily for 14 consecutive days (Q1D× 14)

PK-PD experiment in A431 model:
Tumors were allowed to grow to 250 mm³ size. Compounds were dosed once and PBMCs and tumors were collected at $T_{max}$ for pStat3 estimation. Plasma was also collected to estimate drug concentration estimation.

Efficacy experiment in A431 model:
Dosage:
Group1. Vehicle control
Group2. Compound No. 45—150 MPK
Group3. Gefitinib®-100 MPK Recording of body weight of animals everyday
Tumor volumes recorded three times every week
Observation for clinical signs, morbidity and mortality—twice everyday
Termination of mice at $T_{max}$ (0.75 hrs) on the day of last dose
Observations during necropsy: Gross pathology in internal organs such as lung, liver, kidney, spleen and intestines, histopathology of these organs in case gross pathology is observed. Plasma collected for drug concentration estimation and whole blood was collected to isolate PBMCs to determine pStat3 inhibition by flow cytometry as PD readout. Tumors were snap frozen in liquid nitrogen and stored at −80° C. to estimate pStat3 by flow cytometry as PD readout Determination of Plasma Drug Concentration:
Plasma samples were treated with acetonitrile and centrifuged. The supernatant was evaporated to dryness and reconstituted with the mobile phase and later analysed for drug concentration by LC-MS/MS in MRM mode. Tumour samples were homogenized and later subjected to the same procedure as plasma. A set of calibration standards and quality control samples were used for both plasma and tumour samples.

Quantification of pStat3 in PBMCs and Tumors:
Collection of Blood and Compound Treatment
Venus blood was collected through retro orbital vein to BD vacutainer (buff. Na Citrate 0.109M, 3.2%) BD Franklin (#8019827) and transferred to 6 well plate (Costar#3516). Phosphorylation of Stat3 was stimulated by addition of hIL6 (10 ug/mL) for 30 min at 37° C. Blood was fixed with formaldehyde (final 2% v/v) for 10 min at 370 C.

Separations of PBMCs
Blood was overlaid on warmed Histopaque (Sigma cat#10771, ratio of 1:2, 3.5 ml of blood+7.5 ml of Histopaque). Centrifuged (eppendorf#5810R, rotor A-4-62) at 1500 rpm for 30 min at RT (with zero deceleration). Buffy coat (PBMCs) was separated by aspirating translucent layer using pipetteman and washed twice with PBS-1×

Permeabilization
Pre chilled PBMC's were permeabilized by adding ice cold Methanol, while vortexing gently (final volume 90% MeOH v/v) and incubated for 30 min on ice.

Staining using unlabelled primary and Conjugated Secondary antibodies (Ab).
Permeabilized PBMCs were washed with PBS once. PBMCs re-suspended to $2 \times 10^6$ cells in 200 μL of incubation buffer for 10 min at room temperature (RT). Primary Ab was added (1:100 dilution) and incubated 45 min at RT. Washed as before (twice) and re-suspended in fluorochrome conjugated secondary Ab (1:500 dilution) and incubated at RT in dark for 30 min. Washed and re-suspended in 500 μl PBS.

Analyzing pStat3 by FACS

Measured pStat3 using FACS caliber machine (BD). Unstained PBMCs was used for cytometry settings. PBMCs with primary (Rabbit polyclonal to pSTAT3-phosphor Y705-Abcam # ab30646) and secondary Ab (Goat anti-rabbit IgG-Zymed 81-6111) staining [treated as control (peak M1)], IL-6 alone stimulated cells stained with isotype control were treated as positive control [peak shifts towards right side (M2)]. Compound/inhibitor plus IL6 treated cells peak [shifts towards left side]. Histograms (cell number V/s FL1-H) were plotted. Percentage of cells that are phosphorylated by IL6 stimulation (M2 population), and inhibition of phosphorylation by inhibitor (decrease in M2 population) are calculated on histogram by marking peaks, M1 and M2.

Tumours:

Separate the tumour & 200 mg of tumour was crashed (45 mg per ml) by using IKA 10 at Speed #4 for 10 seconds. Sieve the tumour extract through 100 u, centrifuge at 900 g for 10 min. Re-suspend cells briefly in 0.5-1 ml PBS. Add formaldehyde to a final concentration of 2-4% formaldehyde. Fix for 10 minutes at 37° C. Chill tubes on ice for 1 minute.

Permeabilization

Permeabilize cells by adding ice-cold 100% methanol slowly to pre-chilled cells, while gently vortexing, to a final concentration of 90% methanol. Alternatively, to remove fix prior to permeabilization, pellet cells by centrifugation and re-suspend in 90% methanol. Incubate 30 minutes on ice. Proceed with staining or store cells at −20° C. in 90% methanol. Aliquot 0.5-1×106 cells into each assay tube (by volume). Add 2-3 ml Incubation Buffer to each tube and rinse by centrifugation. Repeat. Re-suspend cells in 100 µl Incubation Buffer per assay tube. Analyze by flow cytometry like PBMCs.

Figure 4:
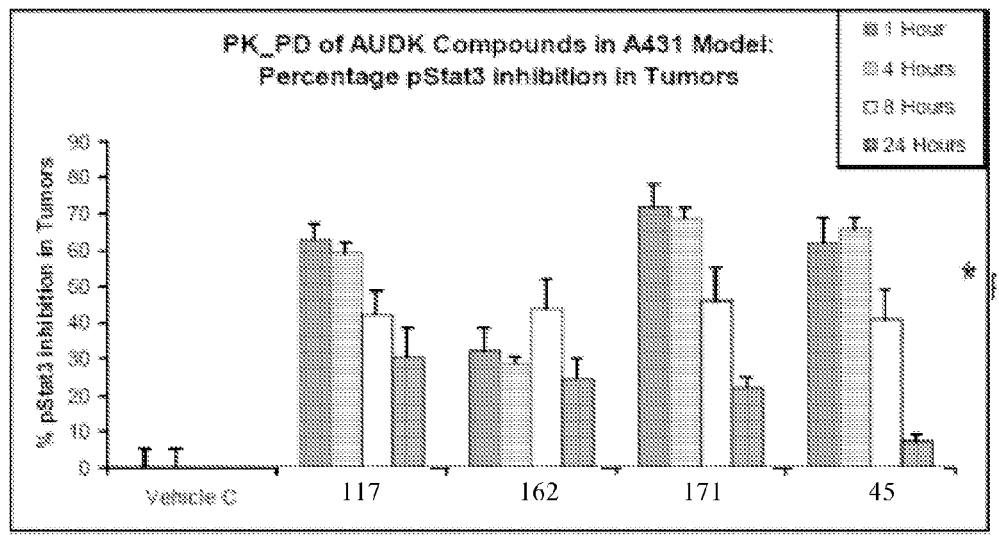
FIG. 4 shows Tyrosine 705 phosphorylated-STAT (pSTAT) inhibition in tumours of the compounds of the invention

Results:

1. Compound No. 45 showed good tolerance (up to 250 MPK) in athymic mice.
2. Compound NO. 45 does not cause pronounced toxicity effects on major organs on upon once-daily 14 days treatment in athymic mice except minor deviations in gastro-intestinal tract.
3. In B16F10 metastasis model, Compound No. 45 showed good anti-tumor activity. Compound No. 45 at 100 MPK caused 75% reduction in metastatic counts on lungs when administered Q1D×14.
4. Anti-tumor activity of Compound No. 45 in B16F10 survival model resulted in a survival advantage of 37.5% which is significant for such an aggressive model (dosing: Q1D×14).
5. In A549 xenograft model Compound No. 45 at 100 MPK (Q1D×14) showed tumor growth inhibition of 64%. Higher dose of 150 MPK resulted in TGI of 54 although not statistically significant from 100 MPK result.
6. No major effects of compound related toxicity were observed up to 150 MPK of Compound No. 45 during A549 efficacy study Further results, obtained with compounds No. 117 and 179, are shown in Table 6 and FIG. 4.

TABLE 6

| Assays | Compound No. 45 | Compound No. 117 | Compound No. 179 |
|---|---|---|---|
| MTD (MPK) | 250 | 100 | 30 |
| % pSTAT3 inhibition in PBMCs (MTD study) | 84% at 100 MPK | 83% at 100 MPK | 65% at 30 MPK |

TABLE 5

| | | B16F10 model | | A549 Xenograft model | | |
|---|---|---|---|---|---|---|
| | | | | % TGI | | |
| Model: | | Metastasis | PBMCs % pStat3 | (Tumor Growth | PBMCs % pStat3 | Tumors % pStat3 |
| Compound | Dose | Inhibition | inhibition | Inhibition) | inhibition | inhibition |
| 45 | 10 MPK | n/d | n/d | 28.90 | 55.61 | 44.46 |
| | 30 MPK | 73% | 66 | 55.62 | 60.66 | 48.92 |
| | 100 MPK | 75% | 73 | 63.86 | 65.28 | 61.51 |
| | 150 MPK | n/d | n/d | 53.74 | 76.56 | 57.08 |
| Taxol | 5 MPK | 32% | 25 | n/a | n/a | n/a |
| Erlotinib | 100 MPK | n/a | n/a | 59.55 | 44.43 | 28.14 |
| Vinorelbine | 8 MPK | n/a | n/a | 51.89 | 28.8 | 25.2 |
| Gefitinib | 100 MPK | n/a | n/a | n/a | n/a | n/a |

| | | A431 Xenograft model | | |
|---|---|---|---|---|
| Model: | | % | PBMCs % pStat3 | Tumors % pStat3 |
| Compound | Dose | TGI | inhibition | inhibition |
| 45 | 10 MPK | n/d | n/d | n/d |
| | 30 MPK | n/d | n/d | n/d |
| | 100 MPK | 52.55 | 56.32 | 44.3 |
| | 150 MPK | n/d | n/d | n/d |
| Taxol | 5 MPK | n/a | n/a | n/a |
| Erlotinib | 100 MPK | n/a | n/a | n/a |
| Vinorelbine | 8 MPK | n/a | n/a | n/a |
| Gefitinib | 100 MPK | 94.25 | 54.1 | 45.44 |

TABLE 6-continued

| Assays | Compound No. 45 | Compound No. 117 | Compound No. 179 |
|---|---|---|---|
| Efficacy - B16F10 at 100 MPK | | | |
| Survival advantage | 9 days | 1 day | 4 days |
| % metastasis inhib. | 75% | 26% | 47% |
| Efficacy - A549 at 100 MPK | | | |
| TGI | 64% at 100 MPK | 56% at 100 MPK | 68% at 30 MPK |
| % pSTAT3 inhib. (tumour) | 62% at 100 MPK | 47% at 100 MPK | 79% at 30 MPK |
| Efficacy - A431 at 100 MPK | | | |
| TGI | 48% | 54% | 67% |
| % pSTAT3 inhib. (tumour) | 45% | 10% | 54% |

Volume Distribution

A high volume of distribution of a compound indicates that the compound penetrates into organs and tissues, being suitable for the treatment of solid tumours, whereas a low distribution volume indicates that the compound presents a lower ability to penetrate into organs and tissues and therefore remains in the blood circulation. Therefore compounds with a weak volume of distribution like the compound N° 171 is more suitable for the treatment of blood (hematological) tumours. Table 8 provides some volume distribution values of the compounds of the present invention.

TABLE 8

| Compound No. | Vd (ml/kg) |
|---|---|
| 45 | 5894 |
| 171 | 794 |
| 185 | 583.2 |
| 17 | 7700 |
| 162 | 3350 |
| 155 | 11807 |
| 131 | 7141 |
| 147 | 20606 |

The invention claimed is:

1. A compound of formula (I) having the structure

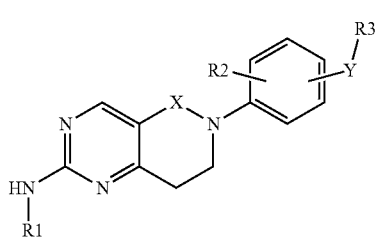

wherein
R1 is H, aryl, substituted aryl, alkyl, substituted alkyl, heteroaryl, substituted heteroaryl, heterocyclyl, substituted heterocyclyl, heterocyclylalkyl or substituted heterocyclylalkyl;
X is $CH_2$ or C=O;
R2 is H, ($C_1$-$C_6$)alkyl, halogen, $CF_3$, or —O—($C_1$-$C_6$)alkyl;
Y is —NHCO—, —CONH—, —$NHSO_2^-$, —NH—, —$NCH_3$—CO—, —$NHCH_2$—, O, —NHCONH— or —$NHCOCH_2$—;
R3 is alkyl, substituted alkyl, aryl, or substituted aryl, heteroaryl, substituted heteroaryl, cycloalkyl, substituted cycloalkyl

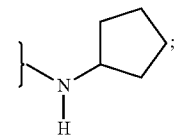

or heterocycloalkyl;
or a pharmaceutically acceptable salt thereof.

2. The compound according to claim 1, of formula (II) having the structure

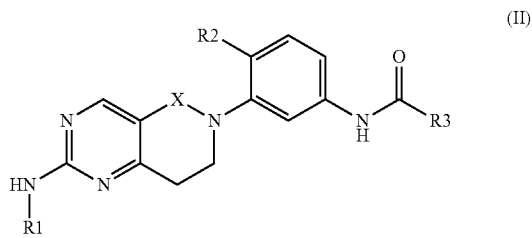

wherein
R1 is hydrogen, ($C_1$-$C_4$)alkyl, phenyl, substituted phenyl, pyridine, or substituted pyridine;
X is $CH_2$ or C=O;
R2 is H, ($C_1$-$C_6$)alkyl, halogen, or —O($C_1$-$C_6$)alkyl;
R3 is ($C_1$-$C_6$)alkyl, cycloalkyl, substituted cycloalkyl, heterocycloalkyl, aryl, substituted aryl, heteroaryl, substituted heteroaryl,

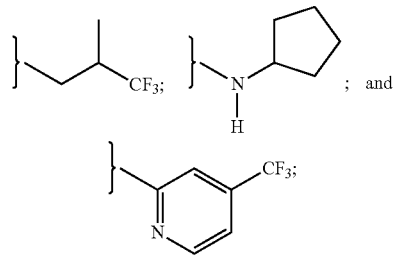

and wherein the substituents are selected from the group consisting of $C_1$-$C_4$ linear or branched alkyl; halo or nitrile substituted $C_1$-$C_4$ alkyl; —O-alkyl($C_1$-$C_4$); and halogen;
or a pharmaceutically acceptable salt thereof.

3. The compound according to claim 1, wherein R3 is selected from the group consisting of:

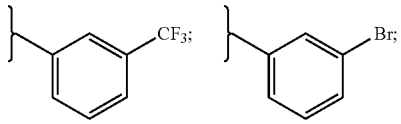

165
-continued

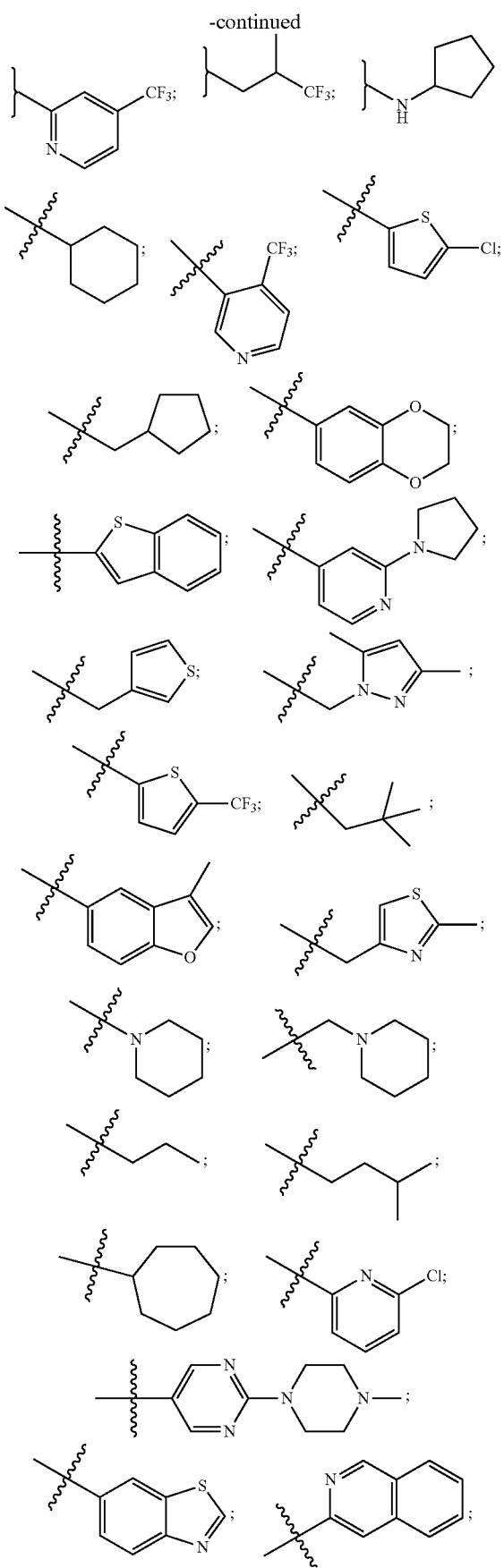

166
-continued

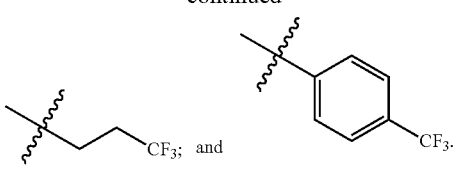

4. The compound according to claim 1, wherein
R1 is substituted phenyl or substituted pyridine;
X is $CH_2$ or C=O;
R2 is H, $CH_3$, Cl or F;
R3 is selected from the group consisting of:

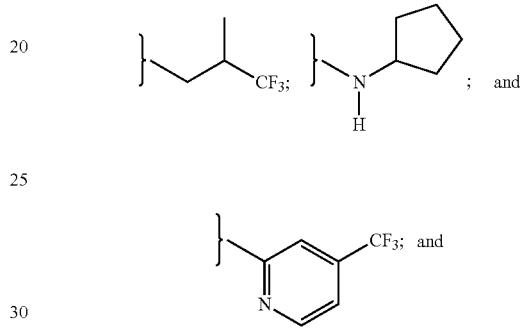

substituted phenyl, wherein the substituents are independently selected from the group consisting of Cl, F, Br, $CF_3$ and $CH_3$.

5. The compound according to claim 1, wherein
R1 is selected from the group consisting of:

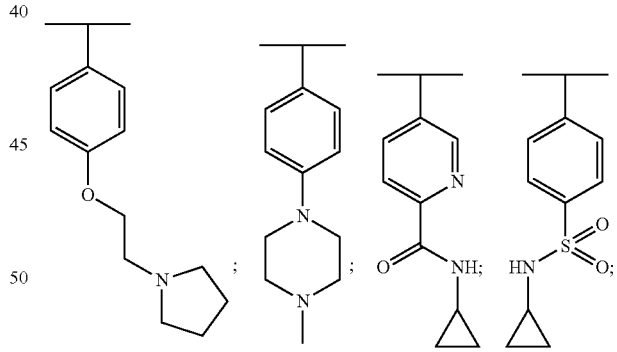

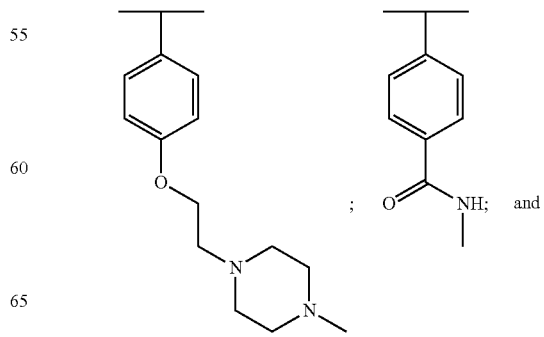

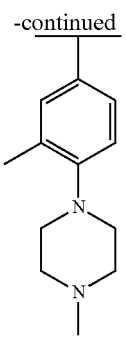

and

R3 is selected from the group consisting of:

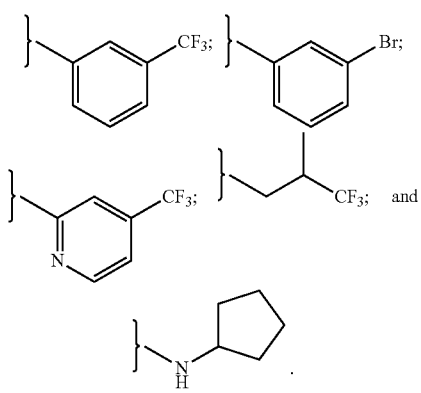

6. The compound according to claim 1, selected from the group consisting of:
- N-(4-Methyl-3-{2-[4-(4-methyl-piperazine-1-carbonyl)-phenylamino]-7,8-dihydro-5H-pyrido[4,3-c]pyrimidin-6-yl}-phenyl)-3-trifluoromethyl-benzamide;
- N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide;
- 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide;
- N-{3-[2-(4-Cyclopropylsulfamoyl-phenylamino)-7,8-dihydro-5H-pyrido[4,3-d]pyrimidin-6-yl]-4-methyl-phenyl}-3-trifluoromethyl-benzamide;
- N-(4-Chloro-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide;
- 4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide;
- 4,4,4-Trifluoro-3-methyl-N-[4-methyl-3-(2-{4-[2-(4-methyl-piperazin-1-yl)-ethoxy]-phenylamino}-7,8-dihydro-5H-pyrido[4,3-d]pyrimidin-6-yl)-phenyl]-butyramide;
- 1-Cyclopentyl-3-(4-methyl-3-{2-[4-(2-pyrrolidin-1-yl-ethoxy)-phenylamino]-7,8-dihydro-5H-pyrido[4,3-d]pyrimidin-6-yl}-phenyl)-urea;
- N-(4-Methyl-3-{5-oxo-2-[4-(2-pyrrolidin-1-yl-ethoxy)-phenylamino]-7,8-dihydro-5H-pyrido[4,3-d]pyrimidin-6-yl}-phenyl)-3-trifluoromethyl-benzamide;
- N-{4-Chloro-3-[2-(4-cyclopropylcarbamoylmethoxy-phenylamino)-5-oxo-7,8-dihydro-5H-pyrido[4,3-d]pyrimidin-6-yl]-phenyl}-3-trifluoromethyl-benzamide;
- N-(4-Chloro-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide;
- 3-Bromo-N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-benzamide; and
- N-(4-Chloro-3-{2-[4-(4-methyl-piperazin-1-ylmethyl)-phenylamino]-5-oxo-7,8-dihydro-5H-pyrido[4,3-d]pyrimidin-6-yl}-phenyl)-3-trifluoromethyl-benzamide;

or a pharmaceutically acceptable salt thereof.

7. The compound according to claim 1, selected from the group consisting of:
- N-(4-Methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide;
- 5-{6-[2-Methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide; and
- 4-Trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide;

or a pharmaceutically acceptable salt thereof.

8. The compound according to claim 1, selected from the group consisting of:
- N-(4-Chloro-3-{2-[3-methyl-4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide; and
- N-{4-Chloro-3-[2-(4-cyclopropylcarbamoylmethoxy-phenylamino)-5-oxo-7,8-dihydro-5H-pyrido[4,3-d]pyrimidin-6-yl]-phenyl}-3-trifluoromethyl-benzamide;

or a pharmaceutically acceptable salt thereof.

9. A pharmaceutical composition comprising a compound or pharmaceutically acceptable salt according to claim 1 and at least one pharmaceutically acceptable excipient, carrier or diluent.

* * * * *